US009095554B2

(12) United States Patent
Lewis et al.

(10) Patent No.: US 9,095,554 B2
(45) Date of Patent: Aug. 4, 2015

(54) BREEDING, PRODUCTION, PROCESSING AND USE OF SPECIALTY CANNABIS

(71) Applicant: Biotech Institute LLC, Westlake Village, CA (US)

(72) Inventors: Mark Anthony Lewis, Westlake Village, CA (US); Michael D Backes, Westlake Village, CA (US); Matthew Giese, Westlake Village, CA (US)

(73) Assignee: Biotech Institute LLC, Los Angeles, CA (US)

( * ) Notice: Subject to any disclaimer, the term of this patent is extended or adjusted under 35 U.S.C. 154(b) by 0 days.

(21) Appl. No.: 14/216,744

(22) Filed: Mar. 17, 2014

(65) Prior Publication Data

US 2014/0287068 A1    Sep. 25, 2014

Related U.S. Application Data

(60) Provisional application No. 61/897,074, filed on Oct. 29, 2013, provisional application No. 61/801,528, filed on Mar. 15, 2013.

(51) Int. Cl.
| | |
|---|---|
| *A01H 5/02* | (2006.01) |
| *A61K 36/185* | (2006.01) |
| *A01H 4/00* | (2006.01) |
| *A01H 1/04* | (2006.01) |
| *A01H 5/12* | (2006.01) |

(52) U.S. Cl.
CPC ............... *A61K 36/185* (2013.01); *A01H 1/04* (2013.01); *A01H 4/00* (2013.01); *A01H 5/02* (2013.01); *A01H 5/12* (2013.01)

(58) Field of Classification Search
None
See application file for complete search history.

(56) References Cited

U.S. PATENT DOCUMENTS

| | | | |
|---|---|---|---|
| 4,279,824 A | 7/1981 | McKinney | |
| 6,403,126 B1 | 6/2002 | Webster et al. | |
| 6,630,507 B1 | 10/2003 | Hampson et al. | |
| 7,968,594 B2 | 6/2011 | Guy et al. | |
| 2004/0049059 A1 | 3/2004 | Mueller | |
| 2008/0103193 A1 | 5/2008 | Castor et al. | |
| 2008/0241339 A1 | 10/2008 | Mitchell et al. | |
| 2009/0035396 A1 | 2/2009 | De Meijer | |
| 2010/0216872 A1 | 8/2010 | Letzel et al. | |
| 2011/0098348 A1 | 4/2011 | De Meijer | |
| 2012/0311744 A1 | 12/2012 | Sirkowski | |
| 2013/0109747 A1 | 5/2013 | Whittle | |
| 2014/0243405 A1 | 8/2014 | Whalley | |
| 2014/0245494 A1 | 8/2014 | Cohen | |
| 2014/0245495 A1 | 8/2014 | Cohen | |
| 2014/0298511 A1* | 10/2014 | Lewis et al. | 800/260 |

FOREIGN PATENT DOCUMENTS

GB    2459125    10/2009

OTHER PUBLICATIONS

CBD-crew Critical Mass (2012) pp. 1-5.*
CBD-crew Sweet and Sour Widow (2012) pp. 1-4.*
CBD-crew Launch Interview (2009) pp. 1-3.*
Fishedick, J. et al. Phytochemistry (2010) vol. 71, pp. 2058-2073.*
Russo, E.B., The British Journal of Pharmacology (2011) vol. 613, pp. 1344-1364.*
CBD Crew Sweet and Sour Widow analysis published Nov. 2, 2013 pp. 1-5.*
CBD Crew Analysis Report; (Critical Mass, Fundacion Canna; Mar. 21, 2012) pp. 1-2.*
CBD Crew Web Pub; (Critical Mass sample available from Northwest Canna Connection; Feb. 26, 2014) pp. 1-5.*
Satyal, P. et al. Journal of Medicinally Active Plants, vol. #3, Issue 1; Dec. 2014; pp. 9-16.*
De Meijer et al., 2003, The Inheritance of Chemical Phenotype in *Cannabis sativa* L. Genetics, 163:335-346.
De Meijer et al., 2005, The Inheritance of Chemical Phenotype in *Cannabis sativa* L. (II) Cannabigerol Predominant Plants. Euphytica, 145:189-198.
De Meijer et al., 2009, The Inheritance of chemical phenotype in *Cannabis sativa* L. (III) Variation in Cannabichromene Proportion Euphytica, 165:293-311.
De Meijer et al., 2009, The Inheritance of Chemical Phenotype in *Cannabis sativa* L. (IV) Cannabinoid-Free Plants, Euphytica, 168:95-112.
2011, Taming THC: potential *Cannabis* synergy and phytocannabinoid-terpenoid entourage effects, British Journal of Pharmacology, 163:1344-1364.
Russo et al. (2006, A tale of two cannabinoids: the therapeutic rationale for combining tetrahydrocannabinol and cannabidiol, Medical Hypothesis, 2006, 66:234-246).
Hazekamp and Fischedick 2010. "Metabolic fingerprinting of *Cannabis sativa* L., cannabinoids and terpenoids for chemotaxonomic and drug standardization purposes" Phytochemistry 2058-73.
McPartland and Russo 2001 *Cannabis* and *Cannabis* Extracts: Greater Than the Sum of Their Parts? Journal of *Cannabis* Therapeutics vol. 1, No. 3/4,2001, pp. 103-132.
RG Pertwee. 2008 "The diverse CB1 and CB2 receptor pharmacology of three plant cannabinoids: delta 9 tetrahydrocannabinol, cannabidiol and delta 9 tetrahydrocannabivarin" Br. J Pharmacol. 153(2):199-215.
CBD Crew "About Us" Printed copy provided as published on Apr. 10, 2012. URL: http://cbdcrew.org/about-us/.
CBD Crew "Varieties" Printed copy provided as published on Mar. 20, 2012. URL: http://cbdcrew.org/varieties/.
International PCT Search Report for PCT/US14/30267, mailed on Nov. 7, 2014.
Seedsman listing of "Sweet and Sour Widow" on May 21, 2013. http://web.archive.org/web/20130521045347/http://www.seedsman.com/en/cbd-sweet-n-sour-widow-regular-5-seeds.
Analytical 360 analysis of Sweet & Sour Widow CBD on Nov. 2, 2013. http://analytical360.com/m/expired/131803.
CBD-crew front page on Nov. 22, 2014. www.cbdcrew.org.

(Continued)

*Primary Examiner* — Russell Kallis
(74) *Attorney, Agent, or Firm* — Cooley LLP

(57) ABSTRACT

The invention provides compositions and methods for the breeding, production, processing and use of specialty *cannabis*.

16 Claims, 19 Drawing Sheets

(56) References Cited

OTHER PUBLICATIONS

Agilent Technologies, Inc "Consideration for Selecting GC/MS or LC/MS for Metabolomics." 2007 Feb. 24, 2007.

Waksmundzka-Hajnos and Monika. "High Performance Liquid Chromatography in Phytochemical Analysis (Chromatographic Science Series)." Published May 14, 2012. p. 582 provided.

The Werc Shop Terpene Profiling Services, Aug. 26, 2012. https://web.archive.org/web/20120826071723/http://thewercshop.com/services/terpene-profiling-services.

Kojoma M et al., DNA polymorphisms in the tetrahydrocannabinolic acid (THCA) synthase gene in "drug-type" and "fiber-type" *Cannabis sative* L, Forensic Science International, Jun. 2, 2006, pp. 132-140, vol. 159, No. 2-3., Elsevier Scientific Publishers Ireland Ltd.

PCT/US2014/046694 International Search Report. Mailed on Jan. 5, 2015.

Bertoli A. et al., "Fibre hemp inflorescences: From crop-residues to essential oil production", Industrial Crops and Products, Nov. 1, 2010, pp. 329-337, vol. 32, No. 3.

Solon, Olivia, "Medical Marijuana Without the High", May 7, 2012, retrieved from the Internet: www.wired.com.

Harm Van Bakel et al., "The draft genome and transcriptome of *Cannabis sativa*", Genome Biology, Oct. 20, 2011, p. R102, vol. 12, No. 10, Biomed Central Ltd., London, GB.

G. of Vancouver island Seed Company, "How to make Clones", Cannabis Culture Magazine published on Tuesday, Apr. 29, 2009. Available online at http://www.cannabisculture.com/content/how-make-clones.

* cited by examiner

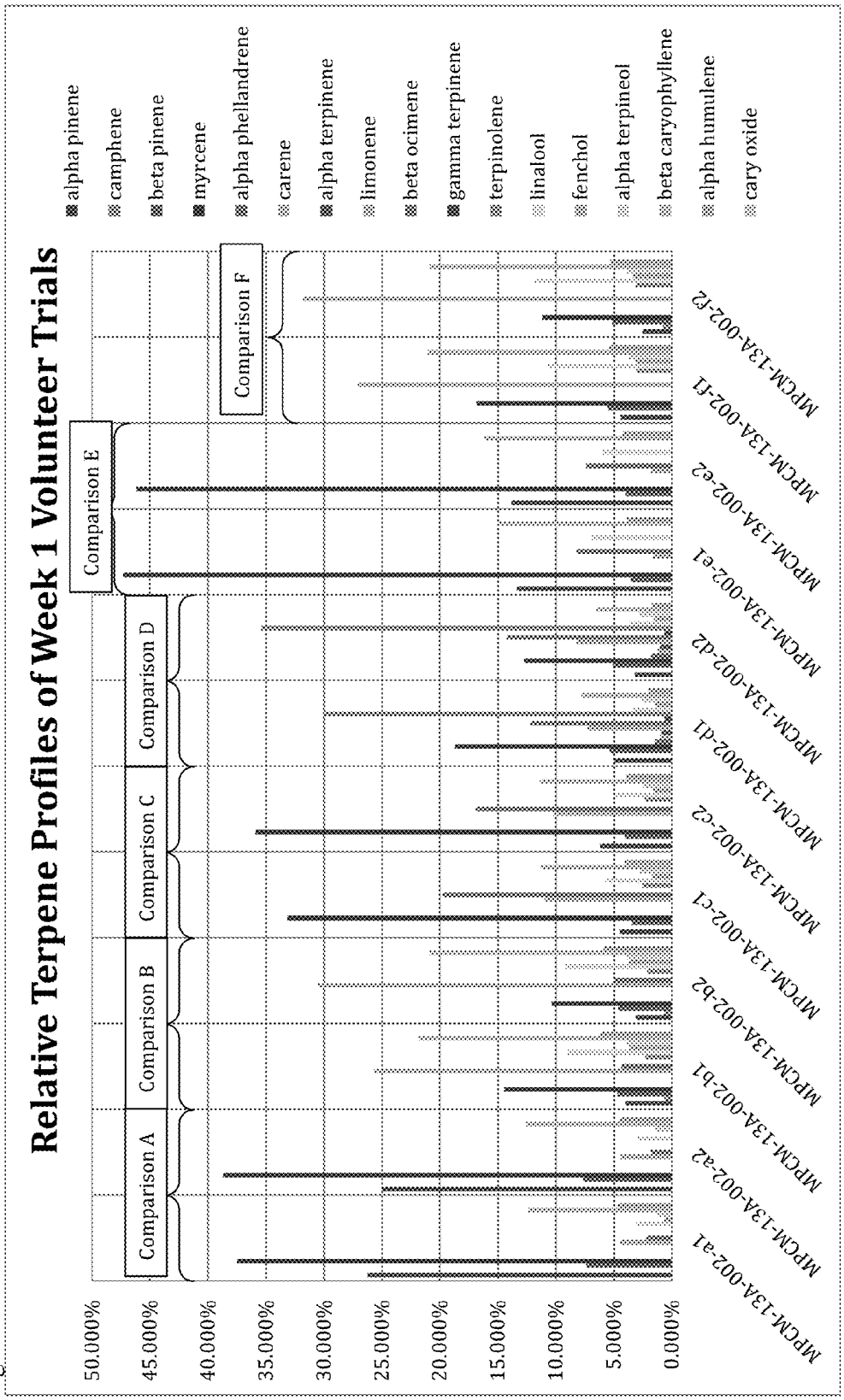

Figure 2

| Critical Feedback Survey | |
|---|---|
| Volunteer: | Sample ID: |
| 1 = Extremely Unpleasant – 10 = Extremely Pleasant | |
| How would you rate the aroma? | 1 2 3 4 5 6 7 8 9 10 |
| How would you describe the aroma? | |
| How would you rate the flavor? | 1 2 3 4 5 6 7 8 9 10 |
| How would you describe the flavor? | |
| 1 = Extremely Weak – 10 = Extremely Strong | |
| How would you rate the mind high? | 1 2 3 4 5 6 7 8 9 10 |
| How would you rate the body high? | 1 2 3 4 5 6 7 8 9 10 |
| 1 = Extremely Low – 10 = Extremely High | |
| How would you rate your level of intoxication? | 1 2 3 4 5 6 7 8 9 10 |
| How would you rate your feeling of calmness? | 1 2 3 4 5 6 7 8 9 10 |
| How would you rate your feeling of alertness? | 1 2 3 4 5 6 7 8 9 10 |
| How would you rate your level of anxiety? | 1 2 3 4 5 6 7 8 9 10 |
| How would you rate your ability to focus? | 1 2 3 4 5 6 7 8 9 10 |
| How would you rate your level of mood enhancement? | 1 2 3 4 5 6 7 8 9 10 |
| How would you rate your energy level? | 1 2 3 4 5 6 7 8 9 10 |
| How would you rate your level of hunger? | 1 2 3 4 5 6 7 8 9 10 |
| How would you rate your level of thirst? | 1 2 3 4 5 6 7 8 9 10 |
| How would you rate your level of physical comfort? | 1 2 3 4 5 6 7 8 9 10 |
| How would you rate your level of emotional comfort? | 1 2 3 4 5 6 7 8 9 10 |
| How would you rate your ability to function normally? | 1 2 3 4 5 6 7 8 9 10 |
| How would you rate your level of sedation? | 1 2 3 4 5 6 7 8 9 10 |
| 1 = Extremely Brief – 10 = Extremely Long | |
| How would you rate the length of your effects? | 1 2 3 4 5 6 7 8 9 10 |
| 1 = Extremely Low – 10 = Extremely High | |
| Rate the perceived level of positive effects you attribute to this sample. | 1 2 3 4 5 6 7 8 9 10 |
| Rate the perceived level of negative effects you attribute to this sample. | 1 2 3 4 5 6 7 8 9 10 |
| Comments: | |

Figure 14
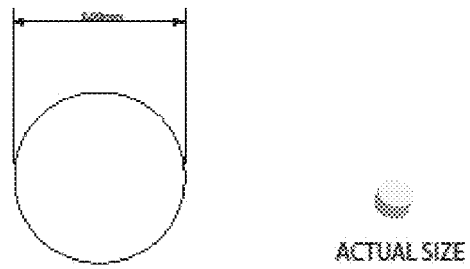
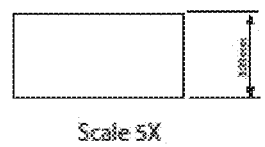
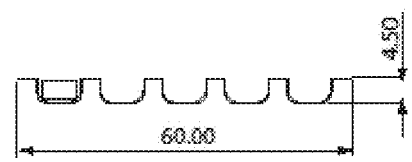
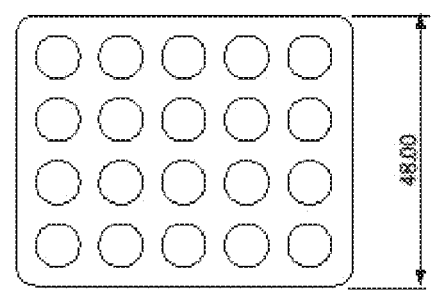

b= diameter of larger base h= height of of cone t= diameter of smaller base

Figure 16
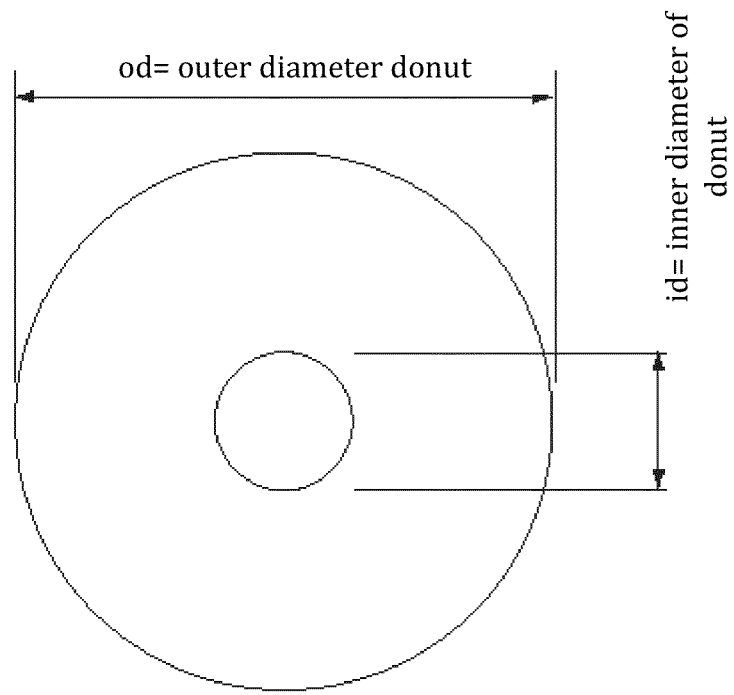
ACTUAL SIZE
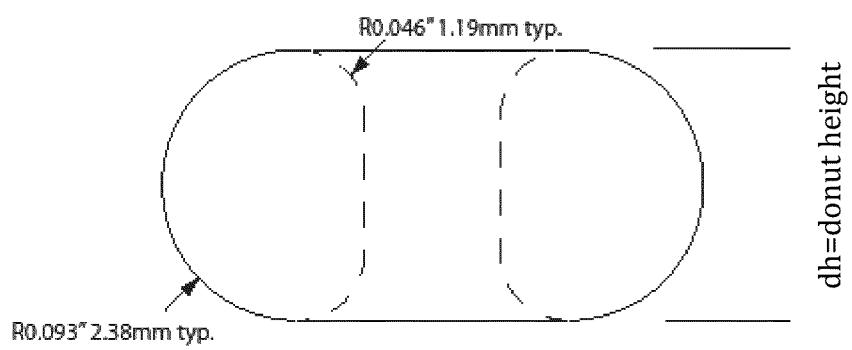

BREEDING, PRODUCTION, PROCESSING AND USE OF SPECIALTY CANNABIS

CROSS-REFERENCE TO RELATED APPLICATIONS

This application claims the benefit of U.S. provisional application No. 61/801,528 filed on Mar. 15, 2013 which is hereby incorporated by reference in its entirety including all descriptions, references, figures, and claims for all purposes. This application also claims the benefit of U.S. provisional application No. 61/897,074 filed on Oct. 29, 2013 which is hereby incorporated by reference in its entirety including all descriptions, references, figures, and claims for all purposes.

FIELD OF THE INVENTION

The invention relates to specialty *cannabis* plants, compositions and methods for making and using said *cannabis* plants and compositions derived thereof.

BACKGROUND OF THE INVENTION

*Cannabis*, more commonly known as marijuana, is a genus of flowering plants that includes at least three species, *Cannabis sativa*, *Cannabis indica*, and *Cannabis ruderalis* as determined by plant phenotypes and secondary metabolite profiles. In practice however, *cannabis* nomenclature is often used incorrectly or interchangeably. *Cannabis* literature can be found referring to all *cannabis* varieties as "sativas" or all cannabinoid producing plants as "indicas". Indeed the promiscuous crosses of indoor *cannabis* breeding programs have made it difficult to distinguish varieties, with most *cannabis* being sold in the United States having features of both sativa and indica species.

The use of *cannabis* for social and medical purposes has been known for almost of all humanity's recorded history. *Cannabis* is most commonly administered via inhalation or consumption of marijuana-infused food and drink. However, since 1972 marijuana has been classified as a Schedule I drug under the U.S. Controlled Substances Act because the U.S. Federal Government considers it to have "no accepted medical use." In stark contrast to this position, 20 of the 50 U.S. states and the District of Columbia have recognized the medical benefits of *cannabis* and have decriminalized its medical use. The 20 U.S. states where medical marijuana has been decriminalized as of the filing date of the present application are as follows: Alaska, Arizona, California, Colorado, Connecticut, Delaware, Hawaii, Illinois, Maine, Massachusetts, Michigan, Montana, Nevada, New Hampshire, New Jersey, New Mexico, Oregon, Rhode Island, Vermont and Washington. The residency requirements, approved list of conditions/diseases, and the other laws/rules regarding the possession and cultivation of medical marijuana generally differ by state.

President Obama has publicly commented on the recreational legalization of *cannabis* in Colorado and Washington stating that "it's important for it to go forward because it's important for society not to have a situation in which a large portion of people have at one time or another broken the law and only a select few get punished". Indeed in the same interview, President Obama remarked about *cannabis* "I don't think it's more dangerous than alcohol. In fact, it is less dangerous than alcohol in terms of its impact on the individual consumer." (Conor Friedersdorf January 2014, "Obama on Pot Legalization: 'It's Important for it to go Forward'" The Atlantic). In line with the President's comments the U.S. Attorney General Eric Holder announced that the federal government would allow states to create a regime that would regulate and implement the legalization of *cannabis*, including loosening banking restrictions for *cannabis* dispensaries and growers (Jacob Sullum "Eric Holder Promises To Reassure Banks About Taking Marijuana Money 'Very Soon'" Forbes January 2014).

In addition to these recent developments, the U.S. government has already set a precedent for patenting *cannabis*, and *cannabis*-related inventions. For example, U.S. Pat. No. 6,630,507 issued on Oct. 7, 2003 and assigned on the patent face to The United States of America, is directed to methods of treating diseases caused by oxidative stress by administering therapeutically effective amounts of a cannabidiol (CBD) cannabinoid from *cannabis* that has substantially no binding to the N-methyl-D-aspartate (NMDA) receptor, wherein the CBD acts as an antioxidant and neuroprotectant. A search of the U.S.P.T.O Patent Application Information Retrieval (PAIR) system also reveals the existence of thousands of *cannabis* related applications and issued patents including U.S. Pat. No. 8,034,843 (use of cannabinoids for treating nausea, vomiting, emesis, motion sickness), U.S. Pat. No. 7,698,594 (cannabinoid compositions for treatment of pain), and U.S. Pat. No. 8,632,825 (anti-tumoural effects of cannabinoid combinations) among many others.

Thus, despite the official position of the U.S. Federal Government, and as recognized by the states that have legalized it, *cannabis* has been shown to provide substantial benefits for medical and recreational uses. *Cannabis* is regularly used by a wide cross-section of society to treat a variety of maladies, conditions and symptoms including, but not limited to, the following: nausea, glaucoma, lack of appetite, mucous membrane inflammation, epilepsy, leprosy, fever, obesity, asthma, urinary tract infections, coughing, anorexia associated with weight loss in AIDS patients, pain, and multiple sclerosis.

*Cannabis* intoxication (i.e., euphoria, relaxation) can occur and other side effects may also accompany its use, particularly with higher doses, specific *cannabis* varieties and/or over prolonged periods of usage. Undesirable side effects of using the available THC-predominant *cannabis* varieties can include, but are not limited to, the following: decreased short-term memory, dry mouth, impaired visual perception and motor skills, erectile dysfunction, lower fertility, red (i.e., blood shot) eyes, increased anxiety, occasional infarction, stroke, paranoia, acute psychosis, lowered mental aptitude, hallucinations, bizarre behavior, irrational panic attacks, irrational thoughts and various other cognitive and social problems.

Some of the negative or undesirable side effects from using available *cannabis* varieties for medical and recreational purposes are related to the plant's content of the chemical $\Delta^9$-tetrahydrocannabinol (THC). A major hurdle to the more widespread acceptance of *cannabis* and its legalization is that the land races and commercially available *cannabis* genotypes (of drug varieties) contain relatively high concentrations of THC. Indeed the average THC content of traditional recreational *cannabis* has risen over the years from an average of 0.74 in 1975, to 3.35% in the 1990's, and average of 6.4% in 2003 (Annual Reports (Nov. 9, 1999 to Nov. 8, 2003) of Mahmoud A. ElSohly, PhD, Director of the National Institute on Drug Abuse (NIDA) Marijuana Project at the National Center for Natural Products Research, School of Pharmacy, University of Mississippi). There is a real need for *cannabis* varieties for potential medical use that produce modulated THC concentrations and varying concentrations of other pharmacologically active substances that reduce the negative side effects of THC and increase the medical benefits realized from its use. There is also a need for healthier *cannabis* for recreational use with reduced negative side effects from THC. The inventions described herein meet that long-felt need.

SUMMARY OF THE INVENTION

According to the methods and compositions of the present invention, plants, plant parts, plant tissues and plant cells are produced to contain pentyl, propyl, C-4, C-1 and monomethylether constituents of cannabinoid families, including but not limited to acidic and neutral forms of the cannabigerol, cannabichromene, cannabidiol, delta-9-tetrahydrocannabinol, delta-8-tetrahydrocannabinol, cannabielsoin, cannabinol and cannabinodiol cannabinoid classes; and, cis and trans terpenoids, including but not limited to myrcene, limonene, linalool, ocimene, beta-pinene, alpha-pinene, beta-caryophyllene, alpha-caryophyllene, delta-3-carene, gamma-bisabolene, alpha-farnesene, beta-fenchol, guajol, alpha-guaiene, terpinolene, beta-eudesmol, alpha-bergamotene, epi-alpha-bisabolol and caryophyllene oxide ranging from 0.1% of dry weight of inflorescences, plant parts, plant tissues and plant cells to 35% of inflorescences and/or 95% of plant parts, plant parts, plant tissues and plant cells.

The present invention provides specialty *cannabis* plants, plant parts, plant tissues and plant cells which provide a way to deliver a consistent and more tolerable and effective ratio of cannabinoids by providing plants that comprise non-THC cannabinoids ("CBs") to patients (e.g., <THC:>CBs than in presently-available *cannabis* varieties).

The present invention provides specialty *cannabis* plants, plant parts, plant cells and plant tissues which have an amount, percentage and/or ratio of cannabinoids that is different from currently available THCA/THC varieties.

The present invention provides Medical *Cannabis* plants, plant parts, plant tissues and plant cells having an alternative cannabinoid (e.g., THCV, CBDV, etc.) to THCA/THC.

In some embodiments, the present invention provides Specialty *Cannabis* plants, plant parts, tissues and cells having a THC content that is ≥2.0% but ≤90.0% based on the dry weight of plant inflorescences; and, a non-THC CBs content based on the dry weight of plant inflorescences that is ≥1.5%. Thus, the specialty *cannabis* plants, plant parts, plant tissues and plant cells of the present invention will have a THC content selected from the group consisting of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89% and 90%; and, a CBs content selected from the group consisting of 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92%, 93%, 94%, 95%, 96%, 97%, and 98%.

In some embodiments, the present invention provides specialty *cannabis* plants, plant parts, tissues and cells having a THC:CBs ratio greater than or equal to of 8:1. In other embodiments, the specialty *cannabis* of the present invention has THC:CBS ratios approaching 1:1, or lower. By comparison, the THC:CBs ratio of the currently available *cannabis* varieties is 20:1 and approaches 25:1, 30:1, 35:1, 40:1 and higher. Thus, the specialty *cannabis* plants, plant parts, plant tissues and plant cells of the present invention will have a THC:CBs ratio of less than 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:9, or below.

The present invention provides Classes of *Cannabis* Varieties developed by selection from landraces of mixed *cannabis* genotypes and resulting from further breeding, wherein these Classes of *Cannabis* Varieties can provide useful patient treatment and also are used as breeding material to develop Specialty *Cannabis* plants and varieties according to the present invention.

The present invention provides Specialty *Cannabis* plants and varieties with increased organoleptic appeal as a result of having specified, predetermined terpene and sesquiterpene profiles and content. In some embodiments of the present invention, the increased organoleptic appeal of the Specialty *Cannabis* is inherited in-whole or in-part as a result of using the Classes of *Cannabis* Varieties in the breeding program to develop the Specialty *Cannabis* plants. For, example, in some embodiments, Classes of *Cannabis* Varieties with specific terpene and sesquiterpene profiles and content are bred with certain *cannabis* varieties with specific CBs profiles and content to develop Specialty *Cannabis* Varieties with the desired combined attributes of the two types of *cannabis* plants.

The present invention also provides methods to determine higher THC adequate to down-regulate the entire Cannabinoid (CB) system. This method uses the 'down-regulation' as therapy for hyper-endocannabinoid systems and to help increase the therapeutic margin. Additionally, the present invention provides for a potential role of dosage and its influence on biosynthesis and build-up of cholesterol; a healthy means of supplementing the endocannabinoid system when consuming an ultra low-cholesterol diet.

The present invention also provides methods for determining the terpene profiles at which 'dosages' are suitable for outcomes related to mood elevation and/or sedation (i.e., high limonene for energy, high myrcene for sleep aid, etc.). Furthermore, according to the present invention, terpenes such as beta-caryophyllene are used in pain studies (anti-inflammatory via PGE) and linalool is used for anxiety (anti-anxiety and sedative).

In some embodiments, the present invention teaches a *cannabis* plant, plant part, tissue, or cell comprising: a cannabidiol (CBD) content that is greater than 1.0% by weight, and a terpene profile in which myrcene is not the dominant terpene, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the cannabinoid and terpene content is measured by GC-FID and calculated based on dry weight of the inflorescence. In some embodiments, the *cannabis* plant, plant part, tissue or cell is chemotype II with $B_T/B_D$ genotype.

In some embodiments, the *cannabis* plant, plant part, tissue or cell of the present invention comprises a tetrahydrocannabinol (THC) content that is at least 1.0% by weight as measured by GC-FID and calculated based on dry weight of the inflorescence.

In some embodiments, the *cannabis* plant, plant part, tissue, or cell of the present invention comprises at least 2% cannabichromene (CBC) content by weight.

In some embodiments, the *cannabis* plant, plant part, tissue or cell of the present invention 1 comprises a CBD content that is at least 5% by weight, and the THC content is at least 5% by weight, as measured by GC-FID and calculated based on dry weight of the inflorescence.

In some embodiments, the *cannabis* plant, plant part, tissue or cell of the present invention comprises a terpene oil content greater than 1.0% by weight wherein the terpene oil content is determined by the additive content of the terpenes in the terpene profile as measured by GC-FID, and calculated based on dry weight of the inflorescence In some embodiments, the *cannabis* plant, plant part, tissue or cell of the present invention comprises a terpene oil content greater than 2% by weight wherein the terpene oil content is determined by the additive content of the terpenes in the terpene profile as measured by GC-FID, and calculated based on dry weight of the inflorescence.

In other embodiments, the present invention teaches a *cannabis* plant, plant part, tissue, or cell comprising a $B_T/B_D$ genotype, and terpene profile in which myrcene is not the dominant terpene, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the terpene content is measured by GC-FID and calculated based on dry weight of the inflorescence.

In other embodiments, the present invention teaches a *cannabis* plant, plant part, tissue, or cell comprising: a $B_T/B_D$ genotype, a myrcene relative content of less than 60% of the terpene profile, and a terpene oil content greater than 1.5% by weight, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the terpene oil content is determined by the additive content of the terpenes in the terpene profile, and wherein the terpene contents are measured by GC-FID and calculated based on dry weight of the inflorescence.

In some embodiments, the *cannabis* plant, plant part, tissue or cell of the present invention comprises a CBD content that is greater than 3% by weight as measured by GC-FID and calculated based on dry weight of the inflorescence.

In some embodiments, the *cannabis* plant, plant part, tissue or cell of the present invention comprises a THC content that is greater than 3% by weight as measured by GC-FID and calculated based on dry weight of the inflorescence.

In yet another embodiment, the present invention teaches a *cannabis* plant, plant part, tissue, or cell comprising: at least one propyl locus A allele ($A_{pr}$), and a terpene oil content greater than 1.5% by weight, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the terpene oil content is determined by the additive content of the terpenes in the terpene profile, and wherein the cannabinoid and terpene contents are measured by GC-FID and calculated based on dry weight of the inflorescence.

In some embodiments, the *cannabis* plant, plant part, tissue, or cell of the present invention comprises at least one $B_o$ allele.

In some embodiments, the *cannabis* plant, plant part, tissue, or cell of the present invention comprises a $B_T/B_D$ genotype.

In some embodiments, the *cannabis* plant, plant part, tissue, or cell of the present invention comprises a $B_D/B_D$ genotype.

In some embodiments, the *cannabis* plant, plant part, tissue, or cell of the present invention comprises a myrcene relative content of less than 60% of the terpene profile.

In some embodiments, the *cannabis* plant, plant part, tissue, or cell of the present invention comprises a terpene profile in which myrcene is not the dominant terpene.

In some embodiments, the *cannabis* plant, plant part, tissue or cell of the present invention comprises a cannabidivarin (CBDV) content that is greater than 1% as measured by GC-FID and calculated based on dry weight of the inflorescence.

In some embodiments, the *cannabis* plant, plant part, tissue or cell of the present invention comprises a CBDV content that is greater than 4% as measured by GC-FID and calculated based on dry weight of the inflorescence.

In some embodiments, the *cannabis* plant, plant part, tissue or cell of the present invention comprises a tetrahydrocannabivarin (THCV) content that is greater than 1% as measured by GC-FID and calculated based on dry weight of the inflorescence.

In some embodiments, the *cannabis* plant, plant part, tissue or cell of the present invention comprises a THCV content that is greater than 4% as measured by GC-FID and calculated based on dry weight of the inflorescence.

In other embodiments, the present invention teaches a *cannabis* plant, plant part, tissue, or cell comprising: at least one Bo allele, and a terpene oil content greater than 1.5% by weight, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the terpene oil content is determined by the additive content of the terpenes in the terpene profile, and wherein the cannabinoid and terpene contents are measured by GC-FID and calculated based on dry weight of the inflorescence.

In some embodiments, the *cannabis* plant, plant part, tissue, or cell of the present invention comprises a second $B_o$ allele.

In some embodiments, the *cannabis* plant, plant part, tissue, or cell of the present invention comprises a $B_D$ allele.

In some embodiments, the *cannabis* plant, plant part, tissue, or cell of the present invention comprises a $B_T$ allele.

In some embodiments, the *cannabis* plant, plant part, tissue or cell of the present invention comprises a Cannabigerol (CBG) content that is greater than 1% as measured by GC-FID and calculated based on dry weight of the inflorescence.

In some embodiments, the *cannabis* plant, plant part, tissue or cell of the present invention comprises a CBG content that is greater than 5% as measured by GC-FID and calculated based on dry weight of the inflorescence.

In some embodiments, the *cannabis* plant, plant part, tissue or cell of the present invention comprises a terpene profile in which the first or second most abundant terpene in the terpene profile is terpinolene.

In some embodiments, the *cannabis* plant, plant part, tissue or cell of the present invention comprises a terpene profile in which the first or second most abundant terpene in the terpene profile is alpha phelladrene.

In some embodiments, the *cannabis* plant, plant part, tissue or cell of the present invention comprises a terpene profile in which the first or second most abundant terpene in the terpene profile is careen.

In some embodiments, the *cannabis* plant, plant part, tissue or cell of the present invention comprises a terpene profile in which the first or second most abundant terpene in the terpene profile is limonene.

In some embodiments, the *cannabis* plant, plant part, tissue or cell of the present invention comprises a terpene profile in which the first or second most abundant terpene in the terpene profile is gamma terpinene.

In some embodiments, the *cannabis* plant, plant part, tissue or cell of the present invention comprises a terpene profile in which the first or second most abundant terpene in the terpene profile is alpha pinene.

In some embodiments, the *cannabis* plant, plant part, tissue or cell of the present invention comprises a terpene profile in which the first or second most abundant terpene in the terpene profile is alpha terpinene.

In some embodiments, the *cannabis* plant, plant part, tissue or cell of the present invention comprises a terpene profile in which the first or second most abundant terpene in the terpene profile is beta pinene.

In some embodiments, the *cannabis* plant, plant part, tissue or cell of the present invention comprises a terpene profile in which the first or second most abundant terpene in the terpene profile is gamma fenchol.

In some embodiments, the *cannabis* plant, plant part, tissue or cell of the present invention comprises a terpene profile in which the first or second most abundant terpene in the terpene profile is camphene.

In some embodiments, the *cannabis* plant, plant part, tissue or cell of the present invention comprises a terpene profile in which the first or second most abundant terpene in the terpene profile is terpineol.

In some embodiments, the *cannabis* plant, plant part, tissue or cell of the present invention comprises a terpene profile in which the first or second most abundant terpene in the terpene profile is alpha humulene.

In some embodiments, the *cannabis* plant, plant part, tissue or cell of the present invention comprises a terpene profile in which the first or second most abundant terpene in the terpene profile is beta caryophyllene.

In some embodiments, the *cannabis* plant, plant part, tissue or cell of the present invention comprises a terpene profile in which the first or second most abundant terpene in the terpene profile is linalool.

In some embodiments, the *cannabis* plant, plant part, tissue or cell of the present invention comprises a terpene profile in which the first or second most abundant terpene in the terpene profile is cary oxide.

In some embodiments, the *cannabis* plant, plant part, tissue or cell of the present invention comprises a terpene profile in which the first or second most abundant terpene in the terpene profile is beta ocimene.

In other embodiments, the present invention teaches a method of breeding *cannabis* plants with non-myrcene dominant terpene profiles and a $B_D$ allele, said method comprising: (i) making a cross between a first *cannabis* plant and a second *cannabis* plant to produce an F1 plant, wherein the first plant comprises: a CBD content that is greater than 1.0% by weight, and a terpene profile in which myrcene is not the dominant terpene, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the cannabinoid and terpene content is measured by GC-FID and calculated based on dry weight of the inflorescence; (ii) harvesting the resulting seed; (iii) growing said seed; and (iv) selecting for the desired phenotypes; wherein the resulting selected *cannabis* plant has a non-myrcene dominant terpene profile, and comprises a $B_D$ allele.

In some embodiments of the breeding methods of the present invention, the first *cannabis* plant is chemotype II with $B_T/B_D$ genotype.

In some embodiments of the breeding methods of the present invention, the first *cannabis* plant, comprises a THC content that is at least 1.0% by weight as measured by GC-FID and calculated based on dry weight of the inflorescence.

In some embodiments of the breeding methods of the present invention, the first *cannabis* plant comprises at least 2% CBC content by weight.

In some embodiments of the breeding methods of the present invention, the first *cannabis* plant comprises a terpene oil content greater than 1.0% by weight wherein the terpene oil content is determined by the additive content of the terpenes in the terpene profile as measured by GC-FID, and calculated based on dry weight of the inflorescence.

In some embodiments of the breeding methods of the present invention, the first *cannabis* plant comprises a terpene oil content greater than 2.0% by weight wherein the terpene oil content is determined by the additive content of the terpenes in the terpene profile as measured by GC-FID, and calculated based on dry weight of the inflorescence.

In some embodiments of the breeding methods of the present invention, the first *cannabis* plant comprises a CBD content that is at least 5% by weight, and the THC content is at least 5% by weight, as measured by GC-FID and calculated based on dry weight of the inflorescence.

In other embodiments, the present invention teaches a method of breeding chemotype II *cannabis* plants with a non myrcene dominant terpene profile, said method comprising: (i) making a cross between a first *cannabis* plant and a second *cannabis* plant to produce an F1 plant, wherein the first plant comprises: a $B_T/B_D$ genotype, and a terpene profile in which myrcene is not the dominant terpene, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the cannabinoid and terpene content is measured by GC-FID and calculated based on dry weight of the inflorescence; (ii) harvesting the resulting seed; (iii) growing said seed; and (iv) selecting for the desired phenotypes; wherein the resulting selected *cannabis* plant is a chemotype II *cannabis* plant with a non-myrcene dominant terpene profile.

In other embodiments, the present invention teaches a method of breeding chemotype II *cannabis* plants with high oil content and low-myrcene content, said method comprising: (i) making a cross between a first *cannabis* plant and a second *cannabis* plant to produce an F1 plant, wherein the first plant comprises: a $B_T/B_D$ genotype, a myrcene relative content of less than 60% of the terpene profile; and, a terpene oil content greater than 1.5% by weight, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the terpene oil content is determined by the additive content of the terpenes in the terpene profile, and wherein the terpene contents are measured by GC-FID and calculated based on dry weight of the inflorescence; (ii) harvesting the resulting seed; (iii) growing said seed; and (iv) selecting for the desired phenotypes; wherein the resulting selected *cannabis* plant is a chemotype II *cannabis* plant with a terpene oil content greater than 1.5% by weight and a myrcene relative content of less than 60%.

In some embodiments of the breeding methods of the present invention, the first *cannabis* plant comprises a CBD content that is greater than 3% by weight as measured by GC-FID and calculated based on dry weight of the inflorescence.

In some embodiments of the breeding methods of the present invention, the first *cannabis* plant comprises a THC content that is greater than 3% by weight as measured by GC-FID and calculated based on dry weight of the inflorescence.

In other embodiments, the present invention teaches a method of breeding *cannabis* plants with propyl cannabinoids and high oil content, said method comprising: (i) making a cross between a first *cannabis* plant and a second *cannabis* plant to produce an F1 plant, wherein the first plant comprises: at least one propyl locus A allele ($A_{pr}$), and a terpene oil content greater than 1.5% by weight; wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of a plant, and wherein the terpene oil content is determined by the additive content of the terpenes in the terpene profile, and wherein the cannabinoid and terpene contents are measured by GC-FID and calculated based on dry weight of the inflorescence; (ii) harvesting the resulting seed; (iii) growing said seed; and (iv) selecting for the desired phenotypes; wherein the resulting selected *cannabis* plant has at least one propyl locus A allele capable of producing at least one propyl cannabinoid, and also has a terpene oil content greater than 1.5% by weight.

In some embodiments of the breeding methods of the present invention, the first *cannabis* plant comprises at least one null locus B allele.

In some embodiments of the breeding methods of the present invention, the first *cannabis* plant comprises a $B_T/B_D$ genotype.

In some embodiments of the breeding methods of the present invention, the first *cannabis* plant comprises a $B_D/B_D$ genotype.

In some embodiments of the breeding methods of the present invention, the first *cannabis* plant, comprises a myrcene relative content of less than 60% of the terpene profile.

In some embodiments of the breeding methods of the present invention, the first *cannabis* plant, comprises a terpene profile in which myrcene is not the dominant terpene.

In some embodiments of the breeding methods of the present invention, the first *cannabis* plant comprises a CBDV content that is greater than 1% as measured by GC-FID and calculated based on dry weight of the inflorescence.

In some embodiments of the breeding methods of the present invention, the first *cannabis* plant comprises a CBDV content that is greater than 4% as measured by GC-FID and calculated based on dry weight of the inflorescence.

In some embodiments of the breeding methods of the present invention, the first *cannabis* plant comprises a THCV content that is greater than 1% as measured by GC-FID and calculated based on dry weight of the inflorescence.

In some embodiments of the breeding methods of the present invention, the first *cannabis* plant comprises a THCV content that is greater than 4% as measured by GC-FID and calculated based on dry weight of the inflorescence.

In some embodiments, the present invention teaches methods of growing *cannabis* plants, said method comprising: obtaining a *cannabis* seed, cutting, or plant cell of any of the specialty *cannabis* varieties of the present invention capable of growing, placing said *cannabis* seed, cutting, or plant cell in an environment conducive to plant growth, and allowing said *cannabis* seed, cutting, or plant to produce a *cannabis* plant, wherein *cannabis* plant contains the same genetic makeup as the *cannabis* seed, cutting, or plant cell from which it was grown.

In some embodiments, the present invention teaches a *cannabis* extract from the *cannabis* plant, plant part, tissue, or cell of the present invention.

In some embodiments, the extract of the present invention is selected from the group consisting of kief, hashish, bubble hash, solvent reduced oils, sludges, e-juice, and tinctures.

In some embodiments, the extract of the present invention retains the terpene profile of the *cannabis* plant, plant part, tissue or cell from which it was made.

In some embodiments, the present invention teaches a *cannabis* edible product produced from the *cannabis* plant, plant part, tissue, or cell of the present invention.

In some embodiments, the present invention teaches a multiplexed *cannabis* mixture (MCM), said MCM comprising: (i) at least one *cannabis* plant base; (ii) one or more stock fortifiers; wherein the mixture is tailored for a specific recreational or medicinal purpose based on the pharmacological properties of the cannabinoid and terpene profiles of the mixture, and wherein the MCM comprises at least 1.5% terpene oil content, wherein the terpene profile consists of terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene of the mixtures, wherein the terpene oil content is determined by the additive content of the terpenes in the terpene profile, and wherein the terpene contents are measured by GC-FID and calculated based on dry weight of the mixture.

In some embodiments, the multiplexed *cannabis* mixture of the present invention comprises at least 0.05% content by weight of at least two terpenes of said terpene profile.

In some embodiments, the multiplexed *cannabis* mixture of the present invention comprises at least 0.05% content by weight of at least three, four, five, six, seven, eight, or nine terpenes of said terpene profile.

In some embodiments, the multiplexed *cannabis* mixture of the present invention comprises at least 2% content by weight of at least two cannabinoids selected from the group consisting of: THC, CBD, CBG, CBC, THCV, CBDV, and cannabigevarin (CBGV).

In some embodiments, the multiplexed *cannabis* mixture of the present invention comprises at least 2% content by weight of at least three, four, or five cannabinoids selected from the group consisting of: THC, CBD, CBG, CBC, THCV, CBDV, CBGV.

In some embodiments, the multiplexed *cannabis* mixture of the present invention has at least one of the stock fortifier that is a cannabinoid fortifier (CB).

In some embodiments, the multiplexed *cannabis* mixture of the present invention has at least one stock fortifier that is a terpene fortifier (EO).

In some embodiments, the present invention teaches a compressed *cannabis* pellet for smoking or vaporization, wherein the pellet comprises the *cannabis* plant parts of the present invention.

In some embodiments, the compressed *cannabis* pellet of the present invention comprises a multiplexed mixture of the present invention.

In some embodiments, the compressed *cannabis* pellet of the present invention comprises *cannabis* extracts of the present invention.

In some embodiments, the compressed *cannabis* pellet of the present invention is in the shape of a truncated cone.

In some embodiments, the compressed *cannabis* pellet of the present invention is a truncated cone, with a height of 2.0 millimeters, a smaller base diameter of 4.0 millimeters, and a larger base diameter of 6.0 millimeters.

In some embodiments, the compressed *cannabis* pellet of the present invention is in the shape of a donut.

In some embodiments, the compressed *cannabis* pellet of the present invention is a donut shape with a height of 2.0 millimeters, an inner donut diameter of 1.5 millimeters, and an outer donut diameter of 6 millimeters.

In some embodiments, the present invention teaches a method of treating Brachial Plexus Avulsion, said method comprising: (i) identifying a patient with Brachial Plexus Avulsion; and (ii) administering a prescribed amount of the *cannabis* of the present invention to a patient; wherein said patient experiences symptom relief due to said *cannabis* administration, with reduced THC side effects, and a pleasing organoleptic experience.

In some embodiments, the present invention teaches a method of treating seizures, said method comprising: (i) identifying a patient with Seizures; and (ii) administering a prescribed amount of the *cannabis* of the present invention to a patient; wherein said patient experiences reduced number of seizures due to said *cannabis* administration, with reduced THC side effects, and a pleasing organoleptic experience.

In some embodiments, the present invention teaches a method of treating Arthritis, said method comprising: (i) identifying a patient with Arthritis; and (ii) administering a prescribed amount of the *cannabis* of the present invention to a patient; wherein said patient experiences joint pain relief due to said *cannabis* administration, with reduced THC side effects and a pleasing organoleptic experience.

In some embodiments, the present invention teaches a method of treating Motion Sickness, said method comprising: (i) identifying a patient with Motion Sickness; and (ii) administering a prescribed amount of the *cannabis* of the present invention to a patient; wherein said patient experiences reduced motion sickness symptoms due to said *cannabis* administration, with reduced THC side effects, and a pleasing organoleptic experience.

In some embodiments, the present invention teaches a method of treating Neuropathic Pain, said method comprising: (i) identifying a patient with Neuropathic Pain; and (ii) administering a prescribed amount of the *cannabis* of the present invention to a patient; wherein said patient experiences reduced pain symptoms due to said *cannabis* administration, with reduced THC side effects, and a pleasing organoleptic experience.

In some embodiments, the present invention teaches a method of losing weight, said method comprising: administering a prescribed amount of the *cannabis* of the present invention to a person wishing to lose weight, wherein said patient experiences accelerated weight loss due to said *cannabis* administration, with reduced THC side effects, and a pleasing organoleptic experience.

In some embodiments, the present invention teaches a method of treating depression, said method comprising: (i) identifying a patient with depression; and (ii) administering a prescribed amount of the *cannabis* of the present invention to a patient; wherein said patient experiences reduced symptoms due to said *cannabis* administration, with reduced THC side effects, and a pleasing organoleptic experience.

In some embodiments, the present invention teaches a method of treating Irritable Bowel Syndrome, said method comprising: (i) identifying a patient with Irritable Bowel Syndrome; and (ii) administering a prescribed amount of the *cannabis* of the present invention to a patient; wherein said patient experiences reduced symptoms due to said *cannabis* administration, with reduced THC side effects, and a pleasing organoleptic experience.

In some embodiments, the present invention teaches a method of treating pain from cancer, said method comprising: (i) identifying a cancer patient experiencing pain; and (ii) administering a prescribed amount of the *cannabis* of the present invention to a patient; wherein said patient experiences reduced pain symptoms due to said *cannabis* administration, with reduced THC side effects, and a pleasing organoleptic experience.

In some embodiments, the present invention teaches a method of improving cholesterol, said method comprising: (i) identifying a patient with high total cholesterol, or low HDL cholesterol; and (ii) administering a prescribed amount of the *cannabis* of the present invention to a patient; wherein said patient experiences a lowering of cholesterol and/or increase in HDL cholesterol due to said *cannabis* administration, with reduced THC side effects, and a pleasing organoleptic experience.

In some embodiments, the present invention teaches a method of treating psychosis related diseases, said method comprising: (i) identifying a patient with a psychosis related disease; and (ii) administering a prescribed amount of the *cannabis* of the present invention to a patient; wherein said patient experiences reduced psychosis symptoms due to said *cannabis* administration, with reduced THC side effects, and a pleasing organoleptic experience.

In some embodiments, the methods of treating diseases of the present invention utilize administer *cannabis* extracts or edibles of the present invention.

In some embodiments, the methods of treating diseases of the present invention administer multiplexed *cannabis* mixtures of the present invention.

In some embodiments, the present invention teaches a bubble packaging for storing and shipping *cannabis* comprising: (i) a sealable storage space to place a *cannabis* plant part, extract, or MCM of the present invention; (ii) a modified atmosphere within said sealable space, wherein said bubble packaging increases the shelf life of said *cannabis* plant part, extract, or MCM beyond that of a control of *cannabis* plant part, extract, or MCM, placed left out, or placed in a traditional jar or bag without the modified atmosphere.

In some embodiments, modified atmosphere of the bubble packaging for storing and shipping *cannabis* comprises a vacuum.

In some embodiments, the present invention teaches a method of vaporizing *cannabis* and MCMs, said method comprising: placing the *cannabis* or MCMs of the present invention in a zero-point delivery device, turning the zero-point delivery device on, and vaporizing said *cannabis* or MCM.

In some embodiments, the cannabinoid contents of the *cannabis* plants, plant parts, plant cells, or plant cultures of the present invention is measured using HPLC.

In some embodiments of the present invention, the cannabinoids are measured via HPLC, and the content of cannabinoids includes the acidic and neutral forms of said cannabinoid.

In some embodiments, the present invention teaches a hybrid *cannabis* plant, or an asexual clone of said hybrid *cannabis* plant, or a plant part, tissue, or cell thereof comprising: a $B_T/B_D$ genotype, a terpene profile in which myrcene is not the dominant terpene, and a terpene oil content greater than about 1.0% by weight; wherein the terpene profile is defined as terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene, and wherein the terpene oil content is determined by the additive content of the terpenes in the terpene profile; and wherein the terpene contents are measured by gas chromatography-flame ionization detection (GC-FID) and calculated based on dry weight of the inflorescence.

In some embodiments, the hybrid *cannabis* plant, or an asexual clone of said hybrid *cannabis* plant, or a plant part, tissue, or cell thereof of the present invention comprises a terpene oil content greater than about 1.5% by weight In some embodiments, the hybrid *cannabis* plant, or an asexual clone of said hybrid *cannabis* plant, or a plant part, tissue, or cell thereof of the present invention comprises a tetrahydrocannabinol (THC) content that is at least 3.0% by weight as measured by GC-FID and calculated based on dry weight of the inflorescence.

In some embodiments, the hybrid *cannabis* plant, or an asexual clone of said hybrid *cannabis* plant, or a plant part, tissue, or cell thereof of the present invention comprises a cannabidiol CBD content that is at least 3.0% by weight as measured by GC-FID and calculated based on dry weight of the inflorescence.

In some embodiments, the hybrid *cannabis* plant, or an asexual clone of said hybrid *cannabis* plant, or a plant part, tissue, or cell thereof of the present invention comprises a tetrahydrocannabinol (THC) content that is at least 6.0% by weight as measured by GC-FID and calculated based on dry weight of the inflorescence.

In some embodiments, the hybrid *cannabis* plant, or an asexual clone of said hybrid *cannabis* plant, or a plant part, tissue, or cell thereof of the present invention comprises a cannabidiol CBD content that is at least 6.0% by weight as measured by GC-FID and calculated based on dry weight of the inflorescence.

In some embodiments, the hybrid *cannabis* plant, or an asexual clone of said hybrid *cannabis* plant, or a plant part, tissue, or cell thereof of the present invention, has a terpene profile in which limonene is the most abundant terpene.

In some embodiments, the hybrid *cannabis* plant, or an asexual clone of said hybrid *cannabis* plant, or a plant part, tissue, or cell thereof of the present invention, has a terpene profile in which terpinolene is the most abundant terpene.

In some embodiments, the hybrid *cannabis* plant, or an asexual clone of said hybrid *cannabis* plant, or a plant part, tissue, or cell thereof of the present invention has a terpene profile in which alpha pinene is the most abundant terpene.

In some embodiments, the hybrid *cannabis* plant, or an asexual clone of said hybrid *cannabis* plant, or a plant part, tissue, or cell thereof of the present invention has a terpene profile in which beta caryophyllene is the most abundant terpene.

In some embodiments, the present invention teaches a method of breeding chemotype II *cannabis* plants with a non-myrcene dominant terpene profile, said method comprising: (i) making a cross between a first hybrid *cannabis* plant, or an asexual clone of said hybrid *cannabis* plant of the present invention and a second *cannabis* plant to produce an F1 seed; (ii) harvesting the resulting seed; (iii) growing said seed; and (iv) selecting a *cannabis* plant with a desired phenotype; wherein the resulting selected *cannabis* plant is a chemotype II *cannabis* plant with a non-myrcene dominant terpene profile.

In some embodiments, the present invention teaches a method of producing a chemotype II *cannabis* plant with a non-myrcene dominant terpene profile, said method comprising: (i) obtaining a *cannabis* seed, cutting, or plant cell, from a hybrid *cannabis* plant, or an asexual clone of said hybrid *cannabis* plant of the present invention; (ii) placing said *cannabis* seed, cutting, or plant cell in an environment conducive to growth; and (iii) allowing said *cannabis* seed, cutting, or plant cell to produce a *cannabis* plant; wherein said produced *cannabis* plant is a chemotype II *cannabis* plant with a non-myrcene dominant terpene profile.

In some embodiments, the present invention teaches a *cannabis* extract from the hybrid *cannabis* plant, or an asexual clone of said hybrid *cannabis* plant, or a plant part, tissue, or cell thereof of the present invention.

In some embodiments, the *cannabis* extract of the present invention is selected from the group consisting of kief, hashish, bubble hash, solvent reduced oils, sludges, e-juice, and tinctures.

In some embodiments, the present invention teaches an edible product comprising *cannabis* tissue from the hybrid *cannabis* plant, or an asexual clone of said hybrid *cannabis* plant, or a plant part, tissue, or cell thereof of the present invention.

In some embodiments, the present invention teaches an edible product comprising the *cannabis* extract of the present invention.

In some embodiments, the present invention teaches plant parts of the hybrid *cannabis* plant, or an asexual clone of said hybrid *cannabis* plant, or a plant part, tissue, or cell thereof of the present invention, wherein said plant part is selected from the group consisting of: trichomes, sun leaves, or inflorescences.

BRIEF DESCRIPTION OF THE DRAWINGS

FIG. 1—Bar graph of the relative terpene contents (y-axis) of *cannabis* blends (x-axis) used for Week 1 volunteer trials. Each sample comparison pair was blended to produce similar terpene profiles so as to compare the effects of added CBD.

FIG. 2—Sample questionnaire used for volunteer trials. Questionnaire was provided to volunteers with each *cannabis* blend sample to measure the effects of the sample when smoked.

FIG. 14—Example diagram of bubble pack dosing. Specialty *cannabis*, multiplexed *cannabis* medicines, *cannabis* extracts, or *cannabis* pellets can be packaged into individual doses for consumers in a modified air or vacuum environment to extend shelf life/quality of product.

FIG. 16—Example diagrams of "donut shape" pressed pellet shapes.

DETAILED DESCRIPTION OF THE INVENTION

Figure 3:
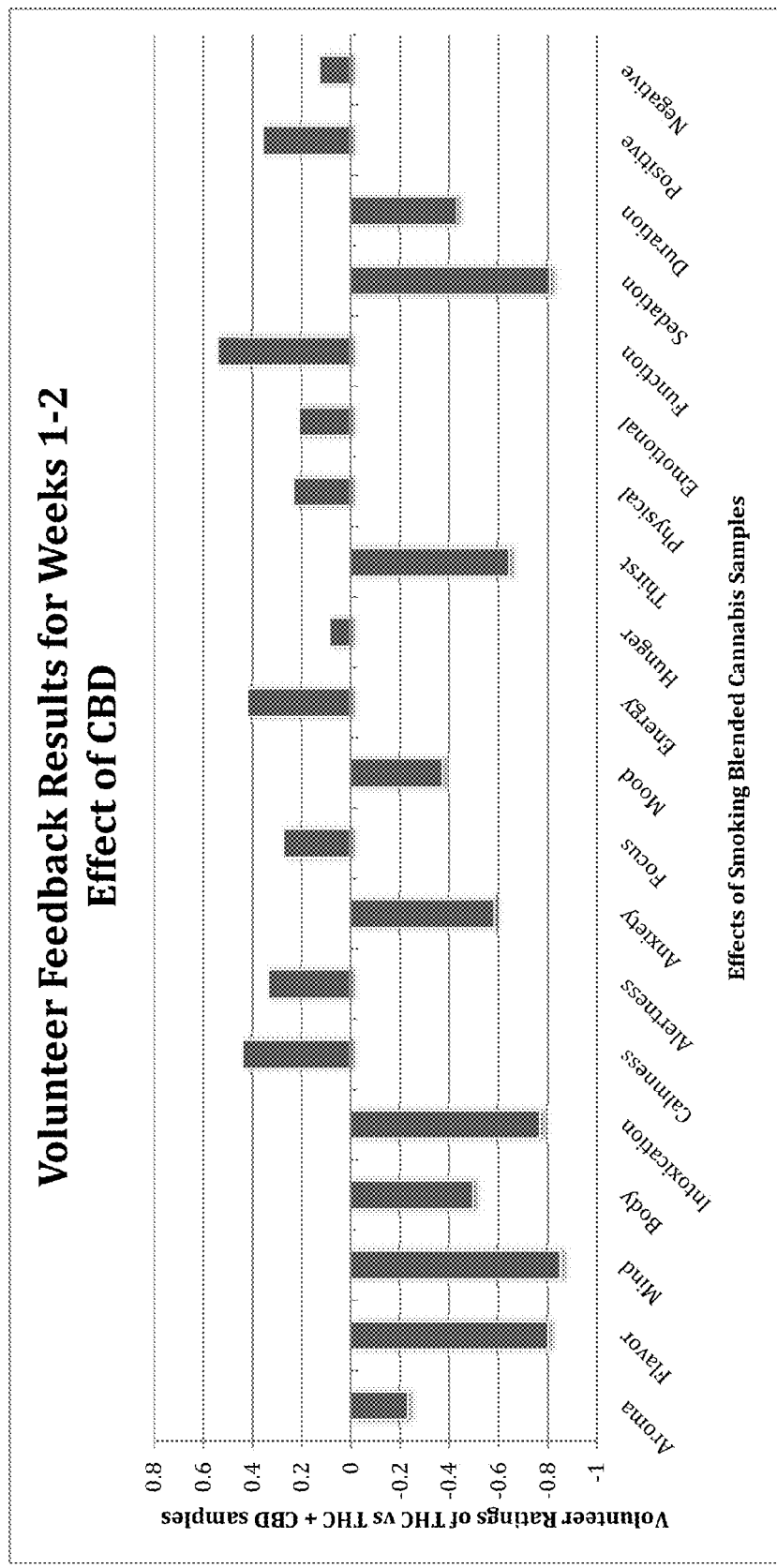
FIG. 3—Bar graph of Weeks 1 and 2 trials feedback results combined. Values are presented as ratings for test sample minus control sample. Higher values indicated increased ratings for a category, while lower values indicated decreased ratings for a category. CBD containing samples showed decrease in mind and body high as well as increased ability to function.

All publications, patents and patent applications, including any drawings and appendices, are herein incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

The invention provides *cannabis* plants. As used herein, the term "plant" refers to plants in the genus of *Cannabis* and plants derived thereof. Such as *cannabis* plants produced via asexual reproduction and via seed production.

The invention provides plant parts. As used herein, the term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots". Plant part may also include certain extracts such as kief or hash which includes *cannabis* trichomes or glands.

As used herein, the term dominant refers to a terpene that is the most abundant in the terpene profile either in absolute content as a % by dry weight, or in relative content as a % of the terpene profile.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, a "landrace" refers to a local variety of a domesticated plant species which has developed largely by natural processes, by adaptation to the natural and cultural environment in which it lives. The development of a landrace may also involve some selection by humans but it differs from a formal breed which has been selectively bred deliberately to conform to a particular formal, purebred standard of traits.

The International Code of Zoological Nomenclature defines rank, in the nomenclatural sense, as the level, for nomenclatural purposes, of a taxon in a taxonomic hierarchy (e.g., all families are for nomenclatural purposes at the same rank, which lies between superfamily and subfamily). While somewhat arbitrary, there are seven main ranks defined by the international nomenclature codes: kingdom, phylum/division, class, order, family, genus, and species.

The invention provides plant cultivars. As used herein, the term "cultivar" means a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "inbreeding" refers to the production of offspring via the mating between relatives. The plants resulting from the inbreeding process are referred to herein as "inbred plants" or "inbreds."

The term LOQ as used herein refers to the limit of quantitation for Gas Chromatography (GC) and High Performance Liquid Chromatography measurements.

The term secondary metabolites as used herein refers to organic compounds that are not directly involved in the normal growth, development, or reproduction of an organism. In other words, loss of secondary metabolites does not result in immediate death of said organism.

The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

The invention provides samples. As used herein, the term "sample" includes a sample from a plant, a plant part, a plant cell, or from a transmission vector, or a soil, water or air sample.

The invention provides offspring. As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The invention provides methods for crossing a first plant with a second plant. As used herein, the term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

The invention provides donor plants and recipient plants. As used herein, "donor plants" refer to the parents of a variety which contains the gene or trait of interest which is desired to be introduced into a second variety (e.g., "recipient plants").

In some embodiments, the present invention provides methods for obtaining plant genotypes comprising recombinant genes. As used herein, the term "genotype" refers to the genetic makeup of an individual cell, cell culture, tissue, organism (e.g., a plant), or group of organisms.

In some embodiments, the present invention provides homozygotes. As used herein, the term "homozygote" refers to an individual cell or plant having the same alleles at one or more loci.

In some embodiments, the present invention provides homozygous plants. As used herein, the term "homozygous" refers to the presence of identical alleles at one or more loci in homologous chromosomal segments.

In some embodiments, the present invention provides hemizygotes. As used herein, the term "hemizygotes" or "hemizygous" refers to a cell, tissue, organism or plant in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present invention provides heterozygotes. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest which is under control of the synthetic regulatory element.

The invention provides methods for obtaining plant lines comprising recombinant genes. As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The invention provides open-pollinated populations. As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

The invention provides self-pollination populations. As used herein, the term "self-crossing", "self pollinated" or "self-pollination" means the pollen of one flower on one plant is applied (artificially or naturally) to the ovule (stigma) of the same or a different flower on the same plant.

The invention provides ovules and pollens of plants. As used herein when discussing plants, the term "ovule" refers to the female gametophyte, whereas the term "pollen" means the male gametophyte.

The invention provides plant tissue. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The invention provides methods for obtaining plants comprising recombinant genes through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The invention provides transformants comprising recombinant genes. As used herein, the term "transformant" refers to a cell, tissue or organism that has undergone transformation. The original transformant is designated as "T0" or "$T_0$." Selfing the T0 produces a first transformed generation designated as "T1" or "$T_1$."

In some embodiments, the present invention provides plant varieties comprising the recombinant genes. As used herein, the term "variety" refers to a subdivision of a species, consisting of a group of individuals within the species that are distinct in form or function from other similar arrays of individuals.

In some embodiments, the present invention provides organisms with recombinant genes. As used herein, an "organism" refers any life form that has genetic material comprising nucleic acids including, but not limited to, prokaryotes, eukaryotes, and viruses. Organisms of the present invention include, for example, plants, animals, fungi, bacteria, and viruses, and cells and parts thereof.

In some embodiments, the specialty *cannabis* varieties of the present invention reduce the myrcene "couch lock" effects. As used herein, the term couch lock is defined as a heavy body high which reduces the ability of users to function, and is associated with lethargy and lack of motivation.

In some embodiments, the present invention teaches the use of *cannabis* sludges. As used herein, *cannabis* sludges are solvent-free *cannabis* extracts made via multigas extraction including the refrigerant 134A, butane, iso-butane and propane in a ratio that delivers a very complete and balanced extraction of cannabinoids and essential oils.

Cannabis

*Cannabis* has long been used for drug and industrial purposes. fiber (hemp), for seed and seed oils, for medicinal purposes, and as a recreational drug. Industrial hemp products are made from *Cannabis* plants selected to produce an abundance of fiber. Some *Cannabis* strains have been bred to produce minimal levels of THC, the principal psychoactive constituent responsible for the psychoactivity associated with marijuana. Marijuana has historically consisted of the dried flowers of *Cannabis* plants selectively bred to produce high levels of THC and other psychoactive cannabinoids. Various extracts including hashish and hash oil are also produced from the plant.

*Cannabis* is diploid, having a chromosome complement of 2n=20, although polyploid individuals have been artificially produced. The first genome sequence of *Cannabis*, which is estimated to be 820 Mb in size, was published in 2011 by a team of Canadian scientists (Bakel et al, "The draft genome and transcriptome of *Cannabis sativa*" Genome Biology 12:R102).

All known strains of *Cannabis* are wind-pollinated and the fruit is an achene. Most strains of *Cannabis* are short day plants, with the possible exception of *C. sativa* subsp. *sativa* var. *spontanea* (=*C. ruderalis*), which is commonly described as "auto-flowering" and may be day-neutral.

The genus *Cannabis* was formerly placed in the Nettle (Urticaceae) or Mulberry (Moraceae) family, and later, along with the *Humulus* genus (hops), in a separate family, the Hemp family (Cannabaceae sensu stricto) Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

*Cannabis* plants produce a unique family of terpeno-phenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *cannabis* plant (Rudolf Brenneisen, 2007, Chemistry and Analysis of Phytocannabinoids (cannabinoids produced produced by *cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or $\Delta^9$-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Cannabinoids are the most studied group of secondary metabolites in *cannabis*. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

The cannabinoids in *cannabis* plants include, but are not limited to, $\Delta^9$-Tetrahydrocannabinol ($\Delta^9$-THC), $\Delta^8$-Tetrahydrocannabinol ($\Delta^8$-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), $\Delta^9$-Tetrahydrocannabivarin (THCV), cannabichromevarin (CBCV), and cannabigerovarin (CBGV). See Holley et al. (Constituents of *Cannabis sativa* L. XI Cannabidiol and cannabichromene in samples of known geographical origin, *J. Pharm. Sci.* 64:892-894, 1975) and De Zeeuw et al. (Cannabinoids with a propyl side chain in *Cannabis*, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

In one embodiment, the present invention provides specialty *cannabis* plants, which are distinct from the traditional recreational marijuana plants.

As used herein, 'specialty *cannabis*' refers to *cannabis* plants, lines, varieties and cultivars having a THC content based on the dry weight of plant inflorescences less than or equal to 90% (i.e., THC ≤90%) and having a CBs content based on the dry weight of plant inflorescences equal to or greater than 1.0% (e.g., CBD, CBDV, THCV, or CBG of ≥1.0%); or, alternatively, having a THC:CBs ratio of 1:20 or greater and approaching 1:1 or greater based on the dry weight of plant inflorescences.

As a result of the present invention, select *cannabis* varieties can be used as a physician-recommended form of medicine or herbal therapy without causing any side effects, or with reduced general or specific side effects when compared to traditional recreational marijuana plants. Methods for administration of medical *cannabis* include, but are not limited, to vapor inhalation, smoking (e.g., dried buds), drinking, eating extracts or food products infused with extracts, and taking capsules.

Cannabis Chemistry

Cannabinoids are a class of diverse chemical compounds that activate cannabinoid receptors. Cannabinoids produced by plants are called phytocannabinoids, a.k.a., natural cannabinoids, herbal cannabinoids, and classical cannabinoids. At least 85 different cannabinoids have been isolated from the *cannabis* plants (El-Alfy et al., 2010, "Antidepressant-like effect of delta-9-tetrahydrocannabinol and other cannabinoids isolated from *Cannabis sativa* L", Pharmacology Biochemistry and Behavior 95 (4): 434-42; Brenneisen, supra). Typical cannabinoids isolated from *cannabis* plants include, but are not limited to, Tetrahydrocannabinol (THC), Cannabidiol (CBD), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and CBGM (Cannabigerol Monomethyl Ether). In the *Cannabis* plant, cannabinoids are synthesized and accumulated as cannabinoid acids (e.g., cannabidiolic acid (CBDA)). When the herbal product is dried, stored, or heated, the acids decarboxylize gradually or completely into neutral forms (e.g., CBDA→CBD).

Known as delta-9-tetrahydrocannabinol (Δ9-THC), THC is the principal psychoactive constituent (or cannabinoid) of the *cannabis* plant. The initially synthesized and accumulated form in plant is THC acid (THCA).

THC has mild to moderate analgesic effects, and *cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003). "Drugs of abuse and the elicitation of human aggressive behavior". *Addictive Behaviors* 28: 1533-1554).

The pharmacological actions of THC result from its partial agonist activity at the cannabinoid receptor $CB_1$, located mainly in the central nervous system, and the $CB_2$ receptor, mainly expressed in cells of the immune system (Pertwee, 2006, "The pharmacology of cannabinoid receptors and their ligands: An overview". *International Journal of Obesity* 30: S13-S18.) The psychoactive effects of THC are primarily mediated by its activation of CB1G-protein coupled receptors, which result in a decrease in the concentration of the second messenger molecule cAMP through inhibition of adenylate cyclase (Elphick et al., 2001, "The neurobiology and evolution of cannabinoid signaling". *Philosophical Transactions of the Royal Society B: Biological Sciences* 356 (1407): 381-408.) It is also suggested that THC has an anticholinesterase action which may implicate it as a potential treatment for Alzheimer's and Myasthenia (Eubanks et al., 2006, "A Molecular Link Between the Active Component of Marijuana and Alzheimer's Disease Pathology". Molecular Pharmaceutics 3 (6): 773-7.)

In the *cannabis* plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC. The pathway for THCA biosynthesis is similar to that which produces the bitter acid humulone in hops. See Fellermeier et al., (1998, "Prenylation of olivetolate by a hemp transferase yields cannabigerolic acid, the precursor of tetrahydrocannabinol". *FEBS Letters* 427 (2): 283-5); de Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112.)

Non-limiting examples of THC variants include:

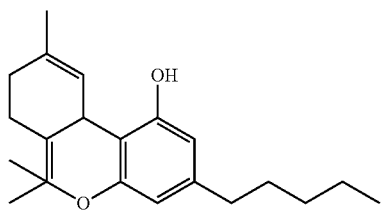

Tetrahydrocannabinol (THC)

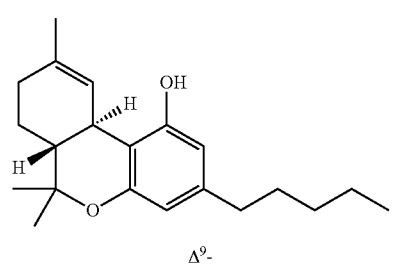

$\Delta^9$-Tetrahydrocannabinol
$\Delta^9$-THC-$C_5$

-continued

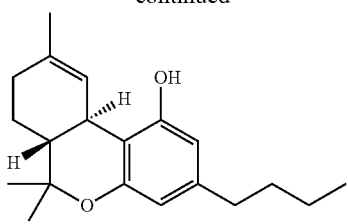

Δ⁹-Tetrahydrocannabinol-C₄
Δ⁹-THC-C₄

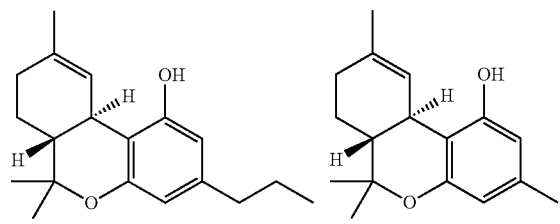

Δ⁹-Tetrahydrocannabivarin
Δ⁹-THCV-C₃

Δ⁹-Tetrahydrocannabiorcol
Δ⁹-THCO-C₁

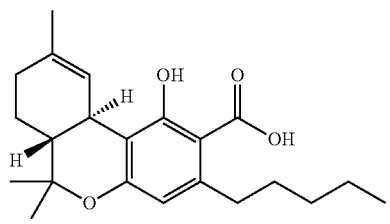

Δ⁹-Tetrahydrocannabinolic acid A
Δ⁹-THCA-C₅ A

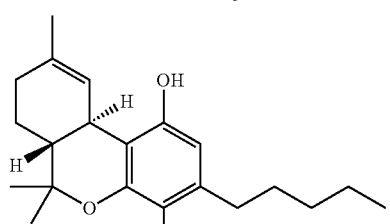

Δ⁹-Tetrahydrocannabinolic acid B
Δ⁹-THCA-C₅ B

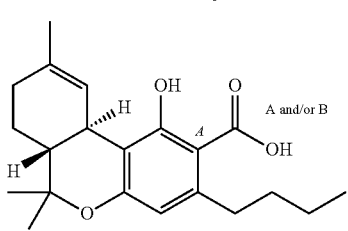

Δ⁹-Tetrahydrocannabinolic acid-C₄ A and/or B
Δ⁹-THCA-C₄ A and/or B

-continued

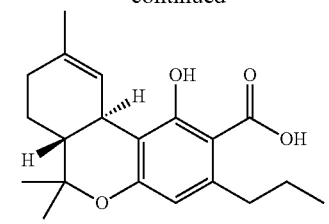

Δ⁹-Tetrahydrocannabivarinic acid A
Δ⁹-THCVA-C₃ A

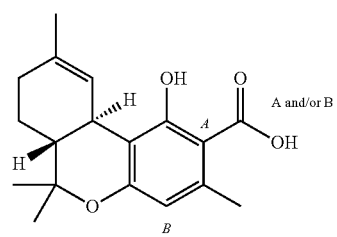

Δ⁹-Tetrahydrocannabiorcolic acid A and/or B
Δ⁹-THCOA-C₁ A and/or B

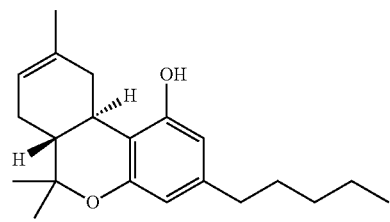

(-)-Δ⁸-trans-(6aR, 10aR)-Δ⁸-Tetrahydrocannabinol
Δ⁸-THC-C₅

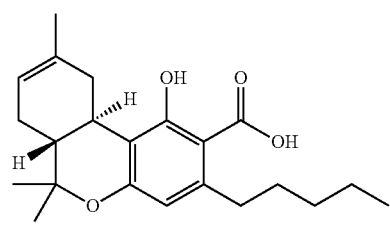

(-)-Δ⁸-trans-(6aR, 10aR)-Tetrahydrocannabinolic acid A
Δ⁸-THCA-C₅ A

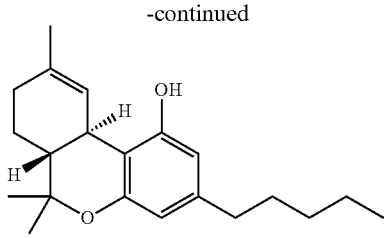

(-)-(6aS, 10aR)-Δ⁹-
Tetrahydrocannabinol
(-)-cis-Δ⁹-THC-C$_5$

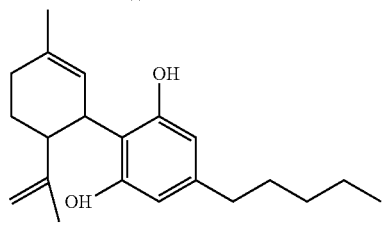

Cannabidiol (CBD)

CBD is a cannabinoid found in *cannabis*. Cannabidiol has displayed sedative effects in animal tests (Pickens, 1981, "Sedative activity of *cannabis* in relation to its delta'-trans-tetrahydrocannabinol and cannabidiol content". *Br. J. Pharmacol.* 72 (4): 649-56). Some research, however, indicates that CBD can increase alertness, and attenuate the memory-impairing effect of THC. (Nicholson et al., June 2004, "Effect of Delta-9-tetrahydrocannabinol and cannabidiol on nocturnal sleep and early-morning behavior in young adults" *J Clin Psychopharmacol* 24 (3): 305-13; Morgan et al., 2010, "Impact of cannabidiol on the acute memory and psychotomimetic effects of smoked *cannabis*: naturalistic study, *The British Journal of Psychiatry*, 197:258-290). It may decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, "Cannabidiol—recent advances". *Chemistry & Biodiversity* 4 (8): 1678-1692.) Recent studies have shown cannabidiol to be as effective as atypical antipsychotics in treating schizophrenia (Zuardi et al., 2006, "Cannabidiol, a *Cannabis sativa* constituent, as an antipsychotic drug" *Braz. J. Med. Biol. Res.* 39 (4): 421-429.). Studies have also shown that it may relieve symptoms of dystonia (Consroe, 1986, "Open label evaluation of cannabidiol in dystonic movement disorders". *The International journal of neuroscience* 30 (4): 277-282). CBD reduces growth of aggressive human breast cancer cells in vitro and reduces their invasiveness (McAllister et al., 2007, "Cannabidiol as a novel inhibitor of Id-1 gene expression in aggressive breast cancer cells". *Mol. Cancer. Ther.* 6 (11): 2921-7.)

Cannabidiol has shown to decrease activity of the limbic system (de Souza Crippa et al., "Effects of Cannabidiol (CBD) on Regional Cerebral Blood Flow". *Neuropsychopharmacology* 29 (2): 417-426.) and to decrease social isolation induced by THC (Malon et al., "Cannabidiol reverses the reduction in social interaction produced by low dose Δ9-tetrahydrocannabinol in rats". Pharmacology Biochemistry and Behavior 93 (2): 91-96.) It's also shown that Cannabidiol reduces anxiety in social anxiety disorder (Bergamaschi et al., 2003, "Cannabidiol Reduces the Anxiety Induced by Simulated Public Speaking in Treatment-Naïve Social Phobia Patients". *Neuropsychopharmacology* 36 (6): 1219-1226).

Cannabidiol has also been shown as being effective in treating an often drug-induced set of neurological movement disorders known as dystonia (Snider et al., 1985, "Beneficial and Adverse Effects of Cannabidiol in a Parkinson Patient with Sinemet-Induced Dystonic Dyskinesia". *Neurology*, (Suppl 1): 201.) Morgan et al. reported that strains of *cannabis* which contained higher concentrations of Cannabidiol did not produce short-term memory impairment vs. strains which contained similar concentrations of THC (2010, "Impact of cannabidiol on the acute memory and psychotomimetic effects of smoked *cannabis*:naturalistic study:naturalistic study [corrected."]. *British Journal of Psychiatry* 197 (4): 285-90.)

Cannabidiol acts as an indirect antagonist of cannabinoid agonists. CBD is an antagonist at the putative new cannabinoid receptor, GPR55. Cannabidiol has also been shown to act as a 5-HT1A receptor agonist, an action which is involved in its antidepressant, anxiolytic, and neuroprotective effects. Cannabidiol is also an allosteric modulator at the Mu and Delta opioid receptor sites.

*Cannabis* produces CBD-carboxylic acid through the same metabolic pathway as THC, until the last step, where CBDA synthase performs catalysis instead of THCA synthase. See Marks et al. (2009, "Identification of candidate genes affecting Δ9-tetrahydrocannabinol biosynthesis in *Cannabis sativa*". Journal of Experimental Botany 60 (13): 3715-3726.) and Meijer et al. I, II, III, and IV. Non-limiting examples of CBD variants include:

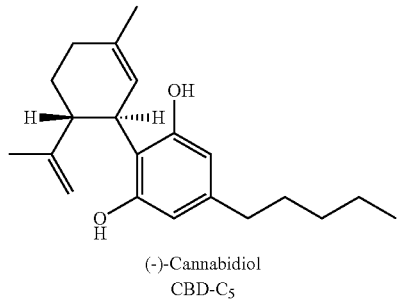

(-)-Cannabidiol
CBD-C$_5$

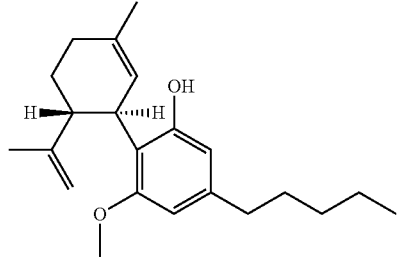

Cannabidiol
momomethyl ether
CBDM-C$_5$

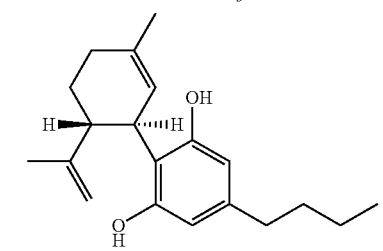

Cannabidiol-C$_4$
CBD-C$_4$

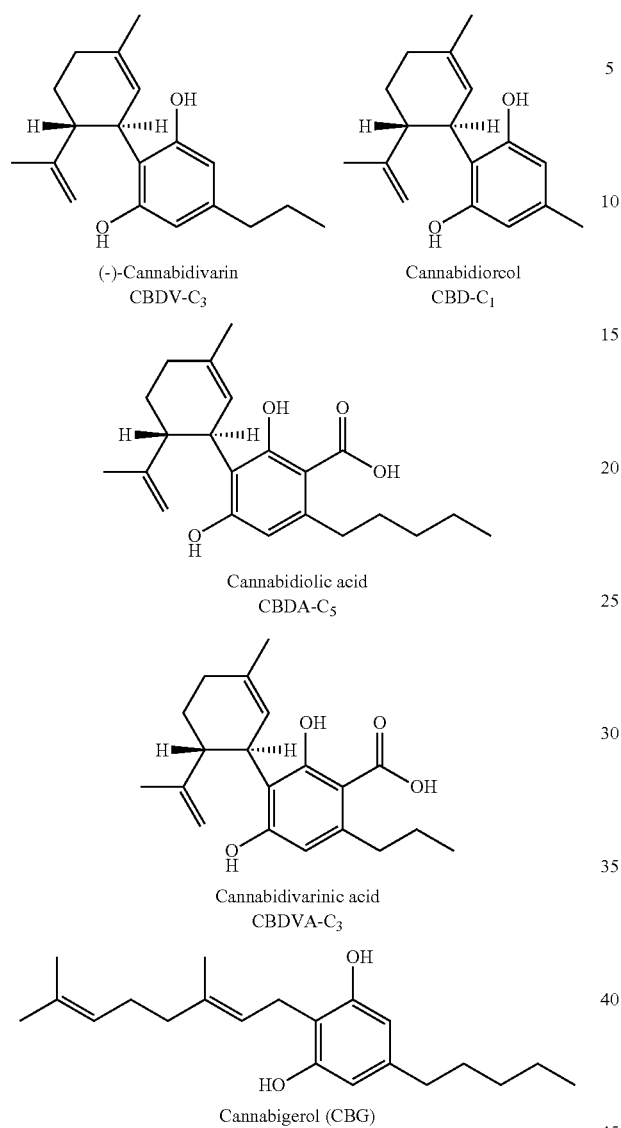

(-)-Cannabidivarin
CBDV-C$_3$

Cannabidiorcol
CBD-C$_1$

Cannabidiolic acid
CBDA-C$_5$

Cannabidivarinic acid
CBDVA-C$_3$

Cannabigerol (CBG)

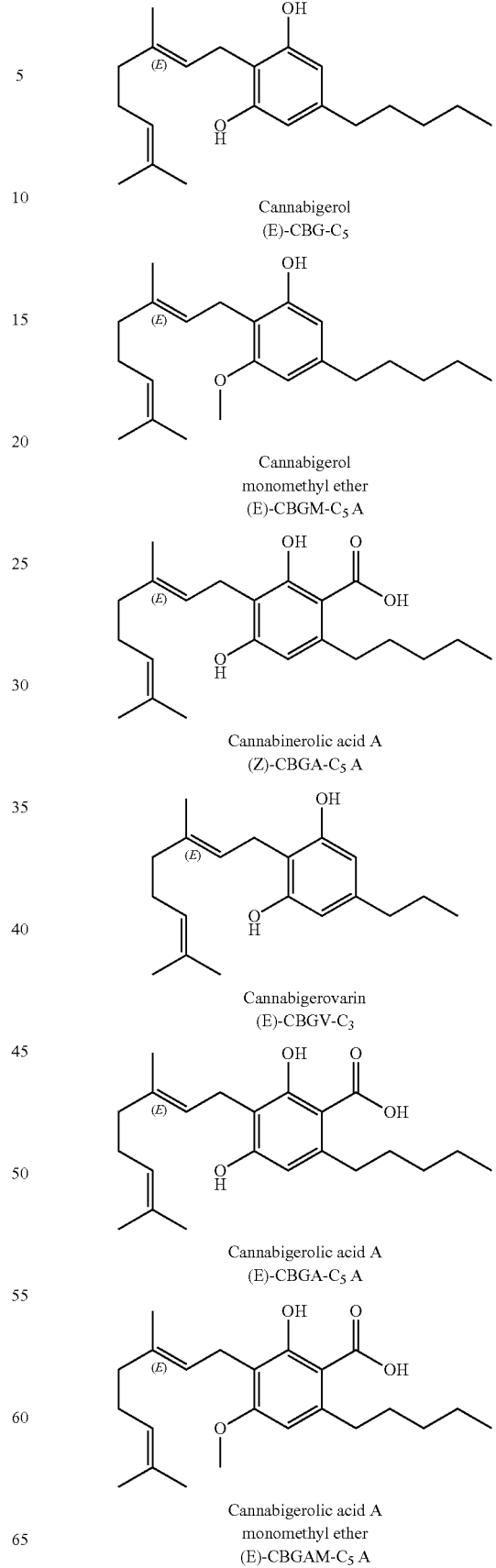

Cannabigerol
(E)-CBG-C$_5$

Cannabigerol
monomethyl ether
(E)-CBGM-C$_5$A

Cannabinerolic acid A
(Z)-CBGA-C$_5$A

Cannabigerovarin
(E)-CBGV-C$_3$

Cannabigerolic acid A
(E)-CBGA-C$_5$A

Cannabigerolic acid A
monomethyl ether
(E)-CBGAM-C$_5$A

CBG is a non-psychoactive cannabinoid found in the *Cannabis* genus of plants. Cannabigerol is found in higher concentrations in hemp rather than in varieties of *Cannabis* cultivated for high THC content and their corresponding psychoactive properties. Cannabigerol has been found to act as a high affinity α2-adrenergic receptor agonist, moderate affinity 5-HT1A receptor antagonist, and low affinity CB$_1$ receptor antagonist. It also binds to the CB$_2$ receptor. Cannabigerol has been shown to relieve intraocular pressure, which may be of benefit in the treatment of glaucoma (Craig et al. 1984, "Intraocular pressure, ocular toxicity and neurotoxicity after administration of cannabinol or cannabigerol" Experimental eye research 39 (3):251-259). Cannabigerol has also been shown to reduce depression in animal models (U.S. patent application Ser. No. 11/760,364). Non-limiting examples of CBG variants include:

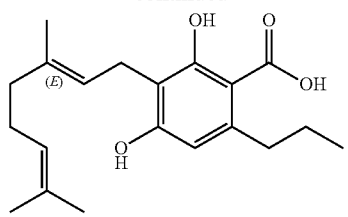

Cannabigerovarinic acid A
(E)-CBGVA-C₃ A

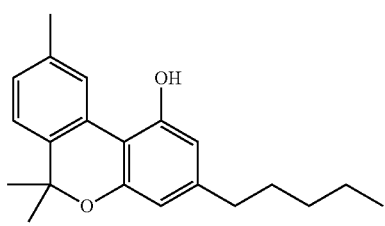

Cannabinol (CBN)

CBN is a psychoactive substance cannabinoid found in *Cannabis sativa* and *Cannabis indica/afghanica*. It is also a metabolite of tetrahydrocannabinol (THC). CBN acts as a weak agonist of the CB1 and CB2 receptors, with lower affinity in comparison to THC. Non-limiting examples of CBN variants include

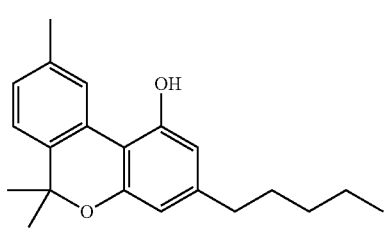

Cannabinol
CBN-C₅

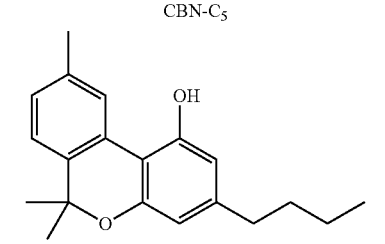

Cannabinol-C₄
CBN-C₄

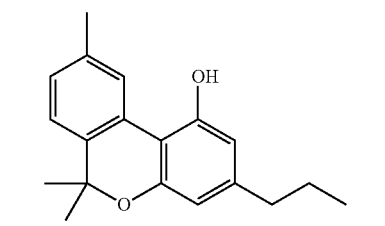

Cannabivarin
CBN-C₃

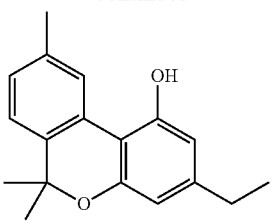

Cannabinol-C₂
CBN-C₂

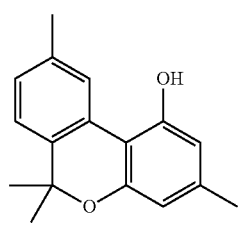

Cannabiorcol
CBN-C₁

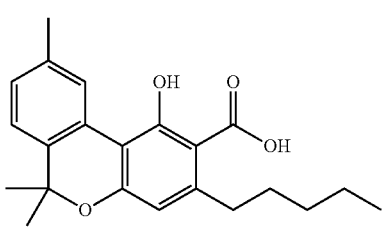

Cannabinolic acid A
CBNA-C₅ A

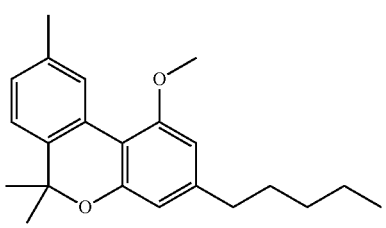

Cannabinol methyl ether
CBNM-C₅

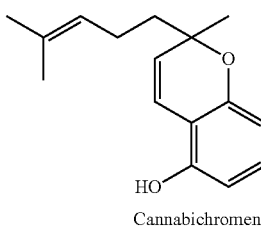

Cannabichromene (CBC)

CBC bears structural similarity to the other natural cannabinoids, including tetrahydrocannabinol, tetrahydrocannabivarin, cannabidiol, and cannabinol, among others. Evidence has suggested that it may play a role in the anti-inflammatory and anti-viral effects of *cannabis*, and may contribute to the overall analgesic effects of *cannabis*. Non-limiting examples of CBC variants include:

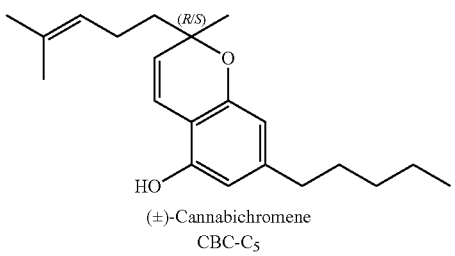

(±)-Cannabichromene
CBC-C$_5$

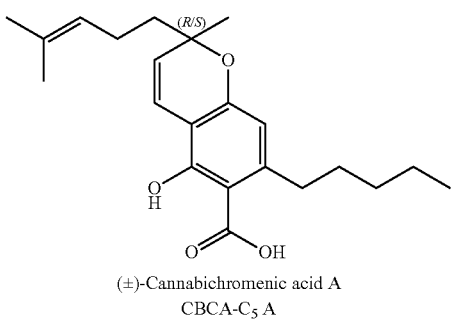

(±)-Cannabichromenic acid A
CBCA-C$_5$ A

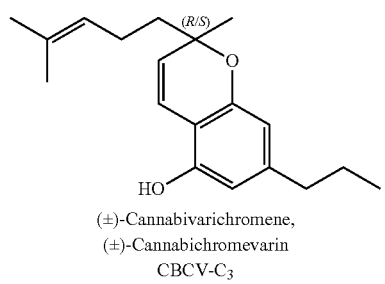

(±)-Cannabivarichromene,
(±)-Cannabichromevarin
CBCV-C$_3$

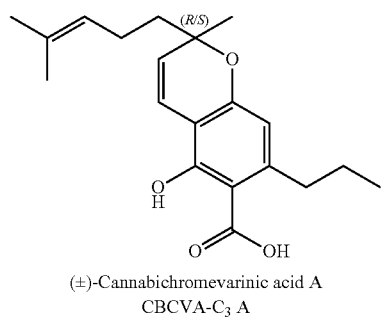

(±)-Cannabichromevarinic acid A
CBCVA-C$_3$ A

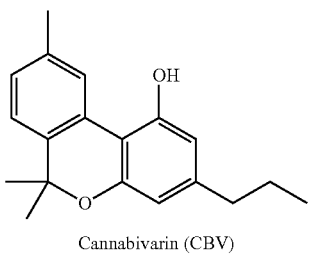

Cannabivarin (CBV)

Cannabivarin, also known as cannabivarol or CBV, is a non-psychoactive cannabinoid found in minor amounts in the hemp plant *Cannabis sativa*. It is an analog of cannabinol (CBN) with the side chain shortened by two methylene bridges (—CH2-). CBV is an oxidation product of tetrahydrocannabivarin (THCV, THV).

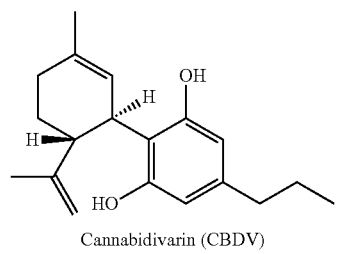 [SMILES: C=C(C)[C@@H]1CCC(C)=C[C@H]1c1c(O)cc(CCC)cc1O]

Cannabidivarin (CBDV)

CBDV is a non-psychoactive cannabinoid found in *Cannabis*. It is a homolog of cannabidiol (CBD), with the side-chain shortened by two methylene bridges (CH2 units). Cannabidivarin has been found reduce the number and severity of seizures in animal models (U.S. patent application Ser. No. 13/075,873). Plants with relatively high levels of CBDV have been reported in feral populations of *C. indica* (=*C. sativa* ssp. *indica* var. *kafiristanica*) from northwest India, and in hashish from Nepal.

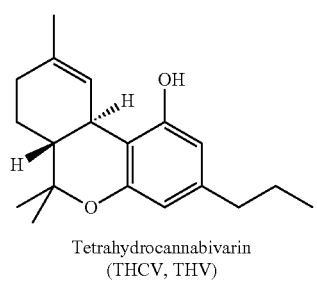 [SMILES: CCCc1cc(O)c2c(c1)OC(C)(C)[C@@H]1CCC(C)=C[C@@H]21]

Tetrahydrocannabivarin
(THCV, THV)

THCV, or THV is a homologue of tetrahydrocannabinol (THC) having a propyl (3-carbon) side chain. This terpeno-phenolic compound is found naturally in *Cannabis*, sometimes in significant amounts. Plants with elevated levels of propyl cannabinoids (including THCV) have been found in populations of *Cannabis sativa* L. ssp. *indica* (=*Cannabis indica* Lam.) from China, India, Nepal, Thailand, Afghanistan, and Pakistan, as well as southern and western Africa. THCV has been shown to be a CB1 receptor antagonist, i.e. it blocks the effects of THC. Tetrahydrocannabinol has been shown to increase metabolism, help weight loss and lower cholesterol in animal models (U.S. patent application Ser. No. 11/667,860)

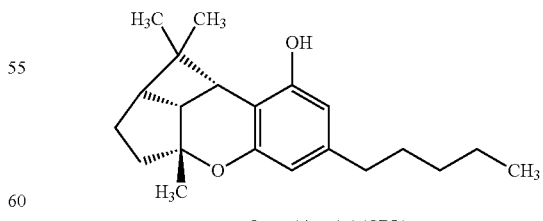

Cannabicyclol (CBL)

Cannabicyclol (CBL) is a non-psychotomimetic cannabinoid found in the *Cannabis* species. CBL is a degradative product like cannabinol. Light converts cannabichromene to CBL. Non-limiting examples of CBL variants include:

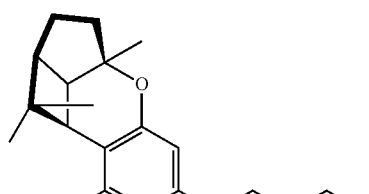

(±)-(1aS,3aR,8bR,8cR)-
Cannabicyclol
CBL-C$_5$

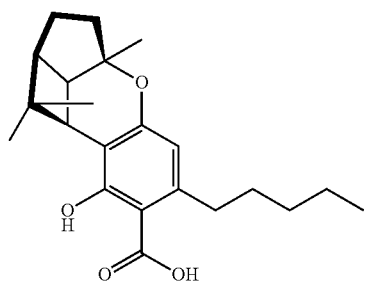

(±)-(1aS,3aR,8bR,8cR)-
Cannabicyclolic acid A
CBLA-C$_5$ A

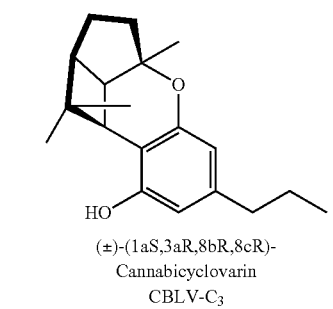

(±)-(1aS,3aR,8bR,8cR)-
Cannabicyclovarin
CBLV-C$_3$

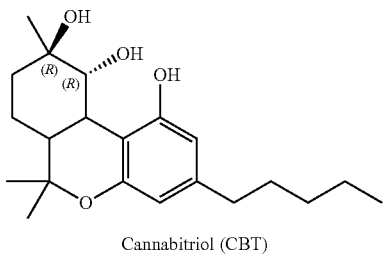

Cannabitriol (CBT)

Non-limiting examples of CBT variants include:

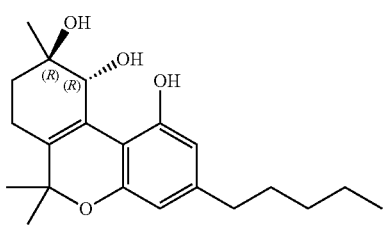

(-)-(9R,10R)-trans-
Cannabitriol
(-)-trans-CBT-C$_5$

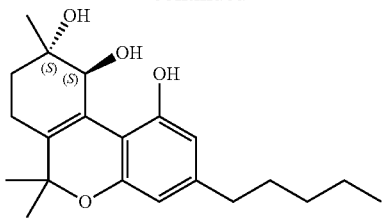

(+)-(9S,10S)-
Cannabitriol
(+)-trans-CBT-C$_5$

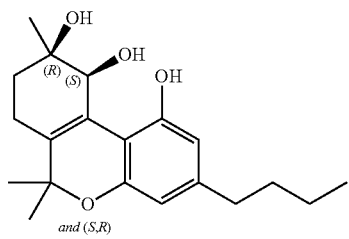

(±)-
(9R,10S/9S,10R)-
Cannabitriol
(±)-cis-CBT-C$_5$

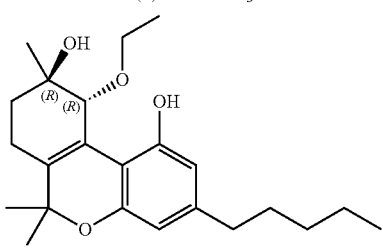

(-)-(9R,10R)-trans-
10-O-Ethyl-
cannabitriol
(-)-trans-CBT-OEt-
C$_5$

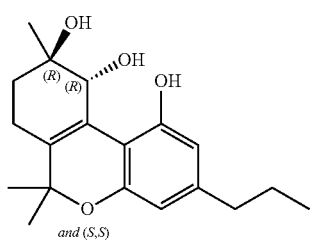

(±)-
(9R,10R/9S,10S)-
Cannabitriol-C$_3$
(±)-trans-CBT-C$_3$

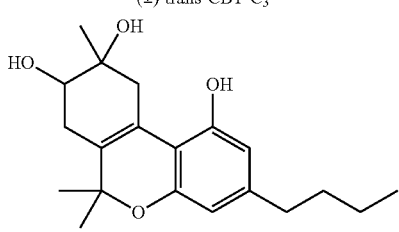

8,9-Dihydroxy-Δ$^{6a(10a)}$-
tetrahydrocannabinol
8,9-Di-OH-CBT-C$_5$

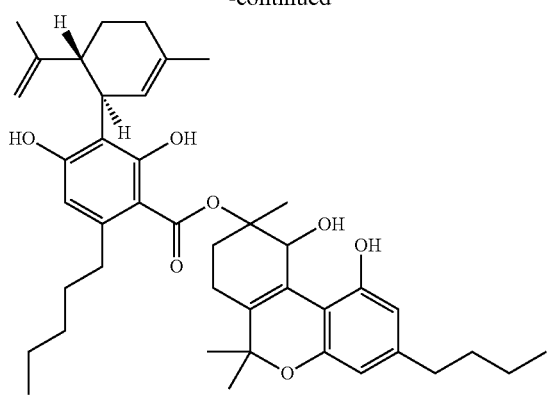

Cannabidiolic acid A
cannabitriol ester
CBDA-C$_5$ 9-OH-CBT-
C$_5$ ester

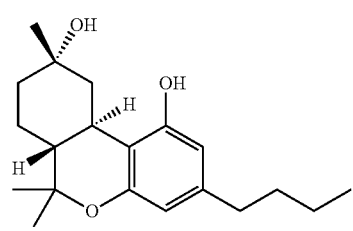

(-)-
(6aR,9S,10S,10aR)-
9,10-Dihydroxy-
hexahydrocannabinol,
Cannabiripsol
Cannabiripsol-C$_5$

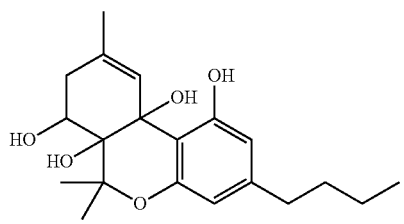

(-)-6a,7,10a-
Trihydroxy-
Δ$^9$-
tetrahydrocannabinol
(-)-Cannabitetrol

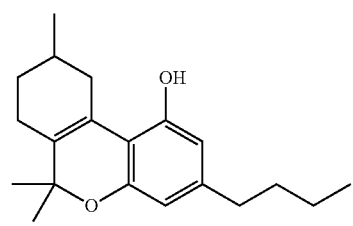

10-Oxo-Δ$^{6a(10a)}$-
tetrahydrocannabinol
OTHC

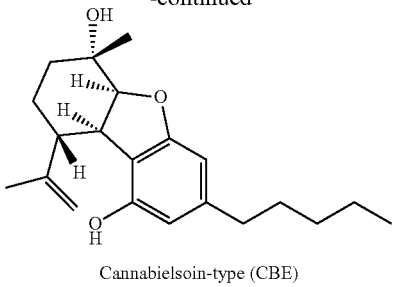

Cannabielsoin-type (CBE)

Non-limiting examples of CBE variants include:

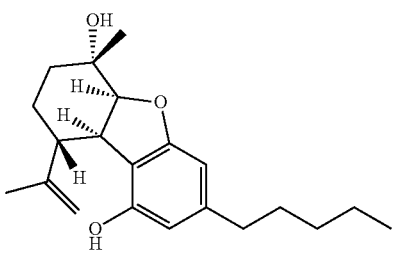

(5aS,6S,9R,9aR)-
Cannabielsoin
CBE-C$_5$

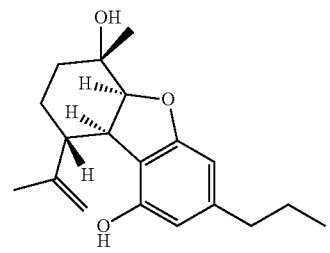

(5aS,6S,9R,9aR)-
C$_3$-Cannabielsoin
CBE-C$_3$

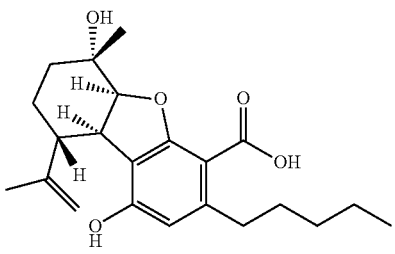

(5aS,6S,9R,9aR)-
Cannabielsoic acid A
CBEA-C$_5$ A

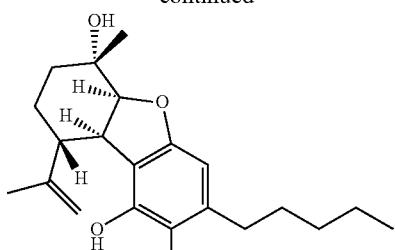

(5aS,6S,9R,9aR)-
Cannabielsoic acid B
CBEA-C₅ B

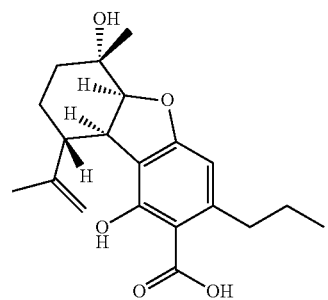

(5aS,6S,9R,9aR)-
C₃-Cannabielsoic
acid B
CBEA-C₃ B

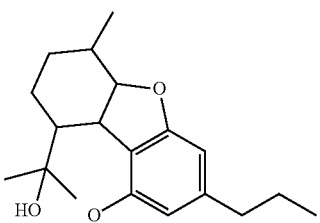

Cannabiglendol-C₃
OH-iso-HHCV-C₃

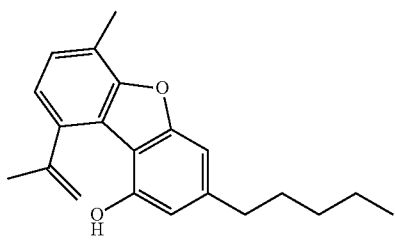

Dehydrocannabifuran
DCBF-C₅

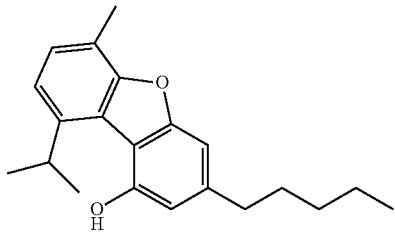

Cannabifuran
CBF-C₅

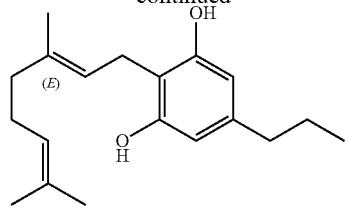

Cannabigerovarin (CBVG)

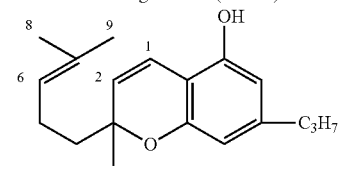

CBCV (Cannabichromevarin)

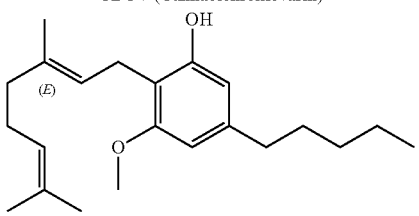

CBGM (Cannabigerol Monomethyl Ether)

Biosynthetic pathway of cannabinoids has been studied. See Meijer et al. I, II, III, and IV (I: 2003, Genetics, 163:335-346; II: 2005, Euphytica, 145:189-198; III: 2009, Euphytica, 165:293-311; and IV: 2009, Euphytica, 168:95-112), each of which is herein incorporated by reference in its entirety for all purposes. According to the current model, phenolic precursors such as geranyl pyrophosphate (GPP) and polyketide, olivetolic acid (OA) are condensed by geranyl pyrophosphate olivetolate geranyltransferase (GOT) to form Cannabigerol acid (CBGA). Alternatively, GPP and divarine acid are condensed by GOT to form Cannabigerovarinic acid (CBGVA). CBGA or CBGAV is transformed to (1) CBC by CBC synthase or CBCV by CBCV synthase; (2) THC by THC synthase or THCV by THCV synthase; or (3) CBD by CBD synthase or CBDV by CBDV synthase. The genes coding for THC synthase and CBD synthase are found on the same B locus. Thus *cannabis* plants can be categorized into THC-CBD chemotypes based on the state of the B locus $B_T/B_T$ (THC producing, chemotype I), $B_D/B_D$ (CBD producing, chemotype III), and $B_T/B_D$ (producing both THC and CBD, chemotype II). Additional information on the genetic regulation of cannabinoids can be found in Meijer et al. I, II, III, and IV (I: 2003, Genetics, 163:335-346; II: 2005, Euphytica, 145:189-198; III: 2009, Euphytica, 165:293-311; and IV: 2009, Euphytica, 168:95-112).

More details of cannabinoids synthesis and the properties and uses of these cannabinoids are described in Russo (2011, Taming THC: potential *cannabis* synergy and phytocannabinoid-terpenoid entourage effects, British Journal of Pharmacology, 163:1344-1364), Russo et al. (2006, A tale of two cannabinoids: the therapeutic rationale for combining tetrahydrocannabinol and cannabidiol, Medical Hypothesis, 2006, 66:234-246), Celia et al. (Impact of cannabidiol on the acute memory and psychotomimetic effects of smoked *cannabis*: naturalistic study, The British Journal of Psychiatry, 201, 197:285-290), de Mello Schier et al., (Cannabidiol, a *cannabis* sativa constituent, as an anxiolytic drug, Rev. Bras. Psiquiatr, 2012, 34(S1):5104-5117), and Zhornitsky et al.

(Cannabidiol in Humans—the Quest for Therapeutic Targets, Pharmaceuticals, 2012, 5:529-552), each of which is herein incorporated by reference in its entirety for all purposes. Please see Table 1 for a non-limiting list of medical uses for cannabinoids.

derived from five-carbon isoprene units assembled and modified in thousands of ways. Most are multicyclic structures that differ from one another not only in functional groups but also in their basic carbon skeletons. Plant terpenoids are used extensively for their aromatic qualities. They play a role in

TABLE 1

Non-limiting list of medical uses for cannabinoids.

| | MEDICAL USES | CANNABINOID | REFERENCES |
|---|---|---|---|
| 1 | Distonia, Akathisia (Anti convulsant) | CBD | (a) Consroe, 1986, *The International journal of neuroscience* 30 (4): 277-282<br>(b) Snider et al., 1985, *Neurology*, (Suppl 1): 201. |
| 2 | Glaucoma (lowers intraocular pressure) | CBD<br>CBG | (a) Colasanti et al, Exp. Eye Res. 30: 251-259, 1984<br>(b) Gen. Pharmac. 15: 479-484, 1984<br>(c) Craig et al. 1984, Experimental eye research 39 (3): 251-259 |
| 3 | Ischemic disease (Alzheimer's, Parkinson's, Down Syndrome, HIV, Dementia) | CBD | (a) U.S. Pat. No. 6,630,507<br>(b) Snider et al., 1985, "Beneficial and Adverse Effects of Cannabidiol in a Parkinson Patient with Sinemet-Induced Dystonic Dyskinesia". *Neurology*, (Suppl 1): 201. |
| 4 | Good for patients treated with oxidant-inducing agents for chemotherapy, radiation. | CBD | (a) U.S. Pat. No. 6,630,507 |
| 5 | Motion Sickness (Anti-emetic) | CBD | (a) U.S. Pat. No. 8,034,843 GW Pharma experiments on Shrews<br>(b) Mechoulam, et al., 2007, *Chemistry & Biodiversity* 4 (8): 1678-1692. |
| 6 | Pain-Brachial plexus avulsion | THC<br>THC:CBD | (a) U.S. Pat. No. 20060135599 GW Pharma |
| 7 | Pain and inflammation-Arthritis | CBD: THC | (a) U.S. Pat. No. 20080139667<br>(b) Mechoulam, et al., 2007, *Chemistry & Biodiversity* 4 (8): 1678-1692. |
| 8 | Anti Cancer-cell movement | CBD: THC<br>CBD | (a) U.S. Pat. No. 20080262099<br>(b) Mechoulam, et al., 2007, *Chemistry & Biodiversity* 4 (8): 1678-1692.<br>(c) McAllister et al., 2007, Mol. Cancer Ther. 6 (11): 2921-7. |
| 9 | Anti Convulsant (against seizures) | CBDV<br>CBD | (a) U.S. Pat. No. 20120004251<br>(b) U.S. Pat. No. 20120165402<br>(d) Mechoulam, et al., 2007, *Chemistry & Biodiversity* 4 (8): 1678-1692.<br>(a) Carlini et al., J. Clin. Pharmacol. 21: 417S-427S, 1981<br>(b) Karler et al., J. Clin. Pharmacol. 21: 437S-448S, 1981<br>(c) Consroe et al., J. Clin Pharmacol. 21: 428S-436S, 1981 |
| 10 | Neurological Pain (MS related) | THC: CBD | (a) U.S. Pat. No. 20100035978 |
| 11 | Weight loss | THCV | (b) U.S. Pat. No. 20090306221<br>(c) U.S. Pat. No. 20080119544 |
| 12 | Anti-Depressant | CBG | (a) U.S. Pat. No. 20080031977<br>(b) U.S. Pat. No. 60/813,814 |
| 13 | Irritable Bowel Syndrome (Crohns) | THC:CBD | (c) EP 1361864<br>(d) EP 1542657<br>(e) U.S. Pat. No. 20100286098 |
| 14 | Type II diabetes | THCV:CBD | (a) U.S. Pat. No. 20110082195<br>(b) |
| 15 | Anti-Psychotic | THCV:CBD | (c) U.S. Pat. No. 20110038958<br>(d) Zuardi et al., 2006, *Braz. J. Med. Biol. Res.* 39 (4): 421-429. |
| 16 | Cancer Pain | THC:CBD | (e) U.S. Pat. No. 20110230549 |
| 17 | Anxiety Reduction | CBD | (a) Mechoulam, et al., 2007, *Chemistry & Biodiversity* 4 (8): 1678-1692.<br>(b) Bergamaschi et al., 2003, *Neuropsychopharmacology* 36 (6): 1219-1226 |

Terpenes and Terpenoids in *Cannabis* Plants

Terpenes are a large and diverse class of organic compounds, produced by a variety of plants. They are often strong smelling and thus may have had a protective function. Terpenes are derived biosynthetically from units of isoprene, which has the molecular formula $C_5H_8$. The basic molecular formulae of terpenes are multiples of that, $(C_5H_8)_n$ where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids.

Terpenoids, a.k.a. isoprenoids, are a large and diverse class of naturally occurring organic chemicals similar to terpenes, traditional herbal remedies and are under investigation for antibacterial, antineoplastic, and other pharmaceutical functions. The terpene Linalool for example, has been found to have anti-convulsant properties (Elisabetsky et al., Phytomedicine, May 6(2):107-13 1999). Well-known terpenoids include citral, menthol, camphor, salvinorin A in the plant Salvia divinorum, and the cannabinoids found in *Cannabis*. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by *cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

In addition to cannabinoids, *cannabis* also produces over 120 different terpenes (Russo 2011, Taming THC: potential *cannabis* synergy and phytocannabinoid-terpenoid entourage effects, *British Journal of Pharmacology*, 163:1344-1364). Within the context and verbiage of this document the terms 'terpenoid' and 'terpene' are used interchangeably. Cannabinoids are odorless, so terpenoids are responsible for the unique odor of *cannabis*, and each variety has a slightly different profile that can potentially be used as a tool for identification of different varieties or geographical origins of samples (Hillig 2004. "A chemotaxonomic analysis of terpenoid variation in *Cannabis*" Biochem System and Ecology 875-891). It also provides a unique and complex organoleptic profile for each variety that is appreciated by both novice users and connoisseurs. In addition to many circulatory and muscular effects, some terpenes interact with neurological receptors. A few terpenes produced by *cannabis* plants also bind weakly to Cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

Generally speaking, terpenes are considered to be pharmacologically relevant when present in concentrations of at least 0.05% in plant material (Hazekamp and Fischedick 2010. "Metabolic fingerprinting of *Cannabis sativa* L., cannabinoids and terpenoids for chemotaxonomic and drug standardization purposes" Phytochemistry 2058-73; Russo 2011, Taming THC: potential *cannabis* synergy and phytocannabinoid-terpenoid entourage effects, *British Journal of Pharmacology*, 163:1344-1364). Thus, although there are an estimated 120 different terpenes, only a few are produced at high enough levels to be detectable, and fewer still which are able to reach pharmacologically relevant levels.

For the purposes of this application, *cannabis* terpene profile will be defined as the absolute and relative values of 17 of the most expressed terpenes: terpinolene, alpha phelladrene, beta ocimene, carene, limonene, gamma terpinene, alpha pinene, alpha terpinene, beta pinene, fenchol, camphene, alpha terpineol, alpha humulene, beta caryophyllene, linalool, cary oxide, and myrcene. A survey of the terpene profiles of several *cannabis* varieties has found that these terpenes express at high enough levels so as to have their own pharmacological effects and also to act in synergy with cannabinoids. Both experts and consumers believe that there are biochemical and phenomenological differences between different varieties of *cannabis*, which are attributed to their unique relative cannabinoid and terpenoid ratios. This is known as the entourage effect and is generally considered to result in plants providing advantages over only using the natural products that are isolated from them (Russo 2011, Taming THC: potential *cannabis* synergy and phytocannabinoid-terpenoid entourage effects, *British Journal of Pharmacology*, 163:1344-1364).

These advantages include synergy with THC, the primary active ingredient, and also mitigation of side effects from THC (McPartland and Russo 2001 "*Cannabis* and *Cannabis* Extracts: Greater Than the Sum of Their Parts?" Hayworth Press). Terpenoids can be extracted from the plant material by steam distillation (giving you essential oil) or vaporization, however the yield varies greatly by plant tissue, type of extraction, age of material, and other variables (McPartland and Russo 2001 "*Cannabis* and *Cannabis* Extracts: Greater Than the Sum of Their Parts?" Hayworth Press). Typically the yield of terpenoids in *cannabis* is less than 1% by weight on analysis; however it is thought that they may comprise up to 10% of the trichome content. Monoterpenoids are especially volatile, thus decreasing their yield relative to sesquiterpenoids (Russo 2011, Taming THC: potential *cannabis* synergy and phytocannabinoid-terpenoid entourage effects, *British Journal of Pharmacology*, 163:1344-1364).

D-Limonene is a monoterpenoid that is widely distributed in nature and often associated with citrus. It has strong anxiolytic properties in both mice and humans, apparently increasing serotonin and dopamine in mouse brain. D-limonene has potent anti-depressant activity when inhaled. It is also under investigation for a variety of different cancer treatments, with some focus on its hepatic metabolite, perillic acid. There is evidence for activity in the treatment of dermatophytes and gastro-oesophageal reflux, as well as having general radical scavenging properties (Russo 2011, Taming THC: potential *cannabis* synergy and phytocannabinoid-terpenoid entourage effects, *British Journal of Pharmacology*, 163:1344-1364).

β-Myrcene is a monoterpenoid also found in *cannabis*, and has a variety of pharmacological effects. It is often associated with a sweet fruit like taste. It reduces inflammation, aids sleep, and blocks hepatic carcinogenesis, as well as acting as an analgesic and muscle relaxant in mice. When β-myrcene is combined with Δ9-THC it could intensify the sedative effects of Δ9-THC, causing the well-known "couch-lock" effect that some *cannabis* users experience (Russo 2011, Taming THC: potential *cannabis* synergy and phytocannabinoid-terpenoid entourage effects, *British Journal of Pharmacology*, 163: 1344-1364).

D-Linalool is a monoterpenoid with very well-known anxiolytic effects. It is often associated with lavender, and frequented used in aromatherapy for its sedative impact. It acts as a local anaesthetic and helps to prevent scarring from burns, is anti-nociceptive in mice, and shows antiglutamatergic and anticonvulsant activity. Its effects on glutamate and GABA neurotransmitter systems are credited with giving it its sedative, anxiolytic, and anticonvulsant activities (Russo 2011, Taming THC: potential *cannabis* synergy and phytocannabinoid-terpenoid entourage effects, *British Journal of Pharmacology*, 163:1344-1364).

α-Pinene is a monoterpene common in nature, also with a plethora of effects on mammals and humans. It acts as an acetylcholinesterase inhibitor which aids memory and counteracts the short-term memory loss associated with $\Delta_9$-THC intoxication, is an effective antibiotic agent, and shows some activity against MRSA. In addition, α-pinene is a bronchodilator in humans and has anti-inflammatory properties via the prostaglandin E-1 pathway (Russo 2011, Taming THC:

potential cannabis synergy and phytocannabinoid-terpenoid entourage effects, *British Journal of Pharmacology*, 163: 1344-1364).

β-Caryophyllene is often the most predominant sesquiterpenoid in *cannabis*. It is less volatile than the monoterpenoids, thus it is found in higher concentrations in material that has been processed by heat to aid in decarboxylation. It is very interesting in that it is a selective full agonist at the CB2 receptor, which makes it the only phytocannabinoid found outside the *cannabis* genus. In addition, it has anti-inflammatory and gastric cytoprotective properties, and may even have anti-malarial activity.

Caryophyllene oxide is another sesquiterpenoid found in *cannabis*, which has antifungal and anti-platelet aggregation properties. As an aside, it is also the molecule that drug-sniffing dogs are trained to find (Russo 2011, Taming THC: potential *cannabis* synergy and phytocannabinoid-terpenoid entourage effects, *British Journal of Pharmacology*, 163: 1344-1364).

Nerolidol is a sesquiterpene that is often found in citrus peels that exhibits a range of interesting properties. It acts as a sedative, inhibits fungal growth, and has potent anti-malarial and antileishmanial activity. It also alleviated colon adenomas in rats (Russo 2011, Taming THC: potential *cannabis* synergy and phytocannabinoid-terpenoid entourage effects, *British Journal of Pharmacology*, 163:1344-1364). Phytol is a diterpene often found in *cannabis* extracts. It is a degradation product of chlorophyll and tocopherol. It increases GABA expression and therefore could be responsible the relaxing effects of green tea and wild lettuce. It also prevents vitamin-A induced teratogenesis by blocking the conversion of retinol to its dangerous metabolite, all-trans-retinoic acid (Russo 2011, Taming THC: potential *cannabis* synergy and phytocannabinoid-terpenoid entourage effects, British Journal of Pharmacology, 163:1344-1364).

Some of the most commonly found terpenoids in *cannabis* are summarized in Table 2, with their individual organoleptic properties as well as their basic pharmacology.

TABLE 2

A non-limiting list of the medical effects of some of the most common terpenes found in cannabis

| Terpenoid | Odor Description | Flavor Description | Suggested Pharmacology |
|---|---|---|---|
| $^a$-pinene | Herbal, piney | Woody, piney, camphoraceous | Anti-inflammatory, bronchodilator, stimulant |
| camphene | Woody, piney | Camphoraceous, cooling, minty | Reduces plasma cholesterol and triglycerides, Antioxidant and free radical scavenger |
| $^b$-pinene | Herbal, cooling, piney | Fresh, piney, woody | Strong antimicrobial |
| myrcene | Spicy, herbaceous | Woody, vegetative, citrus | Anti-inflammatory, sedative, antibiotic, analgesic |
| $^a$-phellandrene | Terpenic, citrus | Terpenic, citrus, lime | Antinociceptive |
| carene | Citrus, sweet | None given | CNS depressant, anti-inflamatory |
| $^a$-terpinene | Woody, citrus, medicinal | Terpenic, woody, piney | Antioxidant |
| limonene | Citrus, fresh | Sweet, orange, citrus | Anxiolytic, antidepressant, immunostimulant |
| $^b$-ocimene | Floral, green | Green, tropical, woody | Possible anti-bacterial |
| $^g$-terpinene | Terpenic, woody | Terpenic, citrus, lime-like | Antioxidant |
| terpinolene | Herbal, woody | Sweet, fresh, piney, citrus | Comforting, calming, anti-oxidant, antifungal |
| linalool | Floral, citrus | Citrus, orange, lemon, floral | Sedative, anxiolytic, immunostimulant |
| fenchol | Camphor, piney | Fresh, piney | Possible stimulant |
| $^a$-terpineol | Floral, piney | None given | Sedative, AChE inhibitor, antioxidant |
| $^b$-caryophyllene | Spicy, woody | Spicy, clove, rosemary | Selective agonist of CB2 receptor, anti-inflammatory, antimalarial |
| $^a$-humulene | Woody | None given | Anti-inflammatory |
| caryophyllene oxide | Woody, sweet | None given | Antifungal, stimulant |

Cannabis Plants

*Cannabis* is an annual, dioecious, flowering herb. The leaves are palmately compound or digitate, with serrate leaflets. *Cannabis* normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in *cannabis*) bear staminate and pistillate structures on individual flowers, whereas monoecious plants bear male and female flowers at different locations on the same plant.

The life cycle of *cannabis* varies with each variety but can be generally summarized into germination, vegetative growth, and reproductive stages. Because of heavy breeding and selection by humans, most *cannabis* seeds have lost dormancy mechanisms and do not require any pre-treatments or winterization to induce germination (See Clarke, R C et al. "*Cannabis*: Evolution and Ethnobotany" University of California Press 2013). Seeds placed in viable growth conditions are expected to germinate in about 3 to 7 days. The first true leaves of a *cannabis* plant contain a single leaflet, with subsequent leaves developing in opposite formation, with increasing number of leafletts. Leaflets can be narrow or broad depending on the morphology of the plant grown. *Cannabis* plants are normally allowed to grow vegetatively for the first 4 to 8 weeks. During this period, the plant responds to increasing light with faster and faster growth. Under ideal conditions, *cannabis* plants can grow up to 2.5 inches a day, and are capable of reaching heights of up to 20 feet. Indoor growth pruning techniques tend to limit *cannabis* size through careful pruning of apical or side shoots.

Although, some *cannabis* varieties will flower without the need for external stimuli, most varieties have an absolute requirement for inductive photoperiods in the form of short days or long nights to induce fertile flowering. The first sign of flowering in *cannabis* is the appearance of undifferentiated flower primordial along the main stem of the nodes. At this stage, the sex of the plants are still not distinguishable. As the flower primordia continue to develop, female (pistillate), and male (staminate) flowers can be distinguished.

For most cannabinoid producing purposes, only female plants are desired. The presence of male flowers is considered undesirable as pollination is known to reduce the cannabinoid yield, and potentially ruin a crop. For this reason, most *cannabis* is grown "sinsemilla" through vegetative (i.e., asexual) propagation. In this way, only female plants are produced and no space is wasted on male plants.

In breeding new varieties of *cannabis*, there are many phenotypic and morphological characteristics one must consider. For example, plants should produce high amounts of cannabinoids. Cannabinoid levels can be measured via chemical analysis of mature plants, but can also be estimated in the field by the number and size of the trichomes produced by a plant's flower clusters. Plants with dense trichome patterns are said to be "frosty", and selected for further breeding. The types of cannabinoids can also be determined in the field via thin layer chromatography (TLC) analysis (see "*Cannabis* Inflorescence & Leaf QC" from The American Herbal Pharmacopeia 2013). The absolute cannabinoid and terpene contents are calculated based on weight of cannabinoid or terpene present in a sample divided by the dried weight of the dried trimmed inflorescence. Dried inflorescences are harvested inflorescence tissue dried to ~10% moisture level. The terp trimmed inflorescence as used herein refers to inflorescences with sun leaves cut off such that only the calyx and reproductive buds remain. Frosty leaves are left on the inflorescence. Trimming can be performed manually, through careful manicuring of harvested tissue, or via automated mechanical methods.

Another important aspect of *cannabis* breeding is the terpene profile of a plant. In some embodiments, the present invention teaches the preference for *cannabis* plant material with diverse terpene profiles which are not dominated by myrcene. In other embodiments, the present invention teaches *cannabis* plants with high terpene essential oil contents. For the purposes of this application, a *cannabis* plant's terpene profile is defined in absolute or relative contents of 17 key terpenes including: terpinolene, alpha phelladrene, beta ocimene, carene, limonene, gamma terpinene, alpha pinene, alpha terpinene, beta pinene, fenchol, camphene, alpha terpineol, alpha humulene, beta caryophyllene, linalool, cary oxide, and myrcene. A myrcene dominant terpene is used to refer to terpene profiles in which myrcene is the most abundant terpene in the terpene profile (i.e., myrcene relative or absolute content is >content of any single one of the 16 other terpenes in the terpene profile). Terpene essential oil contents are measured by adding the absolute contents by weight of the 17 terpenes from the terpene profile as defined above. The absolute terpene content is measured as w/w % value based on dry inflorescences. The present invention is based in part on the discovery that consumers prefer specialty *cannabis* varieties with diverse terpene profiles not dominated by myrcene and with high terpene essential oil contents.

In some embodiments, the specialty *cannabis* of the present invention has greater than 0.1%, 0.2%, 0.3%, 0.4%, 0.5%, 0.6%, 0.7%, 0.8%, 0.9%, 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.3%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, or 8% terpene essential oil content by dry weight. Thus in some embodiments the essential oil content of the specialty *cannabis* varieties of the present invention is between about 0.5% and about 8% by dry weight. In other embodiments the essential oil contents of the specialty *cannabis* varieties of the present invention is between about 1.5% and about 5% by dry weight.

In some embodiments, the specialty *cannabis* of the present invention has an absolute content of any one of the 17 terpenes in the terpene profile that is 0%, 0.01%, 0.02%, 0.04%, 0.06%, 0.08%, 0.1%, 0.12%, 0.14%, 0.16%, 0.18%, 0.2%, 0.22%, 0.24%, 0.26%, 0.28%, 0.3%, 0.32%, 0.34%, 0.36%, 0.38%, 0.4%, 0.42%, 0.44%, 0.46%, 0.48%, 0.5%, 0.52%, 0.54%, 0.56%, 0.58%, 0.6%, 0.62%, 0.64%, 0.66%, 0.68%, 0.7%, 0.72%, 0.74%, 0.76%, 0.78%, 0.8%, 0.82%, 0.84%, 0.86%, 0.88%, 0.9%, 0.92%, 0.94%, 0.96%, 0.98%, 1%, 1.02%, 1.04%, 1.06%, 1.08%, 1.10%, 1.12%, 1.14%, 1.16%, 1.18%, 1.2%, 1.22%, 1.24%, 1.26%, 1.28%, 1.3%, 1.32%, 1.34%, 1.36%, 1.38%, 1.4%, 1.42%, 1.44%, 1.46%, 1.48%, 1.5%, 1.6%, 1.7% 1.8%, 1.9%, 2%, 2.2%, 2.4%, 2.6%, 2.8%, 3%, 3.2%, 3.4%, 3.6%, 3.8%, 4%, 4.2%, 4.3%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, 8%, or greater based on dry weight of inflorescence. Thus in some embodiments the absolute content of any one of the terpenes is between about 0.05% and about 0.85%.

In some embodiments, the specialty *cannabis* of the present invention has a myrcene absolute content of less than 0.02%, 0.04%, 0.06%, 0.08%, 0.1%, 0.12%, 0.14%, 0.16%, 0.18%, 0.2%, 0.22%, 0.24%, 0.26%, 0.28%, 0.3%, 0.32%, 0.34%, 0.36%, 0.38%, 0.4%, 0.42%, 0.44%, 0.46%, 0.48%, 0.5%, 0.52%, 0.54%, 0.56%, 0.58%, 0.6%, 0.62%, 0.64%, 0.66%, 0.68%, 0.7%, 0.72%, 0.74%, 0.76%, 0.78%, 0.8%, 0.82%, 0.84%, 0.86%, 0.88%, 0.9%, 0.92%, 0.94%, 0.96%, 0.98%, 1%, 1.02%, 1.04%, 1.06%, 1.08%, 1.10%, 1.12%, 1.14%, 1.16%, 1.18%, 1.2%, 1.22%, 1.24%, 1.26%, 1.28%, 1.3%, 1.32%, 1.34%, 1.36%, 1.38%, 1.4%, 1.42%, 1.44%, 1.46%, 1.48%, 1.5%, 1.6%, 1.7% 1.8%, 1.9%, 2%, 2.2%, 2.4%, 2.6%, 2.8%, 3%, 3.2%, 3.4%, 3.6%, 3.8%, 4%, 4.2%, 4.3%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, or 8% based on dry weight of inflorescence. Thus in some embodiments the absolute content of any one of myrcene is between about 0.05% and about 0.85%.

In some embodiments the terpene content of the specialty *cannabis* of the present invention is described in relative terms as a % composition of the total terpene profile. Thus for example a specialty *cannabis* with 1.2% absolute terpinolene content and 1.2% myrcene content and no other terpenes would said to have 50% terpinolene and 50% myrcene relative content. In some embodiments, the specialty *cannabis* of the present invention has a relative content of any one of the 17 terpenes in the terpene profile that is greater than or less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. Thus in some embodiments the relative content of any one of the terpenes is between 0% and 100%.

In some embodiments, the specialty *cannabis* of the present invention has a relative myrcene content of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. Thus in some embodiments the specialty *cannabis* of the present invention has less than 60% relative myrcene content.

Another important breeding phenotype is flower color. The accumulation of anthocyanins, carotenoids, or other color-producing compounds in leaves and flowers of *cannabis* can have an effect on consumer visual appeal and flavor. Iconic examples of the appeal of color are the popular "Purple Kush", "Purple Haze", and "Purple Trainwreck" varieties that express anthocyanins in their late maturation stages to produce dark purple leaves. Color selections can also be based on (but not limited to) unique coloration of stem, leaf, inflorescence, calyx, stamen, trichome bodies and finished products including extracts and hash.

Yield is another important factor in breeding. *Cannabis* yield is measured by pounds (lbs), grams (g) or kilograms (Kg) of dried (10% moisture), and trimmed flowers. Yield can be expressed in terms of yield per plant, yield per watt of light, and yield per squared meter of growing area among others. *Cannabis* yield is also dependent on the growing environment. For example yields for a particular *cannabis* strain will vary between outdoor growth long season, outdoor growth short season, or indoor growth. Yield may also be affected by growing conditions such as type of lighting, soil, fertilizer use, size of growing pot, etc.

In some embodiments, the specialty *cannabis* of the present invention produces, 0.1 g, 0.2 g, 0.3 g, 0.4 g, 0.5 g, 0.6 g, 0.7 g, 0.8 g, 0.9 g, 1.0 g, 1.1 g, 1.2 g, 1.3 g, 1.4 g, 1.5 g, 1.6 g, 1.7 g, 1.8 g, 1.9 g, 2.0 g, 2.1 g, 2.2 g, 2.3 g, 2.4 g, 2.5 g, 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, or 5.0 g of dried flowers per watt of light. In some embodiments, the specialty *cannabis* of the present invention produces 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, 100 g, 105 g, 110 g, 115 g, 120 g, 125 g, 130 g, 135 g, 140 g, 145 g, 150 g, 155 g, 160 g, 165 g, 170 g, 175 g, 180 g, 185 g, 190 g, 195 g, 200 g, 210 g, 220 g, 230 g, 240 g, 250 g, 260 g, 270 g, 280 g, 290 g, 300 g, 310 g, 320 g, 330 g, 340 g, 350 g, 360 g, 370 g, 380 g, 390 g, 400 g, 410 g, 420 g, 430 g, 440 g, 450 g, 460 g, 470 g, 480 g, 490 g, 500 g, 550 g, 600 g, 650 g, 700 g, 750 g, 800 g, 850 g, 900 g, 950 g, 1000 g, 2000 g, 3000 g, or 5000 g of dried flowers per plant.

Desirable yield phenotypes include:

High Yield Natural Light Production Long Season—Selection based on yield performance for early ripening varieties during long seasons.

High Yield Natural Light Production Short Season—Selection based on yield performance of late ripening varieties during long season and/or yield of plants that ripen in winter months and at low light levels.

High Yield Indoor Production—Selection based solely on plant yield performance in artificial lighting (e.g., HID). Another important phenotype that is important for *cannabis* production is structural features for easy harvesting.

Other important breeding phenotypes include:

Structure for Manual Trim/Market—Selections are based on the relative ratio by weight of finished flower. This usually is directly related to dense trichome morphology with very few sun leaves.

Structure for Automated Trimming—Selection based on flower morphology that is more kola (continuous long bud) with many sun leaves protruding from large inflorescences. Overall flower size is typically large, but trichomes are less densely packed and overall inflorescence is less dense than what is traditionally selected for manual trim.

Root Structure—Positive root selection is marked by overall root vigor and adventitious root growth, ease of transplant, rate of root development on clonal propagations, and root shooting from tissue culture samples. Root selections can also be based on resistance to soil and hydroponic pathogens including *pythium*.

Vigor—Selection for plant vigor are marked by tremendous grow rates and robust stem/stalk infrastructure. Often times, selection display morphologies that are very much enlarged compared to sibling progeny.

Fungal Resistance—Selections based on plant that exhibit immunity or partial immunity to fungal diseases and pathogens including but not limited to powdery mildew, *botrytis*, downy mildew among others.

For a non-limiting list of cannabinoid phenotypes, please see Marijuana Botany, An Advanced study: The Propagation and Breeding of Distinctive *Cannabis* by Robert Connell Clarke.

The present invention also relates to variants, mutants and modifications of the seeds, plant parts and/or whole plants of the *cannabis* plants of the present invention. Variants, mutants and trivial modifications of the seeds, plants, plant parts, plant cells of the present invention can be generated by methods well known and available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity).

The present invention also relates to a mutagenized population of the *cannabis* plants of the present invention, and methods of using such populations. In some embodiments, the mutagenized population can be used in screening for new *cannabis* lines which comprises one or more or all of the morphological, physiological, biological, and/or chemical characteristics of *cannabis* plants of the present invention. In some embodiments, the new *cannabis* plants obtained from the screening process comprise one or more or all of the morphological, physiological, biological, and/or chemical characteristics of *cannabis* plants of the present invention, and one or more additional or different new morphological, physiological, biological, and/or chemical characteristic.

The mutagenized population of the present invention can be used in Targeting Induced Local Lesions in Genomes (TILLING) screening method, which combines a standard and efficient technique of mutagenesis with a chemical mutagen (e.g., Ethyl methanesulfonate (EMS)) with a sensitive DNA screening-technique that identifies single base mutations (also called point mutations) in a target gene. Detailed description on methods and compositions on TILLING® can be found in Till et al. (Discovery of induced point mutations in maize genes by TILLING, BMC Plant Biology 2004, 4:12), Weil et al., (TILLING in Grass Species, Plant Physiology January 2009 vol. 149 no. 1 158-164), Comai, L. and S. Henikoff ("TILLING: practical single-nucleotide mutation discovery." Plant J 45(4): 684-94), McCallum et al., (Nature Biotechnology, 18: 455-457, 2000), McCallum et al., (Plant Physiology, 123: 439-442, 2000), Colbert et al., (Plant Physiol. 126(2): 480-484, 2001), U.S. Pat. No. 5,994,075, U.S. Patent Application Publication No. 2004/0053236A1, and International Patent Application Publication Nos. WO 2005/055704 and WO 2005/048692, each of which is hereby incorporated by reference for all purposes.

The present invention also provides any compositions or any products made from or isolated from the plants of the present invention. In some embodiments, the compositions/products comprises extract of the plants, wherein the extract contains more than 2% CBD and less than 98% THC. In some embodiments, the extract contains higher percentage of terpenes/terpenoids compared to extract isolated from a control *cannabis* plant variety (e.g., an existing variety, such as a recreational *cannabis* plant variety).

Methods of Using *Cannabis* Plants

The present invention provides methods of using the *cannabis* plants or any parts, any compositions, or any chemicals derived from said plants of the present invention.

In some embodiments, the plants can be used for medical purpose. In other embodiments, the specialty *cannabis* plants of the present invention can be used for recreational purposes. In some embodiments, the plants can be used by patients having a disease. In some embodiments, the diseases includes, but are not limited to, Acquired Hypothyroidism, Acute Gastritis, Agoraphobia, AIDS Related Illness, Alcohol Abuse, Alcoholism, Alopecia Areata, Alzheimer's Disease, Amphetamine Dependency, Amyloidosis, Amyotrophic Lateral Sclerosis (ALS), Angina Pectoris, Ankylosis, Anorexia, Anorexia Nervosa, Anxiety Disorders, any chronic medical symptom that limits major life activities, any Chronic Medical Symptom that Limits Major Life Activities, Arteriosclerotic Heart Disease, Arthritis, Arthritis (Rheumatoid), Arthropathy, gout, Asthma, Attention Deficit Hyperactivity Disorder (ADD/ADHD), Autism/Asperger's, Autoimmune Disease, Back Pain, Back Sprain, Bell's Palsy, Bipolar Disorder, Brain Tumor, Malignant, Bruxism, Bulimia, Cachexia, Cancer, Carpal Tunnel Syndrome, Cerebral Palsy, Cervical Disk Disease, Cervicobrachial Syndrome, Chemotherapy Chronic Fatigue Syndrome, Chronic Pain, Chronic renal failure, Cocaine Dependence, Colitis, Conjunctivitis, Constipation, Crohn's Disease, Cystic Fibrosis, Damage to Spinal Cord Nervous Tissue, Darier's Disease, Degenerative Arthritis, Degenerative Arthropathy, Delirium Tremens, Dermatomyositis, Diabetes, Diabetic Neuropathy, Diabetic Peripheral Vascular Disease, Diarrhea, Diverticulitis, Dysthymic Disorder, Eczema, Emphysema, Emphysema, Endometriosis, Epidermolysis Bullosa, Epididymitis, Epilepsy, Felty's Syndrome, Fibromyalgia, Friedreich's Ataxia, Gastritis, Genital Herpes, Glaucoma, Glioblastoma Multiforme, Graves Disease, Cluster Headaches, Migraine Headaches, Tension Headaches, Hemophilia A, Henoch-Schonlein Purpura, Hepatitis C, Hereditary Spinal Ataxia, HIV/AIDS, Hospice Patients, Huntington's Disease, Hypertension, Hypertension, Hyperventilation, Hypoglycemia, Impotence, Inflammatory autoimmune-mediated arthritis, Inflammatory Bowel Disease (IBD), Insomnia, Intermittent Explosive Disorder (IED), Intractable Pain, Intractable Vomiting, Lipomatosis, Lou Gehrig's Disease, Lyme Disease, Lymphoma, Major Depression, Malignant Melanoma, Mania, Melorheostosis, Meniere's Disease, Motion Sickness, Mucopolysaccharidosis (MPS), Multiple Sclerosis (MS), Muscle Spasms, Muscular Dystrophy, Myeloid Leukemia, Nail-Patella Syndrome, Nightmares, Obesity, Obsessive Compulsive Disorder, Opiate Dependence, Osteoarthritis, Panic Disorder, Parkinson's Disease, Peripheral Neuropathy, Peritoneal Pain, Persistent Insomnia, Porphyria, Post Polio Syndrome (PPS), Post-traumatic arthritis, Post-Traumatic Stress Disorder (PTSD), Premenstrual Syndrome (PMS), Prostatitis, Psoriasis, Pulmonary Fibrosis, Quadriplegia, Radiation Therapy, Raynaud's Disease, Reiter's Syndrome, Restless Legs Syndrome (RLS), Rheumatoid Arthritis, Rheumatoid Arthritis, Rheumatoid Arthritis, Rosacea, Schizoaffective Disorder, Schizophrenia, Scoliosis, Sedative Dependence, Seizures, Senile Dementia, Severe Nausea, Shingles (Herpes Zoster), Sinusitis, Skeletal Muscular Spasticity, Sleep Apnea, Sleep Disorders, Spasticity, Spinal Stenosis, Sturge-Weber Syndrome (SWS), Stuttering, Tardive Dyskinesia (TD), Temporomandibular joint disorder (TMJ), Tenosynovitis, Terminal Illness, Thyroiditis, Tic Douloureux, Tietze's Syndrome, Tinnitus, Tobacco Dependence, Tourette's Syndrome, Trichotillomania, Viral Hepatitis, Wasting Syndrome, Whiplash, Wittmaack-Ekbom's Syndrome, Writers' Cramp, nausea, vomiting, premenstrual syndrome, unintentional weight loss, insomnia, and lack of appetite, spasticity, painful conditions, especially neurogenic pain, movement disorders, asthma, glaucoma, adrenal disease, inflammatory bowel disease, migraines, fibromyalgia, and related conditions, multiple sclerosis, spinal cord injuries. It exhibits antispasmodic and muscle-relaxant properties as well as stimulates appetite. Other studies state that *cannabis* or cannabinoids may be useful in treating alcohol abuse, amyotrophic lateral sclerosis, collagen-induced arthritis, asthma, atherosclerosis, bipolar disorder, colorectal cancer, HIV-Associated Sensory Neuropathy, depression, dystonia, epilepsy, digestive diseases, gliomas, hepatitis C, Huntington's disease, leukemia, skin tumors, methicillin-resistant *Staphylococcus aureus* (MRSA), Parkinson's disease, pruritus, posttraumatic stress disorder (PTSD), psoriasis, sickle-cell disease, sleep apnea, and anorexia nervosa.

In some embodiments, the plants of the present invention provide one or more medical benefits to a person in need without any side effects, or with reduced side effects compared to a traditional recreational marijuana plant variety. In some embodiments, the specialty *cannabis* of the present invention can reduce the effect of *cannabis* use on fetal brain development by providing CBs and terpenes which attenuate the activation of CB1 receptor by THC (Tortoriello et al., 2013 "Miswiring the brain: delta 9 tetrahydrocananbinol disrupts cortical development by inducing an SCG10/stathmin-2 degradation pathway" EMBO 10 Dec. 2013). In some embodiments, the traditional recreational marijuana plant variety is the variety 'White Widow.' In some embodiments, the traditional recreational marijuana plant variety contains at least 98%, at least 98.5%, at least 99%, at least 99.5%, at least 99.6%, at least 99.7%, at least 99.8%, at least 99.9%, or 100% THC in the cannabinoid accumulation in the plant.

In some embodiments, the plants can be used for non-medical purposes. In some embodiments the specialty *cannabis* plants of the present invention can be used for recreational purposes. In some embodiments, the specialty *cannabis* plants of the present invention can be used for industrial purposes. In some embodiments, the plants are used for producing food, oil, wax, resin, rope, cloth, pulp, fiber, feed for livestock, construction material, plastic and composite materials, paper, jewelry, water and soil purification materials, weed control materials, cultivation materials, textiles, clothing, biodegradable plastics, body products, health food and biofuel.

Cannabis Breeding Methods

In some embodiments, the plants of the present invention can be used to produce new plant varieties. In some embodiments, the plants are used to develop new, unique and superior varieties or hybrids with desired phenotypes.

In some embodiments, selection methods, e.g., molecular marker assisted selection, can be combined with breeding methods to accelerate the process. Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. Cannabis genome has been sequenced recently (Bakel et al., The draft genome and transcriptome of Cannabis sativa, Genome Biology, 12(10):R102, 2011). Molecular makers for cannabis plants are described in Datwyler et al. (Genetic variation in hemp and marijuana (Cannabis sativa L.) according to amplified fragment length polymorphisms, J Forensic Sci. 2006 March; 51(2):371-5.), Pinarkara et al., (RAPD analysis of seized marijuana (Cannabis sativa L.) in Turkey, Electronic Journal of Biotechnology, 12(1), 2009), Hakki et al., (Inter simple sequence repeats separate efficiently hemp from marijuana (Cannabis sativa L.), Electronic Journal of Biotechnology, 10(4), 2007), Datwyler et al., (Genetic Variation in Hemp and Marijuana (Cannabis sativa L.) According to Amplified Fragment Length Polymorphisms, J Forensic Sci, March 2006, 51(2):371-375), Gilmore et al. (Isolation of microsatellite markers in Cannabis sativa L. (marijuana), Molecular Ecology Notes, 3(1):105-107, March 2003), Pacifico et al., (Genetics and marker-assisted selection of chemotype in Cannabis sativa L.), Molecular Breeding (2006) 17:257-268), and Mendoza et al., (Genetic individualization of Cannabis sativa by a short tandem repeat multiplex system, Anal Bioanal Chem (2009) 393:719-726), each of which is herein incorporated by reference in its entirety for all purposes.

In some embodiments, molecular markers are designed and made, based on the genome of the plants of the present application. In some embodiments, the molecular markers are selected from Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety for all purposes.

The molecular markers can be used in molecular marker assisted breeding. For example, the molecular markers can be utilized to monitor the transfer of the genetic material. In some embodiments, the transferred genetic material is a gene of interest, such as genes that contribute to one or more favorable agronomic phenotypes when expressed in a plant cell, a plant part, or a plant.

Details of existing cannabis plants varieties and breeding methods are described in Potter et al. (2011, World Wide Weed: Global Trends in Cannabis Cultivation and Its Control), Holland (2010, The Pot Book: A Complete Guide to Cannabis, Inner Traditions/Bear & Co, ISBN1594778981, 9781594778988), Green I (2009, The Cannabis Grow Bible: The Definitive Guide to Growing Marijuana for Recreational and Medical Use, Green Candy Press, 2009, ISBN 1931160589, 9781931160582), Green II (2005, The Cannabis Breeder's Bible: The Definitive Guide to Marijuana Genetics, Cannabis Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive Cannabis, Ronin Publishing, ISBN 091417178X, 9780914171782), Short (2004, Cultivating Exceptional Cannabis: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, Cannabis and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, R C (Cannabis: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Plant Transformation

Plants of the present invention can be further modified by introducing into the plants one or more transgenes which when expressed lead to desired phenotypes. The most common method for the introduction of new genetic material into a plant genome involves the use of living cells of the bacterial pathogen Agrobacterium tumefaciens to literally inject a piece of DNA, called transfer or T-DNA, into individual plant cells (usually following wounding of the tissue) where it is targeted to the plant nucleus for chromosomal integration. There are numerous patents governing Agrobacterium mediated transformation and particular DNA delivery plasmids designed specifically for use with Agrobacterium—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. Agrobacterium-mediated plant transformation involves as a first step the placement of DNA fragments cloned on plasmids into living Agrobacterium cells, which are then subsequently used for transformation into individual plant cells. Agrobacterium-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet.* 79: 625-631 (1990), U.S. Pat. Nos. 4,795,855, 5,378,824 and 6,107,549). In addition, the dhfr gene, which confers resistance to the anticancer agent methotrexate, has been used for selection (Bourouis et al., *EMBO J.* 2(7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety. Other references teaching the transformation of *cannabis* plants and the production of callus tissue include Raharjo et al 2006, "Callus Induction and Phytochemical Characterization of *Cannabis sativa* Cell Suspension Cultures", Indo. J. Chem 6 (1) 70-74; and "The biotechnology of *Cannabis sativa*" by Sam R. Zwenger, electronically published April, 2009.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General transformation methods, and specific methods for transforming certain plant species (e.g., maize) are described in U.S. Pat. Nos. 4,940,838, 5,464,763, 5,149,645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated herein by reference in its entirety for all purposes.

Non-limiting examples of methods for transforming *cannabis* plants and *cannabis* tissue culture methods are described in Zweger (The Biotechnology of *Cannabis sativa*, April 2009); MacKinnon (Genetic transformation of *Cannabis sativa* Linn: a multi purpose fiber crop, doctoral thesis, University of Dundee, Scotland, 2003), MacKinnon et al. (Progress towards transformation of fiber hemp, Scottish Crop Research, 2000), and US 20120311744, each of which is herein incorporated by reference in its entirety for all purposes. The transformation can be physical, chemical and/or biological.

Breeding Methods

Classical breeding methods can be included in the present invention to introduce one or more recombinant expression cassettes of the present invention into other plant varieties, or other close-related species that are compatible to be crossed with the transgenic plant of the present invention.

In some embodiments, said method comprises (i) crossing any one of the plants of the present invention comprising the expression cassette as a donor to a recipient plant line to create a F1 population; (ii) selecting offspring that have expression cassette. Optionally, the offspring can be further selected by testing the expression of the gene of interest.

In some embodiments, complete chromosomes of the donor plant are transferred. For example, the transgenic plant with the expression cassette can serve as a male or female parent in a cross pollination to produce offspring plants, wherein by receiving the transgene from the donor plant, the offspring plants have the expression cassette.

In a method for producing plants having the expression cassette, protoplast fusion can also be used for the transfer of the transgene from a donor plant to a recipient plant. Protoplast fusion is an induced or spontaneous union, such as a somatic hybridization, between two or more protoplasts (cells in which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits. More specifically, a first protoplast can be obtained from a plant having the expression cassette. A second protoplast can be obtained from a second plant line, optionally from another plant species or variety, preferably from the same plant species or variety, that comprises commercially desirable characteristics, such as, but not limited to disease resistance, insect resistance, valuable grain characteristics (e.g., increased seed weight and/or seed size) etc. The protoplasts are then fused using traditional protoplast fusion procedures, which are known in the art to produce the cross.

Alternatively, embryo rescue may be employed in the transfer of the expression cassette from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, In vitro culture of higher plants, Springer, ISBN 079235267x, 9780792352679, which is incorporated herein by reference in its entirety).

In some embodiments, the recipient plant is an elite line having one or more certain desired traits. Examples of desired traits include but are not limited to those that result in increased biomass production, production of specific chemicals, increased seed production, improved plant material quality, increased seed oil content, etc. Additional examples of desired traits includes pest resistance, vigor, development time (time to harvest), enhanced nutrient content, novel growth patterns, flavors or colors, salt, heat, drought and cold tolerance, and the like. Desired traits also include selectable marker genes (e.g., genes encoding herbicide or antibiotic resistance used only to facilitate detection or selection of transformed cells), hormone biosynthesis genes leading to the production of a plant hormone (e.g., auxins, gibberellins, cytokinins, abscisic acid and ethylene that are used only for selection), or reporter genes (e.g. luciferase, β-glucuronidase, chloramphenicol acetyl transferase (CAT, etc.). The recipient plant can also be a plant with preferred chemical compositions, e.g., compositions preferred for medical use or industrial applications.

Classical breeding methods can be used to produce new varieties of *cannabis* according to the present invention. Newly developed F1 hybrids can be reproduced via asexual reproduction.

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagatable by random-mating within itself in isolation. Second, the synthetic variety attains the same end result as population improvement but is not itself propagatable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative*

*Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The numbers of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties. A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

This invention is further illustrated by the following examples which should not be construed as limiting. The contents of all references, patents and published patent applications cited throughout this application, as well as the Figures and the Sequence Listing, are incorporated herein by reference.

Specialty *Cannabis*

The present invention is based in part on the discovery new specialty *cannabis* varieties with unique terpene and cannabinoid profiles can be bred to produce *cannabis* with reduced THC side effects and increased medicinal uses.

Contemporary "recreational" marijuana cultivars that are currently available have been bred and selected primarily for their THC content, without much regard for their terpenoid aroma and flavor chemistry, or for their for their production of the other cannabinoids (CBs), such as CBD, THCV, CBC, CBG, etc. Indeed, almost 99% of *cannabis* sold by dispensaries in California for medical purposes contains less than 1% non-THC CBs. (personal communication with SC Laboratories and Halent Laboratory, 2013).

While THC has considerable medicinal value, it can be responsible for a range of poorly tolerated side effects including anxiety, dizziness, tachycardia, asthenia, etc. It has recently been discovered that administration of CBD reduces or ameliorates some undesirable effects of THC including intoxication, sedation and tachycardia, while contributing analgesic, anti-emetic, and anti-carcinogenic properties (Russo and Guy, 2006, Medical Hypotheses (2006) 66, 234-246). Evidence has also emerged that CBD may contribute anti-anxiety effects to *cannabis* varieties with THC. See "Cannabidiol, a Cannabis sativa constituent, as an anxiolytic drug." (Rev Bras Psiquiatr. 2012; 34(Sup11):S104-S117) Also evidence has emerged that CBD can ameliorate the memory impairment caused by THC. See Morgan, Celia J A, et al. "Impact of cannabidiol on the acute memory and psychotomimetic effects of smoked *cannabis*: naturalistic study." *The British Journal of Psychiatry* 197.4 (2010): 285-290. Other non-THC cannabinoids (CBs) have also been demonstrated to have extensive medicinal uses (Table 1).

THC is produced primarily by narrow and broad-leafleted drug *cannabis* varieties. CBD is produced primarily by narrow and broad leafleted fiber *cannabis* varieties, commonly known as hemp. Other non-THC CBs such as THCv and CBDv can also be found in natural varieties (Meijer and Hammond 2005, Euphytica 145:189-198). CBC production is associated with juvenile *cannabis* and some natural varieties found in India (Meijer and Hammond 2009, Euphytica 165:293-311).

Interbreeding drug and other natural varieties of *cannabis* can produce cultivars that produce both THC and other CBs, in amounts that far exceed landrace *cannabis* drug or fiber varieties (See Clarke, R C et al. "*Cannabis*: Evolution and Ethnobotany" University of California Press 2013). Unfortunately, such crosses have been rare, and have only produced *cannabis* varieties lacking the terpenoid constituents responsible for the appealing aroma and flavor. Moreover, such varieties, also lack the synergistic entourage effects of diverse terpene-cannabinoid combinations (2011, Taming THC:

potential *cannabis* synergy and phytocannabinoid-terpenoid entourage effects, *British Journal of Pharmacology*, 163: 1344-1364, Table 2).

Similar problems have been identified with oral administrations of *cannabis* extracts such as Marinol® (dronabinol), and Sativex®, which have higher side effects, and lower consumer acceptance, partially due to the lack of terpene entourage effects and lack of positive aroma/flavors (see Hazenkamp et al 2013, "The Medicinal Use of *Cannabis* and Cannabinoids—An international Cross-Sectional Survey on Administration forms" Journal of Psychoactive drugs 45 (3) 199-210; McPartland and Russo 2001 "*Cannabis* and *Cannabis* Extracts: Greater Than the Sum of Their Parts?" Hayworth Press).

For example, all known varieties of chemotype II *cannabis* ($B_T/B_D$ genotype) exhibit terpene profiles dominated by myrcene. That is, these *cannabis* varieties produce myrcene at higher levels than any other terpene. As such, these varieties do not exhibit diverse terpene profiles and lack the varied aroma, organoleptic feel of the specialty *cannabis* of the present invention. The aroma and flavors for myrcene dominant varieties tend to be "single tone", with the high myrcene levels dominating the flavor and aroma profile. Moreover, as myrcene is associated with the *cannabis* "couch lock" effect, these varieties have produce less functional highs, with higher sedation.

The present invention provides specialty *cannabis* plants with THC and CBs, and desirable terpene profiles. In some embodiments, the CBs (e.g. CBD, or CBDv) level in dried *cannabis* plants of the present invention is higher compared to that of a dried recreational *cannabis* plants, such as the strain 'White Widow.' In some embodiments, the THC level in the dried *cannabis* plants of the present invention is lower compared to that of a dried recreational *cannabis* plants, such as the strain 'White Widow.' In some embodiments the specialty *cannabis* of the present invention is a chemotype II plant. In some embodiments, the specialty *cannabis* of the present invention produces more than 1.5% of any one CBs. In some embodiments, the specialty *cannabis* plants of the present invention also have terpene profiles that are not dominated by myrcene. In some embodiments, the specialty *cannabis* of the present invention have higher terpene oil contents which overcome high myrcene profiles.

In some embodiments, the specialty *cannabis* varieties of the present invention have been bred to produce high terpene oil contents. In currently available *cannabis* cultivars, increased terpene oil content is largely driven by increased myrcene content, which can increase the "couch-lock" effect and overshadow the effects of the other terpenes. In contrast to current practice, the breeding programs of the present invention were designed to produce specialty *cannabis* varieties with higher terpene oil content with terpene profiles in which myrcene has a relative terpene content of less than two-thirds of the terpene profile. In other embodiments, the breeding programs of the present invention were designed to produce high terpene oil cultivars in which myrcene was not the dominant terpene.

EXAMPLES

Example 1

Chemical Analysis of Cannabinoids and Terpenes

Chemical analyses of the parental and progeny specialty *cannabis* varieties of the present invention was carried out using standard chemical separation techniques well known to those skilled in the arts. Qualitative identification of cannabinoids and terpenes was carried out by GCMS, while quantitative analysis was done by GC-FID and/or HPLC-PDA (Photo Diode Array). Initial field analyses of cannabinoids was performed using thin layer chromatography as described in ("*Cannabis* Inflorescence & Leaf QC" from The American Herbal Pharmacopeia 2013). The in-house assays for cannabinoids included orthogonal methods of GC-FID and HPLC for the highest level of accuracy.

Samples were prepared by grinding ~5 g of dried *cannabis* flower material in a coffee grinder. From this homogenized material, 500±20 mg was placed in a bead beater vial with ~1 g of 2 mm beads and 5 mL of working solution. Each sample was placed in the bead beater (BioSpec Products Inc.) and homogenized on high for 3 minutes. The vials were centrifuged at 1350 xg, decanted into 50 mL falcon tubes, and the process was repeated with fresh working solution. After the second extraction the caps were removed, the vials were decanted into the appropriate falcon tubes, and the vials were rinsed into the falcon tubes with an additional 5 mL of working solution. For samples suspected of having lower concentrations of analytes (i.e. <10% THC or total terpene content ~0.5%), 3 mL portions of working solution could be employed. Approximately 2 mL of the extracts were placed in 2 mL centrifuge tubes, and the vials were centrifuged at 9500 xg for 5 minutes. The supernatant was placed in a GC vial for terpene analysis without dilution. The supernatant was also diluted with working solution for GC and HPLC analysis. A 1:40 dilution provided the appropriate concentration for analysis of cannabinoids present at concentrations above 1.5%, while a 1:3 dilution allowed for analysis of cannabinoids below this level.

i. Terpenoids by Gas Chromatography-Flame Ionization Detector (GC-FID)

Terpenes were quantified by a method developed on a GC-FID instrument from Perkin Elmer (Waltham, Mass.). This method separates and quantifies 17 different terpenoids commonly found in *cannabis* plant tissue. The terpenoids are each quantified by their own individual calibration curves generated with analytical reference standards (Sigma Aldrich) and all use n-nonane as the internal standard.

The instrumentation includes a Clarus 680 gas chromatograph (GC) equipped with an autosampler, an Elite-5 column (Perkin Elmer (Waltham, Mass.), 30 m length, 0.25 mm internal diameter, 0.25 μm thickness film diameter) and a flame ionization detector (FID). Instrument control and data acquisition and analyses was accomplished by TotalChrom software version 1.2.3.4 (Perkin Elmer, Waltham, Mass.).

Calibration curves were generated by injecting each standard in triplicate and the RSDs provided the measure of precision while the absolute accuracy was determined by comparing the concentrations of the standards predicted by the calibration curve to their "known" values determined by dilution ratios. AOAC International standards for accuracy and precision were used as quality guidelines for every calibration. Check standards were run at the start, middle, and end of every analysis, and recalibration was performed when they varied more than +/−5% of their initial average response. Levels that failed the acceptance criteria and analytes were not quantified at those levels until recalibration of the instrument corrected the deficiency. Most of the curves were linear to nearly two orders of magnitude and based on the sample mass extracted (500 mg) and the two possible extraction volumes (3×3 mL or 3×5 mL), this provided quantitation of terpene levels from 0.01-0.9% or 0.02-1.5% (typical) in the plant matrix.

ii. Cannabinoids by GC-FID

Cannabinoids were quantified by an analytical method developed and run on a Perkin Elmer (Waltham, Mass.) GC-FID instrument also. This method was developed to separate six neutral cannabinoids, CBD, CBG, CBN, THC, Δ8-THC, and CBC. The cannabinoids are each quantified by their own individual calibration curves generated with analytical reference standards (Restek) and all use tricosane as the internal standard. The retention time of THCV was determined by analyzing THV01 (vide infra) by GCMS, however since analytical standards were not available it was "quantified" by referencing the calibration curve for THC.

There was no need to consider chromatographic separation of acidic forms of the cannabinoids due to their immediate conversion to neutral form in the heated injector of the instrument, although a thorough study of the conversion efficiency of THCA was performed and is discussed in section iv. (orthogonal analyses of all samples).

The instrumentation includes a Clarus 680 gas chromatograph (GC) equipped with an autosampler, an Elite-1 column (Perkin Elmer (Waltham, Mass.), 30 m length, 0.25 mm internal diameter, 0.25 μm thickness film diameter) and a flame ionization detector (FID). Instrument control and data acquisition and analyses was accomplished by TotalChrom software version 1.2.3.4 (Perkin Elmer, Waltham, Mass.).

Calibration curves were generated by injecting each standard in triplicate and the RSDs provided the measure of precision while the absolute accuracy was determined by comparing the concentrations of the standards predicted by the calibration curve to their "known" values determined by dilution ratios. AOAC International standards for accuracy and precision were used as quality guidelines for every calibration. Check standards were run at the start, middle, and end of every analysis, and recalibration was performed when they varied more than +/−5% of their initial average response. Levels that failed the acceptance criteria and analytes were not quantified at those levels until recalibration of the instrument corrected the deficiency. Due to the very linear nature of the FID detector, the GC-FID cannabinoid assay generally provided satisfactory results over nearly two orders of magnitude (up to 1.0 mg/mL), however in order to use the same calibration solutions and "validation" procedures for both GC and HPLC the range was reduced to that of the HPLC method. Based on the sample mass extracted (500 mg) and a 3×3 mL extraction (low oil samples), a 1:3 dilution provided quantitation of cannabinoid levels from 0.09-1.35% and the 1:40 dilution from 1.15-18% in the plant matrix. A 3×5 mL extraction (high oil samples, typical), a 1:3 dilution provided quantitation of cannabinoid levels from 0.14-2.25% and the 1:40 dilution from 1.9-30% in the plant matrix.

iii. Cannabinoids by High Performance Liquid Chromatography—Photo Diode Array Detector (HPLC-PDA)

An HPLC-PDA (also known as HPLC-DAD, or simply HPLC) assay was developed as an orthogonal method to GC-FID for cannabinoid analyses. This method quantifies six neutral cannabinoids (CBD, CBG, CBN, THC, Δ8-THC, and CBC) as well as THCA based on calibration curves generated with analytical standards and an internal reference standard (ibuprofen). The only acidic cannabinoid that is readily available as an analytical standard in the United States is THCA, so levels of CBDA, CBGA, and THCVA are estimated by reference to THCA calibration.

All HPLC analyses were performed using a Perkin Elmer (Waltham, Mass.) HPLC system comprised of a Flexar FX-15 binary pump, a Flexar 5-CH solvent manager, an FX UHPLC autosampler, and a Peltier LC column oven. UV data was collected at 228 nm and 280 nm with a Flexar FX-PDA UHPLC detector. Chromatography was performed on a Brownlee SPP C18 column (PKI N9308411, 2.7 μm, 3.0×150 mm), protected by a Brownlee SPP C18 guard column (2.7 μm, 2.1×5 mm). HPLC system control, data acquisition and analyses were performed with Chromera software version 3.4.1.5904.

Calibration was achieved by performing a five-point calibration curve (0.016-0.25 mg/mL for each analyte) followed by linear regression analysis. This analysis was performed with Microsoft Excel (Redmond, Wash.) software. The calibration curves were generated by injecting each standard in triplicate and the RSDs provided the measure of precision while the absolute accuracy was determined by comparing the concentrations of the standards predicted by the calibration curve to their "known" values determined by dilution ratios. AOAC International standards for accuracy and precision were used as quality guidelines for every calibration. Check standards were run at the start, middle, and end of every analysis, and recalibration was performed when they varied more than +/−5% of their initial average response.

iv. Orthogonal Analyses of all Samples

The cannabinoid content was quantified by both GC-FID and HPLC. The main difference between GC and HPLC is that GC involves thermal stress and mainly resolves analytes by boiling points while HPLC does not involve heat and mainly resolves analytes by polarity. There are several reasons that this orthogonal approach to analyses is desirable for highly accurate and reproducible results in determining chemotype. The first reason is related to the difference between the cannabinoids produced naturally by the plant (the acidic cannabinoids) and those that are bioactive (the neutral cannabinoids). *Cannabis* biosynthesizes all the cannabinoids in their relatively unstable acidic forms, and these forms are generally not bioactive in the traditional sense. The application of heat (flame, vaporizer, oven, etc) causes a loss of the carboxylic acid group and generates the neutral forms of the cannabinoids, which are generally the bioactive forms that are sought after, however this process is highly variable and not quantitative. If one wants to know the native phytochemical profile of the plant then HPLC should be used since this assay does not involve heat. If one wants to know the possible available amount of bioactive cannabinoids, then GC should be used since conversion to these forms in the injector of the GC is an inherent part of the analytical method.

The second reason is also related to the difference between the acidic and neutral cannabinoids, but has to do with the availability of analytical standards to calibrate the instruments. While all of the neutral cannabinoids (THC, CBG, CBC, CBD, and CBN) are available as analytical standards, THCA is the only acidic cannabinoid available as an analytical standard and the instruments were only calibrated for quantification using actual analytical standards. Technically the HPLC assay could characterize the naturally occurring chemotypes, but the acidic analytes are not available as standards, so this quantification is approximate and considered for information only. The acidic analytes are all quantified by reference to the calibration curve for THCA, and this is not an unreasonable assumption as many of them have approximately the same spectral properties. The GC assay is calibrated with analytical standards, but these are the neutral cannabinoids and their formation from the naturally occurring acidic cannabinoids in the GC injector is not quantitative, which complicates exact characterization of the naturally occurring chemotype.

The final reason is simply to have an internal crosscheck of our results by using orthogonal testing methods. Each type of assay (GC and HPLC) has its strengths and weaknesses, and by using both methods one can compare results and ensure that both the identification and quantitation of the components are accurate. A caveat to this, as mentioned above, is that the conversion of the acidic forms to the neutral forms is not quantitative due to thermal degradation. Under the highly optimized conditions of a GC injector we have found conversion can vary between 75-85% (for analytical THCA standards), while *cannabis* samples generally have a conversion of 70-80%. Similar conversion rates are also described in literature for highly optimized analytical instruments (Dussy et al. 2004). Because of this incomplete conversion our GC results are consistently 20-30% lower than the HPLC results for *cannabis* samples. This same conversion efficiency can be applied to estimate the maximum availability of THC based on THCA content when smoking or vaporizing *cannabis*.

v. Method "Validation"

In order to demonstrate the performance of a method of analysis, a systematic process known and method validation can be carried out. This process demonstrates the method is fit for its intended purpose and is necessary for the confident use of that method, providing assurance that the results that are reported are precise, accurate, and reflective of the sample. Very few labs in the *cannabis* industry attempt to validate their assays and this fact, combined with inappropriate sampling have resulted in erroneous data for several varieties. In order to validate the analytical methods employed for this project, an abbreviated protocol similar to Single Laboratory Validation (SLV) was carried out. Assay "validation" was carried out by spiking blank matrix with the analytes at low, med, and high concentrations and carrying out the assay procedure in replicate (n=5). While some analytes provided better results than others the analyte RSDs, recoveries, and precisions at these concentrations satisfied AOAC guidance (based on mg/mL). In general the RSDs for the terpenes at the low, medium, and high concentrations (varied by terpene but generally 0.016, 0.125, and 1.0 mg/mL) were less than 5%, 4%, and 3% respectively. The absolute bias for these analytes was generally less than 10%, 4%, and 2%. In general the RSDs for the cannabinoids by both GC and HPLC at the low, medium, and high concentrations (0.016, 0.61, and 0.250 mg/mL) were less than 2%, 2%, and 1% respectively. The absolute bias for these analytes was generally less than 10%, 2%, and 2%. The assays all provided satisfactory S/N ratios at the lowest level and this was initially taken as the LOQ. After subsequent re-calibrations (n=3 at each level), the LOQ was taken as the lowest level of the calibration curve that provided acceptable accuracy (<10% error) determined by comparing the known concentration levels (determined by dilution ratios) to the predicted levels (obtained from the signal and calibration curve). The error between the known and measured values establishes the accuracy of the method and verifies that real samples do not present any matrix effects that influence the resulting measurements. The precision, or closeness of individual measurements, of the method is also determined by carrying out all analyses in replicate (n=5). Guidance for acceptable values was taken from publications provided by the AOAC.

The in-house validation revealed that the above-described chemical analysis methods were accurate and reliable, and the use of orthogonal methods of analyses provided an internal check on the assays as well as an understanding of the use of GC to analyze thermally unstable molecules. Using multiple dilution ratios kept samples in the linear ranges of the assays, and method validation verified that precise and accurate results were obtained.

Example 2

Proprietary Parental Variety Phenotypes

More detailed descriptions of the development and characteristics of representative Parental Classes of *Cannabis* Varieties of the present invention are provided below. In some embodiments, the THC parental varieties of the present invention were selected for their morphologies and desirable phenotypes.

GOD13

Description of Breeding Stock. Inflorescences were obtained for a land race of Gold class varieties and seeds from these inflorescences were isolated and put into conditions proper for their germination. The seeds which germinated grew identically. However, upon flower onset, the seedlings were selected for the strongest limonene/Pine-Sol fragrance and narrowed to two phenotypes. Of these, the individual phenotype with the best user experience based on testing was selected to create GO13, a variety classified into the Gold Class.

Hypothesized Genetics. *Cannabis indica* ssp. *afghanica* WLD "Purple Afghan"×*C. indica* ssp. *indica* var. *indochinensis* NLD "Lemon Thai"×*C. indica* ssp. *kafiristanica* NLDA.

Propagation and Vegetative Growth. Cuttings from GO13 are marked by 3-finger leaflet sets with internode buds asymmetrically located on alternate sides on main shoot. In particular, the internode space of this variety tends to be greater than that of other gold class varieties and stems harden quicker. Roots nodes appear with 7-10 days and roots within 10-14 days. The GOD13 grows extremely tall and thin with extreme stretching and asymmetrical bud and leaf sets. When root system is not limited or pruned, this variety of gold class varieties exhibits unparalleled vigor and stretch. Vegetative growth is marked by a deep blue-green (Munsell ID) hue with lime green thin stalks. Petioles are marked by purple pointillism increasing on sides exposed to light and the end closest to palm of the leaflet set. Root bodies are typically full and bright white. Stalks radiate a pungent smell of body odor or urine. Canopy extremely sparse and apical dominance can be disrupted easily with removal of apical meristem. Main stems also exhibit purpling, but inflorescences are not purple.

Onset of Flowering and Inflorescences. Leaves are 3 and 5 leaflet patterns with 3 being predominant and overall decreasing to 1 and to none in the presence of female flowers.

Female flowers are spread out due to the large internode spacing. Upon flower set, buds and supporting structures (stems, leaves, etc.) are quickly covered with an extremely dense field of trichome bodies. Again, this variety tends to be more densely covered with trichome bodies than its parent and other gold class varieties. In fact, the inflorescences are very dense and have large calyxes covered in highly resinous glands that exhibit this variety's distinct lemon Pine-Sol scent after only 7-10 days. As inflorescences mature, the density compact sets give way to foxtailing and 'reaching' by individual calyxes, resulting in an overall increase in surface area dedicated to trichome production. In particular, the oily character of these flowers set this gold class apart from its parent and other gold class varieties. Textures are extremely sticky and fibrous. Stems do not 'break' they tear, but remain attached via intense fiber strands.

Description of Finished Flower. GO13 consistently produces among the highest THCA levels of *cannabis* known in California and is often noted for an intense and crushing physical effect combined with a sublime and inspiring mental flight. Aromas of lemon peel, fuel and Pine-Sol combine to produce a pure menthol exhalation when smoked. Noted for excellent appetite and sexual stimulation often accompanied by uninterrupted sleep.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days). Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying.

Yield Data. Yield determined on a 'per plant' basis and determined by specified cultivation techniques employed. In this case, indoor Controlled Environment Agriculture (CEA) technique following the protocol described elsewhere herein. Flower onset was initiated with 12/12 day/night at approximately 12" in vegetative height. Total biomass ~150 g, finished flowers ~50 g, and/or ~50 g of seed per plant.

Potential Uses of this Line. Potential uses of GO13 include but are not limited to medical applications, as a source for extractions of plant constituents and chemicals, for commercial raw materials, fiber and pulp.

Patient Testimonials/Comments and Visual Observations. Patients rave about the flavor and 'oily' composition by comparison to other Gold class varieties. In fact, besides the extremely high potency from its combined cannabinoid/terpenoid 'entourage effects", this line of gold class has been noted by patients for being particularly effective for sexual and appetite stimulation.

Palatable CBDA varieties with ideal CBDA:THCA ratio can be developed from GO13 to reduce side-effects associated with extant recreational *cannabis* varieties related to GO13. Additionally reduced THCA varieties can be developed that are intended to reduce side-effects from extant recreational *cannabis* varieties related to GO13.

Flavor when smoked includes distinct citrus and mentholated notes. Significant analgesia accompanies its deep range of effects, but with little sedation, but the "rising/falling" physical sensations associated with gold class. Some patients have compared its flavor to bergamot orange. Patients also remark on the "clarity" of this variety's psychoactivity, with less sedation and disorientation, and with considerable euphoria.

Its aroma has been characterized as a tangy, sharp, naphthalene aroma with orange notes and a sweet undertone. Also the range of pharmacologically active terpenoids that this variety produces provide a significant "entourage effect" that accompanies the effects of its THC content. While it stimulates appetite, it does not appear to encourage overeating.

BRO5
Description of Breeding Stock. Inflorescences were obtained for a landrace of Haze and seeds from these inflorescences were isolated and put into conditions proper for their germination.

The seeds which germinated grew identically, being short and squatty with purple leaves and 'sweet' scent, with one exception which was tall and stretchy with a savory and musty scent. There was absolutely no sweetness in the smell of BRO5. Testing proved that its effects were the most enjoyable and virtually myrcene free. The lack of myrcene and presence of pinene and limonene is quite rare and sets this variety apart from most *cannabis* varieties.

Upon flower onset, the seedlings were selected for being short and squatty with purple leaves and 'berry' scent to create BRO5, a variety classified into the Gold Class.

Hypothesized Genetics. "NL#5×Haze ×inbred Thai"

Propagation and Vegetative Growth. Cuttings from BRO5 are marked by 9-finger very thin leaflet sets with internode buds asymmetrically located on alternate sides on main shoot. In particular, the internode space of this variety tends to be extremely large. Stems are tall, frail and stretchy. Cuttings roots appear within 10-14 days. The BRO5 grows tall and stretchy with flimsy stems. It possesses the classic narrow-leafleted morphology associated with 1970's Haze cultivars that were inherited from Haze's tropical drug *cannabis* parents, including Colombian and That varieties.

BRO5 grows with asymmetrical bud and leaf sets. Vegetative growth is marked by a lightened green (Munsell ID) hue with lime green thin stalks. Leaflets are longer and narrower than most of drug *cannabis* varieties.

BRO5 displays vigorous hybrid character.

There is little or no purple on this plant until the final weeks of flowering. Leaves turn deep purple with flowers silvering up as time goes on. Stalks radiate a 'hazy' or musty urine scent. Canopy extremely sparse and topping near flowering is encouraged for even growth.

Onset of Flowering and Inflorescences. Leaves are 9 and 7 leaflet patterns with 7 being predominant and overall decreasing to 1 and to none in the presence of female flowers. In particular, flower onset is very slow with this variety. 'Hairy' flowers are not very dense. Female flowers are spread apart due to the large internode spacing.

Upon flower set, buds and supporting structures (stems, leaves, etc.) take longer than most to become covered with trichome bodies. Everything about this plant takes longer. As inflorescences mature, they become more hardened and dense. In particular, the oily character of these flowers was the driving force for selection.

Description of Finished Flower. BRO5 defines heady, hazy medicine with highly functional mental effects. This variety has the structure and scent of the BRO5 lines famous around the world. With aromas of spice and anise, the hashish flavor when smoked is enlightening.

BRO5 is noted for mood elevation, inspiration and creativity and is also likely to improve home hygiene.

Chemotype Description for Patient. Relative potency: strong. Headspace Terpenes: pinenes, limonene. Caryophyllene content: high.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield determined on a 'per plant' basis and determined by specified cultivation techniques employed. In this case, indoor CEA technique following the protocol described elsewhere herein. Flower onset was initiated with 12/12 day/night at approximately 16" in vegetative height. Organic mix of soil in fabric pots, a regimen of nutrients following standard NPK feeding schedules and addition of proprietary mixture. Flower onset was initiated with 12/12 day/night when plant reached approximately 16" in vegetative height.

Potential Uses of this Line. Potential uses of BRO5 include but are not limited to medical applications, extractions, commercial raw material (chemical), fiber and pulp.

Patient Testimonials/Comments and Visual Observations. Patients rave about the great experience of using BRO5. The effects are mind stimulating with some visual 'crispness'. The patients often comment that this variety is good for the 'new' user because of its lower THC concentration and the 'clarity' of the experience.

SIL04

Description of Breeding Stock. Inflorescences were obtained for a proprietary breeding program and seeds from these inflorescences were isolated and put into conditions proper for their germination. The seeds which germinated grew identically. The resulting plants were then crossed with GO13 plants and seeds were planted and germinated for selection based on oil content of the plants. Plants with higher oil content were selected to create SIL04.

Hypothesized Genetics. "*Cannabis indica* ssp. *afghanica* WLD "SB Purple" ×*C. indica* ssp. *indica* NLD ×*C. indica* ssp. *kafiristanica* NLDA"

Propagation and Vegetative Growth.

Cuttings from SIL04 are marked by 5-finger leaflet sets with internode buds asymmetrically located on alternate sides on main shoot. In particular, the internode space of this variety tends to be longer and stalks thinner (~4-8" veg, decreasing flower onset). Plants are tall, stretchy and productive. Roots of the cuttings appear within 10-14 days.

The SIL04 grows tall and stretchy and exhibits little or no apical dominance. SIL04 grows with asymmetrical bud and leaf sets. Vegetative growth is marked by a lavish green (Munsell ID) hue with green undersides and hard wood like stalks. When healthy, fan leaves are extremely jagged and serrations are very pronounced.

The stems are strong and fibrous, but extremely thin. The standout quality of SIL04 is the amount of trichomes and their density. The flower sets look 'frosty' before most other varieties.

Stalks are vanilla spice scent.

Canopy is extremely sparse with clustered bud formation. Topping extremely encouraged.

Onset of Flowering and Inflorescences. Leaves are 5 leaflet patterns with 5 being predominant and overall decreasing to 1 and to none in the presence of female flowers. In particular, flower onset is fast by comparison to most varieties.

Trichome density and smell are almost immediate. Female flowers are spear-shaped, dense and thick although relatively large internode lengths. Again, this variety tends to be more densely covered with trichome bodies than most other varieties.

The flowers are compact and well-formed in the shape of small pinecones. As inflorescences mature, the density compact sets compound to form bright orange and silver flowers that give way to yellow and purple sun leaves.

Plants are marked by unusually high oil mass content and extremely dense small resinous buds.

Apical inflorescences are often smaller than lowers. Inflorescences particularly are resistant to fungal infestation due to compact oil flowers.

Description of Finished Flower. SIL04 (a.k.a., internally known as 'Heiress' or "Oily Heiress) was bred from a dream team of *cannabis* genetics: Northern Lights×Haze, Santa Barbara Purps, a Midwest G-13 and the aforementioned GO13. The chemotype of this variety is indicative of this diverse genetic heritage. The aroma consists of vanilla, grapefruit, and even has petroleum notes, but a rich creamy vanilla flavor emerges when smoked. Noted for its rare combination of clarity and profound potency, it delivers functional and long lasting inspiration and positivity.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that one is actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis and determined by specified cultivation techniques employed. In this case, indoor CEA technique following the protocol described elsewhere herein. Flower onset was initiated with 12/12 day/night at approximately 16" in vegetative height. Total biomass ~120 g, finished flowers ~40 g, and/or ~30 g of seed per plant.

Potential Uses of this Line. Potential uses of SIL04 include but are not limited to medical applications, extractions, commercial raw material (e.g., chemical), fiber and pulp.

Patient Testimonials/Comments and Visual Observations. Very interesting from an organoleptic standpoint (sweet Amsterdam flavor) and a caryophyllene content standpoint. SIL04 produces a happy laughing high, with the classic combusted aroma of 1990's landrace varieties of the same *cannabis* class.

WHI04

Description of Breeding Stock. Inflorescences were obtained for a landrace of WHI04 and seeds from these inflorescences were isolated and put into conditions proper for their germination. The seeds which germinated grew fairly similarly. However, upon flower onset, the seedlings were selected for trichome density, leaflet width and root vigor to create WHI04.

Hypothesized Genetics. "*Cannabis indica* ssp. *afghanica* WLD"

Propagation and Vegetative Growth. Cuttings from WHI04 are marked by 7-finger leaflet sets with internode buds asymmetrically located on alternate sides on main shoot. In particular, the internode space of this variety tends to be greater than that of other Silver varieties and stems harden more slowly. In particular, the cutting roots more rapidly than other Silver varieties. In fact, the root bodies of the plant are the most robust and vigorous of all *cannabis* plants tested in our laboratory. Root time varies with nodes appearing within 7-10 days and roots within 10-14 days.

The WHI04 grows medium in stature with stocky branches and stalks. Even growth throughout with asymmetrical bud and leaf sets. Vegetative growth is marked by a deep blue-green (Munsell ID) hue with lime green thin stalks. Leaflets are fat and exhibit classic recreational 'indica' look. These broad leaflets are indicative of this variety. Petioles are marked by purple pointillism increasing on sides exposed to light and the end closest to palm of the leaflet set. Root bodies are typically full and bright white. Stalks radiate a pungent smell of bubble gum coffee and green class. Canopy extremely sparse and apical dominance can be clearly observed and removal of apical meristem often results in stunted growth. Main stems may also exhibit purpling, and inflorescences sets are large, but spread out.

Onset of Flowering and Inflorescences. Leaves are 7 and 5 leaflet patterns with 3 being predominant and overall decreasing to 1 and to none in the presence of female flowers. Female flowers are spread out due to the large internode spacing.

Upon flower set, buds and supporting structures (stems, leaves, etc.) are quickly covered with an extremely dense field of trichome bodies. Again, this variety tends to be more densely covered with trichome bodies than its parent and other Silver varieties. In fact, the inflorescences are very dense and have large calyxes covered in highly resinous glands that exhibit this variety's distinct lemon Pine-Sol scent after only 7-10 days.

As inflorescences mature, the dense and compact calyx clusters or flower sets give way to foxtailing and 'reaching' by individual calyxes, resulting in an overall increase in surface area dedicated to trichome production. In particular, the oily character of these flowers set WHI04 apart from its parent and other Silver varieties. Textures are extremely sticky and fibrous. Stems do not 'break' they tear, but remain attached via intense fiber strands.

Description of Finished Flower. WHI04 has descended from the great Afghan hashish *cannabis* cultivars and is a nearly perfect choice for vaporization. The resin content delivers a range of tastes and effects with each draw.

The aroma consists of coffee, spice and exotic incense. This variety is noted for its ability to mellow without sedation or fatigue, excellent analgesic effects and deep introspection.

Chemotype Description for Patient. Relative potency: mild. Headspace Terpenes: pinenes, myrcene, limonene, linalool. Caryophyllene content: medium Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not the 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis and determined by specified cultivation techniques employed. In this case, indoor CEA technique following the protocol described elsewhere herein.

Flower onset was initiated with 12/12 day/night at approximately 12" in vegetative height. Total biomass ~120 g, finished flowers ~30 g, and/or ~15 g of seed per plant.

Potential Uses of this Line. Potential uses of WHI04 include but are not limited to medical applications, extractions, commercial raw material (e.g., chemical), fiber and pulp.

Patient Testimonials/Comments and Visual Observations. Patients rave about the coffee flavor and 'oily' and 'silver' composition of WHI04. In fact, besides the mellow effects, WHI04 is particularly noted for treating pain and inspiration.

RED08

Description of Breeding Stock. Inflorescences were obtained from a DJ Short's Flo (a.k.a. DJ's Flo) pollinated by a hermaphroditic Hawaiian plant and seeds from these inflorescences were isolated and put into conditions proper for their germination.

The seeds which germinated grew very uniformly in appearance. However, the seedlings were selected for vigorous phenotype with highest trichome density and 'oily' feel of resin glands to create RED08.

Hypothesized Genetics. "1995 Hawaiian Bag Seed ×Thai".

Propagation and Vegetative Growth. Cuttings from RED08 are marked by 7-finger leaflet sets with internode buds asymmetrically located on alternate sides on main shoot. In particular, the internode space of this variety tends to be medium-stretchy (~4" veg, decreasing flower onset). Plants are tall, robust and lanky. Cuttings root within 10-14 days.

The RED08 grows tall and stout with mixed apical dominance.

RED08 grows with asymmetrical bud and leaf sets. Vegetative growth is marked by a deeper off green (Munsell ID) hue with deep purple strong hollow stalks.

When healthy, sun leaves are gigantic with magenta and purple under side coloring. Plants have super vigor and hybrid character. RED08's stand-out quality feature is the high amount of trichomes and the high amount of oil. Stalks have a pungent 'medical' scent. Plant canopy is dense with large cola formation. Topping encouraged.

Onset of Flowering and Inflorescences. Leaves are 7 leaflet patterns with 7 being predominant and overall decreasing to 1 and to none in the presence of female flowers. In particular, flower onset is medium-fast by comparison to most varieties.

Trichome density and smell are almost immediate. Female flowers are clustered to do decreased internode spacing. Again, this variety tends to be more densely covered with trichome bodies than its parents and other varieties. In fact, the inflorescences are very dense and have large calyxes covered in highly resinous glands that exhibit this variety's distinct blueberry pine medicine/medicinal scent after only 7-10 days.

As inflorescences mature, the density compact sets compound to form bright green and extremely oily buds. In particular, the oily character of these flowers set this its parent and phenotypes.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins.

The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Potential Uses of this Line. Potential uses of RED08 include but are not limited to medical applications, extractions, commercial raw material (e.g., chemical), fiber and pulp.

Patient Testimonials/Comments and Visual Observations. RED08 is very interesting from an organoleptic standpoint and it is unique in almost all visual categories.

SIL03

Description of Breeding Stock. Inflorescences were obtained from a, and selfed seeds from these plants were germinated. The seeds which germinated grew very similarly. The resulting seedlings were selected for vigor.

Hypothesized Genetics. "*Cannabis indica* ssp. *afghanica* WLD "Cherry Afghan"×*C. indica* ssp. *indica* NLD hybrid Propagation and Vegetative Growth. Cuttings from SIL03 are marked by 7-finger leaflet sets with internode buds asymmetrically located on alternate sides on main shoot. In particular, the internode space of this variety tends to be medium-stretchy (~4" veg, decreasing flower onset). The plants are tall, robust and lanky. Cuttings root within 10-14 days.

The SIL03 grows tall and strong with little apical dominance. SIL03 grows with asymmetrical bud and leaf sets.

Vegetative growth is marked by a lighter shade of green (Munsell ID) hue with deep purple strong hollow stalks. When healthy, sun leaves are point upward toward light source.

The stems are strong and fibrous. The plants are super vigorous and hybrid in character. The stand-out quality is the high amount of trichomes and the high amount of oil. Stalks have a sweet scent. Canopy is dense with large cola formation. Topping encouraged.

Onset of Flowering and Inflorescences. Leaves are 7 leaflet patterns with 7 being predominant and overall decreasing to 1 and to none in the presence of female flowers. In particular, flower onset is medium-fast by comparison to most varieties.

Trichome density and smell are almost immediate. Female flowers are clustered to do decreased internode spacing. Again, this variety tends to be more densely covered with trichome bodies than its parents and other varieties. In fact, the inflorescences are very dense and have large calyxes covered in highly resinous glands that exhibit this variety's distinct blueberry pine medicine/medicinal scent after only 7-10 days.

As inflorescences mature, the dense and compact calyx clusters or flower sets form bright green and extremely oily buds. In particular, the oily character of these flowers set this variety apart from its parent and phenotypes.

Description of Finished Flower. SIL03 combines a beautifully sweet cherry WLD Afghan with a NLD to deliver a strong, cheerful, dreamy psychoactivity. This variety produces a pleasant silliness and a 'where'd I put my keys!?' memory effect and obliterates most patient troubles.

Aroma consists of cherry cough drops, fresh strawberries and just a hint of spice. SIL03 is often noted for long-lasting effects and positive mood impact.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis and determined by specified cultivation techniques employed. In this case, indoor CEA technique following the protocol described elsewhere herein. Flower onset was initiated with 12/12 day/night at approximately 16" in vegetative height. Total biomass ~180 g, finished flowers ~60 g, and/or ~50 g of seed per plant.

Potential Uses of this Line. Potential uses of SIL03 include but are not limited to medical applications, extractions, commercial raw material (e.g., chemical), fiber and pulp.

Patient Testimonials/Comments and Visual Observations. Noted as being very interesting from an organoleptic standpoint. SIL03 is unique in almost all visual categories.

GRE01

Description of Breeding Stock. Inflorescences were obtained and isolated and put into conditions proper for their germination.

The seeds which germinated grew identically. However, the seedlings were selected for the phenotype that is more densely covered in trichomes, where the oil content of the gland heads was higher than other phenotypes of this variety.

Hypothesized Genetics. "*Cannabis indica* ssp. *afghanica* WLD "Afghan #1"×*C. indica* ssp. *indica* NLD hybrid Propagation and Vegetative Growth. Cuttings from GRE01 are marked by 9-finger very thin leaflet sets with internode buds asymmetrically located on alternate sides on main shoot. In particular, the internode space of this variety tends to be extremely large. Plants are tall, frail and stretchy. Cuttings root appears within 10-14 days.

GRE01 grows tall and stretchy with flimsy stems and embodies what it means to be a true hybrid.

GRE01 grows with asymmetrical bud and leaf sets. Vegetative growth is marked by a lush green (Munsell ID) hue with lime green thin stalks.

Leaflets are longer and thinner than varieties. Plants have a vigorous hybrid character. GRE01 has little or no purple color on the plant. The stand-out quality is the high amount of trichomes and the high amount of oil. Plant stalks have a sweet citrus 'creamsicle' scent.

Plant canopy is dense and even topping near flowering is encouraged for even growth.

Onset of Flowering and Inflorescences. Leaves are 9 and 7 leaflet patterns with 7 being predominant and overall decreasing to 1 and to none in the presence of female flowers. In particular, flower onset is fast by comparison to most varieties.

Trichome density and smell are almost immediate. Female flowers are clustered to do decreased internode spacing. Again, this variety tends to be more densely covered with trichome bodies than its parent and other green class varieties. In fact, the inflorescences are very dense and have large calyxes covered in highly resinous glands that exhibit this variety's distinct green class creamsicle scent after only 7-10 days. As inflorescences mature, the density compact sets compound to form orange and bright green extremely oily buds. In particular, the oily character of these flowers set this green class apart from its parent and other green class varieties.

Description of Finished Flower. GRE01 defines sweet, delicious medicine/medicinal with functional mental effects. This variety has resin production akin to Afghan and psychoactivity reminiscent of original Green class.

GRE01 has aromas of citrus, brown sugar, and banana nut bread combine to produce a fantastic fruity hashish flavor when smoked. It is noted for mood elevation and daytime bursts of energy that provide for short-term pain relief.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis and determined by specified cultivation techniques employed. In this case, indoor CEA technique following the protocol described elsewhere herein.

Flower onset was initiated with 12/12 day/night at approximately 16" in vegetative height. Total biomass ~160 g, finished flowers ~50 g, and/or ~50 g of seed per plant.

Potential Uses of this Line. Potential uses of GRE01 include but are not limited to medical applications, extractions, commercial raw material (e.g., chemical), fiber and pulp.

Patient Testimonials/Comments and Visual Observations. Patients rave about the great experience of using this plant. The flowers of GRE01 consistently produce approximately 2.0% CBGA in finished flowers. Its wonderful smell/taste is patient's major reason for appeal.

PUR03

Description of Breeding Stock. Inflorescences were obtained for a landrace of purple class pollinated with a hermaphroditic purple class variety and seeds from these inflorescences were isolated and put into conditions proper for their germination.

The seeds which germinated grew very uniformly in appearance. However, upon flower onset, the seedlings were selected for the two phenotypes that most smelled like 'grape and dank', and producing flowers with the highest trichome density and robust examples of these two phenotypes were subsequently crossed to create PUR03.

Hypothesized Genetics. "2007 SB PUP1×2009 PPS7".

Propagation and Vegetative Growth. Cuttings from PUR03 are marked by 7-finger leaflet sets with internode buds asymmetrically located on alternate sides on main shoot. In particular, the internode space of this variety tends to be decreased. Short, squatty and bushy. Cuttings root within 10-14 days.

The PUR03 grows stout in the traditional 'Christmas tree' shape. PUR03 grows with asymmetrical bud and leaf sets. Vegetative growth is marked by a deeper off green (Munsell ID) hue with lime green thin stalks. Leaflets are longer and thinner than varieties. When healthy, sun leaves are gigantic. It has vigorous hybrid character. The stand-out quality is the high amount of trichomes and the high amount of oil. There is an extremely high cannabinoid content in PUR03. Stalks have a sweet 'dank' scent. Canopy dense and do not need to top.

Onset of Flowering and Inflorescences. Leaves are 7 leaflet patterns with 7 being predominant and overall decreasing to 1 and to none in the presence of female flowers. In particular, flower onset is fast by comparison to most varieties.

Trichome density and smell are almost immediate. Female flowers are clustered to do decreased internode spacing. Again, this variety tends to be more densely covered with trichome bodies than its parents and other purple varieties. In fact, the inflorescences are very dense and have large calyxes covered in highly resinous glands that exhibit this variety's distinct grape lollipop scent after only 7-10 days. As inflorescences mature, the density compact sets compound to form deep purple and dark green extremely oily buds. In particular, the oily character of these flowers set this purple apart from its parent and other green class varieties.

Description of Finished Flower. PUR03 defines sweet, delicious grape flavored medicine with functional mental effects and pain relief. This variety has resin production akin to Afghan and psychoactivity reminiscent of the PUR03.

PUR03 has aromas of grape, sweet sugar, and dank which all combine to produce a fantastic grape flavor when smoked. It is noted for mood elevation, short-term pain relief and hunger stimulation.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis and determined by specified cultivation techniques employed. In this case, indoor CEA technique following the protocol described elsewhere herein.

Flower onset was initiated with 12/12 day/night at approximately 16" in vegetative height. Total biomass ~160 g, finished flowers ~50 g, and/or ~50 g of seed per plant.

Potential Uses of this Line. Potential uses of PUR03 include but are not limited to medical applications, extractions, commercial raw material (e.g., chemical), fiber and pulp.

Patient Testimonials/Comments and Visual Observations. Patients rave about the great experience. This flower consistently produces approximately 2.0% CBGA in finished flowers. Its wonderful smell/taste is patient's major reason for appeal.

YEL03

Description of Breeding Stock. Inflorescences were obtained from an unknown landrace. Seeds from these inflorescences were isolated and put into conditions proper for their germination. The seeds which germinated grew uniformly in appearance. However, the seedlings were selected for their narrow-leafleted tropical *cannabis* morphology and pinene production to create YEL03.

Hypothesized Genetics. "*Cannabis indica* ssp. *indica* NLD "Thai"—*C. indica* ssp. *indica* NLD "Highland Mexican."

Propagation and Vegetative Growth. Cuttings from YEL03 are marked by 9-finger leaflet sets with internode buds asymmetrically located on alternate sides on main shoot. In particular, the internode space of this variety tends to be lengthy and stretchy (~4" veg, decreasing flower onset). The plants are tall, robust and lanky. Cuttings root within 10-14 days.

The YEL03 grows tall and strong with pronounced apical dominance. YEL03 grows with asymmetrical bud and leaf sets. Vegetative growth is marked by a lighter dark green (Munsell ID) hue with purple undersides and strong hollow stalks. When healthy, sun leaves are point upward toward light source at twisted angles. The stems are strong and fibrous. The stand-out quality is the high amount of trichomes and the high amount of oil. YEL03 has stalks with a sweet scent. Plant canopy is sparse with scattered bud formation. Topping encouraged.

Onset of Flowering and Inflorescences. Leaves are 9 leaflet patterns with 9 being predominant and overall decreasing to 1 and to none in the presence of female flowers. In particular, flower onset is fast by comparison to most varieties.

Trichome density and smell are almost immediate. Female flowers are sparse due to large internode spacing. Again, this variety tends to be more densely covered with trichome bodies than its parents and other varieties. The flowers are not compact or well-formed. Inflorescences are spirals of individual foxtails that form a 'coral' looking structure. Although buds are made of individual spirals, the inflorescences are dense and tightly packed. As inflorescences mature, the density compact sets compound to form bright green and extremely oily buds.

Description of Finished Flower. YEL03 has descended from the great Oaxacan and That *cannabis* landrace plants of the 1970's. This variety delivers an intense "up" stimulating effect that can be great for countering the debilitating aspects of many medical conditions. A complex aroma of spicy spruce and lemon peel release a cornucopia of sweet and spicy piney flavors when smoked. It is often characterized by a clear head, accompanied by mood elevation.

Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days). Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis using the specified cultivation techniques employed. In this case, indoor CEA technique following the protocol described elsewhere herein. Flower onset was initiated with 12/12 day/night at approximately 16" in vegetative height. Total biomass ~120 g, finished flowers ~40 g, and/or ~30 g of seed per plant.

Potential Uses of this Line. Potential uses of YEL03 include but are not limited to medical applications, extractions, commercial raw material (e.g., chemical), fiber and pulp.

Patient Testimonials/Comments and Visual Observations. Plants have a very interesting from an organoleptic standpoint and are unique in almost all visual categories.

PUR12

Description of Breeding Stock. Inflorescences were obtained for an unknown landrace. Seeds from these inflorescences were isolated and put into conditions proper for their germination. The seeds which germinated grew uniformly in appearance. However, the seedlings were selected for trichome density and hybrid leaf morphology to create PUR12.

Hypothesized Genetics. "*Cannabis indica* ssp. *afghanica* WLD "Afghan #1"×*Cannabis indica* ssp. *indica* NLD "Brazilian"×*C. indica* ssp. *indica* NLD "Indian."

Propagation and Vegetative Growth. Cuttings from PUR12 are marked by 5-finger leaflet sets with internode buds asymmetrically located on alternate sides on main shoot. In particular, the internode space of this variety tends to be shorter and stout (~2-4" veg, decreasing flower onset). The plants are short, robust and bushy. Cuttings root within 10-14 days.

The PUR12 grows short and bushy with classic 'Christmas tree' apical dominance. PUR12 grows with asymmetrical bud and leaf sets. Vegetative growth is marked by a dark green (Munsell ID) hue with green undersides and hard wood like stalks. When healthy, sun leaves are point upward toward light source and 'reach'. The stems are strong and fibrous. The stand out quality is the high amount of trichomes and the high amount of oil. The flower sets look 'white' before most other varieties. Stalks are sweet scent. Plant canopy is dense with clustered bud formation. Topping discouraged.

Onset of Flowering and Inflorescences. Leaves are 5 leaflet patterns with 5 being predominant and overall decreasing to 1 and to none in the presence of female flowers. In particular, flower onset is fast by comparison to most varieties.

Trichome density and smell are almost immediate. Female flowers are dense and thick due to relatively small internode lengths. Again, this variety tends to be more densely covered with trichome bodies than other varieties in the white class. The flowers are compact and well-formed in the shape of pinecones. Pistils are fat and of high density. As inflorescences mature, the density compact sets compound to form bright neon-green flowers that give way to red-orange hair. It is marked by unusually high sesquiterpene content and extremely resinous buds. Inflorescences are subject to fungal infestation due to large size and extreme density.

Description of Finished Flower. PUR12 produces prodigious amounts of psychoactive resin. This variety was derived from Brazilian, Indian, and Afghan gene pools. Its aroma of green classy, balsamic, pineapple gazpacho delivers a sweet, hashy flavor when smoked. It is noted for fast-onset psychoactivity reminiscent of traditional *cannabis* experiences that will leave you right where it found you. Happiness induced pain relief and considerable relaxation.

Chemotype Description for Patient. Relative potency: very strong. Headspace Terpenes: pinenes, myrcene, limonene, humulene, and naphthalene. Caryophyllene content: very high Description of Planting, Harvesting and Processing of the Plants. This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data. Yield was determined on a 'per plant' basis and determined by specified cultivation techniques employed. In this case, indoor CEA technique following the protocol described elsewhere herein. Flower onset was initiated with 12/12 day/night at approximately 16" in vegetative height. Total biomass ~140 g, finished flowers ~50 g, and/or ~50 g of seed per plant.

Potential Uses of this Line. Potential uses of PUR12 include but are not limited to medical applications, extractions, commercial raw material (e.g., chemical), fiber and pulp.

Patient Testimonials/Comments and Visual Observations. Very interesting from an organoleptic standpoint (sweet Amsterdam flavor) and a caryophyllene content standpoint. Happy laughing high. PUR12 has the burnt scent of 1990's landraces.

Parental Plant Phenotypes

In order to better describe the morphologies of parental *cannabis* lines, plants were grown indoor to maturity at 120 days post transfer under standard production and pruning methods. These plants were assayed for several phenotypes important for *cannabis* production. These phenotypes and their descriptions are listed below, and their measurements for parental varieties summarized in Table 3.

Plant Sex—In order to properly assess the progeny morphology of the female inflorescence important for *cannabis* production, only pistillate plants were allowed to fully develop. Breeding of pistillate flowers was carried out by reversing the sex of a branch of female flowers through the application silver thiosulfate. Sex determination was made during vegetative growth through the identification of the earliest pre-flowers (see Cervantes 2006 "Marijuana Horticulture The indoor/outdoor medical grower's bible" editors Linda Meyer and Estella Cervantes). Male plants were not allowed to develop in order to avoid accidental pollination of female plants.

Plant Height—measured in centimeters from the base of the plant to the top of the apical meristem. Plants were measured 120 days post transfer.

Plant Diameter—measured in centimeters as width of the plant at its widest diameter.

Plants were measured 120 days post transfer.

Number of Leafletts—Leafletts on leaves were counted. The leaf with the most leaflets was recorded at 120 days post transfer.

Leaf Type—Leaves were visually inspected for broad or narrow leaf morphologies. Narrow leaf morphologies produce leaflets less than 1 cm wide (N). This type of leaf morphology is most closely associated with *Cannabis sativa* varieties. Broad leaf morphologies produce leaflets wider than 2 cm (B). This type of leaf morphology is most closely associated with *Cannabis indica*. Leaves were designated as medium (M) morphologies if they fell in between broad and narrow leaf values, indicating the progeny included genetics from both *C. sativa* and *C. indica*.

Average Internodes—Internodes were counted at plant maturity at 120 days. Number of internodes is highly correlated to plant branching and number of inflorescences. Internodes are defined as the sections of stem between nodes.

Node Branching—Node branching was visually determined by inspecting nodes and determining the amount of branching at plant maturity at 120 days post transfer. Higher branching can increase total flower yield, but can also produce plants that cannot be grown closely for indoor production.

Leaf Color—Representative leaves from each plant were harvested and pictures were taken. Colors will be analyzed and will be provided using Royal Horticultural Society color chart values.

Average Number of Inflorescences at Maturity—Inflorescences were visually inspected and counted at plant maturity at 120 days post transfer. Plants were designated as having "low" number of inflorescences if they produced less than 10 inflorescences per plant. Plants were designated as having "medium" number of inflorescences if they produced between 10 and 15 inflorescences per plant. Plants were designated as having "high" number of inflorescences if they produced more than 15 infloresences per plant. In general, higher number of inflorescences are associated with higher *cannabis* flower yield.

Average Non-Apical Inflorescence Size—Inflorescence size was measured by volume by measuring the height and radius of each non-apical inflorescence at plant maturity at 120 days post transfer. These measurements were used to determine volume of the inflorescence using a cylinder shape approximation (formula Pi ×radius$^2$×height). Values for all non-apical inflorescences were averaged. Inflorescences with average volumes of less than 100 cm$^3$ were designated "small". Inflorescences with average volumes between 100 cm$^3$ and 300 cm$^3$ were designated "medium". Inflorescences with volumes greater than 300 cm$^3$ were designated "large".

Average Apical Inflorescence Size—Inflorescence size was measured by volume by measuring the height and radius of apical inflorescences at plant maturity at 120 days post transfer. These measurements were used to determine volume of the inflorescence using a cylinder shape approximation (formula Pi ×radius$^2$×height). Values for apical inflorescences of multiple plants were averaged. Apical inflorescences with average volumes of less than 400 cm$^3$ were designated "small". Apical inflorescences with average volumes between 400 cm$^3$ and 600 cm$^3$ were designated "medium". Inflorescences with volumes greater than 600 cm$^3$ were designated "large".

Floral Cluster Density—Floral cluster density is a measure of how tightly packed floral buds are in a plant inflorescence. This measure is correlated with total yield and is also associated with the amount of labor necessary for trimming the inflorescence post harvest. For parental varieties of this example, floral cluster density was approximated by measuring the time it took for the inflorescences to dry (reach ~10% relative humidity). Faster drying time were associated with "low" floral cluster density. Slower drying times were associated with "high" floral cluster densities. Low density floral clusters dry in 4-5 days, medium density floral clusters take 6-7 days, and dense floral clusters take 8-9 days.

Trichome Density—Trichomes on the inflorescences of mature plants at 120 days post transfer were visually inspected for trichome density and assigned a score of 1-10 based on past experiences of the grower. Lower scores indicated lower trichome densities, whereas higher scores indicated higher trichome densities. Trichome density is also commonly referred to as "frostiness". Inflorescences with scores higher than 7 appear to be completely covered in white trichomes giving a "frost" like appearance. Density scores of 8-10 were equivalent to what could be expected of an OG Kush strain.

TABLE 3

Phenotype table of parental varieties.

| Variety new name | Plant height at maturity (cm) | Plant diameter at maturity (cm) | Leaf type | Avg # inter-nodes | Branching at each node | Avg Number inflorescences at maturity | Avg non-apical inflorescence size | Avg apical inflorescence size (cm) | @ Floral cluster density | # Trichome density (1-10 scale) | Number of Leaflets |
|---|---|---|---|---|---|---|---|---|---|---|---|
| PUR13 | 154 | 63.5 | B | 23 | every node: 1 leaf, 1 branch | Low | Large | High | High | 9 | 5 |
| SIL04 | 145 | 65.2 | B | 27.5 | every node: 1 leaf, 1 branch | High | Large | High | Low | 5 | 5 |
| GRE01 | 95 | 45.7 | M | 29.3 | every node: 1 leaf, 1 branch | Medium | Mediumium | High | Medium | 7 | 5 |
| SIL03 | 133 | 49.8 | B | 26.5 | every node: 1 leaf, 1 branch | Medium | Large | High | Medium | 7 | 7 |
| PUR03 | 71 | 47.4 | B | 23 | every node: 1 leaf, 1 branch | Low | Medium | Medium | High | 5 | 7 |
| SIL01 | 78 | 46.5 | B | 15.7 | every node: 1 leaf, 1 branch | Low | Medium | Low | High | 7 | 5 |
| SIL06 | 83 | 22.9 | B | 21 | every node: 1 leaf, 1 branch | Low | Medium | Low | Low | 9 | 7 |
| YEL03 | 104 | 67.6 | B | 20.8 | every node: 1 leaf, 1 branch | Medium | Large | High | Low | 7 | 9 |
| WHI07 | 112 | 50.2 | B | 29.5 | every node: 1 leaf, 1 branch | Medium | Medium | High | Medium | 9 | 7 |
| GOD13 | 121 | 45.7 | B | 22 | every node: 1 leaf, 1 branch | Medium | Small | Medium | Low | 7 | 5 |
| ORA02 | 135 | 43.2 | B | 32.3 | every node: 1 leaf, 1 branch | High | Small | High | Low | 9 | 5 |
| WHI04 | 103 | 36.2 | B | 19.8 | every node: 1 leaf, 1 branch | Low | Medium | Medium | Medium | 7 | 7 |
| PUR01 | 125 | 39.4 | M | 28.8 | every node: 1 leaf, 1 branch | Medium | Medium | High | Medium | 9 | 7 |
| CBD03 | 89 | 41.5 | M | 26.5 | every node: 1 leaf, 1 branch | High | Small | Low | High | 9 | 7 |
| SIL02 | 94 | 43.8 | M | 28.5 | every node: 1 leaf, 1 branch | High | Medium | Medium | Low | 7 | 5 |
| BRO01 | 118 | 43.2 | M | 27 | every node: 1 leaf, 1 branch | Medium | Medium | High | Low | 9 | 7 |
| PUR12 | 103 | 45.1 | M | 31.7 | every node: 1 leaf, 1 branch | High | Medium | Medium | High | 5 | 5 |
| CBD01 | 125 | 44.9 | M | 38.3 | every node: 1 leaf, 1 branch | High | Small | Low | Low | 2 | 5 |
| PUR06 | 94 | 44.5 | B | 27.3 | every node: 1 leaf, 1 branch | Medium | Medium | Low | Medium | 7 | 7 |
| CBD5 | 132 | 48.3 | B | 37 | every node: 1 leaf, 1 branch | High | Low | Medium | Medium | 7 | 5 |

Example 3

Analysis of Proprietary THC Parental Varieties

One objective of the present invention was to develop *cannabis* varieties with high terpene oil contents and different terpene profiles to meet various aroma/flavor and medicinal needs. The parental varieties developed in the present invention, underwent chemical analyses as described in Example 1. The resulting cannabinoid and terpene profiles were further subjected to agglomerative hierarchal clustering (AHC) using XLStat to classify varieties into "classes". Varieties in a given class of *cannabis* share certain common physiological, chemical and/or morphological characteristics. Thus, according to the present invention, *cannabis* plants are grouped into named classes according to their primary/dominant flavor(s) in order to establish standard *cannabis* classes of plants herein referred to collectively as 'Classes of *Cannabis* Varieties.'

As explained in greater detail below, individual *cannabis* plants of the proprietary *cannabis* varieties were identified, tested and grouped to form class categories of similar varieties. According to the present invention, more than one variety of *cannabis* may have been established within a single *cannabis* class. Selected candidate *cannabis* plants for a specific variety may have been subjected to further breeding and selection before being chosen as a *cannabis* variety for a particular class. The final selected varieties were designated as Classes of *Cannabis* Varieties. Therefore, as used herein, 'Classes of *Cannabis* Varieties' or 'variety classes' or the like each refer to certain *cannabis* varieties originating from proprietary varieties, wherein they were selected based on certain desirable phenotypical characteristics and morphological characteristics for a particular class of *cannabis*. Color class parental *cannabis* tended to be chemotype I plants.

Table 4 summarizes the classes of the *cannabis* varieties provided by the present invention and the Class color, Class name, Class abbreviations ("ABRV"), flavor associated with each class, and the major terpenes measured in each class.

TABLE 5

Changes in variety color classification and naming.

| Old Name | New Name |
|---|---|
| BLU4 | BLU04 |
| BLU8 | RED08 |
| BLU9 | GRE09 |
| GRE1 | GRE01 |
|  | VLT |
| GO13 | GOD13 |
| GOD3 | GOD03 |
| GOD2 | GOD02 |
| GOD11 | GOD11 |
| GOD10 | GOD10 |
| BLU5 | SIL06 |
| GOD12 | SIL12 |
| GOD8 | SIL08 |
| RED2 | SIL03 |
| RED1 | SIL02 |
| SIL1 | SIL01 |
| WHI2 | SIL04 |
| GOD5 | WHI02 |
| WHI7 | WHI07 |
| GOD6 | WHI06 |
| GO14 | WHI14 |
| SIL4 | WHI04 |
| CHM1 | WHI01 |
| SIL05 | WHI05 |
| GOD4 | WHI09 |
| THC01 | BLK01 |
| THC02 | BLK02 |
| THC03 | BLK03 |
| THC04 | BLK04 |
| YEL3 | YEL03 |

TABLE 4

Color class characteristics of THC parental varieties.

| Color | Abbrev | Class Terpene Characteristics | Flavor |
|---|---|---|---|
| Azure | AZR | myrcene>>limonene>caryophyllene | Woody, fruity |
| Black | BLK | caryophyllene>limonene>myrcene | Camphoreous, baked sweets |
| Blue | BLU | pinenes>myrcene>caryophyllene | Berry, terpy, solvent |
| Bronze | BRZ | limonene≈myrcene>caryophyllene | Sweet, lemons |
| Brown | BRO | myrcene>>ocimene>pinene | Musky, sweet, apple cider |
| Fuscia | FSC | myrcene, caryophyllene | Fuel, grass, baked lemon |
| Gold | GOD | limonene =caryophyllene =myrcene | Lemon, pine-sol, fuel |
| Green | GRE | myrcene>limonene≈ocimene | Sweet, cream, citrus, skunk |
| Grey | GRA | myrcene, pinene, limonene | Woody, green, sweet, bubblegum, pine |
| Jade | JAD | terpinolene, myrcene | Sweet, pepper, spice |
| Lemon | LMN | limonene>myrcene≈ocimene≈caryophyllene | Citrus, sweet, spice |
| Magenta | MAG | myrcene>>ocimene>limonene≈caryophyllene | Sweet, orange peel, spice |
| Navy | NVY | myrcene>pinene>limonene≈ocimene | Sweet, pine, citrus |
| Olive | OLV | myrcene>>ocimene≈limonene | Sweet, orange, lemon |
| Orange | ORA | myrcene, terpinolene, ocimene, pinene | Intense orange peel, sweet |
| Pink | PNK | myrcene≈ocimene≈pinene | Sweet, orange, pine |
| Purple | PUR | myrcene, pinene, caryophyllene | Grapes, pine, sweet, pineapple, berry, floral, acrid, menthol |
| Red | RED | ocimene≈limonene≈pinene | Floral, vanilla, skunk |
| Sea | SEA | limonene≈caryophyllene≈myrcene>ocimene | Lemons, pepper, sweet |
| Silver | SIL | limonene,>caryophyllene, myrcene | Lime, pomegranate, creamy, blueberry, spice, menthol |
| Tan | TAN | myrcene>ocimene>limonene>pinene | Sweet, citrus, pine |
| Violet | VLT | myrcene≈ocimene | Sweet, oranges |
| White | WHI | limonene=caryophyllene, >myrcene | Berry, lime, skunk, fuel, incense, citrus, pine |
| Yellow | YEL | terpinolene, ocimene, myrcene | Lemon, pine, skunk |

The analysis of *cannabis* class varieties led to the slightly different abbreviations for color classes and also to the renaming of varieties disclosed in the original filing. Name changes in this application from priority documents (U.S. 61/801,528 and U.S. 61/897,074) are summarized in Table 5. New class categories violet and pink are included in the following table.

TABLE 5-continued

Changes in variety color classification and naming.

| Old Name | New Name |
|---|---|
| YEL05 | YEL05 |
| PUR2 | YEL02 |

TABLE 5-continued

Changes in variety color classification and naming.

| Old Name | New Name |
|---|---|
| JK11 | JAD11 |
| JK12 | JAD12 |
| JCK4 | JAD04 |
| ORA3 | ORA03 |
| ORA2 | ORA02 |
| PUR1 | PUR01 |
| PUR3 | PUR03 |
| PUR5 | PUR05 |
| GRA3 | PUR13 |
| BLU6 | PUR06 |
| GRA1 | PUR11 |
| BRO1 | PUR11 |
| WHI3 | PUR12 |
| GRE2 | FSC04 |
| CHM3 | FSC03 |
| CHM2 | FSC02 |
| GRE30 | BRO01 |
| ORA4 | BRO02 |
|  | PNK |
| GOD7 | GRA07 |
| GRE31 | GRA31 |
| WHI4 | GRA04 |
| WHI5 | GRA05 |

The cannabinoid and terpene profiles of each THC parental variety were determined using both GC-FID and HPLC as described in Example 1. The resulting measurements are summarized in Tables 6, 7, 8, and 9. The GC-FID cannabinoid analysis of Table 6 also included measurements for THCV, CBDV, CBGV, CBN, and delta 8 THC, all of which were measured to be less than 0.05% and were therefore not included in the table. Similarly, the HPLC cannabinoid analysis of Table 7 included measurements for THCV, THCVA, CBDV, CBDVa, CBGV, CBGVA, CBC, CBCA, CBD, and CBN, all of which were measured to be less than 0.01%, and were therefore not included in the table.

TABLE 6

Cannabinoid measurement by GC-FID for THC color class parental varieties. Blank values indicate undetectable levels or 0.

GC-FID THC Color Class Parental Lines

| | THC | | CBD | | CBG | | CBC | | Cannabs by GC | | THC:CBD by GC | | Cannabs/Terps (GC) | |
|---|---|---|---|---|---|---|---|---|---|---|---|---|---|---|
| Sample | Wt % | 95% CI | Wt % | 95% CI | Wt % | 95% CI | Wt % | 95% CI | Wt % | 95% CI | Wt % | 95% CI | Wt % | 95% CI |
| BLK01 | 18.82% |  |  |  | 0.51% |  | 0.23% |  | 19.56% |  |  |  | 13.77 |  |
| BLK02 | 20.23% |  |  |  | 1.37% |  | 0.37% |  | 21.97% |  |  |  | 18.78 |  |
| BLK03 | 16.54% |  |  |  | 0.71% |  | 0.43% |  | 17.67% |  |  |  | 12.06 |  |
| BLK04 | 20.70% |  |  |  | 0.58% |  | 0.19% |  | 21.90% |  |  |  | 12.37 |  |
| BLU04 | 7.52% |  | 0.16% |  | 0.16% |  | 0.10% |  | 7.98% |  | 47.26 |  | 5.94 |  |
| BRO01 | 12.23% | 2.32% |  |  | 0.52% | 0.01% | 0.26% | 0.07% | 13.08% | 2.27% |  |  | 9.01 | 3.27 |
| BRO02 | 13.47% | 0.97% | 0.02% | 0.02% | 0.74% | 0.06% | 0.16% | 0.02% | 14.44% | 0.90% | 1036.07 | 1147.94 | 12.66 | 2.88 |
| FSC04 | 12.49% |  |  |  | 0.34% |  | 0.42% |  | 13.29% |  |  |  | 6.62 |  |
| FSC03 | 16.20% | 1.84% |  |  | 0.29% | 0.14% | 0.16% | 0.03% | 16.71% | 1.91% |  |  | 10.08 | 1.71 |
| FSC02 | 17.57% |  |  |  | 0.51% |  | 0.19% |  | 18.39% |  |  |  | 7.89 |  |
| GOD13 | 19.79% | 2.10% |  |  | 0.53% | 0.07% | 0.18% | 0.02% | 20.55% | 2.17% |  |  | 7.30 | 0.56 |
| GOD03 | 21.12% |  |  |  | 0.82% |  | 0.17% |  | 22.19% |  |  |  | 10.13 |  |
| GOD02 | 19.36% | 1.70% |  |  | 0.64% | 1.08% | 0.16% | 0.01% | 20.22% | 2.75% |  |  | 8.72 | 3.85 |
| GOD11 | 20.45% |  |  |  | 1.00% |  | 0.15% |  | 21.65% |  |  |  | 10.38 |  |
| GOD10 | 21.37% |  |  |  | 0.97% |  | 0.18% |  | 22.58% |  |  |  | 9.00 |  |
| GRA07 | 16.07% | 1.25% |  |  | 0.43% | 0.03% | 0.18% | 0.07% | 16.74% | 1.22% |  |  | 7.71 | 0.83 |
| GRA31 | 11.43% | 2.35% |  |  | 0.13% | 0.09% | 0.21% | 0.09% | 11.81% | 2.54% |  |  | 9.19 | 1.20 |
| GRA04 | 8.30% | 1.56% | 0.01% | 0.00% | 0.06% | 0.01% | 0.15% | 0.01% | 8.54% | 1.56% | 1193.88 | 110.99 | 8.77 | 1.65 |
| GRA05 | 11.52% | 1.45% | 0.01% | 0.00% | 0.14% | 0.05% | 0.32% | 0.03% | 12.02% | 1.50% | 850.84 | 193.14 | 7.01 | 1.50 |
| GRE09 | 7.97% |  |  |  | 0.31% |  | 0.16% |  | 8.48% |  |  |  | 11.30 |  |
| GRE01 | 16.43% | 0.83% |  |  | 1.31% | 0.08% | 0.31% | 0.04% | 18.10% | 0.90% |  |  | 9.59 | 1.57 |
| JAD11 | 12.45% |  |  |  | 0.54% |  | 0.25% |  | 13.28% |  |  |  | 5.41 |  |
| JAD12 | 8.32% |  |  |  | 0.47% |  | 0.19% |  | 9.03% |  |  |  | 5.23 |  |
| JAD04 | 10.29% |  |  |  | 0.67% |  | 0.18% |  | 11.20% |  |  |  | 5.80 |  |
| ORA02 | 11.83% | 0.79% |  |  | 0.50% | 0.04% | 0.13% | 0.01% | 12.50% | 0.83% |  |  | 9.32 | 1.53 |
| ORA03 | 11.60% | 1.23% | 0.03% | 0.04% | 0.20% | 0.04% | 0.18% | 0.01% | 12.03% | 1.25% | 818.90 | 1083.82 | 7.33 | 2.92 |
| PUR03 | 15.52% | 1.12% |  |  | 0.32% | 0.07% | 0.30% | 0.03% | 16.19% | 1.17% |  |  | 9.28 | 0.64 |
| PUR01 | 11.45% | 1.01% |  |  | 0.25% | 0.06% | 0.16% | 0.03% | 11.91% | 0.98% |  |  | 7.06 | 0.81 |
| PUR13 | 16.13% | 2.35% |  |  | 0.75% | 0.06% | 0.19% | 0.02% | 17.14% | 2.38% |  |  | 9.45 | 1.30 |
| PUR06 | 14.08% | 2.66% |  |  | 0.16% | 0.03% | 0.17% | 0.03% | 14.48% | 2.70% |  |  | 9.56 | 2.93 |
| PUR05 | 18.96% | 0.92% |  |  | 0.39% | 0.01% | 0.32% | 0.01% | 19.70% | 0.91% |  |  | 6.45 | 0.30 |
| PUR11 | 13.49% |  |  |  | 0.41% |  | 0.15% |  | 14.09% |  |  |  | 9.93 |  |
| PUR13 | 9.89% |  |  |  | 0.16% |  | 0.18% |  | 10.26% |  |  |  | 6.55 |  |
| PUR12 | 13.89% | 2.42% |  |  | 0.31% | 0.10% | 0.15% | 0.03% | 14.39% | 2.43% |  |  | 12.44 | 2.26 |
| RED08 | 8.42% | 0.88% |  |  | 1.18% | 0.67% | 0.22% | 0.11% | 9.86% | 1.38% |  |  | 14.27 | 2.15 |
| SIL04 | 15.27% | 1.28% |  |  | 0.41% | 0.06% | 0.19% | 0.03% | 15.92% | 1.36% |  |  | 7.02 | 0.68 |
| SIL06 | 11.25% | 1.09% |  |  | 0.39% | 0.03% | 0.40% | 0.07% | 12.09% | 1.14% |  |  | 14.25 | 1.07 |
| SIL08 | 17.15% | 1.43% |  |  | 0.23% | 0.11% | 0.15% | 0.02% | 17.59% | 1.39% |  |  | 10.78 | 2.17 |
| SIL03 | 13.37% | 0.90% |  |  | 0.19% | 0.02% | 0.16% | 0.04% | 13.74% | 0.96% |  |  | 11.07 | 1.80 |
| SIL02 | 15.00% | 2.38% |  |  | 0.12% | 0.00% | 0.17% | 0.02% | 15.30% | 2.39% |  |  | 9.03 | 0.10 |
| SIL01 | 14.23% | 2.05% |  |  | 0.40% | 0.03% | 0.16% | 0.01% | 14.88% | 2.07% |  |  | 10.89 | 1.36 |
| WHI07 | 15.44% | 1.75% |  |  | 0.24% | 0.03% | 0.17% | 0.01% | 15.92% | 1.78% |  |  | 8.73 | 1.05 |
| WHI04 | 15.97% | 1.40% |  |  | 0.50% | 0.20% | 0.16% | 0.02% | 16.76% | 1.65% |  |  | 12.93 | 5.49 |

TABLE 6-continued

Cannabinoid measurement by GC-FID for THC color class parental varieties. Blank values indicate undetectable levels or 0.

GC-FID THC Color Class Parental Lines

| Sample | THC Wt % | 95% CI | CBD Wt % | 95% CI | CBG Wt % | 95% CI | CBC Wt % | 95% CI | Cannabs by GC Wt % | 95% CI | THC:CBD by GC Wt % | 95% CI | Cannabs/Terps (GC) Wt % | 95% CI |
|---|---|---|---|---|---|---|---|---|---|---|---|---|---|---|
| WHI09 | 15.27% | | | | 0.60% | | 0.19% | | 16.22% | | | | 15.22 | |
| WHI01 | 14.83% | 1.74% | | | 0.23% | 0.13% | 0.17% | 0.05% | 15.30% | 1.96% | | | 9.79 | 2.04 |
| WHI14 | 14.40% | 4.04% | | | 0.36% | 0.33% | 0.20% | 0.06% | 15.01% | 4.36% | | | 10.77 | 5.02 |
| WHI05 | 16.15% | | | | 0.45% | | 0.18% | | 16.82% | | | | 17.19 | |
| WHI06 | 14.74% | | 0.03% | | 0.40% | | 0.18% | | 15.37% | | 491.23 | | 8.82 | |
| WHI02 | 18.72% | | 0.16% | | 0.47% | | 0.23% | | 19.60% | | 114.16 | | 13.87 | |
| YEL03 | 13.81% | 0.58% | | | 0.58% | 0.08% | 0.58% | 0.05% | 15.04% | 0.68% | | | 10.61 | 2.06 |
| YEL05 | 16.21% | 2.20% | | | 1.63% | 0.80% | 0.29% | 0.13% | 18.19% | 3.13% | | | 7.60 | 1.66 |
| YEL02 | 11.10% | 1.14% | | | 0.74% | 0.06% | 0.24% | 0.03% | 12.12% | 1.14% | | | 6.21 | 0.50 |

*LOQ for all cannabinoids was 0.14%.

TABLE 7

Cannabinoid measurement by HPLC for THC color class parental varieties. Blank values indicate undetectable levels, or 0.

| Sample | Cannabinoids (UHPLC) THCA Wt % | 95% CI | CBDA Wt % | 95% CI | CBGA Wt % | 95% CI | THC Wt % | 95% CI | CBG Wt % | 95% CI | Cannabs by HPLC Wt % | 95% CI | Cannabs/Terps (HPLC) Ratio | 95% CI |
|---|---|---|---|---|---|---|---|---|---|---|---|---|---|---|
| BLK01 | 27.24% | | | | 0.95% | | 0.34% | | 0.07% | | 28.61% | | 20.15 | |
| BLK02 | 26.11% | | | | 1.94% | | 0.30% | | 0.09% | | 28.44% | | 24.17 | |
| BLK03 | 26.70% | | | | 0.71% | | 1.10% | | 0.05% | | 28.56% | | 19.50 | |
| BLK04 | 26.37% | | | | 0.77% | | 0.74% | | 0.48% | | 28.38% | | 17.02 | |
| BLU04 | 9.94% | | 0.25% | | 0.21% | | 0.16% | | | | 10.60% | | 7.90 | |
| BRO01 | 15.90% | 2.54% | | | 1.08% | 0.81% | 0.47% | 0.21% | | | 17.49% | 1.47% | 11.99 | 3.30 |
| BRO02 | 16.77% | 0.29% | 0.06% | | 0.85% | 0.02% | 0.30% | 0.15% | 0.09% | 0.00% | 18.04% | 0.51% | 15.93 | 5.04 |
| FSC04 | 16.20% | | | | 0.38% | | 0.33% | | | | 16.92% | | 8.43 | |
| FSC03 | 18.33% | 1.30% | | | 0.38% | 0.21% | 1.03% | 0.29% | | | 15.81% | 7.84% | 11.96 | 2.20 |
| FSC02 | 21.04% | | | | 0.72% | | 1.29% | | | | 23.20% | | 9.96 | |
| GOD13 | 24.52% | 2.84% | | | 0.74% | 0.11% | 0.43% | 0.42% | | | 25.82% | 2.54% | 9.17 | 0.64 |
| GOD03 | 24.16% | | | | 1.00% | | 0.60% | | | | 25.83% | | 11.79 | |
| GOD02 | 22.27% | 2.24% | | | 1.29% | 0.29% | 1.30% | 1.47% | 0.11% | | 25.01% | 1.12% | 10.70 | 3.79 |
| GOD11 | 23.57% | | | | 1.17% | | 0.57% | | 0.13% | | 25.49% | | 12.22 | |
| GOD10 | 24.32% | | | | 1.18% | | 0.59% | | 0.13% | | 26.27% | | 10.47 | |
| GRA07 | 20.21% | 1.81% | | | 0.56% | 0.05% | 0.63% | 0.37% | | | 21.55% | 1.47% | 9.93 | 1.08 |
| GRA31 | 15.27% | 2.82% | | | 0.35% | 0.45% | 0.29% | 0.28% | | | 16.02% | 3.47% | 12.47 | 1.60 |
| GRA04 | 10.48% | 1.51% | 0.02% | | 0.10% | 0.02% | 0.37% | 0.03% | | | 10.96% | 1.54% | 11.27 | 1.63 |
| GRA05 | 14.65% | 1.63% | 0.02% | 0.01% | 0.21% | 0.06% | 2.25% | 3.17% | | | 17.13% | 3.76% | 9.97 | 2.62 |
| GRE09 | 9.66% | | | | 0.40% | | 0.14% | | | | 10.21% | | 13.61 | |
| GRE01 | 20.38% | 0.91% | | | 1.55% | 0.19% | 0.52% | 0.27% | 0.12% | 0.00% | 22.55% | 0.83% | 11.94 | 1.90 |
| JAD11 | 15.70% | | | | 0.64% | | 0.61% | | | | 17.05% | | 6.95 | |
| JAD12 | 10.88% | | | | 0.61% | | 0.43% | | | | 11.93% | | 6.91 | |
| JAD04 | 13.53% | | | | 0.91% | | 0.54% | | | | 14.98% | | 7.76 | |
| ORA02 | 14.79% | 0.50% | | | 0.71% | 0.05% | 0.45% | 0.18% | | | 15.88% | 0.50% | 11.78 | 1.43 |
| ORA03 | 14.21% | | 0.01% | | 0.29% | | 0.45% | | | | 7.48% | 14.67% | 7.67 | |
| PUR03 | 19.45% | 1.48% | | | 0.35% | 0.12% | 0.34% | 0.13% | | | 20.26% | 1.46% | 11.60 | 0.69 |
| PUR01 | 14.74% | 1.19% | | | 0.24% | 0.07% | 0.31% | 0.32% | | | 15.31% | 0.98% | 9.10 | 1.18 |
| PUR13 | 21.05% | 2.57% | | | 0.93% | 0.14% | 0.34% | 0.18% | | | 22.41% | 2.56% | 12.44 | 1.87 |
| PUR06 | 18.08% | 3.40% | | | 0.22% | 0.04% | 0.32% | 0.25% | | | 18.70% | 3.27% | 12.34 | 3.72 |
| PUR05 | 23.75% | 1.64% | | | 0.43% | 0.02% | 0.21% | 0.21% | | | 24.48% | 1.31% | 8.02 | 0.43 |
| PUR11 | 16.36% | | | | 0.46% | | 0.54% | | | | 17.57% | | 12.38 | |
| PUR13 | 12.64% | | | | 0.26% | | 0.77% | | | | 13.77% | | 8.78 | |
| PUR12 | 17.55% | 2.71% | | | 0.36% | 0.13% | 0.17% | 0.11% | | | 18.13% | 2.59% | 15.74 | 3.12 |
| RED08 | 11.03% | 1.13% | | | 1.37% | 0.62% | 0.22% | 0.08% | | | 12.67% | 1.66% | 18.37 | 3.05 |
| SIL04 | 19.18% | 2.47% | | | 0.55% | 0.13% | 0.25% | 0.22% | | | 20.04% | 2.42% | 8.81 | 0.59 |
| SIL06 | 14.39% | 1.33% | | | 0.39% | 0.04% | 0.25% | 0.07% | 0.16% | 0.11% | 12.10% | 6.03% | 17.52 | 1.07 |
| SIL08 | 20.75% | 2.44% | | | 0.32% | 0.16% | 0.37% | 0.24% | | | 21.55% | 2.33% | 13.24 | 2.96 |
| SIL03 | 16.70% | 1.32% | | | 0.10% | 0.03% | 0.22% | 0.15% | 0.15% | 0.01% | 17.20% | 1.49% | 13.88 | 2.55 |
| SIL02 | 19.67% | 3.46% | | | 0.07% | 0.04% | | | | | 13.27% | 13.04% | 7.54 | 7.34 |
| SIL01 | 18.25% | 2.53% | | | 0.57% | 0.03% | 0.38% | 0.32% | | | 19.12% | 2.63% | 14.00 | 1.73 |
| WHI07 | 19.31% | 2.48% | | | 0.24% | 0.04% | 0.21% | 0.09% | | | 19.82% | 2.46% | 10.83 | 1.19 |
| WHI04 | 19.76% | 0.77% | | | 0.64% | 0.20% | 0.40% | 0.27% | | | 20.87% | 0.63% | 16.01 | 5.74 |
| WHI09 | 18.99% | | | | 0.80% | | 0.11% | | | | 20.01% | | 18.77 | |
| WHI01 | 17.74% | 2.25% | | | 0.29% | 0.16% | 1.00% | 0.44% | | | 19.06% | 2.73% | 12.13 | 2.22 |
| WHI14 | 17.81% | 4.40% | | | 0.46% | 0.46% | 0.33% | 0.23% | | | 18.67% | 4.78% | 13.34 | 5.63 |
| WHI05 | 19.55% | | | | 0.55% | | 0.20% | | 0.04% | | 20.38% | | 20.84 | |
| WHI06 | 19.25% | | 0.03% | | 0.53% | | 3.97% | | | | 23.78% | | 13.65 | |

TABLE 7-continued

Cannabinoid measurement by HPLC for THC color class parental varieties. Blank values indicate undetectable levels, or 0.

| | Cannabinoids (UHPLC) | | | | | | | | | | Cannabs by HPLC | | Cannabs/Terps (HPLC) | |
|---|---|---|---|---|---|---|---|---|---|---|---|---|---|---|
| | THCA | | CBDA | | CBGA | | THC | | CBG | | | | | |
| Sample | Wt % | 95% CI | Wt % | 95% CI | Wt % | 95% CI | Wt % | 95% CI | Wt % | 95% CI | Wt % | 95% CI | Ratio | 95% CI |
| WHI02 | 22.19% | | | | 0.61% | | 0.15% | | | | 23.09% | | 16.34 | |
| YEL03 | 16.71% | 0.17% | | | 0.74% | 0.03% | 0.33% | 0.10% | | | 17.99% | 0.35% | 12.66 | 1.99 |
| YEL05 | 19.65% | 3.39% | | | 1.93% | 0.41% | 0.85% | 0.11% | | | 22.52% | 3.81% | 9.41 | 2.03 |
| YEL02 | 13.97% | 1.29% | | | 1.19% | 0.33% | 0.20% | 0.14% | | | 12.62% | 5.77% | 6.65 | 3.11 |

*LOQ for all cannabinoids was 0.14%.

TABLE 8

Absolute terpene measurements by GC-FID for THC color class parental varieties. Blank values indicate undetectable levels, or 0.

Terpenes (GC-FID)

| Sample | terpinolene Wt % | terpinolene 95% CI | alpha phellandrene Wt % | alpha phellandrene 95% CI | beta ocimene Wt % | beta ocimene 95% CI | carene Wt % | carene 95% CI | limonene Wt % | limonene 95% CI | gamma terpinene Wt % | gamma terpinene 95% CI | alpha pinene Wt % | alpha pinene 95% CI | alpha terpinene Wt % | alpha terpinene 95% CI | beta pinene Wt % | beta pinene 95% CI | fenchol Wt % | fenchol 95% CI |
|---|---|---|---|---|---|---|---|---|---|---|---|---|---|---|---|---|---|---|---|---|
| BLK01 | | | | | | | | | 0.310% | | | | 0.026% | | | | 0.054% | | 0.038% | |
| BLK02 | | | | | | | | | 0.230% | | | | 0.022% | | | | 0.044% | | 0.036% | |
| BLK03 | | | | | | | | | 0.262% | | | | 0.017% | | | | 0.037% | | 0.031% | |
| BLK04 | | | | | | | | | 0.277% | | | | 0.018% | | | | 0.042% | | 0.040% | |
| BLU04 | 0.014% | | | | | | | | 0.123% | | | | 0.499% | | | | 0.242% | | 0.019% | |
| BRO01 | | | | | 0.211% | 0.070% | | | | | | | 0.055% | 0.011% | | | 0.029% | 0.004% | | |
| BRO02 | | | | | 0.300% | 0.089% | | | | | | | 0.057% | 0.009% | | | 0.026% | 0.007% | | |
| FSC04 | 0.035% | | | | 0.109% | | | | 0.049% | | | | | | | | 0.020% | | | |
| FSC03 | | | | | | | | | 0.210% | 0.033% | | | 0.017% | 0.003% | | | 0.038% | 0.006% | 0.024% | 0.007% |
| FSC02 | 0.026% | | | | | | | | 0.257% | | | | 0.018% | | | | 0.041% | | 0.030% | |
| GOD13 | | | | | | | | | 0.706% | 0.040% | | | 0.063% | 0.004% | | | 0.128% | 0.007% | 0.072% | 0.002% |
| GOD03 | | | | | | | | | 0.699% | | | | 0.056% | | | | 0.107% | | 0.046% | |
| GOD02 | 0.014% | 0.009% | | | | | | | 0.599% | 0.256% | | | 0.050% | 0.019% | | | 0.098% | 0.036% | 0.055% | 0.035% |
| GOD11 | 0.009% | | | | | | | | 0.503% | | | | 0.044% | | | | 0.088% | | 0.042% | |
| GOD10 | 0.012% | | | | | | | | 0.675% | | | | 0.053% | | | | 0.104% | | 0.050% | |
| GRA07 | | | | | | | | | 0.332% | 0.047% | | | 0.030% | 0.005% | | | 0.071% | 0.009% | 0.045% | 0.003% |
| GRA31 | | | | | | | | | 0.102% | 0.032% | | | 0.143% | 0.062% | | | 0.081% | 0.031% | 0.015% | 0.000% |
| GRA04 | | | | | | | | | 0.087% | 0.008% | | | 0.083% | 0.011% | | | 0.049% | 0.001% | 0.012% | 0.007% |
| GRA05 | | | | | | | | | 0.113% | 0.036% | | | 0.238% | 0.063% | | | 0.118% | 0.028% | 0.014% | 0.006% |
| GRE09 | | | | | 0.129% | | | | 0.166% | | | | 0.027% | | | | 0.038% | | 0.017% | |
| GRE01 | | | | | 0.374% | 0.098% | | | 0.233% | 0.032% | | | 0.104% | 0.015% | | | 0.074% | 0.010% | 0.033% | 0.002% |
| JAD11 | | | 0.059% | | 0.017% | | 0.046% | | 0.091% | | 0.027% | | 0.060% | | 0.049% | | 0.108% | | | |
| JAD12 | | | 0.043% | | 0.018% | | 0.034% | | 0.064% | | 0.021% | | 0.047% | | 0.037% | | 0.084% | | | |
| JAD04 | | | 0.045% | | 0.023% | | 0.039% | | 0.070% | | 0.023% | | 0.057% | | 0.039% | | 0.100% | | | |
| ORA02 | 0.277% | 0.043% | 0.016% | 0.002% | 0.212% | 0.023% | 0.014% | 0.001% | 0.074% | 0.027% | 0.009% | 0.001% | 0.068% | 0.009% | 0.016% | 0.000% | 0.060% | 0.010% | 0.013% | 0.003% |
| ORA03 | 0.480% | 0.224% | 0.024% | 0.007% | | | 0.019% | 0.005% | 0.067% | 0.011% | 0.010% | 0.005% | 0.133% | 0.012% | 0.016% | 0.012% | 0.104% | 0.012% | | |
| PUR03 | | | | | 0.127% | 0.028% | | | 0.034% | 0.006% | | | 0.267% | 0.022% | | | 0.067% | 0.006% | | |
| PUR01 | | | | | 0.028% | 0.007% | | | 0.300% | 0.057% | | | 0.188% | 0.031% | | | 0.116% | 0.020% | 0.049% | 0.005% |
| PUR13 | | | | | 0.033% | 0.004% | | | 0.084% | 0.024% | | | 0.510% | 0.094% | | | 0.145% | 0.028% | | |
| PUR06 | | | | | | | | | 0.069% | 0.012% | | | 0.378% | 0.078% | | | 0.175% | 0.037% | 0.014% | 0.001% |
| PUR05 | | | | | 0.259% | 0.000% | | | 0.046% | 0.000% | | | 0.335% | 0.000% | | | 0.104% | 0.000% | | |
| PUR11 | | | | | 0.024% | | | | 0.063% | | | | 0.356% | | | | 0.095% | | | |
| PUR12 | | | | | | | | | 0.186% | | | | | | | | 0.167% | | | |
| RED08 | | | | | 0.188% | 0.051% | | | 0.166% | 0.056% | | | 0.186% | 0.070% | | | 0.101% | 0.040% | 0.022% | 0.010% |
| SIL04 | 0.011% | 0.001% | | | 0.114% | 0.027% | | | 0.132% | 0.019% | | | 0.130% | 0.046% | | | 0.116% | 0.025% | 0.029% | 0.010% |
| SIL06 | | | | | 0.106% | 0.016% | | | 0.702% | 0.031% | | | 0.073% | 0.022% | | | 0.051% | 0.009% | 0.094% | 0.007% |
| SIL08 | | | | | | | | | 0.296% | 0.031% | | | 0.055% | 0.007% | | | 0.074% | 0.009% | 0.051% | 0.007% |
|  | | | | | | | | | 0.572% | 0.151% | | | 0.053% | 0.014% | | | 0.106% | 0.028% | 0.068% | 0.025% |

TABLE 8-continued

Absolute terpene measurements by GC-FID for THC color class parental varieties. Blank values indicate undetectable levels, or 0.

Terpenes (GC-FID)

| Sample | camphene Wt % | 95% CI | alpha terpineol Wt % | 95% CI | alpha humulene Wt % | 95% CI | | | | | | | | |
|---|---|---|---|---|---|---|---|---|---|---|---|---|---|---|
| SIL03 | | | | | 0.393% | 0.064% | | | | | | | | |
| SIL02 | | | | | 0.590% | 0.118% | | | | | | | | |
| SIL01 | | | | | 0.403% | 0.018% | | | | | | | | |
| WHI07 | 0.050% | 0.013% | | | 0.581% | 0.153% | | | | | | | | |
| WHI04 | | | | | 0.443% | 0.237% | | | | | | | | |
| WHI09 | | | | | 0.311% | | | | | | | | | |
| WHI01 | | | | | 0.449% | 0.098% | | | | | | | | |
| WHI14 | | | | | 0.417% | 0.227% | | | | | | | | |
| WHI05 | | | | | 0.282% | | | | | | | | | |
| WHI06 | 0.017% | | | | 0.569% | | | | | | | | | |
| WHI02 | | | | | 0.391% | | | | | | | | | |
| YEL03 | 0.506% | 0.094% | 0.158% | 0.028% | 0.003% | 0.026% | 0.001% | 0.139% | 0.038% | | | | | |
| YEL05 | 1.033% | 0.211% | 0.287% | 0.050% | 0.011% | 0.040% | 0.007% | 0.139% | 0.151% | | | | | |
| YEL02 | 0.690% | 0.077% | 0.299% | 0.035% | 0.003% | 0.028% | 0.003% | 0.173% | 0.016% | | | | | |

Terpenes (GC-FID)

| Sample | beta caryophyllene Wt % | 95% CI | linalool Wt % | 95% CI | cary oxide Wt % | 95% CI | myrcene Wt % | 95% CI | Total identified oil (wt %) Wt % | 95% CI |
|---|---|---|---|---|---|---|---|---|---|---|
| SIL03 | | | 0.036% | 0.006% | | | 0.060% | 0.008% | 0.036% | 0.013% |
| SIL02 | | | 0.052% | 0.007% | | | 0.101% | 0.015% | 0.064% | 0.014% |
| SIL01 | | | 0.037% | 0.003% | | | 0.072% | 0.004% | 0.050% | 0.003% |
| WHI07 | 0.050% | | 0.071% | 0.014% | | | 0.095% | 0.018% | 0.056% | 0.006% |
| WHI04 | | | 0.034% | 0.015% | | | 0.064% | 0.028% | 0.034% | 0.024% |
| WHI09 | | | 0.026% | | | | 0.049% | | 0.027% | |
| WHI01 | | | 0.038% | 0.006% | | | 0.073% | 0.013% | 0.046% | 0.013% |
| WHI14 | | | 0.033% | 0.014% | | | 0.063% | 0.027% | 0.040% | 0.026% |
| WHI05 | | | 0.025% | | | | 0.047% | | 0.025% | |
| WHI06 | | | 0.041% | | | | 0.080% | | 0.054% | |
| WHI02 | | | 0.036% | | | | 0.065% | | 0.035% | |
| YEL03 | 0.022% | 0.004% | 0.049% | 0.001% | 0.018% | 0.003% | 0.076% | 0.003% | 0.066% | 0.107% |
| YEL05 | 0.017% | 0.001% | 0.063% | 0.018% | 0.042% | 0.007% | 0.109% | 0.033% | 0.026% | |
| YEL02 | | | 0.068% | 0.007% | 0.027% | 0.002% | 0.099% | 0.010% | 0.025% | 0.002% |

| Sample | camphene Wt % | 95% CI | alpha terpineol Wt % | 95% CI | alpha humulene Wt % | 95% CI |
|---|---|---|---|---|---|---|
| BLK01 | | | 0.044% | | 0.167% | |
| BLK02 | | | 0.040% | | 0.142% | |
| BLK03 | | | 0.040% | | 0.217% | |
| BLK04 | | | 0.046% | | 0.238% | |
| BLU04 | | | 0.043% | | 0.042% | |
| BRO01 | | | | | 0.017% | 0.009% |
| BRO02 | | | | | 0.024% | 0.001% |
| FSC04 | | | | | 0.168% | |
| FSC03 | | | 0.030% | 0.010% | 0.169% | 0.053% |
| FSC02 | | | 0.039% | | 0.230% | |
| GOD13 | | | 0.086% | 0.001% | 0.130% | 0.009% |
| GOD03 | | | 0.050% | | 0.129% | |
| GOD02 | 0.016% | 0.006% | 0.068% | 0.047% | 0.167% | 0.043% |
| GOD11 | 0.014% | | 0.048% | | 0.133% | |
| GOD10 | | | 0.060% | | 0.157% | |
| GRA07 | | | 0.050% | 0.003% | 0.049% | 0.014% |
| GRA31 | | | 0.035% | 0.015% | 0.016% | 0.002% |
| GRA04 | | | 0.016% | 0.016% | 0.014% | 0.002% |
| GRA05 | | | 0.020% | 0.012% | 0.047% | 0.008% |
| GRE09 | | | 0.019% | | 0.017% | |
| GRE01 | | | 0.047% | 0.007% | 0.087% | 0.007% |
| JAD11 | | | 0.044% | | 0.048% | |
| JAD12 | | | 0.034% | | 0.035% | |
| JAD04 | | | 0.033% | | 0.062% | |
| ORA02 | | | 0.025% | 0.007% | 0.062% | 0.015% |

| Sample | beta caryophyllene Wt % | 95% CI | linalool Wt % | 95% CI | cary oxide Wt % | 95% CI | myrcene Wt % | 95% CI | Total identified oil (wt %) Wt % | 95% CI |
|---|---|---|---|---|---|---|---|---|---|---|
| BLK01 | 0.460% | | 0.144% | | | | 0.177% | | 1.420% | |
| BLK02 | 0.406% | | 0.120% | | | | 0.137% | | 1.170% | |
| BLK03 | 0.603% | | 0.143% | | | | 0.115% | | 1.465% | |
| BLK04 | 0.689% | | 0.156% | | | | 0.161% | | 1.770% | |
| BLU04 | 0.122% | | 0.039% | | | | 0.200% | | 1.343% | |
| BRO01 | 0.043% | 0.024% | 0.053% | 0.012% | | | 1.073% | 0.180% | 1.480% | 0.285% |
| BRO02 | 0.080% | 0.035% | 0.046% | 0.014% | | | 0.624% | 0.182% | 1.161% | 0.335% |
| FSC04 | 0.465% | | 0.059% | | | | 1.026% | | 2.008% | |
| FSC03 | 0.451% | 0.121% | 0.071% | 0.016% | 0.000% | | 0.676% | 0.149% | 1.712% | 0.350% |
| FSC02 | 0.594% | | 0.076% | | 0.077% | | 1.005% | | 2.330% | |
| GOD13 | 0.465% | 0.032% | 0.181% | 0.027% | 0.017% | 0.001% | 0.931% | 0.019% | 2.812% | 0.144% |
| GOD03 | 0.440% | | 0.115% | | | | 0.511% | | 2.190% | |
| GOD02 | 0.392% | 0.172% | 0.139% | 0.077% | 0.018% | 0.012% | 0.593% | 0.037% | 2.406% | 0.749% |
| GOD11 | 0.464% | | 0.129% | | 0.012% | | 0.600% | | 2.086% | |
| GOD10 | 0.548% | | 0.149% | | | | 0.671% | | 2.509% | |
| GRA07 | 0.178% | 0.051% | 0.195% | 0.009% | | | 1.220% | 0.188% | 2.192% | 0.211% |
| GRA31 | 0.056% | 0.010% | 0.068% | 0.001% | | | 0.774% | 0.319% | 1.300% | 0.445% |
| GRA04 | 0.037% | 0.004% | 0.033% | 0.014% | | | 0.641% | 0.027% | 0.974% | 0.005% |
| GRA05 | 0.127% | 0.018% | 0.042% | 0.017% | | | 1.053% | 0.441% | 1.781% | 0.599% |
| GRE09 | 0.055% | | 0.027% | | | | 0.244% | | 0.750% | |
| GRE01 | 0.239% | 0.022% | 0.097% | 0.018% | | | 0.637% | 0.162% | 1.946% | 0.354% |
| JAD11 | 0.129% | | | | 0.088% | | 0.357% | | 2.454% | |
| JAD12 | 0.120% | | | | 0.100% | | 0.173% | | 1.726% | |
| JAD04 | 0.225% | | 0.022% | | 0.053% | | 0.213% | | 1.931% | |
| ORA02 | 0.144% | 0.039% | 0.024% | 0.007% | | | 0.352% | 0.074% | 1.368% | 0.164% |

TABLE 8-continued

Absolute terpene measurements by GC-FID for THC color class parental varieties. Blank values indicate undetectable levels, or 0.

Terpenes (GC-FID)

| | C1 | C2 | C3 | C4 | C5 | C6 | C7 | C8 | C9 | C10 | C11 | C12 | C13 |
|---|---|---|---|---|---|---|---|---|---|---|---|---|---|
| ORA03 | 0.032% | 0.006% | 0.021% | 0.002% | 0.063% | 0.004% | 0.037% | 0.006% | 0.029% | 0.677% | 0.207% | 1.695% | 0.505% |
| PUR03 | | | 0.089% | 0.011% | 0.337% | 0.035% | 0.111% | 0.022% | | 0.712% | 0.080% | 1.758% | 0.161% |
| PUR01 | 0.052% | 0.010% | 0.057% | 0.022% | 0.231% | 0.030% | 0.074% | 0.014% | | 0.604% | 0.143% | 1.711% | 0.301% |
| PUR13 | | | 0.077% | 0.017% | 0.199% | 0.047% | 0.045% | 0.010% | | 0.723% | 0.125% | 1.854% | 0.315% |
| PUR06 | 0.023% | | 0.058% | 0.005% | 0.178% | 0.010% | 0.061% | 0.009% | 0.009% | 0.669% | 0.208% | 1.609% | 0.339% |
| PUR05 | | | 0.109% | 0.000% | 0.419% | 0.000% | 0.183% | 0.000% | 0.002% | 1.520% | 0.000% | 3.053% | 0.000% |
| PUR11 | | | 0.046% | | 0.122% | | 0.030% | | | 0.630% | | 1.419% | |
| PUR13 | | | 0.080% | | 0.187% | | | | | 0.591% | | 1.567% | |
| PUR12 | | | 0.056% | 0.015% | 0.128% | 0.050% | 0.025% | 0.008% | | 0.527% | 0.239% | 1.197% | 0.431% |
| RED08 | 0.021% | 0.003% | 0.022% | 0.008% | 0.076% | 0.037% | 0.023% | 0.008% | | 0.022% | 0.012% | 0.708% | 0.173% |
| SIL04 | 0.092% | 0.003% | 0.138% | 0.005% | 0.487% | 0.004% | 0.213% | 0.025% | | 0.211% | 0.090% | 2.285% | 0.374% |
| SIL06 | 0.050% | 0.005% | 0.021% | 0.003% | 0.074% | 0.012% | 0.022% | 0.006% | | 0.088% | 0.018% | 0.852% | 0.092% |
| SIL08 | 0.065% | 0.028% | 0.055% | 0.009% | 0.185% | 0.033% | 0.268% | 0.091% | | 0.280% | 0.109% | 1.682% | 0.347% |
| SIL03 | 0.037% | 0.012% | 0.050% | 0.015% | 0.175% | 0.056% | 0.175% | 0.044% | | 0.256% | 0.039% | 1.260% | 0.233% |
| SIL02 | 0.072% | 0.020% | 0.097% | 0.016% | 0.372% | 0.047% | 0.221% | 0.017% | | 0.109% | 0.050% | 1.697% | 0.286% |
| SIL01 | 0.060% | 0.001% | 0.074% | 0.008% | 0.271% | 0.027% | 0.186% | 0.002% | | 0.189% | 0.030% | 1.365% | 0.039% |
| WHI07 | 0.071% | 0.015% | 0.157% | 0.022% | 0.585% | 0.101% | 0.054% | 0.019% | | 0.103% | 0.021% | 1.9% | 0.357% |
| WHI04 | 0.038% | 0.028% | 0.098% | 0.012% | 0.376% | 0.036% | 0.107% | 0.063% | | 0.131% | 0.006% | 1.3% | 0.443% |
| WHI09 | | | 0.127% | | 0.355% | | 0.035% | | | 0.106% | | 1.1% | |
| WHI01 | 0.048% | 0.016% | 0.190% | 0.117% | 0.507% | 0.314% | 0.142% | 0.121% | 0.019% | 0.275% | 0.075% | 1.7% | 0.571% |
| WHI14 | 0.053% | 0.023% | 0.152% | 0.046% | 0.420% | 0.135% | 0.017% | 0.007% | | 0.158% | 0.067% | 1.5% | 0.585% |
| WHI05 | 0.023% | | 0.098% | | 0.360% | | 0.055% | 0.013% | | 0.086% | | 1.0% | |
| WHI06 | 0.024% | 0.013% | 0.180% | | 0.502% | | 0.047% | | | 0.194% | | 1.7% | |
| WHI02 | | | 0.177% | | 0.487% | | | | | 0.135% | | 1.4% | |
| YEL03 | 0.030% | 0.013% | 0.031% | 0.010% | 0.110% | 0.034% | 0.025% | 0.007% | 0.033% | 0.157% | 0.025% | 1.438% | 0.209% |
| YEL05 | 0.040% | 0.011% | 0.090% | 0.073% | 0.260% | 0.256% | 0.054% | 0.005% | 0.048% | 0.182% | 0.063% | 2.399% | 0.112% |
| YEL02 | 0.045% | 0.003% | 0.036% | 0.002% | 0.137% | 0.008% | 0.059% | 0.005% | 0.000% | 0.218% | 0.026% | 1.957% | 0.174% |

*LOQ for all terpenes was 0.02% except for alpha-pinene, linalool, and alpha-terpineol which were 0.04%.

TABLE 9

Relative terpene levels as measured by GC-FID for THC color class parental varieties. Blank values indicate undetectable levels, or 0.

| Sample | terpinolene | alpha phellandrene | beta ocimene | carene | limonene | gamma terpinene | alpha pinene | alpha terpinene | beta pinene | fenchol | camphene | alpha terpineol | alpha humulene | beta caryophyllene | linalool | cary oxide | myrcene |
|---|---|---|---|---|---|---|---|---|---|---|---|---|---|---|---|---|---|
| BLK01 | 0% | 0% | 0% | 0% | 22% | 0% | 2% | 0% | 4% | 3% | 0% | 3% | 12% | 32% | 10% | 0% | 12% |
| BLK02 | 0% | 0% | 0% | 0% | 20% | 0% | 2% | 0% | 4% | 3% | 0% | 3% | 12% | 35% | 10% | 0% | 12% |
| BLK03 | 0% | 0% | 0% | 0% | 18% | 0% | 1% | 0% | 3% | 2% | 0% | 3% | 15% | 41% | 10% | 0% | 8% |
| BLK04 | 0% | 0% | 0% | 0% | 16% | 0% | 1% | 0% | 2% | 1% | 0% | 3% | 13% | 39% | 9% | 0% | 9% |
| BLU04 | 1% | 0% | 14% | 0% | 9% | 0% | 37% | 0% | 18% | 0% | 0% | 3% | 3% | 9% | 3% | 0% | 15% |
| BRO01 | 0% | 0% | 26% | 0% | 0% | 0% | 4% | 0% | 2% | 0% | 0% | 0% | 1% | 3% | 4% | 0% | 73% |
| BRO02 | 0% | 0% | 5% | 0% | 0% | 0% | 5% | 0% | 2% | 0% | 0% | 0% | 2% | 7% | 4% | 0% | 54% |
| FSC04 | 2% | 0% | 0% | 0% | 2% | 0% | 0% | 0% | 1% | 0% | 0% | 0% | 8% | 23% | 3% | 0% | 51% |
| FSC03 | 0% | 0% | 0% | 0% | 12% | 0% | 1% | 0% | 2% | 1% | 0% | 2% | 10% | 26% | 4% | 0% | 39% |
| FSC02 | 1% | 0% | 0% | 0% | 11% | 0% | 0% | 0% | 2% | 1% | 0% | 2% | 10% | 25% | 3% | 0% | 43% |
| GOD13 | 0% | 0% | 0% | 0% | 25% | 0% | 2% | 0% | 5% | 3% | 0% | 3% | 5% | 17% | 6% | 1% | 33% |
| GOD03 | 0% | 0% | 0% | 0% | 32% | 0% | 3% | 0% | 5% | 2% | 0% | 2% | 6% | 20% | 5% | 0% | 23% |
| GOD02 | 1% | 0% | 0% | 0% | 25% | 0% | 2% | 0% | 4% | 2% | 1% | 3% | 7% | 25% | 6% | 1% | 25% |
| GOD11 | 0% | 0% | 0% | 0% | 24% | 0% | 2% | 0% | 4% | 2% | 1% | 2% | 6% | 22% | 6% | 1% | 29% |
| GOD10 | 0% | 0% | 0% | 0% | 27% | 0% | 2% | 0% | 4% | 2% | 0% | 2% | 6% | 22% | 6% | 0% | 27% |
| GRA07 | 0% | 0% | 0% | 0% | 15% | 0% | 1% | 0% | 3% | 1% | 0% | 3% | 2% | 8% | 9% | 0% | 56% |
| GRA31 | 0% | 0% | 0% | 0% | 8% | 0% | 11% | 0% | 6% | 1% | 0% | 3% | 1% | 4% | 5% | 0% | 60% |
| GRA04 | 0% | 0% | 0% | 0% | 9% | 0% | 8% | 0% | 5% | 1% | 0% | 2% | 1% | 4% | 3% | 0% | 66% |
| GRA05 | 0% | 0% | 0% | 0% | 6% | 0% | 13% | 0% | 7% | 1% | 0% | 1% | 3% | 7% | 2% | 0% | 59% |
| GRE09 | 0% | 0% | 17% | 0% | 22% | 0% | 4% | 0% | 5% | 2% | 0% | 3% | 2% | 7% | 4% | 0% | 33% |
| GRE01 | 0% | 0% | 19% | 0% | 12% | 1% | 5% | 0% | 4% | 2% | 0% | 2% | 4% | 12% | 5% | 0% | 33% |
| JAD11 | 54% | 2% | 1% | 2% | 4% | 1% | 2% | 2% | 4% | 0% | 0% | 2% | 2% | 5% | 0% | 4% | 15% |
| JAD12 | 53% | 2% | 1% | 2% | 4% | 1% | 3% | 2% | 5% | 0% | 0% | 2% | 2% | 7% | 0% | 6% | 10% |
| JAD04 | 48% | 2% | 1% | 2% | 4% | 1% | 3% | 2% | 5% | 0% | 0% | 2% | 3% | 12% | 1% | 3% | 11% |
| ORA02 | 20% | 1% | 16% | 1% | 5% | 1% | 5% | 1% | 4% | 1% | 0% | 2% | 5% | 11% | 2% | 0% | 26% |
| ORA03 | 28% | 1% | 0% | 1% | 4% | 1% | 8% | 1% | 6% | 0% | 0% | 2% | 1% | 4% | 2% | 2% | 40% |
| PUR01 | 0% | 0% | 7% | 0% | 2% | 0% | 15% | 0% | 4% | 3% | 0% | 0% | 5% | 19% | 6% | 0% | 40% |
| PUR03 | 0% | 0% | 2% | 0% | 18% | 0% | 11% | 0% | 7% | 3% | 0% | 3% | 3% | 14% | 4% | 0% | 35% |
| PUR13 | 0% | 0% | 2% | 0% | 5% | 0% | 27% | 0% | 8% | 3% | 0% | 0% | 4% | 11% | 2% | 0% | 39% |
| PUR06 | 0% | 0% | 0% | 0% | 4% | 0% | 24% | 0% | 11% | 1% | 0% | 1% | 4% | 11% | 4% | 0% | 42% |
| PUR05 | 0% | 0% | 8% | 0% | 2% | 0% | 13% | 0% | 3% | 0% | 0% | 0% | 4% | 14% | 6% | 1% | 50% |
| PUR11 | 0% | 0% | 2% | 0% | 4% | 0% | 24% | 0% | 7% | 0% | 0% | 0% | 3% | 9% | 2% | 0% | 44% |
| PUR13 | 0% | 0% | 2% | 0% | 12% | 0% | 23% | 0% | 11% | 2% | 0% | 0% | 5% | 12% | 0% | 0% | 38% |
| PUR12 | 0% | 0% | 0% | 0% | 14% | 0% | 16% | 0% | 8% | 2% | 0% | 0% | 5% | 11% | 2% | 0% | 44% |
| RED08 | 0% | 0% | 27% | 0% | 19% | 0% | 18% | 0% | 7% | 4% | 0% | 4% | 3% | 11% | 3% | 0% | 3% |
| SIL04 | 0% | 0% | 5% | 0% | 31% | 0% | 3% | 0% | 5% | 4% | 1% | 4% | 6% | 21% | 9% | 0% | 9% |
| SIL06 | 0% | 0% | 12% | 0% | 35% | 0% | 6% | 0% | 9% | 6% | 0% | 6% | 2% | 9% | 3% | 0% | 10% |
| SIL08 | 0% | 0% | 0% | 0% | 34% | 0% | 3% | 0% | 6% | 4% | 0% | 4% | 3% | 11% | 16% | 0% | 17% |
| SIL03 | 0% | 0% | 0% | 0% | 31% | 0% | 3% | 0% | 5% | 3% | 0% | 3% | 4% | 14% | 14% | 0% | 20% |
| SIL02 | 0% | 0% | 0% | 0% | 35% | 0% | 3% | 0% | 6% | 4% | 0% | 4% | 6% | 22% | 13% | 0% | 6% |
| SIL01 | 0% | 0% | 3% | 0% | 30% | 0% | 3% | 0% | 5% | 4% | 0% | 4% | 5% | 20% | 14% | 0% | 14% |
| WHI07 | 0% | 0% | 0% | 0% | 31% | 3% | 4% | 0% | 5% | 3% | 0% | 4% | 8% | 31% | 3% | 0% | 6% |
| WHI04 | 0% | 0% | 0% | 0% | 33% | 0% | 2% | 0% | 5% | 3% | 0% | 3% | 7% | 28% | 8% | 0% | 10% |
| WHI09 | 0% | 0% | 0% | 0% | 29% | 0% | 2% | 0% | 5% | 3% | 0% | 0% | 12% | 33% | 3% | 0% | 10% |

TABLE 9-continued

Relative terpene levels as measured by GC-FID for THC color class parental varieties. Blank values indicate undetectable levels, or 0.

| Sample | terpinolene | alpha phellandrene | beta ocimene | carene | limonene | gamma terpinene | alpha pinene | alpha terpinene | beta pinene | fenchol | camphene | alpha terpineol | alpha humulene | beta caryophyllene | linalool | cary oxide | myrcene |
|---|---|---|---|---|---|---|---|---|---|---|---|---|---|---|---|---|---|
| WHH01 | 0% | 0% | 0% | 0% | 27% | 0% | 2% | 0% | 4% | 3% | 0% | 3% | 11% | 31% | 0% | 0% | 17% |
| WHH14 | 0% | 0% | 0% | 0% | 28% | 0% | 2% | 0% | 4% | 3% | 0% | 4% | 10% | 28% | 10% | 1% | 11% |
| WHH05 | 0% | 0% | 0% | 0% | 29% | 0% | 3% | 0% | 5% | 3% | 0% | 2% | 10% | 37% | 2% | 1% | 9% |
| WHH06 | 1% | 0% | 0% | 0% | 33% | 0% | 2% | 0% | 5% | 3% | 1% | 1% | 10% | 29% | 3% | 1% | 11% |
| WHH02 | 0% | 0% | 0% | 0% | 28% | 0% | 3% | 0% | 5% | 2% | 0% | 0% | 13% | 34% | 2% | 0% | 10% |
| YEL03 | 35% | 2% | 11% | 2% | 10% | 0% | 3% | 1% | 5% | 5% | 0% | 2% | 2% | 8% | 2% | 0% | 11% |
| YEL05 | 43% | 2% | 12% | 2% | 6% | 1% | 3% | 2% | 5% | 1% | 0% | 2% | 4% | 11% | 0% | 1% | 8% |
| YEL02 | 35% | 2% | 15% | 1% | 9% | 1% | 3% | 1% | 5% | 1% | 0% | 2% | 2% | 7% | 3% | 0% | 11% |

Example 4

Analysis of CBs Parental Varieties

A. Proprietary CBs Parental Varieties

One objective of the present invention was to develop *cannabis* varieties producing non-THC cannabinoids (CBs) with high terpene oil contents and different terpene profiles to meet various aroma/flavor and medicinal needs. Chemical analysis of these CBs varieties was conducted as described in Example 1. The cannabinoid and terpene profiles of each CBs parental variety was determined using both GC-FID and HPLC as described in Example 1. The resulting measurements are summarized in Tables 10-22 as average values and 95% confidence interval ranges based on five replicate measurements. The GC-FID cannabinoid analysis of the CBD parental varieties in Table 10 also included measurements for THCV, CBDV, CBGV, CBN, and Delta 8 THC, all of which were measured to be less than 0.01%, and were therefore not included in the table. Similarly, the HPLC cannabinoid analysis of the CBD parental varieties in Table 11 included measurements for CBCA, THCVA, CBDVA, CBGVA, CBC, THCV, CBDV, CBGV, and CBN, all of which were measured to be less than 0.01%, and were therefore not included in the table.

As can be seen in Tables 10 and 11, CBD01, 24, 11, and 13 are chemotype III varieties, with a $B_D/B_D$ genotype responsible for producing CBD, or CBDA (as measured by HPLC). The other parental CBD lines (CBD02-05), have been bred to be chemotype II plants with $B_T/B_D$ genotypes producing both THC and CBD. These proprietary lines were bred for more desirable terpene profiles through multiple rounds of crosses with THC class varieties and selfing to obtain desired genetics. CBD05 exhibits several desirable features such as the production of both THC and CBD, as well as a terpene profile that is not dominated by myrcene (Table 13).

THCV-producing parental line THV01 was also bred for its ability to produce propyl CBGV. THV01 does not accumulate CBGV due to its conversion to THCV by THC synthase. The GC-FID cannabinoid analysis of the THV01 parental line in Table 14 also included measurements for CBDV, CBGV, CBN, and Delta 8 THC, all of which were measured to be less than 0.01%, and were therefore not included in the table. Similarly, the HPLC cannabinoid analysis of the THV01 parental line in Table 15 included measurements for CBDA, CBCA, CBDVA, CBGVA, CBD, CBC, THCV, CBDV, CBGV, CBN, and delta 8 THC, all of which were measured to be 0, and were therefore not included in the table. CBGV is produced by combining divarinic acid and geranylpyrophosphate. This is regulated by locus A which can encode for enzymes to generate pentyl CBG ($A_{pe}$) or propyl CBGV ($A_{pr}$) (De Meijer et al. 2009 *Euphytica*, 165: 293-31). Thus if crossed with a CBD producing chemotype II plant, the THCV locus A is expected to produce both THCV and CBDV. As can be seen in Tables 14 and 15, the parental THV01 line contains at least one allele encoding for propyl cannabinoids with THC and THCV cannabinoids accumulating at roughly equal amounts. The alleles of locus B appear to be $B_T/B_T$ with no significant accumulation of CBD. Further, these THC synthase genes appear to be functioning efficiently converting nearly all CBG and CBGV into THC and THCV respectively. In some embodiments, the THV01 parental line may be crossed with class varieties to produce THCV producing specialty *cannabis* with desirable terpene profiles. In other embodiments of the present invention, the THV01 parental line can be crossed with chemotype II varieties to produce THCV and CBDV cannabinoids. In yet other embodiments, the THV01 parental line can be crossed with CBG accumulating varieties described to produce CBGV accumulating plants.

The present invention also teaches the use of two sources of CBG genetics. The first set of CBG-producing parental lines are plants BLK02, GOD11, GRE01, RED08, and YEL05 of the THC parentals in Table 6. While not wishing to be bound by any one theory, the inventors of the present invention believe that the CBG produced by these plants is due to the incomplete processing of CBG by the THC and CBD synthase enzymes. This may be caused by an over production of CBG, or the inefficient processing of the THC synthase enzymes of the plant. Progeny of these parental lines are expected to produce low levels of CBG in combination with other cannabinoids and desirable terpene profiles.

B. Additional CBs Parental Varieties

Another source of CBG-producing parental lines is CBG variety CBG02 in Table 18. While not wishing to be bound by any one theory, the inventors of the present invention believe that the CBG accumulation in this variety is due to the presence of a null allele ($B_o$). Progeny of these parental varieties are expected to produce higher levels of CBG, alone, or in combination with other cannabinoids and desirable terpene profiles. The HPLC cannabinoid analysis of the CBG02 parental line in Table 19 included measurements for CBDA, CBCA, THCVA, CBDVA, CBGVA, CBD, CBC, THCV, CBDV, CBGV, CBN, and delta 8 THC, all of which were measured to be less than 0.09, and were therefore not included in the table.

A CBC parental variety will be obtained by screening plants for CBC accumulation in mature tissue. While it is believed that CBC biosynthesis is a feature of juvenile tissue, several reports have published reports suggesting the existence of *cannabis* varieties accumulating CBC in older tissue (De Meijer et al., 2009 "The inheritance of chemical phenotype in *Cannabis sativa* L. (III): variation in cannabichromene proportion"). Table 22 outlines some of the publications describing varieties with CBC accumulation that will be analyzed for high CBC accumulation. The best varieties identified through chemical and phenotypical analysis will be designated as CBC01-CBC05.

TABLE 10

Cannabinoid measurement by GC-FID for CBD parental varieties. Blank values indicate undetectable levels or 0.

| | Cannabinoids (GC-FID) | | | | | | | | | | | | | Cannabs by GC | | THC:CBD by GC | | Cannabs/Terps (GC) | |
| | THC | | CBD | | CBG | | CBC | | | | | | | | | | | |
| Sample | Wt % | 95% CI | Wt % | 95% CI | Wt % | 95% CI | Wt % | 95% CI | Wt % | 95% CI | Wt % | 95% CI | Ratio | 95% CI |
|---|---|---|---|---|---|---|---|---|---|---|---|---|---|---|
| CBD01 | 0.42% | 0.08% | 11.13% | 0.01% | 0.41% | 0.10% | 0.60% | 0.05% | 12.56% | 0.23% | 0.04 | 0.01 | 5.33 | 0.36 |
| CBD03 | 3.48% | 0.73% | 6.77% | 1.37% | 0.27% | 0.06% | 0.46% | 0.06% | 10.99% | 2.19% | 0.51 | 0.04 | 11.90 | 2.19 |
| CBD02 | 1.96% | 1.78% | 4.53% | 3.98% | | | 0.35% | 0.28% | 7.08% | 6.36% | 0.43 | 0.02 | 3.81 | 3.37 |
| CBD05 | 4.13% | 0.36% | 7.99% | 0.75% | 0.30% | 0.08% | 0.55% | 0.05% | 12.96% | 0.56% | 0.52 | 0.09 | 8.06 | 1.21 |

TABLE 10-continued

Cannabinoid measurement by GC-FID for CBD parental varieties. Blank values indicate undetectable levels or 0.

| | Cannabinoids (GC-FID) | | | | | | | | | | | | | |
|---|---|---|---|---|---|---|---|---|---|---|---|---|---|---|
| | THC | | CBD | | CBG | | CBC | | Cannabs by GC | | THC:CBD by GC | | Cannabs/Terps (GC) | |
| Sample | Wt % | 95% CI | Wt % | 95% CI | Wt % | 95% CI | Wt % | 95% CI | Wt % | 95% CI | Wt % | 95% CI | Ratio | 95% CI |
| CBD04 | 5.24% | | 5.74% | | 0.16% | | 0.44% | | 11.65% | | 0.91 | | 13.19 | |
| CBD24 | 0.19% | | 8.03% | | 0.19% | | 0.47% | | 8.87% | | 0.02 | | 9.01 | |
| CBD011 | 0.18% | | 6.03% | | 0.10% | | 0.47% | | 6.78% | | 0.03 | | 7.76 | |
| CBD13 | 0.25% | | 8.20% | | 0.14% | | 0.59% | | 9.18% | | 0.03 | | 4.03 | |

*LOQ for all cannabinoids was 0.14%.

TABLE 11

Cannabinoid measurement by HPLC for CBD parental varieties. Blank values indicate undetectable levels or 0.

| | Cannabinoids (UHPLC) | | | | | | | | | |
|---|---|---|---|---|---|---|---|---|---|---|
| | THCA | | CBDA | | CBGA | | THC | | CBD | |
| Sample | Wt % | 95% CI | Wt % | 95% CI | Wt % | 95% CI | Wt % | 95% CI | Wt % | 95% CI |
| CBD01 | 0.38% | 0.13% | 14.87% | 0.05% | 0.50% | 0.17% | 0.05% | 0.06% | 0.43% | 0.06% |
| CBD03 | 4.30% | 1.05% | 9.48% | 1.92% | 0.34% | 0.06% | 0.15% | 0.09% | 0.13% | 0.03% |
| CBD02 | 2.27% | 1.94% | 6.22% | 5.39% | 1.18% | | 0.60% | | 0.42% | |
| CBD05 | 5.24% | 0.19% | 10.77% | 0.83% | 0.30% | 0.14% | 0.20% | 0.13% | 0.14% | 0.02% |
| CBD04 | 8.32% | | 7.53% | | 0.23% | | 0.48% | | 0.16% | |
| CBD24 | 0.24% | | 14.92% | | 0.38% | | 0.03% | | 0.14% | |
| CBD11 | 0.15% | | 10.29% | | 0.14% | | 0.32% | | 0.32% | |
| CBD13 | 0.23% | | 13.67% | | 0.21% | | 0.76% | | 0.36% | |

| | Cannabinoids (UHPLC) | | | | Cannabs by | | THCA:CBDA | | Cannabs/ | |
|---|---|---|---|---|---|---|---|---|---|---|
| | CBG | | D8-THC | | HPLC | | by HPLC | | Terps (HPLC) | |
| Sample | Wt % | 95% CI | Wt % | 95% CI | Wt % | 95% CI | Wt % | 95% CI | Ratio | 95% CI |
| CBD01 | | | 0.16% | | 16.34% | 0.26% | 0.03 | 0.01 | 6.94 | 0.48 |
| CBD03 | | | | | 14.33% | 2.76% | 0.45 | 0.03 | 15.55 | 2.97 |
| CBD02 | | | | | 9.35% | 8.66% | 0.37 | 0.00 | 5.04 | 4.59 |
| CBD05 | | | 0.11% | 0.02% | 16.76% | 0.74% | 0.49 | 0.04 | 10.41 | 1.53 |
| CBD04 | | | | | 16.71% | | 1.10 | | 18.93 | |
| CBD24 | | | | | 15.71% | | 0.02 | | 15.97 | |
| CBD11 | 0.32% | | | | 11.54% | | 0.01 | | 13.20 | |
| CBD13 | 0.04% | | | | 15.27% | | 0.02 | | 6.70 | |

*LOQ for all cannabinoids was 0.14%.

TABLE 12

Absolute terpene measurements by GC-FID for CBD parental varieties. Blank values indicate undetectable levels or 0.

| | Terpenes (GC-FID) | | | | | | | | | | | | | |
|---|---|---|---|---|---|---|---|---|---|---|---|---|---|---|
| | terpinolene | | alpha phellandrene | | beta ocimene | | carene | | limonene | | gamma terpinene | | alpha pinene | |
| Sample | Wt % | 95% CI | Wt % | 95% CI | Wt % | 95% CI | Wt % | 95% CI | Wt % | 95% CI | Wt % | 95% CI | Wt % | 95% CI |
| CBD01 | | | | | | | | | 0.086% | 0.011% | | | 0.447% | 0.087% |
| CBD03 | | | | | | | | | 0.061% | 0.017% | | | 0.213% | 0.078% |
| CBD02 | | | | | | | | | 0.119% | 0.037% | | | 0.421% | 0.173% |
| CBD05 | | | | | 0.122% | 0.071% | | | 0.073% | 0.016% | | | 0.458% | 0.101% |
| CBD04 | | | | | | | | | 0.189% | | | | | |
| CBD24 | | | | | | | | | 0.167% | | | | 0.013% | |
| CBD11 | | | | | | | | | 0.157% | | | | 0.009% | |
| CBD13 | | | | | | | | | 0.179% | | | | 0.186% | |

TABLE 12-continued

Absolute terpene measurements by GC-FID for CBD parental varieties. Blank values indicate undetectable levels or 0.

| | Terpenes (GC-FID) | | | | | | | | | | | |
|---|---|---|---|---|---|---|---|---|---|---|---|---|
| | alpha terpinene | | beta pinene | | fenchol | | camphene | | alpha terpineol | | alpha humulene | |
| Sample | Wt % | 95% CI | Wt % | 95% CI | Wt % | 95% CI | Wt % | 95% CI | Wt % | 95% CI | Wt % | 95% CI |
| CBD01 | | | 0.195% | 0.024% | 0.015% | | | | 0.026% | | | |
| CBD03 | | | 0.085% | 0.029% | 0.016% | 0.001% | | | 0.023% | 0.001% | 0.027% | 0.008% |
| CBD02 | | | 0.182% | 0.068% | | | | | 0.027% | | 0.046% | 0.015% |
| CBD05 | | | 0.119% | 0.019% | 0.229% | | | | | | 0.090% | 0.015% |
| CBD04 | | | 0.027% | | 0.025% | | | | 0.049% | | 0.068% | |
| CBD24 | | | 0.030% | | 0.018% | | | | 0.023% | | 0.042% | |
| CBD11 | | | 0.021% | | 0.013% | | | | 0.044% | | 0.016% | |
| CBD13 | | | 0.100% | | 0.014% | | | | 0.063% | | 0.062% | |

| | Terpenes (GC-FID) | | | | | | | | Total | |
|---|---|---|---|---|---|---|---|---|---|---|
| | beta caryophyllene | | linalool | | cary oxide | | myrcene | | identified oil (wt %) | |
| Sample | Wt % | 95% CI | Wt % | 95% CI | Wt % | 95% CI | Wt % | 95% CI | Wt % | 95% CI |
| CBD01 | 0.269% | 0.003% | 0.029% | | 0.131% | 0.001% | 1.122% | 0.012% | 2.360% | 0.202% |
| CBD03 | 0.077% | 0.022% | 0.034% | 0.005% | 0.030% | 0.005% | 0.419% | 0.097% | 0.949% | 0.204% |
| CBD02 | 0.146% | 0.020% | 0.049% | | 0.054% | | 0.877% | 0.208% | 1.841% | 0.139% |
| CBD05 | 0.234% | 0.048% | 0.092% | 0.049% | 0.014% | | 0.358% | 0.152% | 1.635% | 0.331% |
| CBD04 | 0.216% | | 0.065% | | | | 0.230% | | 0.883% | |
| CBD24 | 0.131% | | 0.057% | | | | 0.503% | | 0.984% | |
| CBD11 | 0.060% | | 0.028% | | | | 0.526% | | 0.874% | |
| CBD13 | 0.204% | | 0.022% | | | | 1.450% | | 2.280% | |

*LOQ for all terpenes was 0.02% except for alpha-pinene, linalool, and alpha-terpineol which were 0.04%.

TABLE 13

Relative terpene levels as measured by GC-FID for CBD parental varieties. Blank values indicate undetectable levels or 0.

| | Terpenes | | | | | | | | |
|---|---|---|---|---|---|---|---|---|---|
| Sample | terpinolene | alpha phellandrene | beta ocimene | carene | limonene | gamma terpinene | alpha pinene | alpha terpinene | beta pinene |
| CBD1 | | | | | 4% | | 19% | | 8% |
| CBD3 | | | | | 6% | | 22% | | 9% |
| CBD2 | | | | | 6% | | 23% | | 10% |
| CBD5 | | | 7% | | 4% | | 28% | | 7% |
| CBD4 | | | | | 21% | | | | 3% |
| CBD24 | | | | | 17% | | 1% | | 3% |
| CBD11 | | | | | 18% | | 1% | | 2% |
| CBD13 | | | | | 8% | | 8% | | 4% |

| | Terpenes | | | | | | | |
|---|---|---|---|---|---|---|---|---|
| Sample | fenchol | camphene | alpha terpineol | alpha humulene | beta caryophyllene | linalool | cary oxide | myrcene |
| CBD1 | 1% | | 1% | | 11% | 1% | 6% | 48% |
| CBD3 | 2% | | 2% | 3% | 8% | 4% | 3% | 44% |
| CBD2 | | | 1% | 2% | 8% | 3% | 3% | 48% |
| CBD5 | 14% | | | 5% | 14% | 6% | 1% | 22% |
| CBD4 | 3% | | 6% | 8% | 24% | 7% | | 26% |
| CBD24 | 2% | | 2% | 4% | 13% | 6% | | 51% |
| CBD11 | 1% | | 5% | 2% | 7% | 3% | | 60% |
| CBD13 | 1% | | 3% | 3% | 9% | 1% | | 64% |

TABLE 14

Cannabinoid measurement by GC-FID for THCV parental varieties.
Blank values indicate undetectable levels.

| | Cannabinoids (GC-FID) | | | | | | | | | | | | | | | |
|---|---|---|---|---|---|---|---|---|---|---|---|---|---|---|---|---|
| | THC | | CBD | | CBG | | CBC | | THCV | | Cannabs by GC | | THC:THCV by GC | | Cannabs/Terps (GC) | |
| Sample | Wt % | 95% CI | Wt % | 95% CI | Wt % | 95% CI | Wt % | 95% CI | Wt % | 95% CI | Wt % | 95% CI | Wt % | 95% CI | Wt % | 95% CI |
| THV01 | 4.52% | 3.22% | 0.01% | | 0.56% | 0.39% | 0.05% | 0.03% | 3.27% | 1.81% | 8.40% | 5.46% | 1.35 | 0.24 | 5.36 | 2.33 |

*LOQ for all cannabinoids was 0.14%.

TABLE 15

Cannabinoid measurement by HPLC for THCV parental varieties. Blank values indicate undetectable levels, or 0.

| | Cannabinoids (UHPLC) | | | | | | | | | | | | | | |
|---|---|---|---|---|---|---|---|---|---|---|---|---|---|---|---|
| | THCA | | CBGA | | THCVA | | THC | | CBG | | Cannabs by HPLC | | THCA:THCVA by HPLC | | Cannabs/Terps (HPLC) |
| Sample | Wt % | 95% CI | Wt % | 95% CI | Wt % | 95% CI | Wt % | 95% CI | Wt % | 95% CI | Wt % | 95% CI | Wt % | 95% CI | Wt % 95% CI |
| THV01 | 4.05% | 0.58% | 3.85% | 0.22% | | | | | 0.06% | | 4.38% | 8.58% | 1.05 | | 6.50 |

*LOQ for all cannabinoids was 0.14%.

TABLE 16

Absolute terpene measurements by GC-FID for THCV parental varieties. Blank values indicate undetectable levels or 0.

| | Terpenes (GC-FID) | | | | | | | | | | | | | |
|---|---|---|---|---|---|---|---|---|---|---|---|---|---|---|
| | terpinolene | | alpha phellandrene | | beta ocimene | | carene | | limonene | | gamma terpinene | | alpha pinene | |
| Sample | Wt % | 95% CI | Wt % | 95% CI | Wt % | 95% CI | Wt % | 95% CI | Wt % | 95% CI | Wt % | 95% CI | Wt % | 95% CI |
| THV01 | | | | | 0.297% | 0.008% | | | 0.192% | 0.031% | | | 0.063% | 0.028% |

| | Terpenes (GC-FID) | | | | | | | | | | | |
|---|---|---|---|---|---|---|---|---|---|---|---|---|
| | alpha terpinene | | beta pinene | | fenchol | | camphene | | alpha terpineol | | alpha humulene | |
| Sample | Wt % | 95% CI | Wt % | 95% CI | Wt % | 95% CI | Wt % | 95% CI | Wt % | 95% CI | Wt % | 95% CI |
| THV01 | | | 0.039% | 0.013% | 0.023% | 0.009% | | | 0.029% | 0.012% | 0.086% | 0.028% |

| | Terpenes (GC-FID) | | | | | | | | Total identified oil (wt %) | |
|---|---|---|---|---|---|---|---|---|---|---|
| | beta caryophyllene | | linalool | | cary oxide | | myrcene | | | |
| Sample | Wt % | 95% CI | Wt % | 95% CI | Wt % | 95% CI | Wt % | 95% CI | Wt % | 95% CI |
| THV01 | 0.175% | 0.098% | 0.029% | 0.012% | | | 0.597% | 0.115% | 1.528% | 0.354% |

TABLE 17

Relative terpene levels as measured by GC-FID for THCV parental varieties.
Blank values indicate undetectable levels or 0.

| | Terpenes | | | | | | | | |
|---|---|---|---|---|---|---|---|---|---|
| Sample | terpinolene | alpha phellandrene | beta ocimene | carene | limonene | gamma terpinene | alpha pinene | alpha terpinene | beta pinene |
| THV01 | | | 19% | | 13% | | 4% | | 3% |

| | Terpenes | | | | | | | |
|---|---|---|---|---|---|---|---|---|
| Sample | fenchol | camphene | alpha terpineol | alpha humulene | beta caryophyllene | linalool | cary oxide | myrcene |
| THV01 | 1% | | 2% | 6% | 11% | 2% | | 39% |

TABLE 18

Cannabinoid measurement by GC-FID for CBG parental varieties.
Blank values indicate undetectable levels or 0.

| | Cannabinoids (GC-FID) | | | | | | | | | | | |
|---|---|---|---|---|---|---|---|---|---|---|---|---|
| | THC | | CBD | | CBG | | CBC | | THCV | | CBDV | |
| Sample | Wt % | 95% CI | Wt % | 95% CI | Wt % | 95% CI | Wt % | 95% CI | Wt % | 95% CI | Wt % | 95% CI |
| CBG02 | 8.41% | | | 0.02% | 2.66% | | 0.17% | | | | | |

| | Cannabinoids (GC-FID) | | | | | | Cannabs by GC | | THC:CBG by GC | | Cannabs/Terps (GC) | |
|---|---|---|---|---|---|---|---|---|---|---|---|---|
| | CBGV | | CBN | | D8-THC | | | | | | | |
| Sample | Wt % | 95% CI | Wt % | 95% CI | Wt % | 95% CI | Wt % | 95% CI | Wt % | 95% CI | Wt % | 95% CI |
| CBG02 | | 0.15% | | | | | 11.40% | | 3.16 | | 13.13 | |

TABLE 19

Cannabinoid measurement by HPLC for CBG parental varieties. Blank values indicate undetectable levels or 0.

| | Cannabinoids (UHPLC) | | | | | | | | Cannabs by HPLC | | THCA:CBGA by HPLC | | Cannabs/Terps (HPLC) | |
|---|---|---|---|---|---|---|---|---|---|---|---|---|---|---|
| | THCA | | CBGA | | THC | | CBG | | | | | | | |
| Sample | Wt % | 95% CI | Wt % | 95% CI | Wt % | 95% CI | Wt % | 95% CI | Wt % | 95% CI | Wt % | 95% CI | Wt % | 95% CI |
| CBG02 | 8.84% | | 3.89% | | 2.59% | | 0.35% | | 15.75% | | 2.27 | | 18.15 | |

*LOQ for all cannabinoids was 0.14%.

TABLE 20

Absolute terpene measurements by GC-FID for CBG parental varieties.
Blank values indicate undetectable levels or 0.

| | Terpenes (GC-FID) | | | | | | | | | |
|---|---|---|---|---|---|---|---|---|---|---|
| | terpinolene | | alpha phellandrene | | beta ocimene | | carene | | limonene | | gamma terpinene |
| Sample | Wt % | 95% CI | Wt % | 95% CI | Wt % | 95% CI | Wt % | 95% CI | Wt % | 95% CI | Wt % | 95% CI |
| CBG02 | | | | | 0.267% | | | | 0.030% | | | |

TABLE 20-continued

Absolute terpene measurements by GC-FID for CBG parental varieties.
Blank values indicate undetectable levels or 0.

| | Terpenes (GC-FID) | | | | | | | | | | | |
|---|---|---|---|---|---|---|---|---|---|---|---|---|
| | alpha pinene | | alpha terpinene | | beta pinene | | fenchol | | camphene | | alpha terpineol | |
| Sample | Wt % | 95% CI | Wt % | 95% CI | Wt % | 95% CI | Wt % | 95% CI | Wt % | 95% CI | Wt % | 95% CI |
| CBG02 | 0.066% | | | | 0.026% | | | | | | | |

| | Terpenes (GC-FID) | | | | | | | | | | Total identified oil (wt %) | |
|---|---|---|---|---|---|---|---|---|---|---|---|---|
| | alpha humulene | | beta caryophyllene | | linalool | | cary oxide | | myrcene | | | |
| Sample | Wt % | 95% CI | Wt % | 95% CI | Wt % | 95% CI | Wt % | 95% CI | Wt % | 95% CI | Wt % | 95% CI |
| CBG02 | 0.076% | | 0.200% | | 0.059% | | | | 0.144% | | 0.868% | |

*LOQ for all terpenes was 0.02% except for alpha-pinene, linalool, and alpha-terpineol which were 0.04%.

TABLE 21

Relative terpene levels as measured by GC-FID for CBG parental varieties.
Blank values indicate undetectable levels or 0.

| | Terpenes | | | | | | | | |
|---|---|---|---|---|---|---|---|---|---|
| Sample | terpinolene | alpha phellandrene | beta ocimene | carene | limonene | gamma terpinene | alpha pinene | alpha terpinene | beta pinene |
| CBG02 | | | 31% | | 3% | | 8% | | 3% |

| | Terpenes | | | | | | | |
|---|---|---|---|---|---|---|---|---|
| Sample | fenchol | camphene | alpha terpineol | alpha humulene | beta caryophyllene | linalool | cary oxide | myrcene |
| CBG02 | | | 9% | 23% | 7% | | | 17% |

TABLE 22

Sources of CBC parental varieties.
Reference for Cannabis Varieties Accumulating CBC Baker, PB et al., (1983) "The Physical and chemical features of *Cannabis* plants grown in the United Kingdom of Great Britain and Northern Ireland from seeds of known origin-Part II: second generation studies." Bull Narc 35: 51-62.
Beutler JA, and Der Marderosian AH (1978) "Chemotaxonomy of *Cananbis* I. Crossbreeding between *Cannabis sativa* and *C. ruderalis*, with analysis of cannabinoid content." Econ Bot 32: 387-394.
Yotoriyama, M et al., (1980) "Plant breeding of *Cannabis*. Determination of cannabinoids by high-pressure liquid chromatography." Yakugaku Zasshi 100: 611-614.
Holley et al., (1975) "Contituents of *Cannabis sativa* L. XI: cannabidiol and cannabichromene in samples of known geographical origin." J Pharm Sci 64: 892-894.

Example 5

Breeding Scheme for New Specialty Cannabis Varieties

In another objective of the present invention, the *cannabis* varieties of Examples 2-4 are used in *cannabis* breeding programs to develop specialty *cannabis* plants and varieties. Furthermore, the specialty *cannabis* varieties developed according to the present invention have specific aromas, flavor(s), and entourage effects in accordance with one of the classes of *cannabis* varieties as discussed above.

This approach was designed in part, as a response to the fact that currently available *cannabis* varieties have been skewed towards higher THC production, which has increased the likelihood of adverse effects from the elevated levels of psychoactivity that these conventional high-THC varieties produce.

Contemporary "recreational" marijuana cultivars have been exclusively bred and selected primarily for their THC acid content, secondarily (if at all) for their terpenoid aroma and flavor chemistry, and rarely for their production of the other cannabinoid acids, such as CBDA.

Cannabidiol (CBD), a cannabinoid that is rare in contemporary *cannabis* varieties, has been shown to reduce and modulate the psychoactivity of THC and also reduce some of THC's other adverse effects including tachycardia, anxiety, memory effects, etc. There is some evidence that CBD may reduce the buildup of tolerance to the effects of THC and also reduce the likelihood of *cannabis* dependency. Other cannabinoids (CBs) such as CBDv, THCv, CBG, CBN, etc have also recently been demonstrated to have a variety of medical and recreational uses.

In some embodiments, the breeding programs of the present invention were designed to combine THC with non-THC CBs. Furthermore, the specialty *cannabis* varieties of the present invention were additionally selected for their ability to produce terpenes that are appealing to patients and that may also provide a pharmacological activity that modifies, enhances or ameliorates the effects of THC. In contrast, publicly-available contemporary hemp varieties that are high in CBD do not produce the pleasing organoleptic attributes of contemporary high-THC marijuana cultivars. Indeed, all known chemotype II or chemotype III plants produce myrcene dominant terpene profiles which do not have pleasing aroma/flavor, and do not have the entourage effects brought on by higher levels of non-myrcene terpenes. Thus, an objective of the present invention is to combine THC with higher CBs and diverse terpene profiles so as to produce specialty *cannabis* varieties with these pleasing aromas and flavors that were unavailable until the present invention.

In other embodiments, the breeding programs of the present invention were designed to produce THC:CBs expressing plants with higher terpene oil content. In some embodiments, the higher oil contents of the specialty *cannabis* of the present invention produce pleasing aromas/flavors. In other embodiments the higher oil levels of the specialty *cannabis* of the present invention allows the terpenes reach high enough levels to reduce THC side effects. In some embodiments, the higher terpene oil contents of the specialty *cannabis* of the present invention increase the amount of entourage effects of the terpenes in the terpene profile. In some embodiments, the specialty *cannabis* plants of the present invention produce myrcene dominant plants with improved aroma/flavor and entourage effects by increasing the terpene oil content.

One embodiment of the present invention is to produce specialty *cannabis* varieties with high essential oil content, in particularly, mono- and sesquiterpenes. The breeding objectives of the present invention are opposite to the face of modern recreational marijuana breeding strategies which have focused almost solely on breeding for higher levels of THC content alone.

According to one embodiment of the present invention a THC class variety is crossed to a CBs producing line to produce F1 seed which were grown to produce F1 progeny. The resultant F1 progeny can be fixed through asexual reproduction and/or used in further breeding schemes. Five CBD lines were chosen to use in the initial breeding program: CBD1, CBD2, CBD3, CBD4 and CBD5 (see Example 3). Similarly, THC class varieties can be crossed to the THV01, CBC01, and CBG01 parental varieties of the present invention. According to one embodiment of the present invention, each of these CBD, THCV, and CBG lines is crossed to one or more *cannabis* varieties which are described above and summarized in Example 3. In another embodiment, the present invention teaches crosses of any of the parental varieties with each other. Thus, for example, one or more GOLD Class varieties are crossed to each of CBD1, CBD2, CBD3, CBD4, CBD5, THV01, CBC01, or CBG plants to produce F1 populations to create (GOLD Class ×CBD; GOLD Class ×THV01; or GOLD Class ×CBG) combinations. In some embodiments, CBs producing parental varieties may also be crossed among themselves (e.g., CBD05 selfed, or CBD05× THV01) Following is a list of the iterations for each of the Class ×CBD, Class ×THV, and Class ×CBG crosses (Tables 23 and 24).

TABLE 23

Example crosses between Color Class cannabis varieties and CBD parental lines.

| CBD01 Crosses | CBD02 Crosses | CBD03 Crosses | CBD04 Crosses | CBD05 Crosses |
|---|---|---|---|---|
| AZURE X CBD01 | AZURE X CBD02 | AZURE X CBD03 | AZURE X CBD04 | AZURE X CBD05 |
| BLACK X CBD01 | BLACK X CBD02 | BLACK X CBD03 | BLACK X CBD04 | BLACK X CBD05 |
| BLUE X CBD01 | BLUE X CBD02 | BLUE X CBD03 | BLUE X CBD04 | BLUE X CBD05 |
| BRONZE X CBD01 | BRONZE X CBD02 | BRONZE X CBD03 | BRONZE X CBD04 | BRONZE X CBD05 |
| BROWN X CBD01 | BROWN X CBD02 | BROWN X CBD03 | BROWN X CBD04 | BROWN X CBD05 |
| FUSCIA X CBD01 | FUSCIA X CBD02 | FUSCIA X CBD03 | FUSCIA X CBD04 | FUSCIA X CBD05 |
| GOLD X CBD01 | GOLD X CBD02 | GOLD X CBD03 | GOLD X CBD04 | GOLD X CBD05 |
| GREEN X CBD01 | GREEN X CBD02 | GREEN X CBD03 | GREEN X CBD04 | GREEN X CBD05 |
| GREY X CBD01 | GREY X CBD02 | GREY X CBD03 | GREY X CBD04 | GREY X CBD05 |
| JADE X CBD01 | JADE X CBD02 | JADE X CBD03 | JADE X CBD04 | JADE X CBD05 |
| LEMON X CBD01 | LEMON X CBD02 | LEMON X CBD03 | LEMON X CBD04 | LEMON X CBD05 |
| MAGENTA X CBD01 | MAGENTA X CBD02 | MAGENTA X CBD03 | MAGENTA X CBD04 | MAGENTA X CBD05 |
| NAVY X CBD01 | NAVY X CBD02 | NAVY X CBD03 | NAVY X CBD04 | NAVY X CBD05 |
| OLIVE X CBD01 | OLIVE X CBD02 | OLIVE X CBD03 | OLIVE X CBD04 | OLIVE X CBD05 |
| ORANGE X CBD01 | ORANGE X CBD02 | ORANGE X CBD03 | ORANGE X CBD04 | ORANGE X CBD05 |
| PINK X CBD01 | PINK X CBD02 | PINK X CBD03 | PINK X CBD04 | PINK X CBD05 |
| PURPLE X CBD01 | PURPLE X CBD02 | PURPLE X CBD03 | PURPLE X CBD04 | PURPLE X CBD05 |
| RED X CBD01 | RED X CBD02 | RED X CBD03 | RED X CBD04 | RED X CBD05 |
| SEA X CBD01 | SEA X CBD02 | SEA X CBD03 | SEA X CBD04 | SEA X CBD05 |
| SILVER X CBD01 | SILVER X CBD02 | SILVER X CBD03 | SILVER X CBD04 | SILVER X CBD05 |
| TAN X CBD01 | TAN X CBD02 | TAN X CBD03 | TAN X CBD04 | TAN X CBD05 |
| VIOLET X CBD01 | VIOLET X CBD02 | VIOLET X CBD03 | VIOLET X CBD04 | VIOLET X CBD05 |
| WHITE X CBD01 | WHITE X CBD02 | WHITE X CBD03 | WHITE X CBD04 | WHITE X CBD05 |
| YELLOW X CBD01 | YELLOW X CBD02 | YELLOW X CBD03 | YELLOW X CBD04 | YELLOW X CBD05 |

TABLE 24

Example crosses between Color Class cannabis varieties and other CBs (THCV/CBDV, CBC, CBG) parental lines.

| THV01 Crosses | CBC01 Crosses | CBG02 Crosses |
|---|---|---|
| AZURE X THV01 | AZURE X CBC01 | AZURE X CBG02 |
| BLACK X THV01 | BLACK X CBC01 | BLACK X CBG02 |
| BLUE X THV01 | BLUE X CBC01 | BLUE X CBG02 |
| BRONZE X THV01 | BRONZE X CBC01 | BRONZE X CBG02 |
| BROWN X THV01 | BROWN X CBC01 | BROWN X CBG02 |
| FUSCIA X THV01 | FUSCIA X CBC01 | FUSCIA X CBG02 |
| GOLD X THV01 | GOLD X CBC01 | GOLD X CBG02 |

TABLE 24-continued

Example crosses between Color Class cannabis varieties and other CBs (THCV/CBDV, CBC, CBG) parental lines.

| THV01 Crosses | CBC01 Crosses | CBG02 Crosses |
| --- | --- | --- |
| GREEN X THV01 | GREEN X CBC01 | GREEN X CBG02 |
| GREY X THV01 | GREY X CBC01 | GREY X CBG02 |
| JADE X THV01 | JADE X CBC01 | JADE X CBG02 |
| LEMON X THV01 | LEMON X CBC01 | LEMON X CBG02 |
| MAGENTA X THV01 | MAGENTA X CBC01 | MAGENTA X CBG02 |
| NAVY X THV01 | NAVY X CBC01 | NAVY X CBG02 |
| OLIVE X THV01 | OLIVE X CBC01 | OLIVE X CBG02 |
| ORANGE X THV01 | ORANGE X CBC01 | ORANGE X CBG02 |
| PINK X THV01 | PINK X CBC01 | PINK X CBG02 |
| PURPLE X THV01 | PURPLE X CBC01 | PURPLE X CBG02 |
| RED X THV01 | RED X CBC01 | RED X CBG02 |
| SEA X THV01 | SEA X CBC01 | SEA X CBG02 |
| SILVER X THV01 | SILVER X CBC01 | SILVER X CBG02 |
| TAN X THV01 | TAN X CBC01 | TAN X CBG02 |
| VIOLET X THV01 | VIOLET X CBC01 | VIOLET X CBG02 |
| WHITE X THV01 | WHITE X CBC01 | WHITE X CBG02 |
| YELLOW X THV01 | YELLOW X CBC01 | YELLOW X CBG02 |

In one representative version of this breeding regime the resultant F1 progeny can be selfed to produce F2 seed which are grown to produce F2 progeny. Selection for desirable phenotypes and/or genotypes can be conducted within the F1, F2, or subsequent progeny since the selections can be maintained (i.e., fixed) via asexual reproduction. Alternatively, the F2 progeny can be crossed among themselves to produce a bulked F3 population from which desired progeny can be selected and/or further generations of crossing can be conducted. In another embodiment, the resultant F1 progeny can by backcrossed to the THC class or CBs variety to further reinforce the traits of other parent. In yet another representative version of this breeding scheme F1, F2, or subsequent progeny may also be crossed to additional CBs varieties to create even more complex cannabinoid combinations. For example, Color Class xTHV01 F1's can be subsequently crossed with a CBD variety in order to produce THV, CBDV progeny. Regardless of the exact crossing/selection procedure, selected lines can be chosen so as to have a total THC content ≤90.0%, a total CBs content ≥1.5%, and a desirable aroma and flavor profiles. In another embodiment of the present invention, regardless of the exact selfing/selection procedure, the selected lines can be chosen so as to have a total THC:CBs ratio of greater than 9:1, 8:1, 7:1, 6:1, 5:1, 4:1, 3:1, 2:1, 1:1, 1:2, 1:3, 1:4, 1:5, 1:6, 1:7, 1:9, and lower, and a desirable aroma and flavor.

According to the present invention, the lines can also be further selected for a specific content of certain other cannabinoids and/or of certain terpenes/terpenoids, and/or for additional phenotypic and genotypic characteristics. Desirable phenotypic characteristics include but are not limited to larger plant size (i.e., greater bulk or biomass), higher production of flower buds, larger flowers, more trichomes, shorter plant stature, ability to tolerate lower and/or higher growing temperatures, greater germination percentage, greater seedling vigor, more efficient water usage, disease resistance, pest resistance, and other desirable agronomic and production traits. For an overview of diseases and pests of importance to *cannabis* production see Clarke et al. (2000) *Hemp Diseases and Pests: Management and Biological Control: An Advanced Treatise* (CABI Publishing).

In an alternative version of this breeding regime the selected F2 progeny are backcrossed to the Class variety as the recurrent parent. Selection for desirable phenotypes and/ or genotypes can be conducted after this initial backcross, after any subsequent backcross (e.g., progeny obtained after 2, 3, 4, 5, 6, 7, 8, 9 or more backcrosses). In some embodiments, selected lines will have a total THC content ≤90.0%, a total CBs content ≥1.5%, and an aroma and flavor profiles typical of its class. In other embodiments of this breeding scheme selected lines can be chosen to have a total THC:CBs ratio of greater than 8:1 and approaching 1:1 and lower, and an aroma and flavor(s) typical of its class. The lines can also be further selected for a specific content of certain other cannabinoids and/or of certain terpenes/terpenoids, and/or for additional phenotypic and genotypic characteristics.

The progeny resulting from any selection stage of either the selfing or backcrossing versions of the breeding regimes of the present invention can be asexually reproduced so as to fix and maintain the desirable THC content, CBs content, the aroma and flavor(s) typical of the desired class, and the other desirable phenotypic and/or genotypic characteristics. The resultant selected lines will be designated as Specialty *Cannabis* Varieties.

The progeny resulting from any stage of either the selfing or backcrossing versions of this regime can also be crossed to other *cannabis* plants/varieties within, between or among the various classes of *cannabis* so as to produce additional plants for selection and maintenance through asexual reproduction. In this way, specialty *cannabis* varieties with various, desired flavor combinations can be produced and subsequently maintained through asexual reproduction.

The resultant specialty *cannabis* plants of the present invention also generally have more terpene essential oil content per plant than contemporary marijuana varieties. More essential oil per plant means less plant matter is required per treatment/administration, thereby also further minimizing any health risks for medical and recreational *cannabis* smokers. This would also further increase production efficiency.

The inventors of the present invention hypothesized that breeding plants with increased CBD, or THCV content would alleviate most of the commonly recognized real and perceived adverse effects of high THC *cannabis*. According to the present invention, a direct result of increased CBD is lower THC content because THC synthase and CBD synthase are allelic. Thus, another objective of the present invention was to create specialty *cannabis* varieties with an 'optimal' dose of THC and resulting in the most efficacious ratio of THC:CBD or THCV:THC.

According to the present invention, it is possible to apply dosage data to creating custom blended granular mixes for rolled delivery, pellets for bowls and house one-hitters, extracts for dabs, etc. with the flowers of these highly resinous newly-developed varieties with designed cannabinoid content so as to reduce adverse effects associated with THC.

Gold Class Breeding Regime for THC:CBD Producing Plants

Example Basic Breeding Scheme. The initial cross for the Gold Class CBD Breeding Regime that can be conducted as follows: P1 (GOLD Line (GO13)×P2 (CBD Line (CBD1). The hybrid cross between Parent 1 (P1) and Parent 2 (P2) could only be achieved by induction of staminate flowers on the pistillate plants by an exogenous application of the chemical silver thiosulfate. This process allows otherwise pistillate (female) plants to be coaxed to produce staminate, pollen bearing flowers. During this process, to investigate and exclude the possibility of maternally inherited genetic factors, reciprocal crosses can be made where both P1 can be induced to produce pollen and fertilize P2 (Line 1A), and P2 can be induced to produce pollen and fertilize P1 (Line 1B).

These crosses result in the production of two F1 populations =CBD-GOLD Lines 1A, 1B. Individuals from the F1 lines of each F1 population can be analyzed via GC/MS to determine their respective chemotypes. It is expected that the F1 populations will comprise individuals that show a Chemotype II cannabinoid distribution, with intermediate levels of both tetrahydrocannabinol (THC) and cannabidiol (CBD).

Plants with suitable terpene contents and profiles can be 'self-fertilized' to create a series F2 segregating populations or families; all non-desirable lines can be rejected from the breeding regimen. In this way, a series of F2's can be created=1AF2a, 1AF2b, 1AF2c, 1BF2a, 1BF2b, 1BF2c, etc.

F2 families can be propagated and screened via GC/MS to determine individual chemotypes; it is expected that in the F2 segregating populations we will see chemotype I, chemotype II, and chemotype III plants. Chemotype I plants can be discarded and only chemotype II and chemotype III plants can be retained and again screened by GC/MS to evaluate their suitability in terms of terpene content and profile.

It may also be desirable to mate selected F1 lines via a backcross scheme to the P1 GO13 to reinforce the GOLD genetic background, although doing so will re-introduce B(t) alleles (i.e., the alleles that encode for THC production) into the breeding population, resulting in a population of chemotype I and II plants.

Similar breeding schemes may be followed to obtain additional class-CBD progeny by repeating the steps described for GO13 with other class varieties and/or CBD parental lines.

Example 6

Development of THC:CBD Specialty *Cannabis* Varieties

Unique parental THC and CBD lines from Examples 2-4 were selected and one of the parental cultivars was treated with silver thiosulfate to coax the pistillate plant to produce staminate, pollen-bearing flowers. The THC and CBD lines were then crossed, the resulting progeny were screened by TLC to identify plants producing both THC and CBD, or CBD alone. Progeny exhibiting the desired chemotype II and III profile were allowed to reach maturity and the flowers were harvested and processed. In general, field observations could detect the crosses with the desired characteristics, however this was verified by chemotype analysis and the final flower was analyzed for cannabinoid and terpene content. Table 25 outlines the initial crosses performed with THC class varieties and CBD parental lines. The crosses produced progeny approaching ratios supporting the single locus model for THC and CBD synthase. TLC results described in the table show the field-determined chemotype of the progeny (chemotype II-THC and CBD producing, and chemotype III-CBD only).

TABLE 25

Crosses performed between class cannabis varieties and other CBD parental lines. TLC result indicates chemotype I, II or III.

P Donor CBD05
P Acceptor

| | CBD05 | | CBD03 | | CBD02 | | CBD02 | | CBD04 | | YEL03 | |
|---|---|---|---|---|---|---|---|---|---|---|---|---|
| | Code | TLC Result | Code | TLC Result | Code | TLC Result | Code | TLC Result | Code | TLC Result | Code | |
| 1 | CBD05xP-01 | III | CBD03xP-01 | III | CBD02xP-01 | – | CBD02xP-31 | II | CBD04xP-01 | + | YEL03xP-01 | – |
| 2 | CBD05xP-02 | II | CBD03xP-02 | – | CBD02xP-02 | – | CBD02xP-32 | II | CBD04xP-02 | II | YEL03xP-02 | – |
| 3 | CBD05xP-03 | – | CBD03xP-03 | II | CBD02xP-03 | – | CBD02xP-33 | – | CBD04xP-03 | II | YEL03xP-03 | – |
| 4 | CBD05xP-04 | – | CBD03xP-04 | – | CBD02xP-04 | – | CBD02xP-34 | – | CBD04xP-04 | + | YEL03xP-04 | – |
| 5 | CBD05xP-05 | II | CBD03xP-05 | II | CBD02xP-05 | II | CBD02xP-35 | – | CBD04xP-05 | + | YEL03xP-05 | – |
| 6 | CBD05xP-06 | – | CBD03xP-06 | – | CBD02xP-06 | – | CBD02xP-36 | – | CBD04xP-06 | +II | YEL03xP-06 | – |
| 7 | CBD05xP-07 | – | CBD03xP-07 | III | CBD02xP-07 | – | CBD02xP-37 | – | CBD04xP-07 | + | YEL03xP-07 | – |
| 8 | CBD05xP-08 | – | CBD03xP-08 | – | CBD02xP-08 | – | CBD02xP-38 | – | | | YEL03xP-08 | – |
| 9 | CBD05xP-09 | – | CBD03xP-09 | II | CBD02xP-09 | II | CBD02xP-39 | – | | | YEL03xP-09 | – |
| 10 | CBD05xP-10 | – | CBD03xP-10 | II | CBD02xP-10 | II | CBD02xP-40 | II | | | YEL03xP-10 | – |
| 11 | CBD05xP-11 | – | CBD03xP-11 | – | CBD02xP-11 | III | CBD02xP-41 | – | | | YEL03xP-11 | – |
| 12 | CBD05xP-12 | – | CBD03xP-12 | – | CBD02xP-12 | II | CBD02xP-42 | – | | | YEL03xP-12 | – |
| 13 | CBD05xP-13 | – | CBD03xP-13 | – | CBD02xP-13 | – | CBD02xP-43 | – | | | YEL03xP-13 | – |
| 14 | CBD05xP-14 | – | CBD03xP-14 | – | CBD02xP-14 | II | CBD02xP-44 | – | | | YEL03xP-14 | – |
| 15 | CBD05xP-15 | – | CBD03xP-15 | – | CBD02xP-15 | II | CBD02xP-45 | – | | | YEL03xP-15 | – |
| 16 | CBD05xP-16 | – | CBD03xP-16 | – | CBD02xP-16 | – | CBD02xP-46 | – | | | YEL03xP-16 | II |

TABLE 25-continued

Crosses performed between class cannabis varieties and other CBD parental lines. TLC result indicates chemotype I, II or III.

| | | | | | | | | | |
|---|---|---|---|---|---|---|---|---|---|
| 17 | CBD05xP-17 | – | CBD03xP-17 | – | CBD02xP-17 | – | CBD02xP-47 | II | YEL03xP-17 | – |
| 18 | CBD05xP-18 | – | CBD03xP-18 | – | CBD02xP-18 | – | CBD02xP-48 | – | YEL03xP-18 | – |
| 19 | CBD05xP-19 | – | CBD03xP-19 | – | CBD02xP-19 | – | CBD02xP-49 | – | YEL03xP-19 | – |
| 20 | CBD05xP-20 | – | CBD03xP-20 | – | CBD02xP-20 | – | CBD02xP-50 | – | YEL03xP-20 | – |
| 21 | CBD05xP-21 | – | CBD03xP-21 | – | CBD02xP-21 | – | CBD02xP-51 | – | YEL03xP-21 | – |
| 22 | CBD05xP-22 | – | CBD03xP-22 | – | CBD02xP-22 | – | CBD02xP-52 | – | YEL03xP-22 | – |
| 23 | CBD05xP-23 | – | CBD03xP-23 | – | CBD02xP-23 | – | CBD02xP-53 | – | YEL03xP-23 | II |
| 24 | CBD05xP-24 | – | CBD03xP-24 | – | CBD02xP-24 | – | CBD02xP-54 | – | YEL03xP-24 | – |
| 25 | | | | | CBD02xP-25 | – | CBD02xP-55 | II | YEL03xP-25 | – |
| 26 | | | | | CBD02xP-26 | – | | | YEL03xP-26 | II |
| 27 | | | | | CBD02xP-27 | – | | | YEL03xP-27 | II |
| 28 | | | | | CBD02xP-28 | II | | | YEL03xP-28 | – |
| 29 | | | | | CBD02xP-29 | – | | | | |
| 30 | | | | | CBD02xP-30 | II | | | | |

P Donor
CBD05
P Acceptor

| | PUR01 | | WHI07 | | SIL08 | | SIL08 | | WHI04 | | WHI01 | |
|---|---|---|---|---|---|---|---|---|---|---|---|---|
| | Code | TLC Result | Code | TLC Result | Code | TLC Result | Code | TLC Result | Code | TLC Result | Code | TLC Result |
| 1 | PUR01xP-01 | – | WHI07xP-01 | II | SIL08xP-01 | II | SIL08xP-31 | – | WHI04xP-01 | – | WHI01xP-18 | |
| 2 | PUR01xP-02 | – | WHI07xP-02 | II | SIL08xP-02 | – | SIL08xP-32 | – | WHI04xP-02 | II | WHI01xP-19 | II |
| 3 | PUR01xP-03 | – | WHI07xP-03 | – | SIL08xP-03 | II | SIL08xP-33 | – | WHI04xP-03 | – | WHI01xP-22 | II |
| 4 | PUR01xP-04 | II | WHI07xP-04 | – | SIL08xP-04 | – | SIL08xP-34 | II | WHI04xP-04 | – | WHI01xP-23 | II |
| 5 | PUR01xP-05 | – | WHI07xP-05 | – | SIL08xP-05 | – | SIL08xP-35 | – | WHI04xP-05 | – | WHI01xP-14 | II |
| 6 | PUR01xP-06 | – | WHI07xP-06 | – | SIL08xP-06 | – | SIL08xP-36 | – | WHI04xP-06 | – | WHI01xP-15 | III |
| 7 | PUR01xP-07 | – | WHI07xP-07 | II | SIL08xP-07 | – | SIL08xP-37 | II | WHI04xP-07 | – | WHI01xP-16 | |
| 8 | PUR01xP-08 | – | WHI07xP-08 | II | SIL08xP-08 | II | SIL08xP-38 | II | WHI04xP-08 | – | WHI01xP-12 | II |
| 9 | PUR01xP-09 | – | WHI07xP-09 | – | SIL08xP-09 | – | SIL08xP-39 | – | WHI04xP-09 | – | | |
| 10 | PUR01xP-10 | II | WHI07xP-10 | – | SIL08xP-10 | – | SIL08xP-40 | – | | | | |
| 11 | PUR01xP-11 | – | WHI07xP-11 | II | SIL08xP-11 | – | SIL08xP-41 | – | | | | |
| 12 | | | WHI07xP-12 | – | SIL08xP-12 | – | SIL08xP-42 | – | | | | |
| 13 | | | | | SIL08xP-13 | – | SIL08xP-33 | – | | | | |
| 14 | | | | | SIL08xP-14 | II | SIL08xP-44 | II | | | | |
| 15 | | | | | SIL08xP-15 | – | | | | | | |
| 16 | | | | | SIL08xP-16 | – | | | | | | |
| 17 | | | | | SIL08xP-17 | – | | | | | | |
| 18 | | | | | SIL08xP-18 | II | | | | | | |
| 19 | | | | | SIL08xP-19 | – | | | | | | |
| 20 | | | | | SIL08xP-20 | – | | | | | | |

TABLE 25-continued

Crosses performed between class cannabis varieties and other CBD parental lines. TLC result indicates chemotype I, II or III.

| | | |
|---|---|---|
| 21 | SIL08xP-21 | – |
| 22 | SIL08xP-22 | – |
| 23 | SIL08xP-23 | – |
| 24 | SIL08xP-24 | – |
| 25 | SIL08xP-25 | – |
| 26 | SIL08xP-26 | – |
| 27 | SIL08xP-27 | II |
| 28 | SIL08xP-28 | – |
| 29 | SIL08xP-29 | – |
| 30 | SIL08xP-30 | II |

Example 7

Chemical Analysis of Cannabinoids and Terpenes of THC:CBD Specialty cannabis Progeny The new specialty cannabis varieties created through crosses described in Examples 5 and 6 were subjected to cannabinoid and terpene chemical analysis as described in Example 1. The levels of cannabinoids were measured by both GC-FID (Table 26) and HPLC (Table 27). Terpenes were measured using GC-FID and are presented as absolute content measurements based on the percent content by weight of dry inflorescences (Table 28) and relative content as a percent of the total terpene profile (Table 29). The GC-FID cannabinoid analysis of Table 26 also included measurements for THCV, CBDV, CBGV, CBN, and Delta 8 THC, all of which were measured to be less than 0.3% and were therefore not included in the table. Similarly, the HPLC cannabinoid analysis of Table 27 included measurements for CBCA, THCVA, CBDVA, CBGVA, CBC, THCV, CBDV, CBGV, CBN and Delta 8 THC all of which were measured to be less than 0.08%, and were therefore not included in the table.

Unlike previously available chemotype II or chemotype III plants, the specialty cannabis of the present invention exhibit chemotype II and III genotypes ($B_T/B_D$, producing both THC and CBD, or $B_D/B_D$, producing CBD but no THC) while producing desirable terpene profiles. That is, the breeding program of the present invention has produced chemotype II and III specialty cannabis plants with desirable terpene profiles in which the myrcene terpene is not dominant. For example, the PUR01xP04, PUR01xP10 and PUR01xP05 have limonene-dominant terpene profiles. In some embodiments, the limonene terpene is expected to impart the specialty cannabis with a citrusy aroma. In other embodiments the limonene terpene is expected to have added anxiolytic properties to combat the side of effects of THC. In yet another embodiment, the reduced myrcene content of the specialty cannabis will reduce the amount of "couch lock" effect produced by myrcene. In other embodiments, the terpene profiles of the other chemotype II and III progeny provide diverse terpene profiles designed to produce desirable aroma/flavors and organoleptic appeal. In other embodiments, the terpene profiles of the chemotype II progeny allow for terpene entourage effects to reduce the side effects of THC.

The breeding scheme described in Example 6 also produced specialty cannabis plants with increased terpene oil content. For example, progeny CBD02xP-11 (chemotype III), and SIL08xP-30 (chemotype II) have terpene oil contents greater than 1.5%. Several other progeny such as CBD05xP-01 (chemotype III), and SIL08xP-34 (chemotype III) have terpene oil contents greater than 2%. In some embodiments, the higher oil content of the specialty cannabis varieties provide "smoother" aromas and flavors and will raise the total terpene levels so as increase the pharmacological entourage effects of said terpenes. The higher oil content results in myrcene becoming the dominant terpene, but it remains less than ⅔ of the relative terpene content providing opportunity for the entourage effects of the other terpenes to emerge. For example despite having a myrcene dominant profile, the SIL08xP-34 specialty cannabis of the present invention is expected to provide a better organoleptic experience than that of myrcene dominant chemotype II varieties currently available which tend to have very low terpene oil levels.

TABLE 26

Cannabinoid values as measured by GC-FID for THC:CBD and CBD (chemotype II and III) specialty cannabis varieties.
Blank values indicate undetectable levels or 0.

| | Cannabinoids (GC-FID) | | | | | | | | Cannabs by GC | | THC:CBD by GC | | |
|---|---|---|---|---|---|---|---|---|---|---|---|---|---|
| | THC | | CBD | | CBG | | CBC | | | | | | |
| Sample | Wt % | 95% CI | Wt % | 95% CI | Wt % | 95% CI | Wt % | 95% CI | Wt % | 95% CI | Wt % | 95% CI | Chemotype |
| WHI01xP-15 | 0.13% | | 4.90% | | 0.05% | | 0.38% | | 5.46% | | 0.03 | | III |
| CBD02xP-11 | 0.25% | 0.10% | 8.88% | 0.68% | 0.15% | 0.05% | 0.55% | 0.22% | 9.83% | 1.04% | 0.03 | 0.01 | III |

TABLE 26-continued

Cannabinoid values as measured by GC-FID for THC:CBD and CBD (chemotype II and III) specialty cannabis varieties. Blank values indicate undetectable levels or 0.

| | Cannabinoids (GC-FID) | | | | | | | | | | THC:CBD | | |
|---|---|---|---|---|---|---|---|---|---|---|---|---|---|
| | THC | | CBD | | CBG | | CBC | | Cannabs by GC | | by GC | | |
| Sample | Wt % | 95% CI | Wt % | 95% CI | Wt % | 95% CI | Wt % | 95% CI | Wt % | 95% CI | Wt % | 95% CI | Chemotype |
| CBD03xP-01 | 0.16% | 0.04% | 5.40% | 1.81% | 0.06% | 0.05% | 0.38% | 0.07% | 6.00% | 1.97% | 0.03 | 0.00 | III |
| CBD03xP-10 | 0.26% | | 8.35% | | 0.23% | | 0.60% | | 9.43% | | 0.03 | | III |
| CBD03xP-07 | 0.17% | | 6.22% | 1.03% | 0.09% | 0.03% | 0.47% | 0.03% | 6.87% | 0.87% | 0.03 | | III |
| CBD04xP-01 | 0.21% | 0.04% | 8.34% | 0.95% | 0.16% | 0.00% | 0.39% | 0.11% | 9.10% | 0.79% | 0.03 | 0.01 | III |
| CBD04xP-09 | 0.22% | | 8.34% | | 0.18% | | 0.42% | | 9.17% | | 0.03 | | III |
| CBD05xP-01 | 0.31% | 0.06% | 11.05% | 1.94% | 0.27% | 0.17% | 0.56% | 0.12% | 12.19% | 1.59% | 0.03 | 0.01 | III |
| CBD05xS-13 | 0.21% | 0.01% | 7.69% | 1.92% | 0.27% | 0.11% | 0.36% | 0.08% | 8.53% | 1.95% | 0.03 | 0.01 | III |
| PUR01xP-06 | 1.59% | | 4.20% | | 0.12% | | 0.28% | | 6.18% | | 0.38 | | II |
| PUR01xP-04 | 2.20% | 0.64% | 6.00% | 1.82% | 0.21% | 0.02% | 0.42% | 0.03% | 8.83% | 2.51% | 0.37 | 0.00 | II |
| PUR01xP-10 | 1.57% | | 4.02% | | 0.21% | | 0.32% | | 6.12% | | 0.39 | | II |
| PUR01xP-05 | 1.55% | | 2.43% | | 0.09% | | 0.32% | | 4.40% | | 0.64 | | II |
| SIL08xP-01 | 1.95% | | 6.20% | | 0.18% | | 0.40% | | 8.73% | | 0.31 | | II |
| SIL08xP-08 | 5.60% | 0.53% | 5.05% | 0.71% | 0.19% | 0.02% | 0.33% | 0.04% | 11.17% | 1.19% | 1.11 | 0.05 | II |
| SIL08xP-30 | 6.20% | | 4.71% | | 0.21% | | 0.35% | | 11.47% | | 1.32 | | II |
| SIL08xP-14 | 2.43% | 0.40% | 8.57% | 1.31% | 0.29% | 0.06% | 0.42% | 0.14% | 11.71% | 1.51% | 0.28 | 0.00 | II |
| SIL08xP-18 | 2.33% | | 7.18% | | 0.35% | | 0.44% | | 10.30% | | 0.32 | | II |
| SIL08xP-34 | 7.65% | | 6.56% | | 0.27% | | 0.53% | | 15.01% | | 1.17 | | II |
| SIL08xP-03 | 3.86% | | 10.75% | | 0.49% | | 0.65% | | 15.75% | | 0.36 | | II |
| SIL08xP-37 | 3.09% | | 8.34% | | 0.44% | | 0.51% | | 12.37% | | 0.37 | | II |
| SIL08xP-38 | 4.40% | | 3.57% | | 0.08% | | 0.31% | | 8.36% | | 1.23 | | II |
| WHI04xP-02 | 2.68% | | 8.10% | | 0.31% | | 0.51% | | 11.60% | | 0.33 | | II |
| WHI07xP-07 | 4.62% | | 4.11% | | 0.17% | | 0.33% | | 9.27% | | 1.12 | | II |
| WHI07xP-11 | 2.20% | | 4.62% | | 0.15% | | 0.35% | | 7.32% | | 0.48 | | II |
| WHI07xP-01 | 6.14% | | 5.26% | | 0.25% | | 0.47% | | 12.13% | | 1.17 | | II |
| WHI07xP-08 | 3.27% | | 3.05% | | 0.15% | | 0.32% | | 6.82% | | 1.07 | | II |
| WHI07xP-02 | 2.12% | | 5.28% | | 0.22% | | 0.42% | | 8.03% | | 0.40 | | II |
| YEL03xP-23 | 3.52% | 0.51% | 6.70% | 1.38% | 0.24% | 0.05% | 0.50% | 0.06% | 10.97% | 1.78% | 0.53 | 0.03 | II |
| YEL03xP-26 | 2.99% | 0.35% | 7.23% | 1.04% | 0.25% | 0.02% | 0.59% | 0.06% | 11.06% | 1.32% | 0.41 | 0.01 | II |
| WHI01xP-22 | 2.60% | | 6.20% | | 0.23% | | 0.56% | | 9.58% | | 0.42 | | II |
| WHI01xP-12 | 3.94% | | 7.67% | | 0.16% | | 0.62% | | 12.39% | | 0.51 | | II |
| WHI01xP-14 | 3.48% | | 6.09% | | 0.23% | | 0.53% | | 10.34% | | 0.57 | | II |
| WHI01xP-19 | 3.89% | | 6.78% | | 0.18% | | 0.59% | | 11.44% | | 0.57 | | II |
| WHI01xP-23 | 1.48% | | 4.63% | | 0.09% | | 0.36% | | 6.56% | | 0.32 | | II |
| CBD02xP-15 | 2.29% | | 5.76% | | 0.25% | | 0.66% | | 8.96% | | 0.40 | | II |
| CBD02xP-16A | 2.93% | | 9.63% | | 0.33% | | 0.84% | | 13.72% | | 0.30 | | II |
| CBD02xP-17 | 1.41% | 0.34% | 4.89% | 0.12% | 0.20% | 0.05% | 0.31% | 0.11% | 6.81% | 0.62% | 0.29 | 0.06 | II |
| CBD02xP-10 | 2.62% | | 7.07% | | 0.30% | | 0.55% | | 10.54% | | 0.37 | | II |
| CBD02xP-12 | 2.39% | | 7.11% | | 0.42% | | 0.50% | | 10.42% | | 0.34 | | II |
| CBD02xP-14 | 1.83% | | 6.40% | | 0.33% | | 0.44% | | 9.00% | | 0.29 | | II |
| CBD02xP-18 | 2.48% | | 6.42% | | 0.15% | | 0.55% | | 9.61% | | 0.39 | | II |
| CBD02xP-31 | 1.79% | | 4.69% | | 0.16% | | 0.38% | | 7.02% | | 0.38 | | II |
| CBD02xP-05 | 1.56% | 0.31% | 5.80% | 1.98% | 0.28% | 0.16% | 0.40% | 0.07% | 8.04% | 2.38% | 0.27 | 0.04 | II |
| CBD02xP-30 | 1.58% | | 5.00% | | 0.25% | | 0.44% | | 7.26% | | 0.32 | | II |
| CBD02xP-32 | 2.14% | 0.11% | 4.67% | 0.52% | 0.15% | 0.06% | 0.40% | 0.13% | 7.35% | 0.57% | 0.46 | 0.03 | II |
| CBD02xP-40 | 1.86% | | 3.85% | | 0.23% | | 0.37% | | 6.31% | | 0.48 | | II |
| CBD02xP-53 | 1.64% | | 3.47% | | 0.16% | | 0.32% | | 5.59% | | 0.47 | | II |
| CBD02xP-09 | 1.93% | | 7.15% | | 0.36% | | 0.46% | | 9.90% | | 0.27 | | II |
| CBD02xP-28 | 2.06% | 0.74% | 6.50% | 1.82% | 0.19% | 0.14% | 0.40% | 0.21% | 9.15% | 2.91% | 0.32 | 0.03 | II |
| CBD02xP-47 | 1.87% | | 6.15% | | 0.15% | | 0.50% | | 8.67% | | 0.30 | | II |
| CBD03xP-03 | 2.12% | | 5.39% | | | | 0.39% | | 7.90% | | 0.39 | | II |
| CBD03xP-05 | 1.35% | | 3.90% | | 0.14% | | 0.30% | | 5.69% | | 0.35 | | II |
| CBD03xP-09 | 1.66% | | 4.63% | | 0.31% | | 0.29% | | 6.90% | | 0.36 | | II |
| CBD04xP-02 | 2.29% | | 3.86% | | 0.13% | | 0.30% | | 6.57% | | 0.59 | | II |
| CBD04xP-03 | 3.36% | | 5.30% | | 0.22% | | 0.32% | | 9.21% | | 0.63 | | II |
| CBD04xP-06 | 2.46% | 0.24% | 4.73% | 0.11% | 0.12% | 0.02% | 0.29% | 0.05% | 7.60% | 0.17% | 0.52 | 0.06 | II |
| CBD05xP-02 | 1.14% | 0.44% | 3.34% | 0.37% | 0.16% | 0.05% | 0.24% | 0.13% | 4.87% | 0.98% | 0.34 | 0.09 | II |
| CBD05xP-05 | 1.57% | 0.20% | 4.87% | 0.05% | 0.32% | 0.09% | 0.31% | 0.12% | 7.23% | 0.03% | 0.32 | 0.04 | II |
| CBD05xS-09 | 1.65% | | 3.58% | | 0.10% | | 0.40% | | 5.73% | | 0.46 | | II |
| CBD05xS-05 | 1.57% | 0.56% | 5.13% | 0.31% | 0.11% | 0.06% | 0.35% | 0.06% | 7.16% | 0.38% | 0.31 | 0.13 | II |
| CBD05xS-11 | 1.63% | 0.05% | 4.71% | 0.39% | 0.08% | 0.00% | 0.38% | 0.20% | 6.80% | 0.13% | 0.35 | 0.04 | II |

TABLE 27

Cannabinoid measurement by HPLC for THC:CBD and CBD (chemotype II and III) specialty cannabis varieties. Blank values indicate undetectable levels or 0.

| | Cannabinoids (UHPLC) | | | | | | | | | |
|---|---|---|---|---|---|---|---|---|---|---|
| | THCA | | CBDA | | CBGA | | THC | | CBD | |
| Sample | Wt % | 95% CI | Wt % | 95% CI | Wt % | 95% CI | Wt % | 95% CI | Wt % | 95% CI |
| WHI01xP-15 | 0.14% | | 7.33% | | 0.06% | | 0.03% | | 0.53% | |
| CBD02xP-11 | 0.27% | 0.12% | 14.83% | 0.28% | 0.18% | 0.02% | 0.01% | 0.03% | 0.15% | 0.08% |
| CBD03xP-01 | 0.18% | 0.07% | 7.90% | 2.35% | 0.09% | 0.06% | 0.02% | 0.00% | 0.10% | 0.02% |
| CBD03xP-10 | | | 12.20% | | | | | | | |
| CBD03xP-07 | 0.19% | | 9.29% | 0.79% | 0.15% | | | | 0.08% | |
| CBD04xP-01 | 0.24% | 0.08% | 13.37% | 4.30% | 0.22% | 0.06% | 0.02% | 0.00% | 0.11% | 0.08% |
| CBD04xP-09 | 0.27% | | 12.00% | | 0.22% | | 0.00% | | 0.06% | |
| CBD05xP-01 | 0.36% | 0.12% | 18.31% | 3.37% | 0.32% | 0.15% | 0.33% | 0.61% | 0.24% | 0.11% |
| CBD05xS-13 | 0.29% | 0.09% | 12.78% | 5.50% | 0.40% | 0.24% | 0.20% | 0.22% | 0.13% | 0.09% |
| PUR01xP-06 | 2.35% | | 6.29% | | 0.19% | | 0.09% | | 0.08% | |
| PUR01xP-04 | 3.29% | 1.07% | 10.39% | 5.43% | 0.21% | 0.09% | 0.07% | 0.00% | 0.05% | 0.01% |
| PUR01xP-10 | 1.76% | | 6.17% | | 0.26% | | 0.02% | | | |
| PUR01xP-05 | 2.01% | | 3.63% | | 0.10% | | 0.08% | | | |
| SIL08xP-01 | 2.93% | | 9.24% | | 0.30% | | 0.04% | | 0.04% | |
| SIL08xP-08 | 7.94% | 0.60% | 8.40% | 2.93% | 0.48% | 0.37% | 0.20% | 0.30% | | |
| SIL08xP-30 | 8.21% | | 6.77% | | 0.26% | | 0.25% | | 0.06% | |
| SIL08xP-14 | 3.38% | 0.35% | 14.12% | 4.73% | 0.42% | 0.05% | 0.07% | 0.01% | 0.07% | 0.02% |
| SIL08xP-18 | 3.28% | | 10.58% | | 0.48% | | 0.12% | | 0.09% | |
| SIL08xP-34 | 10.49% | | 9.58% | | 0.27% | | 0.26% | | 0.07% | |
| SIL08xP-03 | 5.38% | | 15.95% | | 0.68% | | 0.05% | | 0.06% | |
| SIL08xP-37 | 4.37% | | 12.36% | | 0.56% | | 0.04% | | 0.05% | |
| SIL08xP-38 | 6.39% | | 4.55% | | 0.10% | | 0.11% | | | |
| WHI04xP-02 | 3.91% | | 12.23% | | 0.41% | | 0.02% | | 0.05% | |
| WHI07xP-07 | 6.66% | | 6.49% | | 0.22% | | 0.10% | | 0.03% | |
| WHI07xP-11 | 3.34% | | 8.05% | | 0.20% | | 0.07% | | 0.05% | |
| WHI07xP-01 | 8.95% | | 3.70% | | 0.35% | | 0.05% | | | |
| WHI07xP-08 | 5.12% | | 4.70% | | 0.19% | | 0.02% | | | |
| WHI07xP-02 | 3.22% | | 8.46% | | 0.33% | | 0.09% | | 0.06% | |
| YEL03xP-23 | 5.04% | 0.89% | 11.25% | 4.39% | 0.46% | 0.01% | 0.04% | 0.01% | 0.04% | |
| YEL03xP-26 | 4.33% | 0.69% | 12.44% | 5.33% | 0.22% | 0.33% | 0.09% | 0.03% | 0.07% | 0.01% |
| WHI01xP-22 | 4.20% | | 10.44% | | 0.34% | | 0.15% | | 0.10% | |
| WHI01xP-12 | 5.08% | | 11.58% | | 0.29% | | 0.04% | | 0.32% | |
| WHI01xP-14 | 3.64% | | 8.45% | | 0.33% | | 1.06% | | 0.58% | |
| WHI01xP-19 | 5.12% | | 10.41% | | 0.28% | | 0.45% | | 0.21% | |
| WHI01xP-23 | 2.67% | | 8.46% | | 0.17% | | 0.12% | | 0.09% | |
| CBD02xP-15 | 3.60% | | 9.63% | | 0.24% | | 0.06% | | 0.06% | |
| CBD02xP-16A | 4.73% | | 15.65% | | 0.33% | | 0.06% | | 0.08% | |
| CBD02xP-17 | 2.19% | 0.57% | 8.91% | 0.19% | 0.23% | 0.06% | 0.06% | 0.06% | 0.06% | 0.06% |
| CBD02xP-10 | 3.91% | | 11.79% | | 0.38% | | 0.19% | | 0.14% | |
| CBD02xP-12 | 3.59% | | 12.96% | | 0.36% | | 0.13% | | 0.13% | |
| CBD02xP-14 | 2.82% | | 11.68% | | 0.46% | | 0.13% | | 0.13% | |
| CBD02xP-18 | 3.35% | | 10.26% | | 0.18% | | 0.30% | | 0.25% | |
| CBD02xP-31 | 2.24% | | 8.74% | | 0.22% | | 0.11% | | 0.12% | |
| CBD02xP-05 | 2.43% | 0.31% | 10.51% | 3.02% | 0.43% | 0.38% | 0.80% | 1.44% | 0.09% | 0.01% |
| CBD02xP-30 | 3.82% | | 13.70% | | 0.26% | | 0.16% | | 0.14% | |
| CBD02xP-32 | 3.05% | 0.18% | 8.29% | 0.50% | 0.26% | 0.17% | 0.10% | 0.02% | 0.07% | 0.03% |
| CBD02xP-40 | 2.44% | | 7.09% | | 0.29% | | 0.09% | | 0.07% | |
| CBD02xP-53 | 2.08% | | 6.70% | | 0.16% | | 0.13% | | 0.13% | |
| CBD02xP-09 | 2.97% | | 11.37% | | 0.50% | | 0.11% | | 0.13% | |
| CBD02xP-28 | 2.58% | 1.77% | 11.01% | 2.27% | 0.34% | 0.18% | 0.21% | 0.09% | 0.15% | 0.10% |
| CBD02xP-47 | 2.81% | | 10.21% | | 0.32% | | 0.15% | | 0.16% | |
| CBD03xP-03 | 2.64% | | 7.83% | | 0.23% | | 0.09% | | 0.09% | |
| CBD03xP-05 | 1.99% | | 5.98% | | | | | | | |
| CBD03xP-09 | 2.40% | | 6.63% | | | | | | | |
| CBD04xP-02 | 2.72% | | 5.43% | | 0.93% | | 0.15% | | | |
| CBD04xP-03 | 4.70% | | 7.56% | | 0.40% | | 0.13% | | | |
| CBD04xP-06 | 3.54% | 0.09% | 7.76% | 1.88% | 0.22% | 0.06% | 0.05% | 0.04% | 0.04% | |
| CBD05xP-02 | 1.42% | 0.59% | 6.13% | 0.90% | 0.24% | 0.01% | 0.05% | 0.04% | 0.07% | |
| CBD05xP-05 | 2.01% | 0.93% | 8.85% | 0.12% | 0.35% | 0.01% | 0.48% | 0.73% | 0.07% | 0.04% |
| CBD05xS-09 | 2.74% | | 6.81% | | 0.13% | | 0.11% | | 0.09% | |
| CBD05xS-05 | 2.06% | 1.34% | 8.78% | 1.24% | 0.16% | 0.10% | 0.10% | 0.08% | 0.09% | 0.06% |
| CBD05xS-11 | 2.11% | 0.55% | 7.63% | 1.56% | 0.13% | 0.06% | 0.13% | 0.03% | 0.12% | 0.10% |

TABLE 27-continued

Cannabinoid measurement by HPLC for THC:CBD and CBD (chemotype II and III) specialty cannabis varieties. Blank values indicate undetectable levels or 0.

| Sample | Cannabinoids (UHPLC) CBG | | Cannabs by HPLC | | THCA:CBDA by HPLC | | Chemotype |
|---|---|---|---|---|---|---|---|
| | Wt % | 95% CI | Wt % | 95% CI | Ratio | 95% CI | |
| WHI01xP-15 | | | 8.10% | | 0.02 | | III |
| CBD02xP-11 | 0.06% | 0.05% | 15.51% | 0.55% | 0.02 | 0.01 | III |
| CBD03xP-01 | | | 8.29% | 2.50% | 0.02 | 0.00 | III |
| CBD03xP-10 | | | 12.20% | | | | III |
| CBD03xP-07 | | | 9.50% | 0.39% | 0.02 | | III |
| CBD04xP-01 | 0.05% | | 13.99% | 4.15% | 0.02 | 0.01 | III |
| CBD04xP-09 | 0.06% | | 12.70% | | 0.02 | | III |
| CBD05xP-01 | 0.11% | 0.10% | 19.68% | 3.48% | 0.02 | 0.01 | III |
| CBD05xS-13 | 0.03% | 0.01% | 13.83% | 5.77% | 0.02 | 0.02 | III |
| PUR01xP-06 | 0.03% | | 9.03% | | 0.37 | | II |
| PUR01xP-04 | 0.08% | 0.01% | 14.09% | 6.57% | 0.33 | 0.07 | II |
| PUR01xP-10 | 0.05% | | 8.26% | | 0.28 | | II |
| PUR01xP-05 | | | 5.81% | | 0.55 | | II |
| SIL08xP-01 | | | 12.55% | | 0.32 | | II |
| SIL08xP-08 | 0.05% | 0.03% | 17.06% | 3.42% | 0.97 | 0.27 | II |
| SIL08xP-30 | 0.08% | | 15.65% | | 1.21 | | II |
| SIL08xP-14 | 0.06% | 0.04% | 18.13% | 5.02% | 0.24 | 0.06 | II |
| SIL08xP-18 | 0.05% | | 14.65% | | 0.31 | | II |
| SIL08xP-34 | 0.16% | | 20.91% | | 1.09 | | II |
| SIL08xP-03 | 0.08% | | 22.21% | | 0.34 | | II |
| SIL08xP-37 | 0.09% | | 17.45% | | 0.35 | | II |
| SIL08xP-38 | 0.04% | | 11.18% | | 1.40 | | II |
| WHI04xP-02 | 0.08% | | 16.71% | | 0.32 | | II |
| WHI07xP-07 | 0.04% | | 13.58% | | 1.03 | | II |
| WHI07xP-11 | 0.04% | | 11.77% | | 0.42 | | II |
| WHI07xP-01 | 0.10% | | 13.14% | | 2.42 | | II |
| WHI07xP-08 | 0.05% | | 10.06% | | 1.09 | | II |
| WHI07xP-02 | 0.03% | | 12.20% | | 0.38 | | II |
| YEL03xP-23 | 0.05% | 0.00% | 16.84% | 5.33% | 0.46 | 0.10 | II |
| YEL03xP-26 | 0.05% | 0.00% | 17.20% | 5.73% | 0.36 | 0.10 | II |
| WHI01xP-22 | 0.04% | | 15.28% | | 0.40 | | II |
| WHI01xP-12 | 0.05% | | 17.38% | | 0.44 | | II |
| WHI01xP-14 | 0.08% | | 14.19% | | 0.43 | | II |
| WHI01xP-19 | 0.04% | | 16.51% | | 0.49 | | II |
| WHI01xP-23 | | | 11.50% | | 0.32 | | II |
| CBD02xP-15 | 0.09% | | 13.68% | | 0.37 | | II |
| CBD02xP-16A | 0.11% | | 20.96% | | 0.30 | | II |
| CBD02xP-17 | 0.09% | | 11.50% | 0.91% | 0.25 | 0.06 | II |
| CBD02xP-10 | 0.11% | | 16.56% | | 0.33 | | II |
| CBD02xP-12 | 0.26% | | 17.48% | | 0.28 | | II |
| CBD02xP-14 | 0.08% | | 15.35% | | 0.24 | | II |
| CBD02xP-18 | 0.05% | | 14.43% | | 0.33 | | II |
| CBD02xP-31 | 0.03% | | 11.49% | | 0.26 | | II |
| CBD02xP-05 | 0.03% | 0.01% | 14.29% | 5.13% | 0.23 | 0.04 | II |
| CBD02xP-30 | 0.08% | | 18.17% | | 0.28 | | II |
| CBD02xP-32 | 0.03% | | 11.79% | 0.40% | 0.37 | 0.04 | II |
| CBD02xP-40 | 0.04% | | 10.02% | | 0.34 | | II |
| CBD02xP-53 | 0.07% | | 9.26% | | 0.31 | | II |
| CBD02xP-09 | 0.05% | | 15.14% | | 0.26 | | II |
| CBD02xP-28 | 0.05% | | 14.35% | 4.51% | 0.23 | 0.11 | II |
| CBD02xP-47 | 0.03% | | 13.72% | | 0.28 | | II |
| CBD03xP-03 | | | 10.90% | | 0.34 | | II |
| CBD03xP-05 | | | 7.98% | | 0.33 | | II |
| CBD03xP-09 | | | 9.02% | | 0.36 | | II |
| CBD04xP-02 | 0.08% | | 9.32% | | 0.50 | | II |
| CBD04xP-03 | | | 12.79% | | 0.62 | | II |
| CBD04xP-06 | 0.03% | | 11.60% | 1.73% | 0.46 | 0.12 | II |
| CBD05xP-02 | 0.05% | 0.03% | 7.92% | 1.64% | 0.23 | 0.06 | II |
| CBD05xP-05 | 0.13% | 0.05% | 11.89% | 0.16% | 0.23 | 0.11 | II |
| CBD05xS-09 | 0.04% | | 9.93% | | 0.40 | | II |
| CBD05xS-05 | 0.02% | | 11.24% | 0.44% | 0.24 | 0.19 | II |
| CBD05xS-11 | | | 10.12% | 2.05% | 0.28 | 0.02 | II |

TABLE 28

Absolute terpene measurements by GC-FID for THC:CBD and CBD (chemotype II and III) specialty cannabis varieties. Blank values indicate undetectable levels or 0.

| | Terpenes (GC-FID) | | | | | | | | | | | | | | | | | | | |
|---|---|---|---|---|---|---|---|---|---|---|---|---|---|---|---|---|---|---|---|---|
| | terpinolene | | alpha phellandrene | | beta ocimene | | carene | | limonene | | gamma terpinene | | alpha pinene | | alpha terpinene | | beta pinene | | fenchol | |
| Sample | Wt % | 95% CI | Wt % | 95% CI | Wt % | 95% CI | Wt % | 95% CI | Wt % | 95% CI | Wt % | 95% CI | Wt % | 95% CI | Wt % | 95% CI | Wt % | 95% CI | Wt % | 95% CI |
| WHI01xP-15 | | | | | | | | | 0.156% | | | | 0.011% | | | | 0.024% | | 0.016% | |
| CBD02xP-11 | | | | | | | | | 0.120% | 0.024% | | | 0.146% | 0.051% | | | 0.074% | 0.022% | 0.011% | 0.000% |
| CBD03xP-01 | | | | | | | | | 0.057% | 0.005% | | | 0.158% | 0.029% | | | 0.067% | 0.010% | 0.009% | |
| CBD03xP-10 | | | | | | | | | 0.074% | | | | 0.171% | | | | 0.076% | | 0.011% | |
| CBD03xP-07 | | | | | 0.100% | 0.012% | | | 0.089% | 0.025% | | | 0.203% | 0.000% | | | 0.058% | 0.003% | 0.010% | 0.003% |
| CBD04xP-01 | | | | | 0.138% | 0.031% | | | 0.094% | 0.014% | | | 0.253% | 0.030% | | | 0.075% | 0.005% | | |
| CBD04xP-09 | | | | | | | | | 0.197% | | | | 0.012% | | | | 0.022% | | 0.017% | |
| CBD05xP-01 | | | | | 0.128% | 0.021% | | | 0.239% | 0.005% | | | 0.267% | 0.111% | | | 0.135% | 0.041% | 0.020% | 0.004% |
| CBD05xS-13 | | | | | | | | | 0.112% | 0.008% | | | 0.266% | 0.084% | | | 0.081% | 0.022% | 0.013% | 0.001% |
| PUR01xP-06 | | | | | | | | | 0.126% | | | | 0.104% | | | | 0.057% | | 0.013% | |
| PUR01xP-04 | | | | | 0.103% | 0.018% | | | 0.569% | 0.020% | | | 0.087% | 0.012% | | | 0.087% | 0.005% | 0.044% | 0.006% |
| PUR01xP-10 | | | | | 0.068% | | | | 0.333% | | | | 0.058% | | | | 0.052% | | 0.026% | |
| PUR01xP-05 | | | | | 0.113% | | | | 0.276% | | | | 0.022% | | | | 0.034% | | 0.023% | |
| SIL08xP-01 | | | | | | | | | 0.194% | | | | 0.013% | | | | 0.026% | | 0.015% | |
| SIL08xP-08 | | | | | | | | | 0.208% | 0.012% | | | 0.013% | 0.003% | | | 0.027% | 0.005% | 0.017% | 0.003% |
| SIL08xP-30 | | | | | | | | | 0.177% | | | | 0.203% | | | | 0.108% | | 0.018% | |
| SIL08xP-14 | | | | | 0.142% | 0.050% | | | 0.111% | 0.008% | | | 0.400% | 0.206% | | | 0.109% | 0.046% | 0.010% | |
| SIL08xP-18 | | | | | 0.121% | | | | 0.110% | | | | 0.338% | | | | 0.093% | | 0.010% | |
| SIL08xP-34 | | | | | 0.162% | | | | 0.200% | | | | 0.499% | | | | 0.140% | | 0.017% | |
| SIL08xP-03 | 0.046% | | | | | | | | 0.417% | | | | 0.027% | | | | 0.052% | | 0.026% | |

TABLE 28-continued

Absolute terpene measurements by GC-FID for THC:CBD and CBD (chemotype II and III) specialty cannabis varieties.
Blank values indicate undetectable levels or 0.

| Variety | | | | | | | | | | | | | | | | | | | | |
|---|---|---|---|---|---|---|---|---|---|---|---|---|---|---|---|---|---|---|---|---|
| SIL08xP-37 | | | | | 0.309% | | 0.019% | | | | 0.039% | | 0.025% | | | | | | | |
| SIL08xP-38 | | | | | 0.287% | | 0.020% | | | | 0.042% | | 0.025% | | | | | | | |
| WHI04xP-02 | | | | | 0.258% | | 0.017% | | | | 0.032% | | 0.022% | | | | | | | |
| WHI07xP-07 | | | 0.176% | | 0.182% | | 0.286% | | | | 0.091% | | 0.016% | | | | | | | |
| WHI07xP-11 | | | 0.101% | | 0.087% | | 0.204% | | | | 0.063% | | 0.011% | | | | | | | |
| WHI07xP-01 | | | | | 0.386% | | 0.025% | | | | 0.049% | | 0.028% | | | | | | | |
| WHI07xP-08 | | | | | 0.188% | | 0.011% | | | | 0.022% | | 0.012% | | | | | | | |
| WHI07xP-02 | | | 0.042% | | 0.208% | | 0.139% | | | | 0.075% | | 0.020% | | | | | | | |
| YEL03xP-23 | | | 0.155% | 0.069% | 0.320% | 0.013% | 0.028% | 0.000% | | | 0.041% | | 0.025% | 0.001% | | | | | | |
| YEL03xP-26 | 0.712% | 0.085% | 0.226% | 0.074% | 0.142% | 0.023% | 0.042% | 0.006% | 0.022% | 0.001% | 0.074% | 0.011% | 0.015% | 0.001% | | | | | | |
| WHI01xP-22 | | | | | 0.209% | | 0.015% | | | | 0.030% | | 0.019% | | | | | | | |
| WHI01xP-12 | | | | | 0.137% | | 0.153% | | | | 0.083% | | 0.017% | | | | | | | |
| WHI01xP-14 | | | | | 0.267% | | 0.319% | | | | 0.154% | | 0.022% | | | | | | | |
| WHI01xP-19 | | | | | 0.153% | | 0.149% | | | | 0.081% | | 0.015% | | | | | | | |
| WHI01xP-23 | | | | | 0.091% | | 0.083% | | | | 0.050% | | 0.014% | | | | | | | |
| CBD02xP-15 | | | | | 0.285% | | 0.018% | | | | 0.035% | | 0.025% | | | | | | | |
| CBD02xP-16A | | | | | 0.430% | | 0.030% | | | | 0.054% | | 0.032% | | | | | | | |
| CBD02xP-17 | | | 0.217% | | 0.200% | 0.114% | 0.012% | 0.008% | | | 0.027% | 0.017% | 0.016% | 0.007% | | | | | | |
| CBD02xP-10 | | | 0.139% | | 0.154% | | 0.287% | | | | 0.092% | | 0.015% | | | | | | | |
| CBD02xP-12 | | | 0.163% | | 0.126% | | 0.296% | | | | 0.091% | | 0.013% | | | | | | | |
| CBD02xP-14 | | | 0.134% | | 0.107% | | 0.258% | | | | 0.083% | | 0.011% | | | | | | | |
| CBD02xP-18 | | | | | 0.146% | | 0.146% | | | | 0.134% | | 0.014% | | | | | | | |
| CBD02xP-31 | | | 0.136% | | 0.094% | | 0.200% | | | | 0.085% | | | | | | | | | |
| CBD02xP-05 | | | | | 0.141% | 0.047% | 0.187% | 0.083% | | | 0.090% | 0.033% | 0.015% | 0.001% | | | | | | |
| CBD02xP-30 | | | | | 0.133% | | 0.132% | | | | 0.073% | | 0.014% | | | | | | | |

TABLE 28-continued

Absolute terpene measurements by GC-FID for THC:CBD and CBD (chemotype II and III) specialty cannabis varieties.
Blank values indicate undetectable levels or 0.

| Sample | camphene Wt % | 95% CI | alpha terpineol Wt % | 95% CI | alpha humulene Wt % | 95% CI | beta caryophyllene Wt % | 95% CI | linalool Wt % | 95% CI | cary oxide Wt % | 95% CI | myrcene Wt % | 95% CI | Total identified oil (wt %) Wt % | 95% CI |
|---|---|---|---|---|---|---|---|---|---|---|---|---|---|---|---|---|
| CBD02xP-32 | | | | | | | 0.093% | 0.022% | | | 0.091% | 0.012% | 0.051% | 0.001% | 0.013% | 0.003% |
| CBD02xP-40 | | | | | | | 0.181% | | | | 0.170% | | 0.089% | | 0.018% | |
| CBD02xP-53 | | | | | | | 0.099% | | | | 0.126% | | 0.067% | | 0.013% | |
| CBD02xP-09 | | | | | | | 0.094% | | | | 0.193% | | 0.090% | | 0.014% | |
| CBD02xP-28 | | | | | | | 0.121% | 0.043% | | | 0.394% | 0.119% | 0.166% | 0.031% | 0.013% | 0.005% |
| CBD02xP-47 | | | | | | | 0.123% | | | | 0.297% | | 0.131% | | 0.016% | |
| CBD03xP-03 | | | | | | | 0.106% | | | | 0.228% | | 0.107% | | 0.013% | |
| CBD03xP-05 | | | | | | | 0.056% | | | | 0.140% | | 0.063% | | | |
| CBD03xP-09 | | | | | | | 0.066% | | | | 0.161% | | 0.075% | | | |
| CBD04xP-02 | | | | | | | 0.075% | | | | 0.122% | | 0.061% | | 0.010% | |
| CBD04xP-03 | | | | | | | 0.094% | | | | 0.125% | | 0.065% | | 0.013% | |
| CBD04xP-06 | | | | | | | 0.188% | 0.064% | | | 0.012% | 0.006% | 0.023% | 0.008% | 0.016% | 0.004% |
| CBD05xP-02 | 0.336% | 0.075% | | | | | 0.145% | 0.048% | | | 0.043% | 0.009% | 0.027% | 0.005% | 0.015% | 0.005% |
| CBD05xP-05 | 0.534% | 0.025% | | | | | 0.164% | 0.055% | | | 0.081% | 0.008% | 0.039% | 0.004% | 0.017% | 0.007% |
| CBD05xS-09 | 0.100% | | | | | | 0.060% | | | | | | 0.040% | | | |
| CBD05xS-05 | 0.342% | 0.025% | | | | | 0.007% | 0.008% | | | 0.467% | 0.271% | 0.116% | 0.064% | | |
| CBD05xS-11 | 0.294% | 0.029% | | | | | 0.005% | 0.004% | | | 0.517% | 0.432% | 0.125% | 0.099% | | |

| Sample | alpha terpineol Wt % | 95% CI | alpha humulene Wt % | 95% CI | beta caryophyllene Wt % | 95% CI | linalool Wt % | 95% CI | cary oxide Wt % | 95% CI | myrcene Wt % | 95% CI | Total identified oil (wt %) Wt % | 95% CI | Chemotype |
|---|---|---|---|---|---|---|---|---|---|---|---|---|---|---|---|
| WHI01xP-15 | 0.025% | | 0.045% | | 0.045% | | 0.027% | | | | 0.768% | | 1.117% | | III |
| CBD02xP-11 | 0.029% | 0.003% | 0.044% | 0.004% | 0.166% | 0.010% | 0.026% | 0.002% | | | 0.939% | 0.164% | 1.554% | 0.278% | III |
| CBD03xP-01 | | | 0.008% | 0.000% | 0.019% | 0.001% | 0.020% | 0.001% | | | 0.630% | 0.135% | 0.962% | 0.171% | III |

TABLE 28-continued

Absolute terpene measurements by GC-FID for THC:CBD and CBD (chemotype II and III) specialty cannabis varieties. Blank values indicate undetectable levels or 0.

| Sample | C1 | C2 | C3 | C4 | C5 | C6 | C7 | C8 | C9 | C10 | C11 | C12 | Chemotype |
|---|---|---|---|---|---|---|---|---|---|---|---|---|---|
| CBD03xP-10 | | | | | | | | | | 0.754% | 1.086% | | III |
| CBD03xP-07 | 0.022% | | 0.051% | 0.002% | 0.095% | 0.017% | 0.030% | 0.003% | | 0.307% | 0.105% | 0.951% | 0.180% III |
| CBD04xP-01 | 0.057% | 0.007% | 0.030% | 0.000% | 0.086% | 0.001% | 0.051% | 0.011% | | 0.628% | 0.094% | 1.410% | 0.107% III |
| CBD04xP-09 | 0.024% | | | | 0.184% | | 0.068% | | | 0.060% | | 0.584% | III |
| CBD05xP-01 | 0.064% | 0.008% | 0.059% | 0.019% | 0.156% | 0.021% | 0.068% | 0.004% | | 1.484% | 0.263% | 2.490% | 0.067% III |
| CBD05xS-13 | 0.022% | 0.001% | 0.115% | 0.002% | 0.086% | 0.151% | 0.058% | 0.008% | | 0.384% | 0.136% | 1.263% | 0.416% III |
| PUR01xP-06 | 0.020% | | 0.057% | | 0.228% | | 0.041% | | | 0.862% | | 1.508% | II |
| PUR01xP-04 | 0.049% | 0.001% | 0.083% | 0.025% | 0.265% | 0.085% | 0.079% | 0.001% | | 0.168% | 0.005% | 1.542% | 0.121% II |
| PUR01xP-10 | 0.030% | | 0.039% | | 0.143% | | 0.039% | | | 0.096% | | 0.884% | II |
| PUR01xP-05 | 0.028% | | 0.067% | | 0.223% | | 0.047% | | | 0.182% | | 1.015% | II |
| SIL08xP-01 | 0.023% | | 0.098% | | 0.379% | | 0.079% | | | 0.145% | | 0.972% | II |
| SIL08xP-08 | 0.023% | 0.001% | 0.139% | 0.038% | 0.402% | 0.113% | 0.055% | 0.003% | | 0.070% | 0.004% | 0.951% | 0.134% II |
| SIL08xP-30 | 0.025% | | 0.030% | | 0.096% | | 0.042% | | | 0.984% | | 1.683% | II |
| SIL08xP-14 | 0.021% | 0.002% | 0.047% | 0.010% | 0.158% | 0.037% | 0.067% | 0.017% | | 0.706% | 0.085% | 1.764% | 0.451% II |
| SIL08xP-18 | 0.019% | | 0.035% | | 0.116% | | 0.044% | | | 0.503% | | 1.389% | II |
| SIL08xP-34 | 0.025% | | 0.057% | | 0.137% | | 0.087% | | | 0.832% | | 2.156% | II |
| SIL08xP-03 | 0.038% | | 0.069% | | 0.247% | | 0.132% | | | 0.147% | | 1.201% | II |
| SIL08xP-37 | 0.031% | | 0.097% | | 0.244% | | 0.062% | | | 0.135% | | 0.961% | II |
| SIL08xP-38 | 0.031% | | 0.072% | | 0.176% | | 0.102% | | | 0.323% | | 1.078% | II |
| WHI04xP-02 | 0.031% | | 0.054% | | 0.194% | | 0.122% | | | 0.050% | | 0.780% | II |
| WHI07xP-07 | 0.021% | | 0.050% | | 0.145% | | 0.030% | | | 0.540% | | 1.537% | II |
| WHI07xP-11 | | | 0.026% | | 0.084% | | 0.046% | | | 0.636% | | 1.258% | II |
| WHI07xP-01 | 0.033% | | 0.037% | | 0.125% | | 0.085% | | | 0.289% | | 1.057% | II |
| WHI07xP-08 | 0.023% | | 0.064% | | 0.236% | | 0.033% | | | 0.059% | | 0.648% | II |
| WHI07xP-02 | 0.029% | | 0.056% | | 0.142% | | 0.037% | | | 0.867% | | 1.615% | II |

TABLE 28-continued

Absolute terpene measurements by GC-FID for THC:CBD and CBD (chemotype II and III) specialty cannabis varieties.
Blank values indicate undetectable levels or 0.

| Sample | | | | | | | | | | | | | |
|---|---|---|---|---|---|---|---|---|---|---|---|---|---|
| YEL03xP-23 | 0.033% | 0.001% | 0.053% | 0.007% | 0.165% | 0.036% | 0.083% | 0.022% | 0.215% | 0.050% | 1.115% | 0.196% | II |
| YEL03xP-26 | 0.034% | 0.004% | 0.037% | 0.001% | 0.105% | 0.000% | 0.029% | 0.002% | 0.244% | 0.022% | 1.752% | 0.236% | II |
| WHI01xP-22 | | | | 0.012% | | | 0.029% | | 0.305% | | 0.619% | | II |
| WHI01xP-12 | 0.056% | | 0.007% | | | | 0.025% | | 1.600% | | 2.078% | | II |
| WHI01xP-14 | 0.022% | | 0.009% | | 0.080% | | 0.028% | | 1.760% | | 2.661% | | II |
| WHI01xP-19 | | | 0.009% | | 0.060% | | 0.024% | | 1.494% | | 1.985% | | II |
| WHI01xP-23 | | | 0.038% | | 0.156% | | 0.023% | | 0.727% | | 1.182% | | II |
| CBD02xP-15 | 0.027% | | 0.072% | | 0.201% | | 0.046% | | 0.113% | | 0.822% | | II |
| CBD02xP-16A | 0.036% | | 0.064% | | 0.272% | | 0.085% | | 0.194% | | 1.197% | | II |
| CBD02xP-17 | 0.025% | 0.006% | 0.075% | 0.009% | 0.166% | 0.036% | 0.052% | 0.005% | 0.205% | 0.207% | 0.775% | 0.318% | II |
| CBD02xP-05 | 0.022% | | 0.073% | | 0.198% | | 0.050% | | 0.737% | | 1.845% | | II |
| CBD02xP-10 | 0.022% | | 0.025% | | 0.069% | | 0.053% | | 0.769% | | 1.603% | | II |
| CBD02xP-12 | | | 0.048% | | 0.143% | | 0.040% | | 0.777% | | 1.630% | | II |
| CBD02xP-14 | 0.030% | | 0.028% | | 0.078% | | 0.050% | | 1.780% | | 2.540% | | II |
| CBD02xP-18 | 0.057% | | 0.073% | | 0.180% | | 0.038% | | 1.257% | | 2.120% | | II |
| CBD02xP-31 | 0.034% | 0.007% | 0.042% | 0.019% | 0.143% | 0.045% | 0.027% | 0.006% | 0.903% | 0.379% | 1.580% | 0.620% | II |
| CBD02xP-30 | 0.040% | | 0.036% | | 0.108% | | 0.046% | | 1.062% | | 1.644% | | II |
| CBD02xP-32 | 0.043% | 0.005% | 0.045% | 0.007% | 0.108% | 0.011% | 0.032% | 0.003% | 0.693% | 0.022% | 1.166% | 0.045% | II |
| CBD02xP-40 | 0.023% | | 0.023% | | 0.072% | | 0.058% | | 1.214% | | 1.848% | | II |
| CBD02xP-53 | | | 0.044% | | 0.108% | | 0.026% | | 0.623% | | 1.106% | | II |
| CBD02xP-09 | 0.028% | | 0.011% | | 0.031% | | 0.030% | | 1.161% | | 1.652% | | II |
| CBD02xP-28 | 0.030% | 0.005% | 0.011% | 0.002% | 0.028% | 0.007% | 0.034% | 0.006% | 1.486% | 0.465% | 2.281% | 0.382% | II |
| CBD02xP-47 | 0.023% | | 0.016% | | 0.046% | | 0.030% | | 1.419% | | 2.101% | | II |
| CBD03xP-03 | 0.019% | | 0.017% | | 0.064% | | 0.023% | | 1.225% | | 1.802% | | II |
| CBD03xP-05 | | | 0.024% | | 0.066% | | 0.022% | | 0.825% | | 1.196% | | II |

TABLE 28-continued

Absolute terpene measurements by GC-FID for THC:CBD and CBD (chemotype II and III) specialty cannabis varieties.
Blank values indicate undetectable levels or 0.

| Sample | | | | | | | | | | |
|---|---|---|---|---|---|---|---|---|---|---|
| CBD03xP-09 | | 0.016% | | 0.057% | | 0.021% | | 0.751% | 1.147% | II |
| CBD04xP-02 | | 0.026% | | 0.065% | | 0.021% | | 0.727% | 1.107% | II |
| CBD04xP-03 | 0.039% | 0.026% | | 0.059% | | 0.053% | | 0.858% | 1.332% | II |
| CBD04xP-06 | 0.023% | 0.000% | 0.102% | 0.002% | 0.298% | 0.006% | 0.051% | 0.002% | 0.096% | 0.003% | 0.808% | 0.094% | II |
| CBD05xP-02 | 0.023% | | 0.041% | 0.017% | 0.044% | 0.010% | 0.041% | 0.010% | 0.443% | 0.153% | 1.144% | 0.132% | II |
| CBD05xP-05 | 0.023% | 0.004% | 0.085% | 0.000% | 0.160% | 0.037% | 0.040% | 0.002% | 0.746% | 0.170% | 1.888% | 0.241% | II |
| CBD05xS-09 | | | 0.070% | | 0.206% | | 0.044% | | 0.673% | 1.308% | II |
| CBD05xS-05 | | 0.057% | 0.001% | 0.113% | 0.008% | 0.044% | 0.011% | 0.616% | 0.083% | 1.759% | 0.398% | II |
| CBD05xS-11 | | 0.057% | 0.027% | 0.112% | 0.035% | 0.037% | 0.008% | 0.431% | 0.038% | 1.577% | 0.581% | II |

TABLE 29

Relative terpene levels as measured by GC-FID for THC:CBD and CBD (chemotype II and III) specialty cannabis varieties. Blank values indicate undetectable levels or 0.

| Sample | terpinolene | alpha phellandrene | beta ocimene | carene | limonene | gamma terpinene | alpha pinene | alpha terpinene | beta pinene | fenchol | camphene | alpha terpineol | alpha humulene | beta caryophyllene | linalool | cavy oxide | myrcene | Chemotype |
|---|---|---|---|---|---|---|---|---|---|---|---|---|---|---|---|---|---|---|
| WHI01xP-15 | | | | | 14% | | 1% | | 2% | 1% | | 2% | 4% | 4% | 2% | | 69% | III |
| CBD02xP-11 | | | | | 8% | | 9% | | 5% | 1% | | 2% | 3% | 11% | 2% | | 60% | III |
| CBD03xP-01 | | | | | 6% | | 16% | | 7% | 1% | | | 1% | 2% | 2% | | 65% | III |
| CBD03xP-10 | | | | | 7% | | 16% | | 7% | 1% | | | | | | | 69% | III |
| CBD03xP-07 | | | 11% | | 9% | | 21% | | 6% | 1% | | | | | | | | |
| CBD04xP-01 | | | 10% | | 7% | | 18% | | 5% | | | | | | | | | |
| CBD04xP-09 | | | | | 34% | | 2% | | 4% | 3% | | | | | | | | |
| CBD05xP-01 | | | | | 10% | | 11% | | 5% | 1% | | | | | | | | |
| CBD05xS-13 | | | 10% | | 9% | | 21% | | 6% | 1% | | | | | | | | |
| PUR01xP-06 | | | | | 8% | | 7% | | 4% | 1% | | | | | | | | |
| PUR01xP-04 | | | 7% | | 37% | | 6% | | 6% | 3% | | | | | | | | |
| PUR01xP-10 | | | 8% | | 38% | | 7% | | 6% | 3% | | | | | | | | |
| PUR01xP-05 | | | 11% | | 27% | | 2% | | 3% | 2% | | | | | | | | |
| SIL08xP-01 | | | | | 20% | | 1% | | 3% | 2% | | | | | | | | |
| SIL08xP-08 | | | | | 22% | | 1% | | 3% | 2% | | | | | | | | |
| SIL08xP-30 | | | | | 11% | | 12% | | 6% | 1% | | | | | | | | |
| SIL08xP-14 | | | 8% | | 6% | | 23% | | 6% | 1% | | | | | | | | |
| SIL08xP-18 | | | 9% | | 8% | | 24% | | 7% | 1% | | | | | | | | |
| SIL08xP-34 | | | 8% | | 9% | | 23% | | 6% | 1% | | | | | | | | |
| SIL08xP-03 | 4% | | | | 35% | | 2% | | 4% | 2% | | | | | | | | |
| SIL08xP-37 | | | | | 32% | | 2% | | 4% | 3% | | | | | | | | |
| SIL08xP-38 | | | | | 27% | | 2% | | 4% | 2% | | | | | | | | |
| WHI04xP-02 | | | | | 33% | | 2% | | 4% | 3% | | | | | | | | |
| WHI07xP-07 | | | 11% | | 12% | | 19% | | 6% | 1% | | | | | | | | |
| WHI07xP-11 | | | 8% | | 7% | | 16% | | 5% | 1% | | | | | | | | |
| WHI07xP-01 | | | | | 37% | | 2% | | 5% | 3% | | | | | | | | |
| WHI07xP-08 | | | | | 29% | | 2% | | 3% | 2% | | | | | | | | |
| WHI07xP-02 | | | 3% | | 13% | | 9% | | 5% | 1% | | | | | | | | |
| YEL03xP-23 | | | 14% | | 29% | | 3% | | 4% | 2% | | | | | | | | |
| YEL03xP-26 | 41% | 2% | 13% | 1% | 8% | 1% | 2% | 1% | 4% | 1% | | | | | | | | |
| WHI01xP-22 | | | | | 34% | | 2% | | 5% | 3% | | | | | | | | |
| WHI01xP-12 | | | | | 7% | | 7% | | 4% | 1% | | | | | | | | |
| WHI01xP-14 | | | | | 10% | | 12% | | 6% | 1% | | | | | | | | |
| WHI01xP-19 | | | | | 8% | | 8% | | 4% | 1% | | | | | | | | |
| WHI01xP-23 | | | | | 8% | | 7% | | 4% | 1% | | | | | | | | |
| CBD02xP-15 | | | | | 35% | | 2% | | 4% | 3% | | | | | | | | |
| CBD02xP-16A | | | | | 36% | | 3% | | 5% | 3% | | | | | | | | |
| CBD02xP-17 | | | | | 26% | | 2% | | 3% | 2% | | | | | | | | |
| CBD02xP-10 | | | 12% | | 8% | | 16% | | 5% | 1% | | | | | | | | |
| CBD02xP-12 | | | 9% | | 8% | | 18% | | 6% | 1% | | | | | | | | |
| CBD02xP-14 | | | 10% | | 7% | | 16% | | 5% | 1% | | | | | | | | |
| CBD02xP-18 | | | 5% | | 6% | | 6% | | 5% | 1% | | | | | | | | |
| CBD02xP-31 | | | 6% | | 4% | | 9% | | 4% | | | | | | | | | |
| CBD02xP-05 | | | | | 9% | | 12% | | 6% | 1% | | | | | | | | |
| CBD02xP-30 | | | | | 8% | | 8% | | 4% | 1% | | | | | | | | |
| CBD02xP-32 | | | | | 8% | | 8% | | 4% | 1% | | | | | | | | |
| CBD02xP-40 | | | | | 10% | | 9% | | 5% | 1% | | | | | | | | |
| CBD02xP-53 | | | | | 9% | | 11% | | 6% | 1% | | | | | | | | |
| CBD02xP-09 | | | | | 6% | | 12% | | 5% | 1% | | | | | | | | |
| CBD02xP-28 | | | | | 5% | | 17% | | 7% | 1% | | | | | | | | |
| CBD02xP-47 | | | | | 6% | | 14% | | 6% | 1% | | | | | | | | |
| CBD03xP-03 | | | | | 6% | | 13% | | 6% | 1% | | | | | | | | |
| CBD03xP-05 | | | | | 5% | | 12% | | 5% | | | | | | | | | |
| CBD03xP-09 | | | | | 6% | | 14% | | 7% | | | | | | | | | |
| CBD04xP-02 | | | | | 7% | | 11% | | 6% | 1% | | | | | | | | |
| CBD04xP-03 | | | | | 7% | | 9% | | 5% | 1% | | | | | | | | |
| CBD04xP-06 | | | | | 23% | | 1% | | 3% | 2% | | | | | | | | |
| CBD05xP-02 | | | 29% | | 13% | | 4% | | 2% | 1% | | | | | | | | |
| CBD05xP-05 | | | 28% | | 9% | | 4% | | 2% | 1% | | | | | | | | |
| CBD05xS-09 | | | 8% | | 5% | | 9% | | 3% | | | | | | | | | |
| CBD05xS-05 | | | 19% | | 0% | | 27% | | 7% | | | | | | | | | |
| CBD05xS-11 | | | 19% | | 0% | | 33% | | 8% | | | | | | | | | |

TABLE 29-continued

Relative terpene levels as measured by GC-FID for THC:CBD and CBD (chemotype II and III) specialty cannabis varieties. Blank values indicate undetectable levels or 0.

| Name | | | | | | | Chemotype |
|---|---|---|---|---|---|---|---|
| CBD03xP-07 | | 2% | 5% | 10% | 3% | 32% | III |
| CBD04xP-01 | | 4% | 2% | 6% | 4% | 45% | III |
| CBD04xP-09 | | 4% | | 32% | 12% | 10% | III |
| CBD05xP-01 | | 3% | 2% | 6% | 3% | 60% | III |
| CBD05xS-13 | | 2% | 9% | 7% | 5% | 30% | III |
| PUR01xP-06 | | 1% | 4% | 15% | 3% | 57% | II |
| PUR01xP-04 | 1% | 3% | 5% | 17% | 5% | 11% | II |
| PUR01xP-10 | | 3% | 4% | 16% | 4% | 11% | II |
| PUR01xP-05 | | 3% | 7% | 22% | 5% | 18% | II |
| SIL08xP-01 | | 2% | 10% | 39% | 8% | 15% | II |
| SIL08xP-08 | | 2% | 15% | 42% | 6% | 7% | II |
| SIL08xP-30 | | 1% | 2% | 6% | 2% | 58% | II |
| SIL08xP-14 | | 1% | 3% | 9% | 4% | 40% | II |
| SIL08xP-18 | | 1% | 3% | 8% | 3% | 36% | II |
| SIL08xP-34 | | 1% | 3% | 6% | 4% | 39% | II |
| SIL08xP-03 | | 3% | 6% | 21% | 11% | 12% | II |
| SIL08xP-37 | | 3% | 10% | 25% | 6% | 14% | II |
| SIL08xP-38 | | 3% | 7% | 16% | 9% | 30% | II |
| WHI04xP-02 | | 4% | 7% | 25% | 16% | 6% | II |
| WHI07xP-07 | | 1% | 3% | 9% | 2% | 35% | II |
| WHI07xP-11 | | | 2% | 7% | 4% | 51% | II |
| WHI07xP-01 | | 3% | 4% | 12% | 8% | 27% | II |
| WHI07xP-08 | | 4% | 10% | 36% | 5% | 9% | II |
| WHI07xP-02 | | 2% | 3% | 9% | 2% | 54% | II |
| YEL03xP-23 | | 3% | 5% | 15% | 7% | 19% | II |
| YEL03xP-26 | | 2% | 2% | 6% | 2% | 14% | II |
| WHI01xP-22 | | | 2% | | 5% | 49% | II |
| WHI01xP-12 | | 3% | 0% | | 1% | 77% | II |
| WHI01xP-14 | | 1% | 0% | 3% | 1% | 66% | II |
| WHI01xP-19 | | | 0% | 3% | 1% | 75% | II |
| WHI01xP-23 | | | 3% | 13% | 2% | 62% | II |
| CBD02xP-15 | | 3% | 9% | 24% | 6% | 14% | II |
| CBD02xP-16A | | 3% | 5% | 23% | 7% | 16% | II |
| CBD02xP-17 | | 3% | 10% | 21% | 7% | 26% | II |
| CBD02xP-10 | | 1% | 4% | 11% | 3% | 40% | II |
| CBD02xP-12 | | 1% | 2% | 4% | 3% | 48% | II |
| CBD02xP-14 | | | 3% | 9% | 2% | 48% | II |
| CBD02xP-18 | | 1% | 1% | 3% | 2% | 70% | II |
| CBD02xP-31 | | 3% | 3% | 8% | 2% | 59% | II |
| CBD02xP-05 | | 2% | 3% | 9% | 2% | 57% | II |
| CBD02xP-30 | | 2% | 2% | 7% | 3% | 65% | II |
| CBD02xP-32 | | 4% | 4% | 9% | 3% | 59% | II |
| CBD02xP-40 | | 1% | 1% | 4% | 3% | 66% | II |
| CBD02xP-53 | | | 4% | 10% | 2% | 56% | II |
| CBD02xP-09 | | 2% | 1% | 2% | 2% | 70% | II |
| CBD02xP-28 | | 1% | 0% | 1% | 1% | 65% | II |
| CBD02xP-47 | | 1% | 1% | 2% | 1% | 68% | II |
| CBD03xP-03 | | 1% | 1% | 4% | 1% | 68% | II |
| CBD03xP-05 | | | 2% | 6% | 2% | 69% | II |
| CBD03xP-09 | | | 1% | 5% | 2% | 65% | II |
| CBD04xP-02 | | | 2% | 6% | 2% | 66% | II |
| CBD04xP-03 | | 3% | 2% | 4% | 4% | 64% | II |
| CBD04xP-06 | | 3% | 13% | 37% | 6% | 12% | II |
| CBD05xP-02 | | 2% | 4% | 4% | 4% | 39% | II |
| CBD05xP-05 | | 1% | 5% | 8% | 2% | 39% | II |
| CBD05xS-09 | | | 5% | 16% | 3% | 51% | II |
| CBD05xS-05 | | | 3% | 6% | 2% | 35% | II |
| CBD05xS-11 | | | 4% | 7% | 2% | 27% | II |

Example 8

Phenotypic Analysis THC:CBD and CBD Specialty *Cannabis* Progeny

The new specialty *cannabis* varieties created through crosses described in Examples 5 and 6 were subjected to phenotypic analysis as described in Example 2. Seeds were allowed to germinate in indoor facilities for 10 days and were then transferred to grow in an outdoor growing facility. Plants were allowed to grow for 120 days after germination until maturity and were analyzed as described in Example 2. Measurements were conducted as described in Example 2 unless noted otherwise.

The progeny of this example were grown during the "short season" defined as November through February in California (~36.67° N). The 2013-2014 short was marked by record lows and a run of cloudy days that dramatically reduced growth, flower production, trichome formation. These factors combined with low light angles reduced yields and oil production significantly. However, the cooler temperatures combined with higher precipitation weather also provide excellent conditions for fungal pathogens and provide researchers with a great environment to select for resistance to both cold weather, low light levels and fungal pathogens. Table 30 outlines the results of the phenotypic analysis.

Node Branching—Node branching was visually determined by inspecting nodes and determining the amount of branching at plant maturity at 120 days post transfer. For this example branching was notated with a Y to indicate branching at nodes and N to indicate low or no branching at nodes.

Apical Inflorescence Size—For this example, inflorescence size was visually estimated and assigned a score of 1-10 with higher numbers corresponding to larger inflorescences. Due to the short growth season, relative comparisons were used for assessing progeny for future production and/or breeding schemes.

Floral Cluster Density—Floral cluster density is a measure of how tightly packed floral buds are in a plant inflorescence. For this example, floral cluster density was visually estimated and assigned a score of 1-10 with higher numbers corresponding to denser clusters. Due to the short growth season, relative comparisons were used for assessing progeny for future production and/or breeding schemes.

Ripening Mode—Ripening Mode was determined by tracking the ripening of mature inflorescences. All progeny exhibited relatively short and uniform ripening times. The ripening for all progeny was even among all the inflorescences. This is in contrast with other *cannabis* which can exhibit staged ripening in which various inflorescences ripen at different times.

Average Calyx Length—Calyx length was measured in centimeters from the base of the calyx to the tip of the leaf but not the pistil. Measurements were taken from mature plants at 120 days post germination.

Initial selections were conducted based on measured phenotypes and chemical analysis described in Example 7. Cuttings of desirable progeny were preserved for subsequent growth trials during a longer warmer season. These cuttings are also being used for subsequent breeding as described in Example 5, 19, and 20. Phenotypic results for these cuttings and their F2 and S2 progeny will be grown outdoors during the upcoming season as described in this example or through indoor growth as described in Example 2. Year round production to maximize natural light production is greatly dependent upon short season trials to select progeny that perform well in the conditions outlined above. Many of the selected progeny of several lines are being propagated and flowered in controlled indoor environments to determine more standardized growth metrics.

TABLE 30

Phenotype table of THC:CBD, and CBD (chemotype II and III) progeny.

| Cultivar ID | Plant Height at maturity (cm) | Plant Diameter at maturity (cm) | Number of Leaflets | Leaf Type | Ave # of Internodes | Node Branching | Number of Inflorescence | Apical Inflorescence Size (1-10) | Flower Cluster Density (1-10) | Trichome Density | Ripening Mode | Flower Color & Notes |
|---|---|---|---|---|---|---|---|---|---|---|---|---|
| SIL08xP-01 | 65 | 45 | 7 | B | 7 | N | L | 2 | 9 | 8 | Short, Even | Normal color |
| SIL08xP-03 | 78 | 72 | 7 | B | 9 | Y | M | 2 | 9 | 7 | Short, Even | Normal color |
| SIL08xP-08 | 96 | 62 | 7 | B | 8 | Y | M | 3 | 8 | 7 | Short, Even | Normal color |
| SIL08xP-14 | 74 | 39 | 5 | B | 7 | N | M | 3 | 9 | 8 | Short, Even | Normal color |
| SIL08xP-27 | 80 | 54 | 5 | B | 8 | Y | H | 3 | 10 | 9 | Short, Even | Normal color |
| SIL08xP-30 | 72 | 40 | 5 | B | 8 | N | M | 4 | 9 | 9 | Short, Even | Normal color |
| SIL08xP-34 | 120 | 49 | 7 | B | 8 | Y | M | 2 | 8 | 8 | Short, Even | Normal color, Vigor+ |
| SIL08xP-37 | 97 | 48 | 5 | B | 9 | N | M | 3 | 9 | 8 | Short, Even | Normal color |
| SIL08xP-38 | 97 | 47 | 5 | B | 11 | Y | M | 3 | 8 | 9 | Short, Even | Normal color |
| YEL03xP-16 | 99 | 48 | 9 | B | 10 | Y | M | 6 | 7 | 8 | Short, Even | Normal color |
| YEL03xP-23 | 110 | 80 | 11 | B | 9 | Y | M | 5 | 6 | 8 | Short, Even | Normal color |
| YEL03xP-26 | 92 | 39 | 9 | B | 9 | N |  | 6 | 6 | 7 | Short, Even | Normal color |
| YEL03xP-27 | 95 | 60 | 9 | B | 9 | N | M | 4 | 7 | 7 | Short, Even | Normal color |
| PUR01xP-04 | 65 | 48 | 7 | B | 7 | N | H | 1 | 5 | 5 | Short, Even | Purple Flowers |
| PUR01xP-06 | 50 | 30 | 5 | B | 8 | Y | M | 2 | 4 | 6 | Short, Even | Normal color |
| PUR01xP-10 | 62 | 51 | 9 | B | 8 | N | M | 3 | 6 | 7 | Short, Even | Black Leaves, Vigorous growth |
| KRYA-1 | 82 | 42 | 6 | B | 8 | Y | M | 5 | 7 | 7 | Short, Even | Leaf Serrations |
| WHI07-02 | 90 | 39 | 7 | B | 7 | Y | H | 5 | 5 | 8 | Short, Even | Normal color, Vigorous growth |
| WHI07-03 | 93 | 50 | 7 | B | 7 | Y | M | 3 | 5 | 6 | Short, Even | Normal color |
| WHI07-07 | 80 | 60 | 7 | B | 9 | Y | H | 5 | 6 | 6 | Short, Even | Normal color |
| WHI07xP-11 | 45 | 28 | 5 | B | 6 | N | M | 5 | 6 | 6 | Short, Even | Normal color |
| SIL04xP-01 | 47 | 40 | 7 | B | 7 | Y | M | 7 | 8 | 7 | Short, Even | Normal color, Sweet terpene smell |
| SIL04xP-02 | 50 | 31 | 5 | B | 6 | N | L | 6 | 8 | 8 | Short, Even | Normal color |
| CBD04xP-1 | 70 | 64 | 5 | B | 9 | Y | H | 4 | 5 | 8 | Short, Even | Normal color, Sweet and mint terpene smells |
| CBD04xP-2 | 74 | 40 | 5 | B | 6 | Y | M | 4 | 8 | 8 | Short, Even | Normal color |
| CBD04xP-3 | 77 | 40 | 7 | B | 7 | Y | M | 6 | 6 | 7 | Short, Even | Normal color |
| CBD04xP-4 | 83 | 67 | 7 | B | 8 | Y | H | 4 | 5 | 7 | Short, Even | Normal color, Production, High Yield |
| CBD04xP-6 | 96 | 46 | 7 | B | 6 | Y | H | 3 | 8 | 6 | Short, Even | Normal color, Vigorous growth |
| CBD03xP-01 | 55 | 27 | 5 | B | 6 | N | M | 6 | 4 | 5 | Short, Even | Normal color |
| CBD03xP-03 | 100 | 100 | 7 | B | 9 | Y | M | 4 | 8 | 7 | Short, Even | Normal color, Vigorous growth |

TABLE 30-continued

Phenotype table of THC:CBD, and CBD (chemotype II and III) progeny.

| Cultivar ID | Plant Height at maturity (cm) | Plant Diameter at maturity (cm) | Number of Leaflets | Leaf Type | Ave # of Inter-nodes | Node Branching | Number of Inflo-res-cence | Apical Inflores-cence Size (1-10) | Flower Cluster Density (1-10) | Trichome Density | Ripening Mode | Flower Color & Notes |
|---|---|---|---|---|---|---|---|---|---|---|---|---|
| CBD03xP-05 | 82 | 76 | 5 | B | 10 | Y | H | 6 | 7 | 8 | Short, Even | Normal color, Vigorous growth |
| CBD03xP-07 | 73 | 56 | 7 | B | 8 | Y | H | 7 | 6 | 7 | Short, Even | Normal color |
| CBD03xP-09 | 96 | 70 | 5 | B | 8 | Y | M | 6 | 7 | 8 | Short, Even | Normal color, Vigorous growth, Sweet smell |
| CBD03xP-10 | 93 | 42 | 5 | B | 6 | Y | M | 7 | 6 | 8 | Short, Even | Normal color |
| CBD03xP-11 | 84 | 42 | 7 | B | 7 | Y | M | 5 | 5 | 5 | Short, Even | Normal color |
| CBD02xP-05 | 100 | 74 | 7 | B | 8 | Y | H | 7 | 5 | 7 | Short, Even | Normal color, Vigorous growth |
| CBD02xP-10 | 80 | 61 | 7 | H | 9 | Y | H | 5 | 7 | 6 | Short, Even | Normal color |
| CBD02xP-11 | 78 | 62 | 7 | H | 10 | N | M | 5 | 5 | 7 | Short, Even | Blue flower color |
| CBD02xP-12 | 80 | 69 | 7 | H | 9 | Y | H | 5 | 6 | 6 | Short, Even | Blue flower color |
| CBD02xP-15 | 87 | 85 | 11 | H | 11 | Y | H | 7 | 6 | 6 | Short, Even | Normal color, Production, High yield |
| CBD02xP-16a | 78 | 60 | 7 | H | 10 | Y | H | 7 | 6 | 6 | Short, Even | Normal color |
| CBD02xP-16 | 84 | 56 | 5 | H | 8 | N | M | 7 | 6 | 6 | Short, Even | Normal color |
| CBD02xP-17 | 81 | 40 | 5 | H | 6 | Y | M | 4 | 5 | 6 | Short, Even | Normal color |
| CBD02xP-18 | 92 | 64 | 5 | H | 11 | Y | H | 4 | 4 | 6 | Short, Even | Normal color, Production, High yield |
| CBD02xP-28 | 89 | 59 | 9 | H | 8 | Y | M | 6 | 7 | 6 | Short, Even | Normal color |
| CBD02xP-30 | 76 | 86 | 5 | H | 8 | Y | H | 4 | 7 | 6 | Short, Even | Normal color |
| CBD02xP-31 | 81 | 96 | 5 | H | 9 | Y | H | 6 | 7 | TBD | Short, Even | Blue flower color |
| CBD05xP-01 | 92 | 81 | 5 | H | 6 | Y | M | 5 | 9 | 8 | Short, Even | Normal color |
| CBD05xP-02 | 120 | 105 | 7 | H | 9 | Y | M | 7 | 5 | 7 | Short, Even | Normal color |
| CBD05xP-05 | 150 | 126 | 7 | H | 6 | Y | M | 7 | 5 | 8 | Short, Even | Normal color, Vigor+ |
| CBD05xS-05 | 71 | 54 | 7 | B | 7 | Y | M | 7 | 7 | 7 | Short, Even | Normal color |
| CBD05xS-11 | 86 | 39 | 7 | B | 9 | N | M | 7 | 8 | 7 | Short, Even | Normal color, Cherry Pie |
| CBD05xS-13 | 59 | 33 | 7 | B | 7 | Y | M | 7 | 8 | 7 | Short, Even | Normal color |
| CBD02xP-32 | 80 | 53 | 7 | H | 5 | N | L | 6 | 6 | 6 | Short, Even | Normal color, Astringent Cherry |
| CBD02xP-40 | 49 | 38 | 5 | B | 6 | N | M | 6 | 6 | 6 | Short, Even | Normal color |
| CBD02xP-47 | 72 | 55 | 5 | B | 6 | Y | M | 4 | 6 | 6 | Short, Even | Normal color |
| CBD02xP-55 | 73 | 48 | 5 | B | 8 | Y | H | 4 | 6 | 6 | Short, Even | Blue flower color |
| WHI01xP18 | 80 | 64 | 5 | B | 9 | Y | H | 4 | 5 | 6 | Short, Even | Normal color |
| WHI01xP19 | 79 | 59 | 7 | B | 10 | Y | H | 3 | 3 | 4 | Short, Even | Normal color, Bubblegum flavor |
| WHI01xP-22 | 81 | 61 | 7 | B | 9 | Y | H | 4 | 3 | 6 | Short, Even | Normal color |
| WHI01xP-23 | 65 | 50 | 5 | B | 10 | N | L | 32 | 6 | 4 | Short, Even | Normal color |
| CBD24 | 59 | 47 | 5 | B | 10 | Y | H | 2 | 3 | 3 | Short, Even | Normal color |
| CBD11 | 61 | 45 | 7 | H | 7 | N | M | 2 | 4 | 6 | Short, Even | Normal color |
| CBD13 | 60 | 31 | 7 | H | 8 | Y | M | 3 | 6 | 4 | Short, Even | Normal color |
| WHI01xP-15 | 100 | 57 | 5 | H | 10 | Y | H | 3 | 7 | 4 | Short, Even | Normal color, Production, High yield |

Example 9

Volunteer Trials Using THC:CBD Specialty *Cannabis*. Effect of Added CBD

In order to demonstrate the added utility of the specialty *cannabis* varieties of the present invention, volunteer comparison trials were conducted. During these trials, volunteers were provided with *cannabis* flower blends with varying terpene and cannabinoid profiles to determine the effect of *cannabis* with CBD, effect of higher terpene oil content, and the effect of diverse terpene profiles with reduced myrcene contents. The trials were split into two parts. The first part (Weeks 1-2) compared volunteer responses to THC-only cultivars and cultivars that contained THC plus a small amount of CBD.

The volunteer trial for CBD was conducted over 2 weeks. Volunteers were split into six groups (1-6). Each volunteer in the group was given two samples (a control and a comparator blend). For instance, they were given a1 and a2, or b1 and b2, or c1 and c2, or d1 and d2, or e1 and e2, or f1 and f2 (see Table 31 for trial design). In this trial, the control comparator blends were prepared to contain nearly identical levels of THC and terpenes, but each week the comparator had either 1.5% CBD, or 2.5% CBD added in. For the higher percentages of CBD, a cannabinoid rich form of hash known as kief was used rather than flower so a higher concentration could be added without affecting the terpene profile as significantly as adding whole *cannabis* flowers.

TABLE 31

CBD Effect Trial Overview for Weeks 1 and 2.

| Week 1 THC or THC + 1.5% CBD | Week 2 THC or THC + 2.5% CBD | Terpene Class | Control and Comparator Terpenes | Base Cultivar | Control ID | Comp ID |
|---|---|---|---|---|---|---|
| Group 1 | Group 6 | a | myrcene, pinene | GRA8 | a1 | a2 |
| Group 2 | Group 1 | b | limonene, linalool, caryophyllene, humulene | WHI2 | b2 | b1 |
| Group 3 | Group 2 | c | ocimene, myrcene | GRE1 | c1 | c2 |
| Group 4 | Group 3 | d | terpinolene, ocimene | PUR2 | d2 | d1 |
| Group 5 | Group 4 | e | myrcene, pinene, ocimene, linalool, caryophyllene | PUR5 | e1 | e2 |
| Group 6 | Group 5 | f | limonene, caryophyllene, myrcene, linalool | RED1 | f2 | f1 |

The samples were prepared by first assaying the individual cultivars for their cannabinoid and terpene levels. Once levels were determined the mass ratios of the cultivars needed to attain the desired analyte levels could be predicted. The appropriate amounts of materials were combined in a coffee grinder. A finer grind was needed during the first four-week section to mask the addition of the kief. The material was split into 1.0-1.5 g samples and stored at −20 until distribution (typically within 24 hours). Enough of each blend was made to analyze the samples in triplicate to verify the cannabinoid and terpene levels (See Table 32 and 33 for terpene and cannabinoid analysis of blends given to patients). The controls (THC only) are in bold face and it can be seen the levels of THC are roughly similar within a group. It also can be seen that the blending process produced consistent levels of cannabinoids and terpenes that were close to predicted values.

TABLE 32

Cannabinoid levels of cannabis blends for Week 1 and Week 2 trials as measured by GC-FID and HPLC. Blank values indicate undetectable levels or 0.

| | Sample | Cannabinoids (GC-FID) | | | | | | Cannabinoids (UHPLC) | | | | | |
|---|---|---|---|---|---|---|---|---|---|---|---|---|---|
| | | THC | | CBD | | THC:CBD by GC | | THCA | | CBDA | | THCA:CBDA by HPLC | |
| | | Wt % | 95% CI | Wt % | 95% CI | Wt % | 95% CI | Wt % | 95% CI | Wt % | 95% CI | Wt % | 95% CI |
| Week 1 | MPCM-13A-002-a1 | 20.90% | 0.91% | | | | | 24.04% | 0.44% | | | | |
| | MPCM-13A-002-a2 | 18.14% | 0.50% | 1.82% | 0.04% | 9.98 | 0.24 | 21.32% | 0.49% | 2.14% | 0.10% | 9.96 | 0.34 |
| | MPCM-13A-002-b1 | 15.82% | 1.11% | 1.60% | 0.06% | 9.90 | 0.98 | 19.17% | 0.71% | 1.90% | 0.14% | 10.14 | 1.01 |
| | MPCM-13A-002-b2 | 17.51% | 0.58% | | | | | 20.80% | 0.65% | | | | |
| | MPCM-13A-002-c1 | 19.10% | 0.19% | | | | | 22.91% | 0.27% | | | | |
| | MPCM-13A-002-c2 | 17.24% | 0.66% | 1.65% | 0.07% | 10.50 | 0.86 | 20.67% | 1.04% | 2.02% | 0.02% | 10.22 | 0.58 |
| | MPCM-13A-002-d1 | 10.67% | 0.31% | 1.75% | 0.04% | 6.11 | 0.16 | 13.24% | 0.23% | 2.17% | 0.17% | 6.11 | 0.44 |
| | MPCM-13A-002-d2 | 12.22% | 0.96% | | | | | 15.27% | 1.15% | | | | |
| | MPCM-13A-002-e1 | 20.90% | 0.56% | | | | | 24.69% | 0.47% | | | | |
| | MPCM-13A-002-e2 | 18.41% | 0.99% | 1.80% | 0.08% | 10.23 | 0.74 | 21.86% | 0.85% | 2.23% | 0.16% | 9.84 | 0.67 |
| | MPCM-13A-002-f1 | 15.83% | 0.58% | 1.83% | 0.07% | 8.68 | 0.45 | 19.30% | 0.87% | 2.28% | 0.11% | 8.46 | 0.37 |
| | MPCM-13A-002-f2 | 17.92% | 0.55% | | | | | 21.21% | 0.62% | | | | |
| Week 2 | MPCM-13A-003-a1 | 19.17% | 0.84% | | | | | 25.48% | 1.14% | | | | |
| | MPCM-13A-003-a2 | 20.09% | 0.68% | 2.76% | 0.18% | 7.28 | 0.26 | 25.45% | 1.00% | 3.31% | 0.33% | 7.72 | 0.67 |
| | MPCM-13A-003-b1 | 16.81% | 0.19% | 2.69% | 0.04% | 6.26 | 0.05 | 21.46% | 0.76% | 3.18% | 0.14% | 6.75 | 0.53 |
| | MPCM-13A-003-b2 | 16.60% | 0.69% | | | | | 22.28% | 0.98% | | | | |
| | MPCM-13A-003-c1 | 18.92% | 0.55% | | | | | 24.57% | 0.35% | | | | |
| | MPCM-13A-003-c2 | 18.59% | 0.34% | 2.93% | 0.30% | 6.37 | 0.63 | 23.56% | 0.11% | 3.53% | 0.43% | 6.72 | 0.85 |
| | MPCM-13A-003-d1 | 14.50% | 0.67% | 2.93% | 0.27% | 4.97 | 0.48 | 18.51% | 0.71% | 3.47% | 0.40% | 5.37 | 0.62 |
| | MPCM-13A-003-d2 | 11.45% | 0.63% | | | | | 16.09% | 0.60% | | | | |
| | MPCM-13A-003-e1 | 20.97% | 1.09% | | | | | 27.28% | 0.60% | | | | |
| | MPCM-13A-003-e2 | 20.18% | 0.53% | 2.80% | 0.15% | 7.21 | 0.21 | 25.58% | 0.78% | 3.24% | 0.22% | 7.90 | 0.30 |
| | MPCM-13A-003-f1 | 17.72% | 0.24% | 3.05% | 0.10% | 5.82 | 0.13 | 22.96% | 0.24% | 3.60% | 0.20% | 6.39 | 0.40 |
| | MPCM-13A-003-f2 | 17.07% | 0.16% | | | | | 22.80% | 0.26% | | | | |

TABLE 33

Terpene contents of cannabis blends for Week 1 and Week 2 trials as measured by GC-FID. Blank values indicate undetectable levels or 0.

| | | Terpenes (GC-FID) | | | | | | | | | | | | | | | | |
|---|---|---|---|---|---|---|---|---|---|---|---|---|---|---|---|---|---|---|
| | | alpha pinene | | camphene | | beta pinene | | myrcene | | alpha phellandrene | | carene | | alpha terpinene | | limonene | | beta ocimene | | gamma terpinene | |
| Sample | | Wt % | 95% CI | Wt % | 95% CI | Wt % | 95% CI | Wt % | 95% CI | Wt % | 95% CI | Wt % | 95% CI | Wt % | 95% CI | Wt % | 95% CI | Wt % | 95% CI | Wt % | 95% CI |
| Week 1 | MPCM-13A-002-a1 | 0.489% | 0.005% | | | 0.138% | 0.002% | 0.698% | 0.010% | | | | | | | 0.084% | 0.002% | 0.041% | 0.001% | | |
| | MPCM-13A-002-a2 | 0.440% | 0.008% | | | 0.135% | 0.003% | 0.682% | 0.013% | | | | | | | 0.078% | 0.002% | 0.032% | 0.000% | | |
| | MPCM-13A-002-b1 | 0.090% | 0.005% | 0.014% | 0.001% | 0.105% | 0.005% | 0.324% | 0.014% | | | | | | | 0.575% | 0.020% | 0.098% | 0.003% | | |
| | MPCM-13A-002-b2 | 0.074% | 0.001% | 0.018% | 0.001% | 0.112% | 0.004% | 0.249% | 0.006% | | | | | | | 0.736% | 0.030% | 0.118% | 0.005% | | |
| | MPCM-13A-002-c1 | 0.092% | 0.003% | | | 0.071% | 0.001% | 0.677% | 0.015% | | | | | | | 0.2224% | 0.006% | 0.404% | 0.010% | | |
| | MPCM-13A-002-c2 | 0.135% | 0.006% | | | 0.088% | 0.003% | 0.778% | 0.029% | | | | | | | 0.2221% | 0.007% | 0.367% | 0.010% | | |
| | MPCM-13A-002-d1 | 0.091% | 0.005% | | | 0.098% | 0.001% | 0.340% | 0.003% | 0.027% | 0.000% | 0.019% | 0.000% | 0.016% | 0.001% | 0.132% | 0.002% | 0.221% | 0.004% | 0.011% | 0.000% |
| | MPCM-13A-002-d2 | 0.057% | 0.005% | | | 0.090% | 0.007% | 0.224% | 0.013% | 0.032% | 0.003% | 0.023% | 0.002% | 0.018% | 0.001% | 0.145% | 0.011% | 0.251% | 0.018% | 0.012% | 0.001% |
| | MPCM-13A-002-e1 | 0.353% | 0.016% | | | 0.094% | 0.004% | 1.250% | 0.059% | | | | | | | 0.044% | 0.002% | 0.217% | 0.009% | | |
| | MPCM-13A-002-e2 | 0.329% | 0.023% | | | 0.095% | 0.007% | 1.097% | 0.103% | | | | | | | 0.043% | 0.005% | 0.176% | 0.020% | | |
| | MPCM-13A-002-f1 | 0.071% | 0.005% | | | 0.089% | 0.005% | 0.269% | 0.012% | | | | | | | 0.432% | 0.020% | | | | |
| | MPCM-13A-002-f2 | 0.041% | 0.003% | 0.013% | 0.001% | 0.083% | 0.005% | 0.180% | 0.008% | | | | | | | 0.512% | 0.027% | | | | |
| Week 2 | MPCM-13A-003-a1 | 0.387% | 0.021% | | | 0.109% | 0.006% | 0.560% | 0.030% | | | | | | | 0.066% | 0.004% | 0.035% | 0.002% | | |
| | MPCM-13A-003-a2 | 0.339% | 0.005% | | | 0.096% | 0.001% | 0.469% | 0.005% | | | | | | | 0.063% | 0.001% | | | | |
| | MPCM-13A-003-b1 | 0.073% | 0.002% | | | 0.093% | 0.002% | 0.201% | 0.003% | | | | | | | 0.540% | 0.010% | 0.090% | 0.001% | | |
| | MPCM-13A-003-b2 | 0.073% | 0.003% | | | 0.112% | 0.005% | 0.245% | 0.009% | | | | | | | 0.731% | 0.040% | 0.126% | 0.007% | | |
| | MPCM-13A-003-c1 | 0.097% | 0.003% | | | 0.070% | 0.002% | 0.680% | 0.022% | | | | | | | 0.223% | 0.008% | 0.383% | 0.013% | | |
| | MPCM-13A-003-c2 | 0.091% | 0.002% | | | 0.060% | 0.001% | 0.516% | 0.010% | | | | | | | 0.178% | 0.005% | 0.277% | 0.006% | | |
| | MPCM-13A-003-d1 | 0.061% | 0.003% | | | 0.072% | 0.005% | 0.169% | 0.009% | 0.018% | 0.001% | | | | | 0.160% | 0.017% | 0.143% | 0.008% | | |
| | MPCM-13A-003-d2 | 0.050% | 0.003% | | | 0.078% | 0.004% | 0.190% | 0.007% | 0.022% | 0.001% | | | | | 0.114% | 0.000% | 0.189% | 0.008% | | |

TABLE 33-continued

Terpene contents of *cannabis* blends for Week 1 and Week 2 trials as measured by GC-FID. Blank values indicate undetectable levels or 0.

| Sample | terpinolene Wt% | 95% CI | linalool Wt% | 95% CI | fenchol Wt% | 95% CI | alpha terpineol Wt% | 95% CI | beta caryophyllene Wt% | 95% CI | alpha humulene Wt% | 95% CI | cary oxide Wt% | 95% CI | Total identified oil Wt% | 95% CI | Relative myrcene |
|---|---|---|---|---|---|---|---|---|---|---|---|---|---|---|---|---|---|
| MPCM-13A-003-e1 | 0.337% | 0.016% | | | 0.087% | 0.005% | 1.061% | 0.048% | | | | | 0.040% | 0.001% | 0.177% | 0.006% | |
| MPCM-13A-003-e2 | 0.276% | 0.006% | | | 0.072% | 0.001% | 0.879% | 0.019% | | | | | 0.046% | 0.000% | 0.145% | 0.002% | |
| MPCM-13A-003-f1 | 0.051% | 0.002% | | | 0.072% | 0.001% | 0.148% | 0.002% | | | | | 0.409% | 0.009% | | | |
| MPCM-13A-003-f2 | 0.040% | 0.001% | 0.013% | 0.000% | 0.081% | 0.002% | 0.146% | 0.004% | | | | | 0.474% | 0.010% | | | |

Terpenes (GC-FID)

| | Sample | terpinolene Wt% | 95% CI | linalool Wt% | 95% CI | fenchol Wt% | 95% CI | alpha terpineol Wt% | 95% CI | beta caryophyllene Wt% | 95% CI | alpha humulene Wt% | 95% CI | cary oxide Wt% | 95% CI | Total identified oil Wt% | 95% CI | Relative myrcene |
|---|---|---|---|---|---|---|---|---|---|---|---|---|---|---|---|---|---|---|
| Week 1 | MPCM-13A-002-a1 | | | 0.057% | 0.002% | 0.013% | 0.000% | 0.024% | 0.001% | 0.231% | 0.015% | 0.087% | 0.005% | | | 1.861% | 0.027% | 38% |
| | MPCM-13A-002-a2 | | | 0.052% | 0.001% | | | 0.025% | 0.001% | 0.222% | 0.004% | 0.080% | 0.002% | | | 1.762% | 0.031% | 39% |
| | MPCM-13A-002-b1 | 0.051% | 0.002% | 0.202% | 0.008% | 0.082% | 0.003% | 0.087% | 0.003% | 0.489% | 0.018% | 0.138% | 0.006% | | | 2.238% | 0.119% | 14% |
| | MPCM-13A-002-b2 | 0.051% | 0.001% | 0.222% | 0.017% | 0.089% | 0.007% | 0.094% | 0.006% | 0.503% | 0.035% | 0.142% | 0.009% | | | 2.408% | 0.117% | 10% |
| | MPCM-13A-002-c1 | 0.052% | 0.002% | 0.116% | 0.003% | 0.035% | 0.001% | 0.057% | 0.001% | 0.231% | 0.009% | 0.083% | 0.003% | | | 2.043% | 0.044% | 33% |
| | MPCM-13A-002-c2 | 0.050% | 0.003% | 0.107% | 0.003% | 0.035% | 0.001% | 0.054% | 0.002% | 0.246% | 0.004% | 0.086% | 0.002% | | | 2.167% | 0.069% | 36% |
| | MPCM-13A-002-d1 | 0.546% | 0.013% | 0.062% | 0.002% | 0.027% | 0.001% | 0.048% | 0.002% | 0.141% | 0.006% | 0.038% | 0.001% | | | 1.816% | 0.027% | 19% |
| | MPCM-13A-002-d2 | 0.625% | 0.044% | 0.064% | 0.003% | 0.027% | 0.001% | 0.050% | 0.002% | 0.115% | 0.007% | 0.030% | 0.002% | | | 1.763% | 0.118% | 13% |
| | MPCM-13A-002-e1 | | | 0.185% | 0.010% | | | | | 0.397% | 0.027% | 0.103% | 0.008% | | | 2.643% | 0.122% | 47% |
| | MPCM-13A-002-e2 | | | 0.143% | 0.019% | | | | | 0.385% | 0.064% | 0.100% | 0.017% | | | 2.376% | 0.262% | 46% |
| | MPCM-13A-002-f1 | 0.049% | 0.003% | 0.172% | 0.006% | 0.050% | 0.002% | 0.058% | 0.002% | 0.336% | 0.016% | 0.087% | 0.005% | | | 1.596% | 0.101% | 17% |
| | MPCM-13A-002-f2 | 0.050% | 0.000% | 0.192% | 0.009% | 0.055% | 0.003% | 0.063% | 0.003% | 0.337% | 0.018% | 0.085% | 0.004% | | | 1.609% | 0.079% | 11% |
| Week 2 | MPCM-13A-003-a1 | | | | | | | | | 0.160% | 0.009% | 0.061% | 0.004% | | | 1.453% | 0.089% | 39% |
| | MPCM-13A-003-a2 | | | | | | | | | 0.171% | 0.002% | 0.063% | 0.001% | | | 1.319% | 0.013% | 36% |
| | MPCM-13A-003-b1 | 0.046% | 0.002% | 0.155% | 0.002% | 0.069% | 0.001% | 0.072% | 0.002% | 0.337% | 0.007% | 0.095% | 0.002% | | | 1.786% | 0.026% | 11% |
| | MPCM-13A-003-b2 | 0.050% | 0.001% | 0.195% | 0.011% | 0.085% | 0.005% | 0.087% | 0.004% | 0.407% | 0.027% | 0.114% | 0.007% | | | 2.246% | 0.115% | 11% |

TABLE 33-continued

Terpene contents of *cannabis* blends for Week 1 and Week 2 trials as measured by GC-FID. Blank values indicate undetectable levels or 0.

| | | | | | | | | | | | | | | |
|---|---|---|---|---|---|---|---|---|---|---|---|---|---|---|
| MPCM-13A-003-c1 | 0.049% | 0.002% | 0.108% | 0.006% | | 0.051% | 0.001% | 0.197% | 0.011% | 0.071% | 0.004% | 1.961% | 0.068% | 35% |
| MPCM-13A-003-c2 | | | 0.091% | 0.001% | | 0.047% | 0.001% | 0.179% | 0.003% | 0.064% | 0.001% | 1.534% | 0.028% | 34% |
| MPCM-13A-003-d1 | 0.314% | 0.027% | | | 0.026% | 0.002% | 0.044% | 0.003% | 0.113% | 0.011% | 0.031% | 0.003% | 1.203% | 0.061% | 14% |
| MPCM-13A-003-d2 | 0.387% | 0.019% | 0.055% | 0.002% | 0.023% | 0.001% | 0.042% | 0.001% | 0.097% | 0.003% | 0.025% | 0.001% | 1.318% | 0.030% | 14% |
| MPCM-13A-003-e1 | | | 0.151% | 0.005% | | | | | 0.346% | 0.012% | 0.088% | 0.003% | 2.291% | 0.089% | 46% |
| MPCM-13A-003-e2 | | | 0.127% | 0.001% | 0.013% | 0.001% | 0.024% | 0.001% | 0.290% | 0.006% | 0.076% | 0.001% | 1.955% | 0.039% | 45% |
| MPCM-13A-003-f1 | | | 0.162% | 0.002% | 0.050% | 0.001% | 0.057% | 0.000% | 0.297% | 0.005% | 0.078% | 0.001% | 1.328% | 0.023% | 11% |
| MPCM-13A-003-f2 | | | 0.184% | 0.002% | 0.054% | 0.001% | 0.061% | 0.001% | 0.319% | 0.007% | 0.081% | 0.002% | 1.455% | 0.030% | 10% |

The controls (a1, b2, c1, d2, e1, and f2) had only THC while the comparators (a2, b1, c2, d1, e2, and f1) had approximately the same amount of THC plus a small percentage of CBD. In Week One approximately 1.5% of CBD was added, in Week Two 3% of CBD was added. These non-THC cannabinoids have demonstrated pharmacology (such as CBR antagonist and 5HT-1a agonist) that were hypothesized to attenuate some of the negative side effects of THC by blocking the action of THC itself or by activating alternative pathways.

The controls and comparators in Weeks 1-2 were also blended to have very similar terpene profiles in order to ensure both samples had similar aroma, flavor, and putative entourage effects, so as not to predispose the volunteer to thinking one or the other would be different based on organoleptic properties. Both Table 33, and FIG. 1 (with comparison pairs indicated with brackets) of relative terpene content show the precision with which the blends were engineered to have comparable terpene profiles. The blends were always prepared so the myrcene content was below 60% and the total identified essential oil content was about 1.5%.

The amount of added CBD was kept below 3% since adding more of the myrcene-rich CBD cultivar would have significantly altered the terpene profile and all the groups would have become myrcene dominant. Adding more of the myrcene-rich CBD cultivar would have also diluted the relative amount of THC, and at this stage it was desired to ensure any changes in effect were due to the addition of CBD rather than a significant reduction in THC content.

Thirty volunteers were recruited and asked to fill out demographic surveys. Each week the volunteers were given a control and a comparator, two corresponding surveys (FIG. 2), and asked to fill out the survey forms as they administered the samples over the following week. This was designed to be a head-to-head comparison and the results were then tabulated in Excel and analyzed both as absolute ratings and as differences between the control and comparator. The results of Weeks 1 and 2 (control vs. comparator) are summarized in Table 34 as averages followed by 95% confidence intervals.

The results are presented as the difference in feedback scores between control samples with just THC cannabinoid, to comparator samples with added CBD cannabinoid (see Table 34 and FIG. 3). Several feedback trends can be seen in the comparison of the two samples. Most notably, there appeared to be an obvious decrease in the level of "mind high", "body high", "intoxication", "sedation", and "duration" for *cannabis* blends containing CBD. There also appeared to be an increase in the ability to "function normally" for *cannabis* blends containing CBD. There was also a decrease in "anxiety" and an increase in "energy" level for these blends. Each comparison control and comparator sample contained equal amounts of THC and nearly identical terpene profiles. Thus the differences outlined in Table 34 and FIG. 3 are attributed to the relatively small amount of CBD added to comparator samples.

The observed trends suggest that the addition of a non-THC cannabinoid, such as found in chemotype II cultivars, can help reduce the feelings associated with being "high", reduce intoxication, reduce the duration, reduce sedation, and improve the ability to function normally while under the influence of THC. Thus in some embodiments, the specialty *cannabis* of the present invention with CBD has the potential to reduce adverse effects and provide a larger margin of safety for a number of applications wherein the specialty *cannabis* is provided as a blend or as flower material from an individual variety. In some embodiments, the CBD containing specialty *cannabis* can be used at times when users wish to still be able to function after smoking. In other embodiments the specialty *cannabis* of the present invention can be used for medicinal applications. Many times patients attempting to use *cannabis* for medical treatment discontinue use due to the aforementioned "negative" side effects, such as being "high" or intoxicated, and these ratios have demonstrated a clear potential to mitigate these effects.

The decrease in flavor feedback for the CBD blends was likely due to the addition of unpalatable CBD-rich plant material and kief to reach the desired cannabinoid levels. This result further reinforces our original hypothesis of the need

TABLE 34

Combined feedback results for Week 1-2 trials.

| Question | A | 95% CI | B | 95% CI | C | 95% CI | D | 95% CI | E | 95% CI | F | 95% CI | TOTAL | 95% CI |
|---|---|---|---|---|---|---|---|---|---|---|---|---|---|---|
| Aroma | −1 | 1.42 | 0 | 0.98 | −0.9 | 1.59 | −0.75 | 1.27 | 2 | 1.76 | −0.5 | 2.07 | −0.23 | 0.65 |
| Flavor | −1.86 | 1.98 | −0.13 | 1.14 | −1.6 | 1.55 | −1 | 1.74 | 0.857 | 1.45 | −0.83 | 1.71 | −0.8 | 0.67 |
| Mind | −1.57 | 1.12 | −0.11 | 1.40 | −1.6 | 1.61 | −1.63 | 0.74 | −0.43 | 1.27 | 0.429 | 1.70 | −0.85 | 0.58 |
| Body | −0.43 | 0.72 | 0.222 | 1.52 | −1.2 | 1.62 | −1.38 | 1.33 | 1.143 | 1.93 | −1.14 | 1.79 | −0.5 | 0.65 |
| Intoxication | −1.14 | 1.00 | −0.56 | 1.27 | −1 | 1.13 | −1.5 | 0.74 | 0.286 | 1.02 | −0.57 | 1.41 | −0.77 | 0.46 |
| Calmness | −0.71 | 2.13 | 0.444 | 1.09 | −0.6 | 1.06 | 2.25 | 1.73 | 1.143 | 0.79 | 0.286 | 0.70 | 0.438 | 0.59 |
| Alertness | 0 | 1.42 | −0.33 | 1.27 | 1 | 1.87 | −0.38 | 1.52 | 1.143 | 1.00 | 0.571 | 1.53 | 0.333 | 0.62 |
| Anxiety | −0.29 | 0.93 | 0.333 | 1.03 | 0.6 | 1.14 | −3 | 1.74 | −0.86 | 0.79 | −0.71 | 1.95 | −0.58 | 0.61 |
| Focus | 0 | 0.96 | 0.222 | 0.91 | −0.7 | 1.40 | 0.75 | 1.65 | 0.857 | 0.51 | 0.857 | 1.45 | 0.271 | 0.51 |
| Mood | −2.43 | 1.70 | 0.222 | 0.79 | −1.4 | 1.61 | −0.13 | 1.14 | 0.714 | 0.56 | 1 | 2.01 | −0.38 | 0.63 |
| Energy | 0.143 | 1.31 | 1.111 | 0.89 | −0.3 | 1.34 | 0.25 | 1.03 | 0.286 | 1.02 | 1.143 | 1.84 | 0.417 | 0.51 |
| Hunger | −0.71 | 2.17 | 1.222 | 1.30 | 0.4 | 1.81 | −0.38 | 1.23 | 0 | 1.54 | −0.43 | 2.45 | 0.083 | 0.71 |
| Thirst | −0.14 | 2.16 | −0.56 | 1.14 | −0.7 | 1.94 | −1.5 | 1.23 | −0.57 | 1.34 | −0.29 | 1.90 | −0.65 | 0.66 |
| Physical | −0.57 | 1.53 | 0.667 | 1.22 | −0.1 | 0.85 | 0.5 | 1.48 | 1.143 | 1.00 | −0.29 | 2.21 | 0.229 | 0.56 |
| Emotional | −1.43 | 1.34 | 0 | 0.86 | −0.3 | 1.24 | 0.625 | 1.28 | 1.429 | 1.04 | 1.143 | 2.03 | 0.208 | 0.57 |
| Function | 0.714 | 1.33 | −0.33 | 1.22 | 0.8 | 0.96 | −0.38 | 1.11 | 1.429 | 1.04 | 1.286 | 1.85 | 0.542 | 0.52 |
| Sedation | −0.57 | 1.70 | −0.22 | 0.63 | −1.7 | 1.73 | −1.13 | 1.59 | −0.57 | 1.53 | −0.43 | 1.81 | −0.81 | 0.61 |
| Duration | −1 | 1.54 | 0 | 1.70 | −0.44 | 0.93 | −0.29 | 1.85 | −0.29 | 1.46 | −0.67 | 1.31 | −0.43 | 0.57 |
| Positive | −0.71 | 2.08 | 0.778 | 1.56 | −0.6 | 1.68 | 0.75 | 1.47 | 1 | 0.74 | 1.143 | 2.20 | 0.354 | 0.69 |
| Negative | 0.286 | 2.83 | −0.67 | 0.92 | 1.6 | 1.92 | −0.5 | 1.85 | 0.143 | 1.51 | −0.43 | 2.93 | 0.125 | 0.82 | for specialty *cannabis* varieties which contain CBD with desirable terpene profiles to create pleasing aromas/flavors and reduced side effects. Patients may discontinue use of previously available medicinal CBD marijuana due to unpleasant aromas and poor organoleptic feel. Currently existing THC:CBD cultivars have terpene profiles and total oil content that result in organoleptic properties and entourage effects that are less appealing than the THC-only cultivars. In one embodiment, patients wishing to use the specialty *cannabis* of the present invention for medicinal purposes will prefer the improved aroma and flavor.

While it has been known that CBD is an antagonist to the CB1 and CB2 receptor (Mechoulam et al., 2007 "Cannabidiol-recent advances" Chem biodivers 4(8) 1678-92), studies between CBD producing varieties have often compared varieties with high CBD contents and varying THC contents. Thus it has been difficult to distinguish the effects of the addition of CBD, to that of the reduction of THC. In this study, we have shown that beneficial trends can be seen with the addition of small amount of CBD, and that, unexpectedly, these effects do not require a substantially diminished THC content.

Example 10

Volunteer Trials Using Specialty *Cannabis*. Effect of Added High Terpene Oil

The fifth and sixth week of the trials were designed to test the effect of higher terpene oil content on *cannabis* plants. For this trial, the same groups (1-6) used in Example 9 were asked to compare the more oil rich profiles of (a-f) to the "typical" terpene profile of (g) found in currently existing THC:CBD or CBD varieties (Tables 35 and 36, and FIG. 4). This "typical" profile was represented by a known chemotype II variety "Harlequin" (Week 5), or by mimicking the terpene profile with a blend of CBD01 and BLU06 varieties (Week 6), which allowed the THC:CBD ratio to be adjusted. For each week, the control and the comparator samples had nearly identical ratios of THC:CBD. On Week five, the THC:CBD ratio of the samples being tested was ~1:2 (Harlequin). On Week six, the THC:CBD ratio of the samples was ~2:1 (BLU6 and CBD1 blend). The terpene profile of the control was the typical low oil myrcene-dominated profile of the mixed cannabinoid cultivars, while the comparators had higher oil content representative of the specialty *cannabis* plants of the present invention.

Samples for the trials were generated as described in Example 9. However, for this example, samples were ground by hand. As before, each sample was analyzed via GC-FID and HPLC before being provided to volunteers in order to ensure consistency (Tables 35 and 36, and FIG. 4). The same questionnaire that was used in Example 9 (i.e., as provided in FIG. 2) was used to assess the volunteer feedback on the tested blends.

Figure 4:
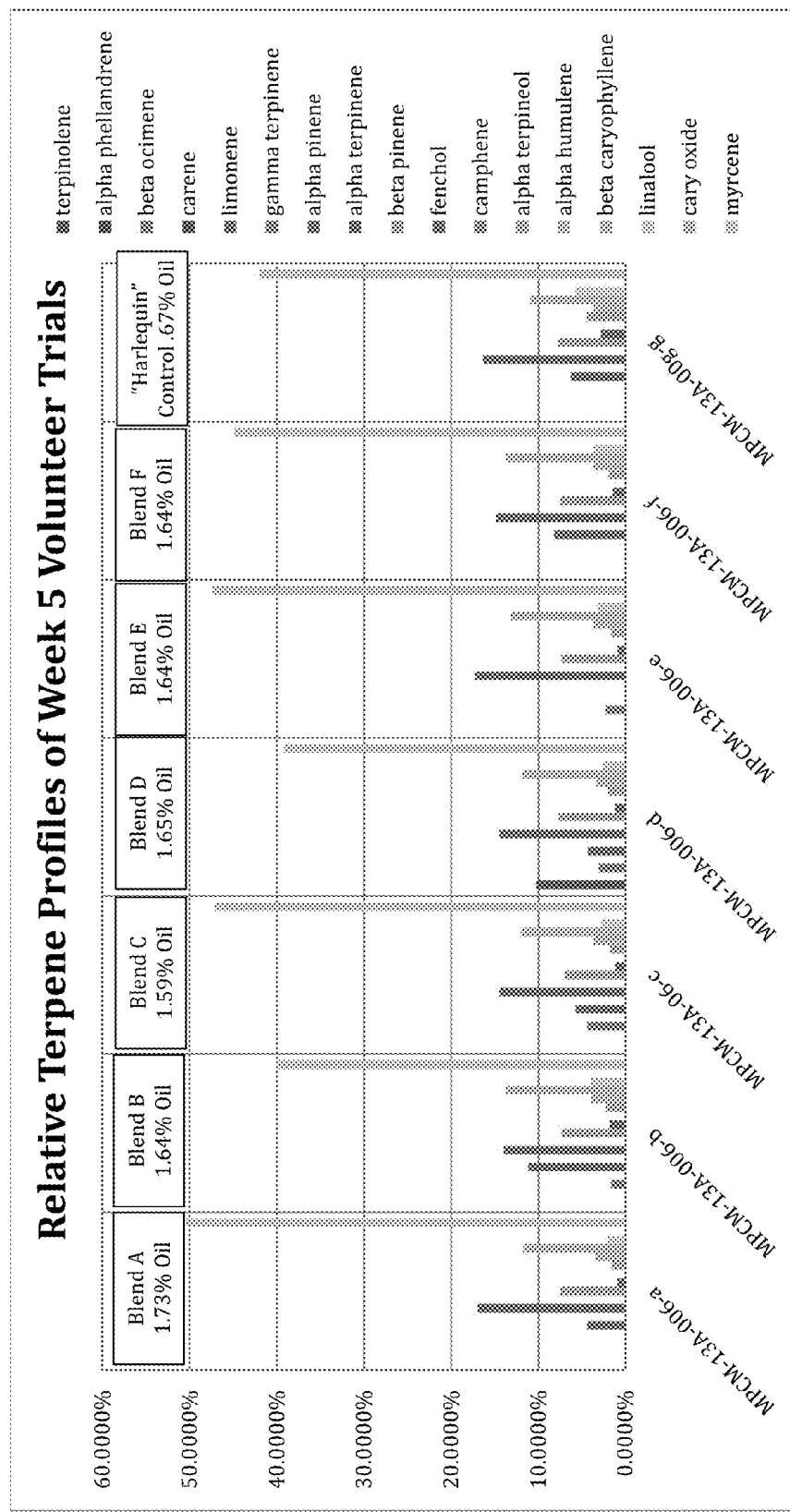
FIG. 4—Bar graph of the relative terpene contents (y-axis) of *cannabis* blends (x-axis) used for Week 5 volunteer trials. Each sample comparison pair was blended to produce similar terpene profiles so as to compare the effects of increased terpene oil contents.

The sample ID of the control sample is highlighted (Tables 35 and 36) and the relative terpene profile is labeled in FIG. 4. Week 5 of this study compared a typical low oil 1:2 THC:CBD variety (Harlequin in this case) to higher oil blends prepared from a parental CBD line (CBD01) and various parental THC lines. Because the mass ratios required to create the 1:2 THC:CBD ratio were approximately 1:4, the terpene profiles were all dominated by myrcene from CBD01, and this is observed in the analytical results. While all the relative terpene profiles were similar and dominated by myrcene, the absolute content was significantly different, with the control (Harlequin) having less than 1% and all of the comparators having greater than 1.5%.

Week six compared a typical low oil 2:1 THC:CBD variety (mimicked by blending BLU06:CBD01) to higher oil blends prepared from a parental CBD line (CBD01) and various parental THC lines. More diversity can now be seen in the terpene profiles of the comparators and the control. The control samples had lower terpene oil contents of ~1%, while the comparators were generally between 1.5-2%.

TABLE 35

Cannabinoid levels of cannabis blends for Week 5 and 6 trials as measured by GC-FID and HPLC. Blank values indicate undetectable levels or 0.

| | | Cannabinoids (GC-FID) | | | | | | Cannabinoids (UHPLC) | | | | | |
|---|---|---|---|---|---|---|---|---|---|---|---|---|---|
| | | THC | | CBD | | THC:CBD by GC | | THCA | | CBDA | | THCA:CBDA by HPLC | |
| | Sample | Wt % | 95% CI | Wt % | 95% CI | Wt % | 95% CI | Wt % | 95% CI | Wt % | 95% CI | Wt % | 95% CI |
| Week 5 | MPCM-13A-006-a | 3.24% | 0.09% | 10.37% | 0.11% | 0.31 | 0.01 | 4.65% | 0.05% | 14.20% | 0.24% | 0.33 | 0.00 |
| | MPCM-13A-006-b | 3.49% | 0.53% | 8.69% | 0.16% | 0.40 | 0.07 | 4.93% | 0.75% | 11.99% | 0.33% | 0.41 | 0.07 |
| | MPCM-13A-06-C | 3.65% | 0.09% | 8.87% | 0.51% | 0.41 | 0.02 | 5.29% | 0.09% | 12.24% | 0.93% | 0.43 | 0.03 |
| | MPCM-13A-006-d | 3.42% | 1.38% | 10.41% | 3.61% | 0.33 | 0.02 | 4.90% | 1.86% | 13.56% | 2.99% | 0.36 | 0.05 |
| | MPCM-13A-006-e | 4.04% | 0.48% | 9.26% | 0.24% | 0.44 | 0.06 | 5.99% | 0.60% | 12.90% | 0.13% | 0.46 | 0.05 |
| | MPCM-13A-006-f | 3.13% | 0.07% | 9.64% | 0.47% | 0.33 | 0.01 | 4.71% | 0.07% | 13.29% | 0.57% | 0.35 | 0.01 |
| | MPCM-13A-00g-g | 4.57% | 0.12% | 9.97% | 0.15% | 0.46 | 0.00 | 6.59% | 0.00% | 14.15% | 0.08% | 0.47 | 0.00 |
| Week 6 | MPCM-13A-007-a | 9.79% | 0.35% | 4.58% | 0.39% | 2.15 | 0.15 | 14.66% | 0.94% | 6.99% | 0.03% | 2.10 | 0.14 |
| | MPCM-13A-007-b | 9.09% | 0.44% | 4.70% | 0.22% | 1.94 | 0.16 | 12.33% | 0.63% | 6.40% | 0.28% | 1.93 | 0.16 |
| | MPCM-13A-007-C | 9.63% | 0.41% | 5.90% | 0.30% | 1.63 | 0.15 | 13.04% | 0.40% | 8.12% | 0.50% | 1.61 | 0.15 |
| | MPCM-13A-007-d | 7.39% | 0.31% | 5.14% | 0.27% | 1.44 | 0.13 | 11.00% | 1.47% | 7.74% | 1.95% | 1.44 | 0.16 |
| | MPCM-13A-007-e | 10.83% | 0.71% | 7.14% | 0.38% | 1.52 | 0.18 | 14.61% | 1.66% | 9.60% | 0.69% | 1.52 | 0.18 |
| | MPCM-13A-007-f | 8.06% | 0.57% | 5.27% | 0.30% | 1.53 | 0.02 | 13.05% | 1.42% | 8.38% | 1.10% | 1.56 | 0.04 |
| | MPCM-13A-007-g | 8.13% | 0.37% | 4.10% | 0.07% | 1.98 | 0.11 | 12.94% | 0.85% | 5.33% | 0.58% | 2.43 | 0.15 |

TABLE 36

Terpene contents of cannabis blends for Week 5 and 6 trials as measured by GC-FID. Blank values indicate undetectable levels or 0.

Terpenes (GC-FID)

| | Sample | alpha pinene Wt % | 95% CI | camphene Wt % | 95% CI | beta pinene Wt % | 95% CI | myrcene Wt % | 95% CI | alpha phellandrene Wt % | 95% CI | carene Wt % | 95% CI | alpha terpinene Wt % | 95% CI | limonene Wt % | 95% CI | beta ocimene Wt % | 95% CI | gamma terpinene Wt % | 95% CI |
|---|---|---|---|---|---|---|---|---|---|---|---|---|---|---|---|---|---|---|---|---|---|
| Week 5 | MPCM-13A-006-a | 0.294% | 0.013% | | | 0.129% | 0.003% | 0.871% | 0.016% | | | | | | | 0.076% | 0.003% | | | | |
| | MPCM-13A-006-b | 0.229% | 0.007% | | | 0.120% | 0.005% | 0.656% | 0.018% | | | | | | | 0.182% | 0.005% | 0.027% | 0.001% | | |
| | MPCM-13A-006-c | 0.229% | 0.013% | | | 0.111% | 0.005% | 0.748% | 0.031% | | | | | | | 0.091% | 0.001% | 0.069% | 0.006% | | |
| | MPCM-13A-06-c | 0.238% | 0.068% | | | 0.126% | 0.038% | 0.643% | 0.193% | | | | | | | 0.071% | 0.022% | 0.051% | 0.016% | | |
| | MPCM-13A-006-d | 0.283% | 0.007% | | | 0.120% | 0.003% | 0.775% | 0.014% | | | | | | | | | 0.037% | 0.001% | | |
| | MPCM-13A-006-e | 0.243% | 0.025% | | | 0.123% | 0.011% | 0.734% | 0.066% | | | | | | | 0.134% | 0.012% | | | | |
| | MPCM-13A-006-f | 0.110% | 0.003% | | | 0.052% | 0.001% | 0.282% | 0.003% | | | | | | | 0.042% | 0.002% | | | | |
| | MPCM-13A-00g-g | 0.323% | 0.004% | | | 0.113% | 0.004% | 0.517% | 0.025% | | | | | | | 0.049% | 0.009% | 0.024% | 0.001% | | |
| | MPCM-13A-007-a | 0.162% | 0.007% | | | 0.108% | 0.003% | 0.416% | 0.014% | | | | | | | 0.314% | 0.010% | 0.047% | 0.001% | | |
| | MPCM-13A-007-b | 0.192% | 0.007% | | | 0.097% | 0.001% | 0.637% | 0.005% | | | | | | | 0.126% | 0.003% | 0.152% | 0.005% | | |
| | MPCM-13A-007-c | 0.161% | 0.006% | | | 0.104% | 0.005% | 0.439% | 0.021% | 0.015% | 0.001% | | | 0.009% | 0.007% | 0.103% | 0.029% | 0.106% | 0.005% | 0.005% | 0.001% |
| | MPCM-13A-007-d | 0.351% | 0.015% | | | 0.125% | 0.005% | 1.030% | 0.033% | | | | | | | 0.075% | 0.002% | 0.087% | 0.002% | | |
| | MPCM-13A-007-e | 0.169% | 0.006% | | | 0.104% | 0.001% | 0.509% | 0.008% | | | | | | | 0.248% | 0.006% | | | | |
| | MPCM-13A-007-f | 0.218% | 0.011% | | | 0.094% | 0.005% | 0.506% | 0.026% | | | | | | | 0.055% | 0.007% | | | | |
| Week 6 | MPCM-13A-007-g | | | | | | | | | | | | | | | | | | | | |

Terpenes (GC-FID)

| | Sample | terpinolene Wt % | 95% CI | linalool Wt % | 95% CI | fenchol Wt % | 95% CI | alpha terpineol Wt % | 95% CI | beta caryophyllene Wt % | 95% CI | beta humulene Wt % | 95% CI | cary oxide Wt % | 95% CI | Total identified oil (wt %) Wt % | 95% CI | Relative myrcene |
|---|---|---|---|---|---|---|---|---|---|---|---|---|---|---|---|---|---|---|
| Week 5 | MPCM-13A-006-a | | | 0.036% | 0.002% | 0.016% | 0.001% | 0.028% | 0.001% | 0.202% | 0.010% | 0.060% | 0.002% | | | 1.727% | 0.010% | 50% |

TABLE 36-continued

Terpene contents of cannabis blends for Week 5 and 6 trials as measured by GC-FID. Blank values indicate undetectable levels or 0.

| | Sample | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| | MPCM-13A-006-b | | | 0.065% | 0.002% | 0.030% | 0.001% | 0.036% | 0.001% | 0.224% | 0.006% | 0.064% | 0.002% | 1.635% | 0.042% | 40% |
| | MPCM-13A-006-c | | | 0.044% | 0.001% | 0.019% | 0.001% | 0.029% | 0.001% | 0.190% | 0.008% | 0.058% | 0.002% | 1.587% | 0.050% | 47% |
| | MPCM-13A-06-c | 0.169% | 0.051% | 0.043% | 0.013% | 0.020% | 0.007% | 0.033% | 0.009% | 0.196% | 0.059% | 0.055% | 0.017% | 1.645% | 0.493% | 39% |
| | MPCM-13A-006-d | | | 0.053% | 0.001% | 0.015% | 0.001% | 0.027% | 0.002% | 0.215% | 0.005% | 0.060% | 0.001% | 1.639% | 0.029% | 47% |
| | MPCM-13A-006-e | | | 0.060% | 0.003% | 0.024% | 0.001% | 0.032% | 0.001% | 0.225% | 0.014% | 0.062% | 0.004% | 1.635% | 0.137% | 45% |
| | MPCM-13A-006-f | | | 0.039% | 0.003% | 0.019% | 0.002% | 0.030% | 0.004% | 0.073% | 0.002% | 0.025% | 0.000% | 0.470% | 0.002% | 42% |
| | MPCM-13A-00g-g | | | | | | | | | 0.164% | 0.012% | 0.056% | 0.004% | 1.290% | 0.046% | 40% |
| Week 6 | MPCM-13A-007-a | | | 0.107% | 0.001% | 0.048% | 0.001% | 0.053% | 0.001% | 0.277% | 0.005% | 0.078% | 0.001% | 1.610% | 0.041% | 26% |
| | MPCM-13A-007-b | | | 0.066% | 0.006% | | | | | 0.194% | 0.031% | 0.063% | 0.011% | 1.588% | 0.051% | 40% |
| | MPCM-13A-007-c | | | 0.046% | 0.001% | 0.021% | 0.001% | 0.036% | 0.002% | 0.142% | 0.008% | 0.039% | 0.002% | 1.498% | 0.066% | 29% |
| | MPCM-13A-007-d | 0.265% | 0.007% | 0.090% | 0.002% | 0.014% | 0.000% | 0.025% | 0.000% | 0.264% | 0.004% | 0.071% | 0.001% | 2.131% | 0.061% | 48% |
| | MPCM-13A-007-e | | | 0.108% | 0.011% | 0.035% | 0.004% | | | 0.257% | 0.029% | 0.068% | 0.008% | 1.541% | 0.061% | 33% |
| | MPCM-13A-007-f | | | 0.046% | 0.001% | 0.016% | 0.001% | 0.024% | 0.000% | 0.077% | 0.001% | 0.025% | 0.001% | 1.040% | 0.050% | 48% |
| | MPCM-13A-007-g | | | | | | | | | | | | | | | |

Figure 5:
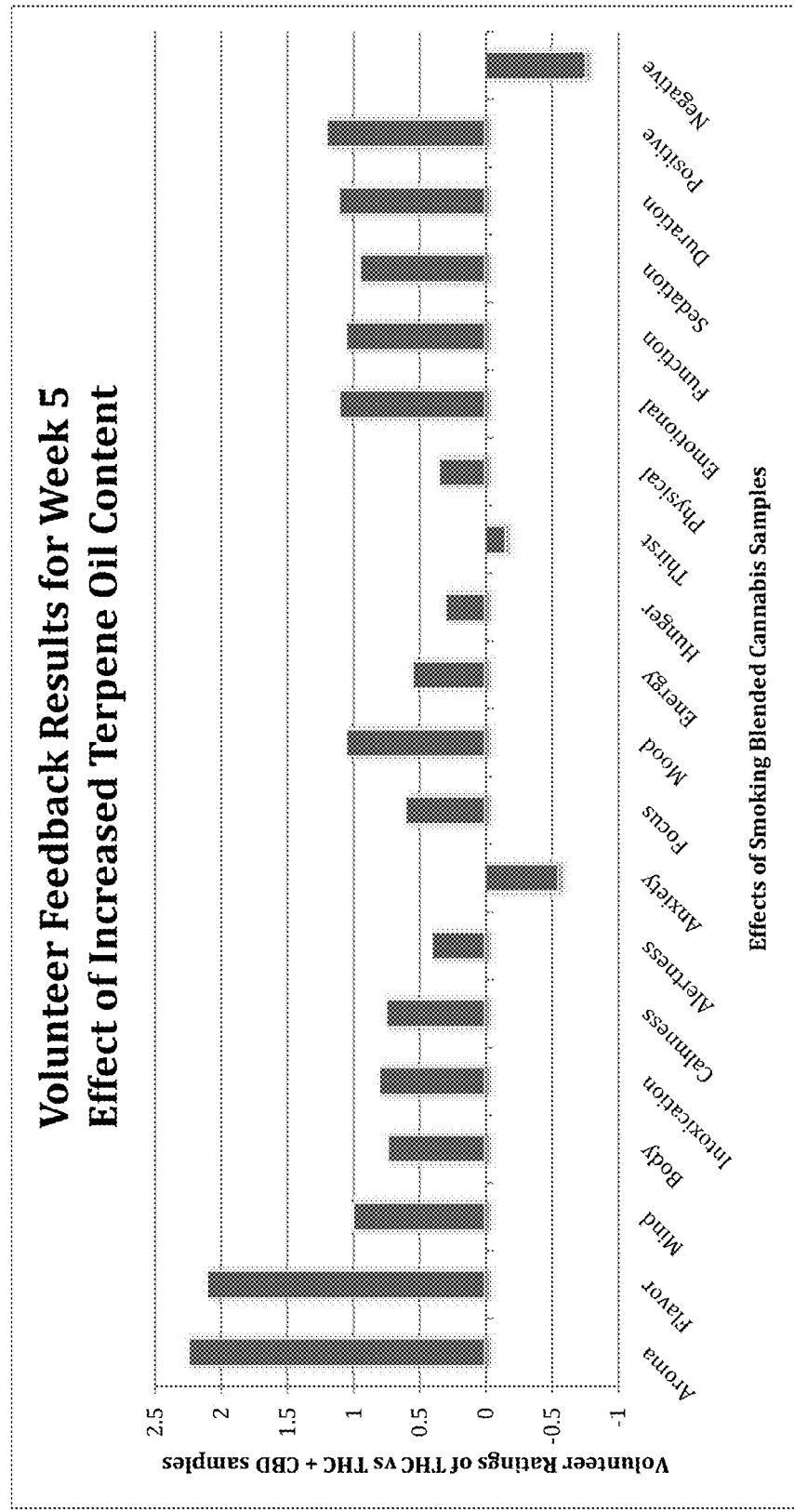
FIG. 5—Bar graph of Week 5 trial feedback results. Values are presented as ratings for test sample minus control sample. Higher values indicate increased ratings for a category, while lower values indicate decreased ratings for a category. Samples containing higher oil showed increase in aroma and flavor and overall positive ratings.

The survey results are shown in Table 37 and FIG. 5.

TABLE 37

Feedback results for Week 5 and 6 trials.

| | Question | A | 95% CI | B | 95% CI | C | 95% CI | D | 95% CI | E | 95% CI | F | 95% CI | TOTAL | 95% CI |
|---|---|---|---|---|---|---|---|---|---|---|---|---|---|---|---|
| Week 5 | Aroma | 3 | 0.80 | 4 | 5.88 | 1.2 | 1.69 | 0.667 | 5.58 | 4 | 4.08 | 1.667 | 1.73 | 2.25 | 1.21 |
| | Flavor | 1.75 | 0.49 | 6 | | 1 | 1.39 | 3 | 2.99 | 3 | 2.99 | 1.333 | 1.73 | 2.105 | 0.90 |
| | Mind | 1 | 1.39 | −1 | 1.96 | 0.25 | 0.49 | 2.333 | 2.85 | 0.333 | 1.73 | 2.667 | 3.27 | 1 | 0.87 |
| | Body | 0.75 | 1.67 | −0.5 | 0.98 | 0 | 0.80 | 0 | 2.26 | 2.333 | 2.85 | 1.667 | 4.28 | 0.737 | 0.93 |
| | Intoxication | 1.75 | 0.94 | 0 | 1.96 | 0.2 | 1.14 | 0.667 | 2.36 | 0.667 | 0.65 | 1.333 | 0.65 | 0.8 | 0.54 |
| | Calmness | 0.5 | 0.57 | −0.5 | 0.98 | 2.4 | 1.92 | 0 | 4.53 | 2.333 | 2.36 | −1.67 | 3.27 | 0.75 | 1.11 |
| | Alertness | 0.75 | 2.32 | 1 | 1.96 | 0.8 | 0.73 | −0.33 | 3.97 | 1.333 | 2.61 | −1.33 | 3.64 | 0.4 | 0.97 |
| | Anxiety | −0.25 | 0.49 | −1.5 | 2.94 | −2 | 1.64 | −2.67 | 2.85 | 1.333 | 2.61 | 2.333 | 5.58 | −0.55 | 1.24 |
| | Focus | 1 | 2.12 | 1.5 | 2.94 | 2.2 | 2.66 | 0.333 | 4.57 | 0 | 1.13 | −2.33 | 2.85 | 0.6 | 1.21 |
| | Mood | 1.5 | 1.27 | 3.5 | 0.98 | −0.4 | 3.37 | 2.333 | 2.85 | 0 | 2.26 | 1 | 1.13 | 1.05 | 1.10 |
| | Energy | 0.25 | 0.49 | 1 | 1.96 | 0.8 | 1.14 | −0.33 | 6.63 | 1 | 1.13 | 0.667 | 1.31 | 0.55 | 0.94 |
| | Hunger | 1.5 | 1.27 | 1 | 1.96 | −2 | 2.06 | 0.667 | 1.31 | −0.67 | 1.31 | 2.667 | 2.85 | 0.3 | 1.01 |
| | Thirst | 0.75 | 0.94 | 4.5 | 2.94 | −2.4 | 2.37 | −1.67 | 3.27 | −2 | 0.00 | 2.667 | 2.85 | −0.15 | 1.34 |
| | Physical | 0.25 | 0.94 | −1 | 1.96 | −0.2 | 2.00 | 0.333 | 1.73 | 1.333 | 1.73 | 1.333 | 1.73 | 0.35 | 0.71 |
| | Emotional | 1 | 1.13 | 1.5 | 0.98 | 1 | 2.63 | 1 | 1.96 | 0.667 | 0.65 | 1.667 | 1.31 | 1.1 | 0.72 |
| | Function | 1 | 2.65 | 2 | 3.92 | 0.6 | 0.78 | 2.333 | 2.85 | 0.667 | 2.36 | 0.333 | 0.65 | 1.05 | 0.81 |
| | Sedation | 0.75 | 1.23 | 0.5 | 0.98 | 0.75 | 2.45 | 1 | 2.99 | 0.333 | 0.65 | 2.333 | 4.71 | 0.947 | 0.95 |
| | Duration | 0.5 | 0.57 | 0 | 0.00 | 0.75 | 1.47 | 1.333 | 1.73 | 1.667 | 1.73 | 2.333 | 2.36 | 1.105 | 0.63 |
| | Positive | 2 | 0.80 | 0.5 | 2.94 | 1.2 | 1.44 | 1.667 | 2.36 | 0.667 | 2.36 | 0.667 | 1.73 | 1.2 | 0.68 |
| | Negative | −1 | 1.13 | −1 | 1.96 | −0.2 | 2.00 | −3 | 3.39 | 0.333 | 5.10 | 0 | 1.96 | −0.75 | 1.07 |
| Week 6 | Aroma | −0.4 | 1.59 | 3 | 1.13 | 3.333 | 2.85 | 3.25 | 0.94 | 2.333 | 1.31 | 2.667 | 1.73 | 2.143 | 0.87 |
| | Flavor | 0.4 | 0.48 | 3 | 1.13 | 2.667 | 5.10 | 0 | 4.08 | 3 | 3.92 | 2.333 | 0.65 | 1.684 | 1.10 |
| | Mind | −0.6 | 1.71 | 0 | 1.13 | 0.5 | 4.90 | 1.25 | 2.45 | 4.667 | 3.64 | 1 | 1.13 | 1 | 1.14 |
| | Body | 0 | 0.88 | 1.667 | 1.31 | 1.5 | 6.86 | 1.25 | 2.93 | 3 | 5.88 | 1.333 | 1.73 | 1.3 | 1.16 |
| | Intoxication | 0.2 | 2.09 | 0.333 | 1.73 | 0.333 | 2.61 | 2.5 | 3.05 | 3.333 | 5.58 | 1.667 | 0.65 | 1.333 | 1.16 |
| | Calmness | −0.2 | 2.00 | 0.667 | 1.31 | −0.67 | 1.73 | 0.25 | 1.47 | 1.667 | 0.65 | −0.33 | 3.97 | 0.19 | 0.81 |
| | Alertness | −0.2 | 0.39 | −0.67 | 2.85 | 0.667 | 0.65 | −3.5 | 2.47 | 0.333 | 1.73 | 0.667 | 1.31 | −0.57 | 0.89 |
| | Anxiety | −1.8 | 3.12 | −1.33 | 1.73 | −2 | 2.26 | −1.5 | 3.80 | −1 | 1.96 | 2 | 1.96 | −1.05 | 1.24 |
| | Focus | −0.2 | 0.73 | −1 | 3.39 | 1 | 1.13 | −2.75 | 0.94 | −1.67 | 7.19 | −2 | 2.99 | −1.1 | 1.18 |
| | Mood | −0.8 | 1.14 | 2 | 2.99 | 1 | 3.92 | −0.5 | 1.70 | 0.667 | 3.46 | 1.667 | 1.73 | 0.476 | 0.96 |
| | Energy | 0.2 | 0.39 | −1 | 1.96 | 1.333 | 2.36 | −2 | 2.53 | 1.333 | 0.65 | −0.33 | 1.31 | −0.14 | 0.79 |
| | Hunger | 0 | 0.62 | 0 | 1.96 | 0.333 | 0.65 | 1.75 | 2.17 | 1 | 1.13 | −0.33 | 2.85 | 0.476 | 0.67 |
| | Thirst | −0.2 | 0.73 | −0.33 | 2.36 | −1 | 2.99 | 3.25 | 2.58 | −3 | 2.99 | −0.67 | 4.28 | −0.14 | 1.22 |
| | Physical | 0.4 | 0.78 | −0.67 | 0.65 | −2 | 1.96 | −1 | 1.79 | 1.667 | 4.28 | 1 | 1.13 | −0.1 | 0.85 |
| | Emotional | −0.2 | 1.57 | −0.67 | 0.65 | −1.33 | 1.31 | 0.25 | 3.34 | 1 | 1.96 | 1 | 1.96 | 0 | 0.83 |
| | Function | −1 | 1.52 | −1 | 1.13 | 1.333 | 1.73 | −2 | 1.79 | 1.333 | 1.31 | −0.33 | 1.73 | −0.43 | 0.78 |
| | Sedation | 0 | 0.88 | 2 | 2.99 | 0 | 1.96 | 0.75 | 2.81 | 0.333 | 0.65 | 1.667 | 0.65 | 0.75 | 0.76 |
| | Duration | 0.2 | 0.73 | 1 | 2.26 | 3.5 | 4.90 | 2.25 | 2.17 | 0.333 | 2.85 | 2 | 2.26 | 1.35 | 0.91 |
| | Positive | 0.6 | 0.48 | 2 | 1.13 | 0.667 | 0.65 | 1 | 2.65 | 1.333 | 1.31 | 0.667 | 2.85 | 1 | 0.65 |
| | Negative | −0.6 | 0.78 | −1 | 1.13 | 0.333 | 2.85 | −1.75 | 1.47 | 0 | 2.99 | −1.33 | 0.65 | −0.76 | 0.67 |

For Week five, both the control and the comparator had nearly the same levels of THC and CBD, so that any observed change in effect can be attributed to the higher terpene oil contents. The major trend observed in this case is a more pleasing aroma, flavor, and overall positive assessment of the high oil blends compared to the currently available low oil chemotype II "Harlequin". Additionally, high oil blends showed increased scores for ability to focus, calmness, energy levels, emotional comfort, and ability to function. This is result demonstrates that our hypothesis that the higher terpene oil contents of the specialty *cannabis* of the present invention mixed THC:CB cultivars will be found more appealing to *cannabis* users than the currently available low oil varieties.

Example 11

Volunteer Trials Using Specialty *Cannabis*. Effect of Added Diverse Terpene Profiles The seventh Week of the trials was designed to test the effect of diverse terpene profiles on *cannabis* plants. For this trial, the same groups (1-6) used in Examples 9 and 10 were asked to compare the diverse terpene profile of samples (a-f) to the myrcene dominant terpene profile of (g) found in currently existing THC:CBD and CBD varieties (Table 38 and 39, and FIG. 6). This study compared a 5:1 THC:CBD cannabinoid ratio with a myrcene dominated terpene profile (a blend of BLU06:CBD01 in this case) to blends prepared from a parental CBD line (CBD01) and various parental THC lines. Samples for the trials were prepared as described in Example 10 by hand grinding and blending *cannabis*. As before, each sample was analyzed via GC-FID and HPLC before being provided to volunteers in order to ensure consistency (Table 38 and 39, and FIG. 6). The same questionnaire that was used in Example 9 (i.e., as provided in FIG. 2) was used to assess the volunteer feedback on the tested blends.

Figure 6:
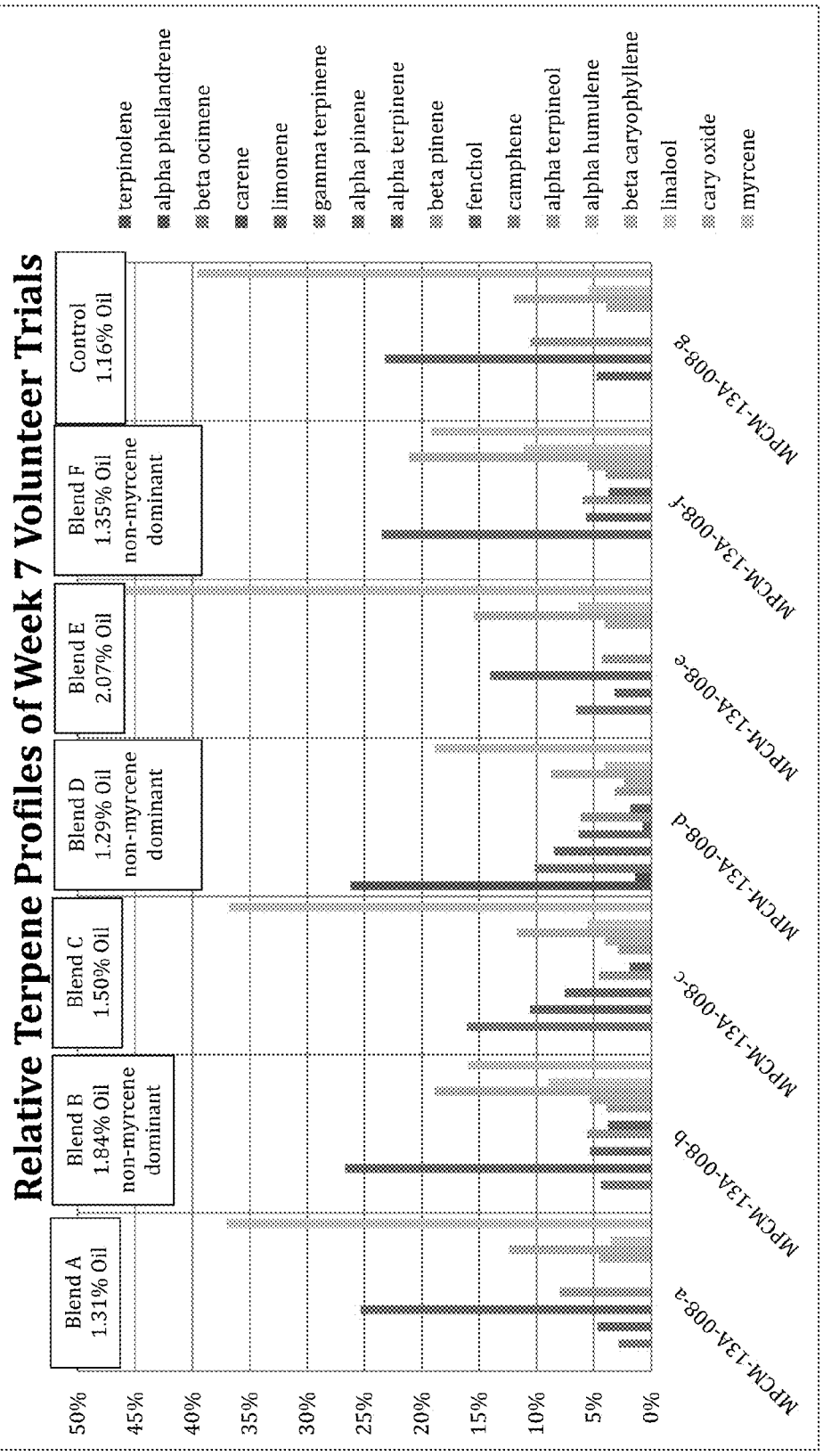
FIG. 6—Bar graph of the relative terpene contents (y-axis) of *cannabis* blends (x-axis) used for Week 7 volunteer trials. Each sample was blended to produce similar cannabinoid profiles so as to compare the effects of different terpene profiles. Control Sample g representative of traditional myrcene dominant terpene profiles.

The sample ID of the control is highlighted in (Tables 38 and 39) and also labeled in (FIG. 6). This study compared a typical high myrcene terpene profile to higher more desirable terpene profiles with other terpenes. Samples b, d, and f in particular exhibited desirable terpene profiles in which myrcene was not the dominant terpene.

TABLE 38

Cannabinoid levels of cannabis blends for Week 7 trials as measured by GC-FID and HPLC.

| | Cannabinoids (GC-FID) | | | | | | Cannabinoids (UHPLC) | | | | | |
|---|---|---|---|---|---|---|---|---|---|---|---|---|
| | THC | | CBD | | THC:CBD by GC | | THCA | | CBDA | | THCA:CBDA by HPLC | |
| Sample | Wt % | 95% CI | Wt % | 95% CI | Wt % | 95% CI | Wt % | 95% CI | Wt % | 95% CI | Wt % | 95% CI |
| MPCM-13A-008-a | 16.59% | 0.65% | 2.10% | 0.09% | 7.92 | 0.52 | 21.20% | 0.42% | 2.57% | 0.16% | 8.26 | 0.57 |
| MPCM-13A-008-b | 14.57% | 1.27% | 2.02% | 0.20% | 7.30 | 1.38 | 18.82% | 0.91% | 2.48% | 0.41% | 7.71 | 1.60 |
| MPCM-13A-008-c | 15.47% | 0.60% | 1.86% | 0.18% | 8.39 | 0.99 | 20.27% | 0.17% | 2.32% | 0.10% | 8.76 | 0.32 |
| MPCM-13A-008-d | 11.10% | 0.80% | 1.53% | 0.06% | 7.27 | 0.81 | 14.99% | 0.60% | 2.09% | 0.10% | 7.17 | 0.53 |
| MPCM-13A-008-e | 17.24% | 1.03% | 2.15% | 0.12% | 8.03 | 0.79 | 22.86% | 1.22% | 2.86% | 0.08% | 7.98 | 0.43 |
| MPCM-13A-008-f | 13.21% | 0.54% | 2.07% | 0.14% | 6.42 | 0.69 | 17.62% | 1.04% | 2.46% | 0.14% | 7.19 | 0.69 |
| MPCM-13A-008-g | 14.67% | 0.62% | 1.60% | 0.22% | 9.25 | 1.31 | 19.75% | 0.54% | 1.87% | 0.26% | 10.67 | 1.28 |

TABLE 39

Terpene contents of cannabis blends for Week 7 trials as measured by GC-FID. Blank values indicate undetectable levels or 0.

Terpenes (GC-FID)

| Sample | alpha pinene Wt % | 95% CI | camphene Wt % | 95% CI | beta pinene Wt % | 95% CI | myrcene Wt % | 95% CI | alpha phellandrene Wt % | 95% CI | carene Wt % | 95% CI | alpha terpinene Wt % | 95% CI | limonene Wt % | 95% CI | beta ocimene Wt % | 95% CI | gamma terpinene Wt % | 95% CI | terpinolene Wt % | 95% CI |
|---|---|---|---|---|---|---|---|---|---|---|---|---|---|---|---|---|---|---|---|---|---|---|
| MPCM-13A-008-a | 0.333% | 0.008% | | | 0.105% | 0.002% | 0.487% | 0.008% | | | | | | | 0.061% | 0.002% | 0.037% | 0.001% | | | | |
| MPCM-13A-008-b | 0.098% | 0.005% | | | 0.103% | 0.002% | 0.293% | 0.007% | | | | | | | 0.490% | 0.014% | 0.080% | 0.002% | | | | |
| MPCM-13A-008-c | 0.113% | 0.006% | | | 0.068% | 0.003% | 0.551% | 0.021% | | | | | | | 0.158% | 0.003% | 0.240% | 0.004% | | | | |
| MPCM-13A-008-d | 0.082% | 0.002% | | | 0.079% | 0.002% | 0.243% | 0.005% | 0.018% | 0.001% | | | 0.010% | 0.000% | 0.109% | 0.031% | 0.131% | 0.003% | | | | |
| MPCM-13A-008-e | 0.291% | 0.019% | | | 0.088% | 0.005% | 0.953% | 0.048% | | | | | | | 0.066% | 0.011% | 0.136% | 0.007% | | | | |
| MPCM-13A-008-f | 0.077% | 0.003% | | | 0.081% | 0.003% | 0.260% | 0.010% | | | | | | | 0.318% | 0.011% | | | | | | |
| MPCM-13A-008-g | 0.270% | 0.007% | | | 0.123% | 0.006% | 0.460% | 0.023% | | | | | | | 0.055% | 0.003% | | | | | 0.338% | 0.011% |

Terpenes (GC-FID)

| Sample | linalool Wt % | 95% CI | fenchol Wt % | 95% CI | alpha terpineol Wt % | 95% CI | beta caryophyllene Wt % | 95% CI | alpha humulene Wt % | 95% CI | cary oxide Wt % | 95% CI | Total identified oil (wt %) Wt % | 95% CI | Relative myrcene |
|---|---|---|---|---|---|---|---|---|---|---|---|---|---|---|---|
| MPCM-13A-008-a | 0.046% | 0.001% | | | | | 0.163% | 0.006% | 0.060% | 0.002% | | | 1.313% | 0.016% | 37% |
| MPCM-13A-008-b | 0.164% | 0.003% | 0.069% | 0.002% | 0.072% | 0.002% | 0.347% | 0.018% | 0.098% | 0.004% | | | 1.835% | 0.073% | 16% |
| MPCM-13A-008-c | 0.083% | 0.001% | 0.028% | 0.001% | 0.043% | 0.000% | 0.175% | 0.001% | 0.061% | 0.000% | | | 1.497% | 0.030% | 37% |
| MPCM-13A-008-d | 0.053% | 0.001% | 0.023% | 0.001% | 0.041% | 0.001% | 0.112% | 0.005% | 0.030% | 0.001% | | | 1.290% | 0.027% | 19% |
| MPCM-13A-008-e | 0.132% | 0.005% | | | | | 0.320% | 0.012% | 0.084% | 0.004% | | | 2.070% | 0.104% | 46% |
| MPCM-13A-008-f | 0.151% | 0.009% | 0.050% | 0.003% | 0.054% | 0.003% | 0.286% | 0.022% | 0.075% | 0.005% | | | 1.351% | 0.064% | 19% |
| MPCM-13A-008-g | 0.063% | 0.005% | | | | | 0.140% | 0.023% | 0.045% | 0.007% | | | 1.162% | 0.057% | 40% |

Figure 7:
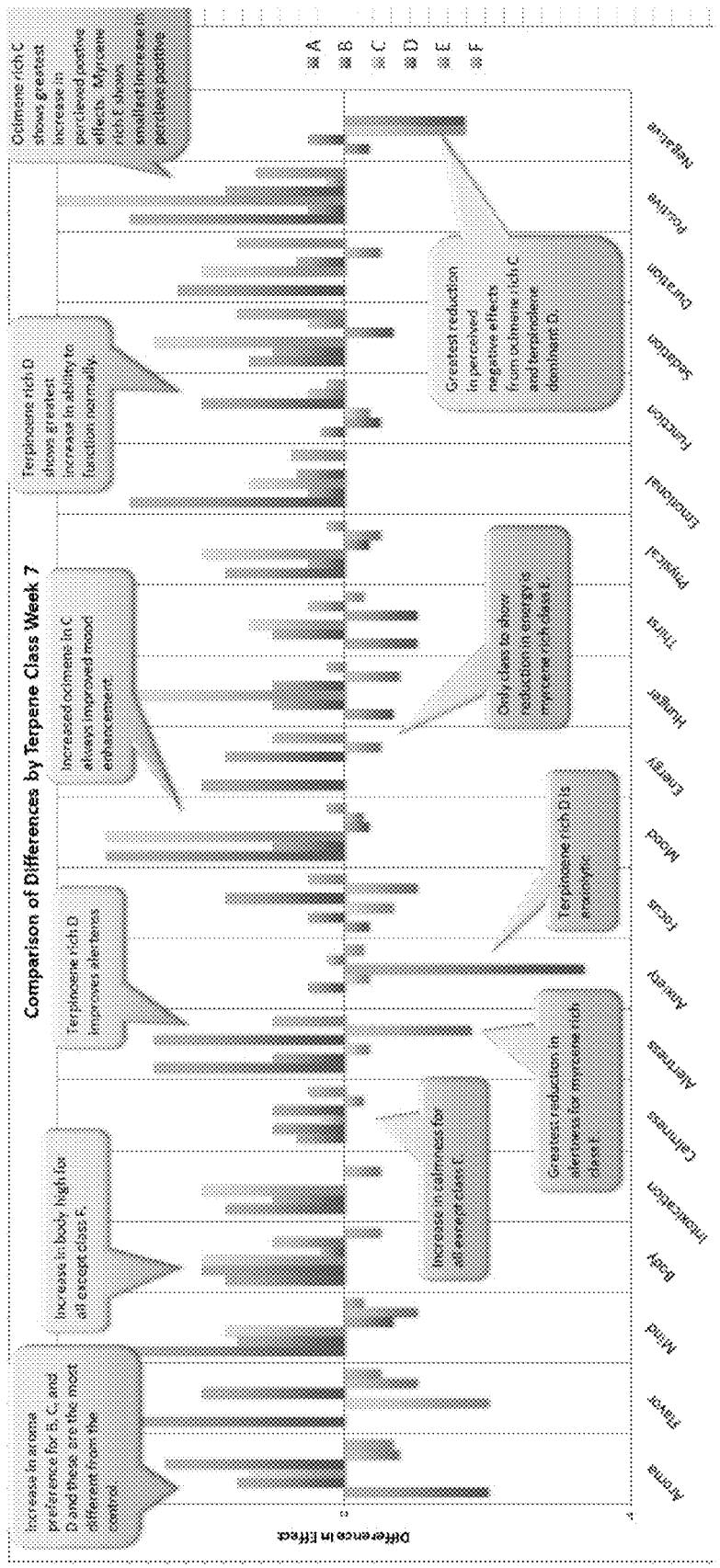
FIG. 7—Bar graph of Week 7 trial feedback results. Values are presented as ratings for each test sample minus control sample. Higher values indicated increased ratings for a category, while lower values indicated decreased ratings for a category. Samples labeled A-F correspond to the chemical analysis *cannabis* blends a-f of FIG. 6. Samples containing lower relative myrcene contents showed increased positive ratings. Diverse and desirable terpene profiles demonstrated improved scores for recreational and medical uses. Terpinolene dominant terpene profiles showed increased scores for alertness and reduced anxiety. Ocimene terpene profiles showed increased mood scores.

The survey results are shown in Table 40 and FIG. 7.

TABLE 40

Feedback results for Week 7 trials.

| | Averages for Week 7 | | | | | | | | | | | | | |
|---|---|---|---|---|---|---|---|---|---|---|---|---|---|---|
| Question | A | 95% CI | B | 95% CI | C | 95% CI | D | 95% CI | E | 95% CI | F | 95% CI | TOTAL | 95% CI |
| Aroma | −2 | 4.08 | 1.5 | 0.98 | 1.333 | 1.73 | 2.5 | 0.98 | −0.75 | 1.47 | −0.67 | 0.65 | 0.059 | 1.04 |
| Flavor | 3.5 | 6.86 | 0 | | −2 | | 2 | 3.92 | −1 | 1.13 | −0.5 | 0.98 | 0.455 | 1.59 |
| Mind | 3.333 | 5.58 | 1.5 | 0.98 | 1.667 | 2.85 | −0.67 | 1.31 | −1 | 2.40 | −0.25 | 0.49 | 0.579 | 1.20 |
| Body | 1.667 | 2.36 | 2 | 1.96 | 2 | 1.96 | 0.333 | 1.31 | 1 | 2.12 | −0.5 | 1.70 | 0.947 | 0.81 |
| Intoxication | 1.667 | 4.28 | 1 | 0.00 | 2 | 3.39 | 0 | 2.26 | −0.5 | 1.70 | 0 | 0.80 | 0.579 | 0.96 |
| Calmness | 0.667 | 2.36 | 1 | 0.00 | 0.333 | 1.31 | 1 | 0.00 | −0.25 | 1.23 | 0.5 | 0.57 | 0.474 | 0.48 |
| Alertness | 2.667 | 6.23 | 1 | 0.00 | −0.33 | 2.61 | 2.667 | 1.73 | −1.75 | 2.17 | 1 | 1.96 | 0.737 | 1.31 |
| Anxiety | 0 | 0.00 | 0.5 | 0.98 | −0.33 | 0.65 | −3.33 | 3.27 | 0.25 | 0.94 | −0.25 | 2.45 | −0.56 | 0.93 |
| Focus | −0.33 | 6.23 | 0.5 | 0.98 | −0.67 | 2.36 | 1.667 | 0.65 | −1 | 0.80 | 0.5 | 0.98 | 0.053 | 1.01 |
| Mood | 3.333 | 5.58 | 1 | 1.96 | 3.333 | 1.73 | −0.33 | 3.27 | −0.25 | 2.45 | 0.25 | 0.49 | 1.105 | 1.24 |
| Energy | 2 | 2.26 | 0 | 0.00 | 0 | 2.99 | 1.667 | 2.36 | −0.5 | 1.88 | 1 | 1.39 | 0.684 | 0.85 |
| Hunger | −0.67 | 0.65 | 1 | 1.96 | 3 | 2.26 | 1 | 1.13 | −0.75 | 1.23 | 0.25 | 0.94 | 0.526 | 0.75 |
| Thirst | −1 | 1.13 | 1 | 1.96 | 1.333 | 0.65 | −1 | 2.26 | 0.5 | 1.70 | −0.25 | 1.47 | 0.053 | 0.69 |
| Physical | 1.667 | 1.73 | 0.5 | 0.98 | 2 | 1.96 | −0.33 | 2.36 | −0.5 | 0.57 | 0.25 | 1.23 | 0.444 | 0.68 |
| Emotional | 3 | 5.88 | 0.5 | 0.98 | 1.333 | 1.31 | 0.667 | 3.46 | 0 | 0.80 | 0.75 | 2.17 | 1 | 1.11 |
| Function | 0.333 | 0.65 | −0.5 | 0.98 | −0.33 | 2.85 | 2 | 1.96 | 0.5 | 1.70 | 0.25 | 1.23 | 0.421 | 0.71 |
| Sedation | 1.333 | 3.64 | 1 | 0.00 | 2.667 | 5.35 | −0.67 | 2.36 | 0.5 | 3.80 | 1.5 | 2.33 | 1.053 | 1.32 |
| Duration | 2.333 | 3.64 | 0 | 0.00 | 2 | 4.08 | 0.667 | 0.65 | −0.5 | 1.27 | 1.5 | 2.47 | 1 | 1.02 |
| Positive | 3 | 5.88 | 0.5 | 0.98 | 4.333 | 0.65 | 1.667 | 2.36 | 0.25 | 1.86 | 1.25 | 1.67 | 1.789 | 1.17 |
| Negative | −0.33 | 2.85 | 0.5 | 0.98 | −1.67 | 2.36 | −1.67 | 3.27 | 0 | 1.39 | 0 | 1.39 | −0.53 | 0.84 |

Since both the control and the comparator had nearly the same levels of THC and CBD, any observed change in effect could be attributed to the varied terpene profiles. In general, non-myrcene dominant profiles showed increases in energy and alertness, associated with less "couch lock". Moreover, analysis of each terpene profile separately revealed several terpene specific effects. For example, there were large increases in the aroma preference for classes b and d which had profiles dominated by terpenes other than myrcene (limonene and terpinolene, respectively). There was also an increase in calmness for all classes except e, which was the only class to have substantially more myrcene than the control sample. Terpinolene rich d is more anxiolytic which agrees with studies showing terpinolene to have a calming effect on mice (Ito et al. 2013 "The sedative effect of inhaled terpinolene in mice and its structure-activity relationships" J Nat Med 67:833-837. Increased ocimene in C always improved mood enhancement. Ocimene has been suggested to be an anxiolytic in mice (Okoli et al., 2010 "Anticonvulsant and anxiolytic evaluation of leaf extracts of *Ocimum gratissimum*, a culinary herb). These results show that non-myrcene dominant profiles can increase the amount of energy and alertness after consuming *cannabis* by overcoming the "couch lock" effect of myrcene. In addition, the reduction in myrcene also allows for entourage effects of other terpenes to create unique specialty *cannabis* tailored to a desired medicinal or recreational effect.

Example 12

Development of THC:THCv/CBDv Specialty *Cannabis* Varieties

Unique parental THC, CBD, and THC:THCV lines from Examples 2-4 were selected and one of the parental cultivars was treated with silver thiosulfate to coax the pistillate plant to produce staminate, pollen-bearing flowers. The THC:CBD, or THC class varieties were crossed with THV01 lines. The resulting progeny were screened by TLC to identify plants producing more than one cannabinoid (e.g., THC:THCV, or THCV:CBDV). Progeny exhibiting desired cannabinoid profiles were allowed to reach maturity and the flowers were harvested and processed. In general, field observations could detect the crosses with the desired characteristics, however this was verified by chemotype analysis and the final flower was analyzed for cannabinoid and terpene content. Table 41 outlines the initial crosses performed with THC class or CBD varieties and THCV parental lines. The crosses produced progeny approaching ratios supporting the separate loci for the control of THC/CBD and THCv as suggested by de Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112). TLC results are indicated as + or −, where + indicates the production of THCV with at least one other cannabinoid.

TABLE 41

Crosses performed between THC:CBD parental and THCV producing parental lines.
TLC result of + indicates presence of THCV with at least one other cannabinoid.

| | P Donor | | | | | | | |
|---|---|---|---|---|---|---|---|---|
| | THV01 | | | | | | CBD05 | |
| | P Acceptor | | | | | | | |
| | SIL08xP | | GRE01 | | YEL03 | | THV01 | |
| | Code | TLC Result | Code | TLC Result | Code | TLC Result | Code | TLC Result |
| 1 | SIL08xTP-01 | − | GRE01xTP-01 | − | YEL03xTP-01 | − | THV01xTP-01 | + |
| 2 | SIL08xTP-02 | + | GRE01xTP-02 | − | YEL03xTP-02 | − | THV01xTP-02 | − |
| 3 | SIL08xTP-03 | − | GRE01xTP-03 | − | YEL03xTP-03 | − | THV01xTP-03 | − |
| 4 | | | GRE01xTP-04 | − | YEL03xTP-04 | − | THV01xTP-04 | + |
| 5 | | | | | YEL03xTP-05 | + | THV01xTP-05 | + |
| 6 | | | | | YEL03xPT-06 | − | THV01xTP-06 | + |
| 7 | | | | | | | THV01xTP-07 | + |
| 8 | | | | | | | THV01xTP-08 | + |
| 9 | | | | | | | THV01xTP-09 | − |
| 10 | | | | | | | THV01xTP-10 | + |
| 11 | | | | | | | THV01xTP-11 | − |
| 12 | | | | | | | THV01xTP-12 | + |
| 13 | | | | | | | THV01xTP-13 | + |
| 14 | | | | | | | THV01xTP-14 | − |
| 15 | | | | | | | THV01xTP-15 | − |
| 16 | | | | | | | THV01xTP-16 | + |
| 17 | | | | | | | THV01xTP-17 | − |
| 18 | | | | | | | THV01xTP-18 | − |
| 19 | | | | | | | THV01xTP-19 | + |
| 20 | | | | | | | THV01xTP-20 | + |
| 21 | | | | | | | THV01xTP-21 | + |
| 22 | | | | | | | THV01xTP-22 | + |
| 23 | | | | | | | THV01xP-23 | − |
| 24 | | | | | | | THV01xTP-24 | + |

Example 13

Chemical Analysis of Cannabinoids and Terpenes of THC:THCV Specialty cannabis Progeny The new specialty cannabis varieties created through crosses described in Examples 5 and 12 were subjected to cannabinoid and terpene chemical analysis as described in Example 1. The levels of cannabinoids were measured by both GC-FID (Table 42) and HPLC (Table 43). Terpenes were measured using GC-FID and are presented as absolute content measurements based on the percent content by weight of dry inflorescences (Table 44) and relative content as a percent of the total terpene profile (Table 45). The GC-FID cannabinoid analysis of Table 42 also included measurements for CBGV, CBN, and Delta 8 THC, all of which were measured to be less than 0.06% and were therefore not included in the table. Similarly, the HPLC cannabinoid analysis of Table 43 included measurements for CBCA, CBGVA, CBC, THCV, CBDV, CBGV, CBN and Delta 8 THC all of which were measured to be less than 0.08%, and were therefore not included in the table.

The specialty cannabis produced by the crosses described in Example 12 contain THCV or CBDV cannabinoids while also producing desirable terpene profiles. For example, the YEL03xTP05 plant of Tables 44 and 45 has a non-myrcene dominant terpene profile. Thus in some embodiments, the specialty cannabis of the present invention has THCV with a non-myrcene dominant terpene profile. In some embodiments, the reduced myrcene content of the specialty cannabis will reduce the amount of "couch lock" effect produced by myrcene. In other embodiments, the terpene profiles of the other THCV and CBDV progeny provide diverse terpene profiles designed to produce desirable aroma/flavors and organoleptic appeal. In other embodiments, the terpene profiles of the THCV and CBDV progeny allow for terpene entourage effects to reduce the side effects of THC. For example the THV01×P07, THV01×P02, THV01×P18, and THV01×P11 have increased levels of ocimene terpene. In some embodiments higher ocimene levels will impart woody and floral aromas/flavors to the specialty cannabis of the present invention.

The breeding scheme described in Example 12 also produced specialty cannabis plants with increased terpene oil content. For example, progeny plant THV01×P-03 has a terpene oil content greater than 2%. In some embodiments, the higher oil content of the specialty cannabis varieties provide "smoother" aromas and flavors and will raise the total terpene levels so as increase the pharmacological entourage effects of said terpenes. For example despite having a myrcene dominant profile, the THV01×P-03 specialty cannabis of the present invention is expected to provide a better organoleptic experience than that of the myrcene dominant THCV varieties currently available which tend to have low terpene oil levels.

TABLE 42

Cannabinoid values as measured by GC-FID for THC:THCV and CBDV specialty cannabis varieties.
Blank values indicate undetectable levels or 0.

| | Cannabinoids (GC-FID) | | | | | | | | |
|---|---|---|---|---|---|---|---|---|---|
| Sample | THC Wt % | CBD Wt % | CBG Wt % | CBC Wt % | THCV Wt % | CBDV Wt % | Cannabs by GC Wt % | THC:THCV by GC Wt % | Cannabs/Terps (GC) Wt % |
| THV01xP-01 | 4.81% | | 0.41% | 0.09% | 0.80% | | 6.10% | 6.00 | 4.26 |
| THV01xP-06 | 1.63% | 2.87% | 0.17% | 0.25% | 0.27% | 0.32% | 5.51% | 6.13 | 4.53 |
| THV01xP-08 | 5.63% | | 0.35% | 0.06% | 1.04% | | 7.08% | 5.39 | 4.31 |
| THV01xP-16 | 1.78% | 3.58% | 0.20% | 0.32% | | 0.21% | 6.09% | | 4.55 |
| THV01xP-17 | 6.42% | 0.00% | 0.43% | 0.08% | 1.01% | | 7.93% | 6.35 | 5.89 |
| THV01xP-19 | 1.83% | 4.10% | 0.16% | 0.28% | 0.29% | 0.43% | 7.10% | 6.44 | 6.29 |
| THV01xP-20 | 2.18% | 5.21% | 0.44% | 0.32% | 0.24% | 0.39% | 8.77% | 8.95 | 5.20 |
| THV01xP-21 | 2.27% | 4.54% | 0.28% | 0.31% | 0.42% | 0.52% | 8.34% | 5.42 | 5.37 |
| THV01xP-10 | 1.77% | 3.79% | 0.44% | 0.29% | | 0.29% | 6.57% | | 3.65 |
| THV01xP-22 | 6.11% | | 0.69% | 0.10% | 0.87% | | 7.76% | 7.06 | 4.61 |
| THV01xP-23 | 4.10% | | 0.48% | 0.07% | 0.91% | | 5.56% | 4.48 | 4.33 |
| THV01xP-07 | 5.36% | | 0.56% | 0.22% | 0.53% | | 6.67% | 10.17 | 4.04 |
| THV01xP-02 | 3.94% | | 0.40% | 0.05% | 0.40% | | 4.78% | 9.84 | 3.50 |
| THV01xP-18 | 1.26% | 4.17% | 0.27% | 0.27% | 0.24% | 0.57% | 6.76% | 5.30 | 5.45 |
| THV01xP-24 | 2.02% | 4.64% | 0.23% | 0.32% | 0.64% | 1.00% | 8.86% | 3.14 | 6.92 |
| THV01xP-14 | 3.24% | | 0.36% | 0.29% | 0.05% | | 3.94% | 63.55 | 4.02 |
| THV01xP-15 | 5.67% | 0.01% | 1.03% | 0.26% | 0.66% | | 7.63% | 8.54 | 4.62 |
| THV01xP-09 | 5.39% | 0.01% | 0.60% | 0.17% | 0.63% | | 6.81% | 8.58 | 4.55 |
| THV01xP-03 | 7.01% | 0.00% | 0.77% | 0.23% | 0.35% | | 8.37% | 19.87 | 3.88 |
| THV01xP-04 | 1.54% | 4.17% | 0.24% | 0.28% | 0.27% | 0.49% | 6.98% | 5.73 | 3.74 |
| THV01xP-05 | 1.65% | 3.32% | 0.15% | 0.26% | | 0.48% | 5.86% | | 3.76 |
| THV01xP-11 | 5.03% | 0.01% | 0.64% | 0.21% | 0.18% | | 6.06% | 28.41 | 3.50 |
| THV01xP-12 | 1.58% | 3.87% | 0.23% | 0.32% | 0.19% | 0.30% | 6.49% | 8.33 | 4.11 |
| THV01xP-13 | 5.49% | | 1.06% | 0.21% | 0.30% | | 7.06% | 18.17 | 3.55 |
| SIL08xTP-02 | 11.14% | 0.03% | 0.33% | 0.15% | 0.25% | | 11.93% | 44.74 | 7.35 |
| YEL03xTP-05 | 4.82% | 0.00% | 0.53% | 0.06% | 4.12% | | 9.59% | 1.17 | 8.78 |

*LOQ for all cannabinoids was 0.14%.

TABLE 43

Cannabinoid measurement by HPLC for THC:CBDV and CBDV specialty cannabis varieties.
Blank values indicate undetectable levels or 0.

| | Cannabinoids (UHPLC) | | | | | | | | | | |
|---|---|---|---|---|---|---|---|---|---|---|---|
| Sample | THCA Wt % | CBDA Wt % | CBGA Wt % | THCVA Wt % | CBDVA Wt % | THC Wt % | CBD Wt % | CBG Wt % | Cannabs by HPLC Wt % | THCA:THCVA by HPLC Wt % | Cannabs/ Terps (HPLC) ratio |
| THV01xP-01 | 7.50% | 0.00% | 0.74% | 1.45% | | 0.07% | | 0.04% | 9.80% | 5.16 | 6.85 |
| THV01xP-06 | 1.96% | 5.05% | 0.29% | 0.46% | 0.69% | 0.03% | | | 8.48% | 4.24 | 6.97 |
| THV01xP-08 | 8.00% | | 0.60% | 1.78% | | 0.14% | | | 10.53% | 4.49 | 6.40 |
| THV01xP-16 | 2.08% | 6.17% | 0.28% | 0.27% | 0.46% | 0.04% | 0.04% | 0.05% | 9.39% | 7.70 | 7.01 |
| THV01xP-17 | 9.31% | | 0.82% | 1.77% | | 0.09% | | 0.03% | 12.02% | 5.25 | 8.92 |
| THV01xP-19 | 2.06% | 5.96% | 0.25% | 0.48% | 0.77% | 0.02% | 0.04% | 0.05% | 9.62% | 4.28 | 8.53 |
| THV01xP-20 | 2.46% | 7.47% | 0.55% | 0.41% | 0.71% | | 0.05% | 0.12% | 11.77% | 5.97 | 6.97 |
| THV01xP-21 | 2.71% | 6.58% | 0.47% | 0.70% | 0.97% | 0.02% | 0.04% | 0.04% | 11.52% | 3.87 | 7.41 |
| THV01xP-10 | 2.29% | 6.59% | 0.63% | 0.34% | 0.59% | 0.04% | 0.04% | 0.04% | 10.56% | 6.65 | 5.86 |
| THV01xP-22 | 8.49% | | 0.93% | 1.20% | | | | 0.08% | 10.71% | 7.08 | 6.37 |
| THV01xP-23 | 5.60% | | 0.74% | 1.49% | | 0.19% | | | 8.03% | 3.75 | 6.26 |
| THV01xP-07 | 7.90% | | 0.82% | 1.96% | | 0.08% | | 0.09% | 10.85% | 4.04 | 6.58 |
| THV01xP-02 | 6.14% | | 0.60% | 0.80% | | 0.07% | | 0.06% | 7.66% | 7.72 | 5.60 |
| THV01xP-18 | 1.23% | 5.94% | 0.29% | 0.34% | 0.91% | 0.07% | 0.04% | 0.09% | 8.91% | 3.59 | 7.18 |
| THV01xP-24 | 2.30% | 6.67% | 0.47% | 1.05% | 1.85% | 0.09% | | | 12.43% | 2.19 | 9.72 |
| THV01xP-14 | 5.13% | | 0.64% | 0.93% | | 0.08% | | 0.06% | 6.84% | 5.51 | 6.97 |
| THV01xP-15 | 8.54% | | 1.58% | 1.21% | | 0.15% | | 0.13% | 11.60% | 7.07 | 7.02 |
| THV01xP-09 | 8.15% | | 0.99% | 1.15% | | 0.12% | | 0.11% | 10.52% | 7.07 | 7.04 |
| THV01xP-03 | 10.25% | 0.01% | 1.20% | 1.49% | | 0.19% | | 0.10% | 13.25% | 6.89 | 6.14 |
| THV01xP-04 | 1.79% | 7.49% | 0.36% | 0.51% | 1.26% | 0.03% | 0.04% | 0.10% | 11.61% | 3.50 | 6.21 |
| THV01xP-05 | 1.79% | 5.92% | 0.19% | 0.57% | 1.10% | 0.06% | | 0.06% | 9.69% | 3.16 | 6.21 |
| THV01xP-11 | 7.39% | 0.02% | 1.02% | 1.18% | | 0.12% | | 0.06% | 9.78% | 6.29 | 5.63 |
| THV01xP-12 | 1.93% | 6.81% | 0.36% | 0.38% | 0.75% | 0.03% | 0.04% | 0.07% | 10.36% | 5.08 | 6.56 |
| THV01xP-13 | 8.13% | | 1.61% | 1.30% | | 0.20% | | 0.17% | 11.41% | 6.26 | 5.73 |
| YEL03xTP-05 | 6.19% | 0.17% | 0.70% | 6.44% | | 0.72% | | 0.09% | 14.36% | 0.96 | 13.15 |

TABLE 44

Absolute terpene measurements by GC-FID for THC:CBDV and CBDV specialty cannabis varieties.
Blank values indicate undetectable levels or 0.

| | Terpenes (GC-FID) | | | | | | | | |
|---|---|---|---|---|---|---|---|---|---|
| Sample | terpinolene Wt % | alpha phellandrene Wt % | beta ocimene Wt % | carene Wt % | limonene Wt % | gamma terpinene Wt % | alpha pinene Wt % | alpha terpinene Wt % | beta pinene Wt % |
| THV01xP-01 | | | 0.120% | | 0.137% | | 0.073% | | 0.044% |
| THV01xP-06 | | | 0.109% | | 0.103% | | 0.060% | | 0.034% |
| THV01xP-08 | | | 0.124% | | 0.157% | | 0.095% | | 0.053% |
| THV01xP-16 | | | 0.142% | | 0.106% | | 0.100% | | 0.048% |
| THV01xP-17 | | | 0.100% | | 0.121% | | 0.061% | | 0.039% |
| THV01xP-19 | | | 0.092% | | 0.105% | | 0.059% | | 0.034% |
| THV01xP-20 | | | 0.173% | | 0.136% | | 0.111% | | 0.054% |
| THV01xP-21 | | | 0.129% | | 0.119% | | 0.096% | | 0.050% |
| THV01xP-10 | | | 0.181% | | 0.130% | | 0.099% | | 0.051% |
| THV01xP-22 | | | 0.179% | | 0.123% | | 0.122% | | 0.058% |
| THV01xP-23 | | | 0.127% | | 0.083% | | 0.120% | | 0.055% |
| THV01xP-07 | | | 0.410% | | 0.156% | | 0.057% | | 0.034% |
| THV01xP-02 | | | 0.336% | | 0.145% | | 0.032% | | 0.026% |
| THV01xP-18 | | | 0.357% | | 0.151% | | 0.040% | | 0.026% |
| THV01xP-24 | | | 0.259% | | 0.160% | | 0.035% | | 0.028% |
| THV01xP-14 | | | 0.240% | | 0.125% | | 0.025% | | 0.022% |
| THV01xP-15 | | | 0.392% | | 0.151% | | 0.050% | | 0.031% |
| THV01xP-09 | | | 0.360% | | 0.119% | | 0.087% | | 0.039% |
| THV01xP-03 | | | 0.494% | | 0.153% | | 0.165% | | 0.063% |
| THV01xP-04 | | | 0.418% | | 0.145% | | 0.088% | | 0.040% |
| THV01xP-05 | | | 0.335% | | 0.117% | | 0.084% | | 0.035% |
| THV01xP-11 | | | 0.480% | | 0.159% | | 0.055% | | 0.033% |
| THV01xP-12 | | | 0.419% | | 0.167% | | 0.041% | | 0.030% |
| THV01xP-13 | | | 0.487% | | 0.194% | | 0.055% | | 0.037% |
| SIL08xP-02 | | | 0.080% | | 0.734% | | 0.068% | | 0.111% |
| YEL03xP-05 | 0.175% | | 0.052% | 0.117% | | | | 0.094% | 0.077% |

| | Terpenes (GC-FID) | | | | | | | | |
|---|---|---|---|---|---|---|---|---|---|
| Sample | fenchol Wt % | camphene Wt % | alpha terpineol Wt % | alpha humulene Wt % | beta caryophyllene Wt % | linalool Wt % | cary oxide Wt % | myrcene Wt % | Total identified oil (wt %) Wt % |
| THV01xP-01 | 0.015% | | | 0.021% | 0.063% | 0.024% | | 0.934% | 1.431% |
| THV01xP-06 | 0.012% | | | 0.017% | 0.026% | 0.022% | | 0.834% | 1.217% |
| THV01xP-08 | 0.017% | | 0.023% | 0.036% | 0.052% | 0.030% | | 1.058% | 1.645% |
| THV01xP-16 | 0.014% | | 0.021% | 0.023% | 0.064% | | | 0.820% | 1.338% |
| THV01xP-17 | 0.014% | | 0.020% | 0.017% | 0.034% | | | 0.941% | 1.347% |
| THV01xP-19 | 0.014% | | | 0.020% | 0.044% | | | 0.760% | 1.128% |
| THV01xP-20 | 0.017% | | 0.024% | 0.020% | 0.070% | 0.031% | | 1.051% | 1.687% |
| THV01xP-21 | 0.016% | | 0.023% | 0.032% | 0.060% | 0.030% | | 0.999% | 1.554% |
| THV01xP-10 | 0.016% | | 0.023% | 0.049% | 0.142% | 0.034% | | 1.078% | 1.803% |
| THV01xP-22 | 0.014% | | 0.022% | 0.050% | 0.150% | 0.031% | | 0.933% | 1.682% |
| THV01xP-23 | 0.011% | | | 0.036% | 0.095% | 0.019% | | 0.737% | 1.283% |
| THV01xP-07 | 0.016% | | 0.024% | 0.073% | 0.120% | 0.055% | | 0.705% | 1.650% |
| THV01xP-02 | 0.015% | | | 0.046% | 0.133% | 0.034% | | 0.600% | 1.367% |
| THV01xP-18 | 0.016% | | 0.023% | 0.032% | 0.043% | 0.041% | | 0.512% | 1.241% |
| THV01xP-24 | 0.018% | | 0.024% | 0.089% | 0.075% | 0.033% | | 0.558% | 1.279% |
| THV01xP-14 | 0.014% | | 0.021% | 0.023% | 0.033% | 0.033% | | 0.445% | 0.981% |
| THV01xP-15 | 0.017% | | 0.024% | 0.070% | 0.161% | 0.064% | | 0.691% | 1.651% |
| THV01xP-09 | 0.014% | | 0.023% | 0.037% | 0.058% | 0.029% | | 0.729% | 1.495% |
| THV01xP-03 | 0.016% | | 0.022% | 0.066% | 0.101% | 0.031% | | 1.046% | 2.157% |
| THV01xP-04 | 0.015% | | 0.022% | 0.046% | 0.062% | 0.052% | | 0.981% | 1.869% |
| THV01xP-05 | 0.013% | | | 0.041% | 0.038% | 0.041% | | 0.856% | 1.560% |
| THV01xP-11 | 0.016% | | 0.023% | 0.077% | 0.193% | 0.048% | | 0.651% | 1.735% |
| THV01xP-12 | 0.017% | | 0.025% | 0.056% | 0.146% | 0.045% | | 0.633% | 1.579% |
| THV01xP-13 | 0.021% | | 0.026% | 0.060% | 0.197% | 0.071% | | 0.842% | 1.990% |
| SIL08xP-02 | 0.094% | 0.019% | 0.093% | 0.044% | 0.165% | 0.135% | 0.005% | 0.076% | 1.624% |
| YEL03xP-05 | | 0.086% | 0.036% | | 0.032% | 0.330% | 0.093% | | 1.092% |

*LOQ for all terpenes was 0.02% except for alpha-pinene, linalool, and alpha-terpineol which were 0.04%.

TABLE 45

Relative terpene levels as measured by GC-FID for THC:CBDV and CBDV specialty cannabis varieties. Blank values indicate undetectable levels or 0.

| | Terpenes | | | | | | | | |
|---|---|---|---|---|---|---|---|---|---|
| Sample | terpinolene | alpha phellandrene | beta ocimene | carene | limonene | gamma terpinene | alpha pinene | alpha terpinene | beta pinene |
| THV01xP-01 | | | 8% | | 10% | | 5% | | 3% |
| THV01xP-06 | | | 9% | | 8% | | 5% | | 3% |
| THV01xP-08 | | | 8% | | 10% | | 6% | | 3% |
| THV01xP-16 | | | 11% | | 8% | | 7% | | 4% |
| THV01xP-17 | | | 7% | | 9% | | 5% | | 3% |
| THV01xP-19 | | | 8% | | 9% | | 5% | | 3% |
| THV01xP-20 | | | 10% | | 8% | | 7% | | 3% |
| THV01xP-21 | | | 8% | | 8% | | 6% | | 3% |
| THV01xP-10 | | | 10% | | 7% | | 5% | | 3% |
| THV01xP-22 | | | 11% | | 7% | | 7% | | 3% |
| THV01xP-23 | | | 10% | | 6% | | 9% | | 4% |
| THV01xP-07 | | | 25% | | 9% | | 3% | | 2% |
| THV01xP-02 | | | 25% | | 11% | | 2% | | 2% |
| THV01xP-18 | | | 29% | | 12% | | 3% | | 2% |
| THV01xP-24 | | | 20% | | 13% | | 3% | | 2% |
| THV01xP-14 | | | 24% | | 13% | | 3% | | 2% |
| THV01xP-15 | | | 24% | | 9% | | 3% | | 2% |
| THV01xP-09 | | | 24% | | 8% | | 6% | | 3% |
| THV01xP-03 | | | 23% | | 7% | | 8% | | 3% |
| THV01xP-04 | | | 22% | | 8% | | 5% | | 2% |
| THV01xP-05 | | | 21% | | 8% | | 5% | | 2% |
| THV01xP-11 | | | 28% | | 9% | | 3% | | 2% |
| THV01xP-12 | | | 27% | | 11% | | 3% | | 2% |
| THV01xP-13 | | | 24% | | 10% | | 3% | | 2% |
| SIL08xTP-02 | | | 5% | | 45% | | 4% | | 7% |
| YEL03xTP-05 | 8% | | 7% | | 9% | | 16% | | 5% |

| | Terpenes | | | | | | | |
|---|---|---|---|---|---|---|---|---|
| Sample | fenchol | camphene | alpha terpineol | alpha humulene | beta caryophyllene | linalool | cary oxide | myrcene |
| THV01xP-01 | 1% | | | 1% | 4% | 2% | | 65% |
| THV01xP-06 | 1% | | | 1% | 2% | 2% | | 69% |
| THV01xP-08 | 1% | | 1% | 2% | 3% | 2% | | 64% |
| THV01xP-16 | 1% | | 2% | 2% | 5% | | | 61% |
| THV01xP-17 | 1% | | 1% | 1% | 3% | | | 70% |
| THV01xP-19 | 1% | | | 2% | 4% | | | 67% |
| THV01xP-20 | 1% | | 1% | 1% | 4% | 2% | | 62% |
| THV01xP-21 | 1% | | 1% | 2% | 4% | 2% | | 64% |
| THV01xP-10 | 1% | | 1% | 3% | 8% | 2% | | 60% |
| THV01xP-22 | 1% | | 1% | 3% | 9% | 2% | | 55% |
| THV01xP-23 | 1% | | | 3% | 7% | 1% | | 57% |
| THV01xP-07 | 1% | | 1% | 4% | 7% | 3% | | 43% |
| THV01xP-02 | 1% | | | 3% | 10% | 2% | | 44% |
| THV01xP-18 | 1% | | 2% | 3% | 3% | 3% | | 41% |
| THV01xP-24 | 1% | | 2% | 7% | 6% | 3% | | 44% |
| THV01xP-14 | 1% | | 2% | 2% | 3% | 3% | | 45% |
| THV01xP-15 | 1% | | 1% | 4% | 10% | 4% | | 42% |
| THV01xP-09 | 1% | | 2% | 2% | 4% | 2% | | 49% |
| THV01xP-03 | 1% | | 1% | 3% | 5% | 1% | | 48% |
| THV01xP-04 | 1% | | 1% | 2% | 3% | 3% | | 52% |
| THV01xP-05 | 1% | | | 3% | 2% | 3% | | 55% |
| THV01xP-11 | 1% | | 1% | 4% | 11% | 3% | | 38% |
| THV01xP-12 | 1% | | 2% | 4% | 9% | 3% | | 40% |
| THV01xP-13 | 1% | | 1% | 3% | 10% | 4% | | 42% |
| SIL08xTP-02 | 6% | 1% | 6% | 3% | 10% | 8% | 0% | 5% |
| YEL03xTP-05 | | | 3% | 9% | 30% | 3% | | 11% |

Example 14

Volunteer Trials Using THC:THCV Specialty Cannabis. Effect of Added THCV

In order to demonstrate the added utility of the specialty cannabis varieties of the present invention, volunteer comparison trials were conducted. During these trials, volunteers were provided with cannabis flower blends with varying terpene and cannabinoid profiles to determine the effect of specialty cannabis with added THCv.

The volunteer trial for THCV was conducted in two weeks. Volunteers were split into six groups (1-6). Each volunteer in the group was given two samples (a control and a comparator blend). For instance, they were given a1 and a2, or b1 and b2, or c1 and c2, or d1 and d2, or e1 and e2, or f1 and f2 (see Table 46 for trial design). In this trial, the control comparator blends were prepared to contain nearly identical levels of THC and terpenes, but each week the comparator had either 1.5% THCV, or 2.5% THCV, added in.

TABLE 46

THCV effect trial overview for Weeks 3 and 4.

| Week | | | | | | |
|---|---|---|---|---|---|---|
| 3 THC or THC + 1.5% THCV | 4 THC or THC + 2.5% THCV | Terpene Class | Control and Comparator Terpenes | Base Cultivar | Control ID | Comp ID |
| Group 5 | Group 4 | a | myrcene, pinene | GRA8 | a1 | a2 |
| Group 6 | Group 5 | b | limonene, linalool, caryophyllene, humulene | WHI2 | b2 | b1 |
| Group 1 | Group 6 | c | ocimene, myrcene | GRE1 | c1 | c2 |
| Group 2 | Group 1 | d | terpinolene, ocimene | PUR2 | d2 | d1 |
| Group 3 | Group 2 | e | myrcene, pinene, ocimene, linalool, caryophyllene | PUR5 | e1 | e2 |
| Group 4 | Group 3 | f | limonene, caryophyllene, myrcene, linalool | RED1 | f2 | f1 |

Figure 8:
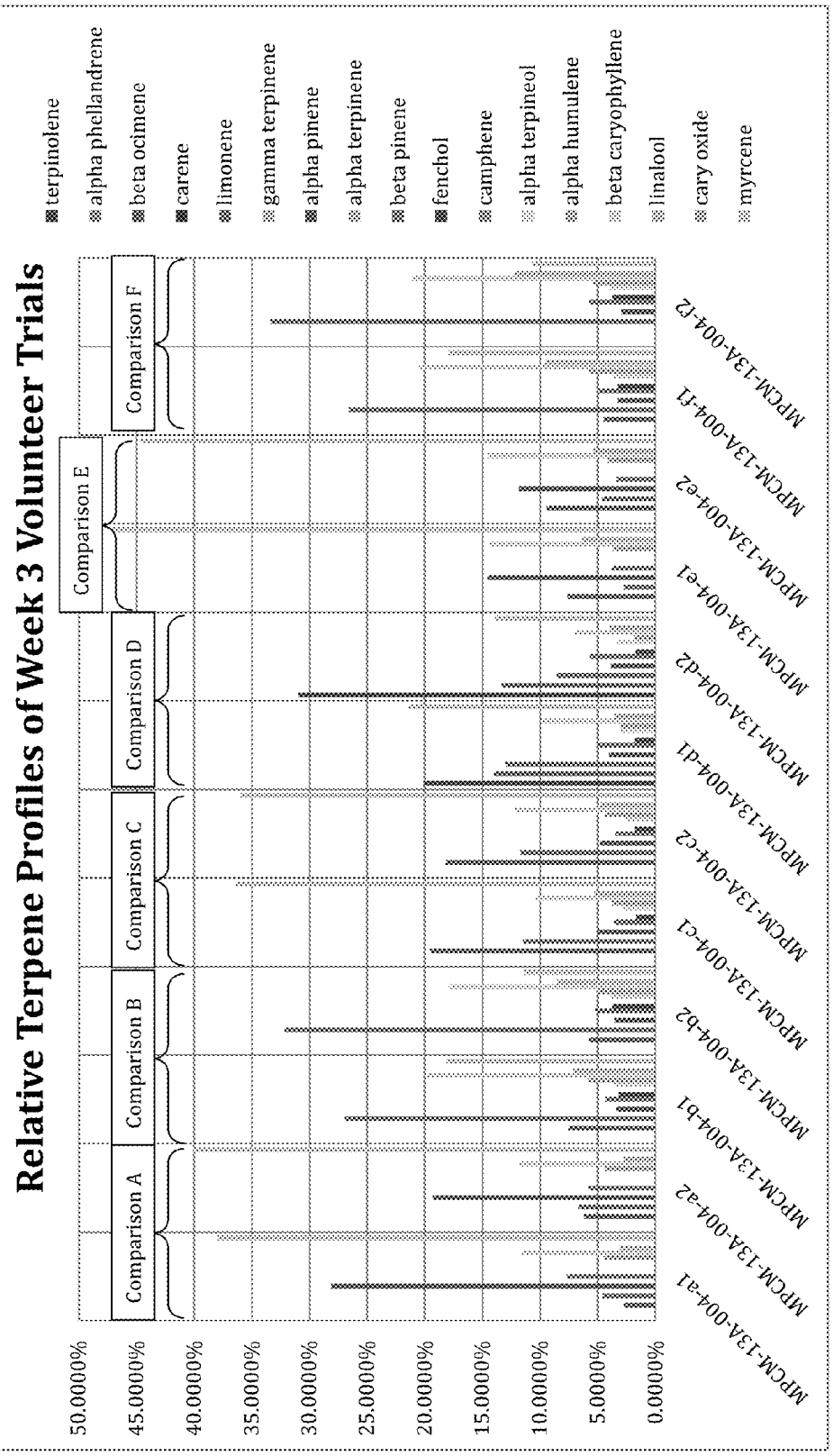
FIG. 8—Bar graph of the relative terpene contents (y-axis) of *cannabis* blends (x-axis) used for Week 3 volunteer trials. Each sample comparison pair was blended to produce similar terpene profiles so as to compare the effects of added THCV.

Samples for the trials were prepared as described in Example 10 by hand grinding and blending *cannabis* flowers. As before, each sample was analyzed via GC-FID and HPLC before being provided to volunteers in order to ensure consistency (Table 47 and 48, and FIG. 8). The same questionnaire that was used in Example 8 was used to assess the volunteer feedback on the tested blends.

TABLE 47

Cannabinoid levels of cannabis blends for Week 3 and Week 4 trials as measured by GC-FID and HPLC. Control samples highlighted. Blank values indicate undetectable levels or 0.

| | Cannabinoids (GC-FID) | | | | | | Cannabinoids (UHPLC) | | | | | |
|---|---|---|---|---|---|---|---|---|---|---|---|---|
| | THC | | THCV | | THC:THCV by GC | | THCA | | THCVA | | THCA:THCVA by HPLC | |
| Sample | Wt % | 95% CI | Wt % | 95% CI | Wt % | 95% CI | Wt % | 95% CI | Wt % | 95% CI | Wt % | 95% CI |
| Week 3 | | | | | | | | | | | | |
| MPCM-13A-004-a1 | 19.02% | 0.56% | | | | | | | | | | |
| MPCM-13A-004-a3 | 16.36% | 0.49% | 1.48% | 0.03% | 11.05 | 0.53 | | | | | | |
| MPCM-13A-004-b1 | 13.96% | 1.15% | 1.38% | 0.04% | 10.11 | 0.51 | | | | | | |
| MPCM-13A-004-b2 | 16.34% | 1.85% | | | | | HPLC measurements not conducted for Week 3 samples | | | | | |
| MPCM-13A-004-c1 | 17.04% | 0.61% | | | | | | | | | | |
| MPCM-13A-004-c2 | 14.85% | 0.86% | 1.33% | 0.05% | 11.17 | 0.70 | | | | | | |
| MPCM-13A-004-d1 | 10.46% | 0.26% | 1.37% | 0.10% | 7.64 | 0.40 | | | | | | |
| MPCM-13A-004-d2 | 10.34% | 0.91% | | | | | | | | | | |
| MPCM-13A-004-e1 | 19.61% | 0.42% | | | | | | | | | | |
| MPCM-13A-004-e2 | 16.46% | 0.56% | 1.41% | 0.04% | 11.50 | 0.49 | | | | | | |
| MPCM-13A-004-f1 | 14.12% | 0.69% | 1.40% | 0.03% | 10.12 | 0.43 | | | | | | |
| MPCM-13A-004-f2 | 15.50% | 0.59% | | | | | | | | | | |
| Week 4 | | | | | | | | | | | | |
| MPCM-13A-005-a1 | 19.02% | 0.56% | | | | | | | | | | |
| MPCM-13A-005-a3 | 21.03% | 0.38% | 2.75% | 0.26% | 7.68 | 0.60 | 27.38% | 0.68% | 4.45% | 0.39% | 6.17 | 0.46 |
| MPCM-13A-005-b1 | 19.31% | 1.78% | 2.72% | 0.20% | 7.12 | 0.98 | 24.96% | 1.53% | 4.44% | 0.33% | 5.64 | 0.55 |
| MPCM-13A-005-b2 | 16.34% | 1.85% | | | | | 24.27% | 2.32% | | | | |
| MPCM-13A-005-c1 | 17.04% | 0.61% | | | | | 25.16% | 0.79% | | | | |
| MPCM-13A-005-c2 | 20.83% | 0.63% | 2.99% | 0.12% | 6.97 | 0.50 | 26.09% | 1.32% | 4.83% | 0.16% | 5.41 | 0.39 |
| MPCM-13A-005-d1 | 15.29% | 0.52% | 2.67% | 0.06% | 5.73 | 0.32 | 20.57% | 0.20% | 4.34% | 0.07% | 4.74 | 0.12 |
| MPCM-13A-005-d2 | 10.34% | 0.91% | | | | | 16.06% | 0.98% | | | | |
| MPCM-13A-005-e1 | 19.61% | 0.42% | | | | | 28.10% | 0.26% | | | | |
| MPCM-13A-005-e2 | 22.93% | 1.44% | 2.96% | 0.04% | 7.76 | 0.58 | 28.72% | 1.10% | 4.70% | 0.02% | 6.11 | 0.22 |
| MPCM-13A-005-f1 | 19.00% | 0.79% | 2.75% | 0.45% | 7.02 | 1.25 | 24.70% | 0.36% | 4.37% | 0.79% | 5.75 | 1.01 |
| MPCM-13A-005-f2 | 15.50% | 0.59% | | | | | 23.47% | 0.79% | | | | |

TABLE 48

Terpene contents of cannabis blends for Week 3 and Week 4 trials as measured by GC-FID.
Blank values indicate undetectable levels or 0.

| | | Terpenes (GC-FID) | | | | | | | | | | | | | | | | |
|---|---|---|---|---|---|---|---|---|---|---|---|---|---|---|---|---|---|---|
| | | alpha pinene | | camphene | | beta pinene | | myrcene | | alpha phellandrene | | carene | | alpha terpinene | | limonene | | beta ocimene | | gamma terpinene | |
| | Sample | Wt % | 95% CI | Wt % | 95% CI | Wt % | 95% CI | Wt % | 95% CI | Wt % | 95% CI | Wt % | 95% CI | Wt % | 95% CI | Wt % | 95% CI | Wt % | 95% CI | Wt % | 95% CI |
| Week 3 | MPCM-13A-004-a1 | 0.428% | 0.011% | | | 0.117% | 0.002% | 0.578% | 0.002% | | | | | | | 0.070% | 0.000% | 0.041% | 0.001% | | |
| | MPCM-13A-004-a2 | 0.326% | 0.019% | | | 0.099% | 0.006% | 0.678% | 0.031% | | | | | | | 0.113% | 0.004% | 0.105% | 0.003% | | |
| | MPCM-13A-004-b1 | 0.067% | 0.005% | | | 0.085% | 0.006% | 0.357% | 0.019% | | | | | | | 0.531% | 0.032% | 0.148% | 0.006% | | |
| | MPCM-13A-004-b2 | 0.079% | 0.009% | | | 0.115% | 0.012% | 0.252% | 0.019% | | | | | | | 0.710% | 0.069% | 0.128% | 0.012% | | |
| | MPCM-13A-004-c1 | 0.093% | 0.003% | | | 0.066% | 0.001% | 0.672% | 0.020% | | | | | | | 0.212% | 0.006% | 0.361% | 0.015% | | |
| | MPCM-13A-004-c2 | 0.085% | 0.003% | | | 0.061% | 0.001% | 0.630% | 0.008% | | | | | | | 0.205% | 0.005% | 0.318% | 0.008% | | |
| | MPCM-13A-004-d1 | 0.054% | 0.001% | | | 0.066% | 0.001% | 0.284% | 0.008% | | | | | | | 0.173% | 0.003% | 0.185% | 0.003% | | |
| | MPCM-13A-004-d2 | 0.047% | 0.005% | | | 0.069% | 0.006% | 0.170% | 0.011% | | | | | | | 0.105% | 0.009% | 0.163% | 0.013% | | |
| | MPCM-13A-004-e1 | 0.316% | 0.013% | | | 0.082% | 0.003% | 1.022% | 0.018% | | | | | | | 0.060% | 0.001% | 0.166% | 0.004% | | |
| | MPCM-13A-004-e2 | 0.239% | 0.015% | | | 0.069% | 0.002% | 0.900% | 0.018% | | | | | | | 0.093% | 0.002% | 0.190% | 0.001% | | |
| | MPCM-13A-004-f1 | 0.047% | 0.002% | | | 0.071% | 0.003% | 0.258% | 0.010% | | | | | | | 0.383% | 0.022% | 0.065% | 0.003% | | |
| | MPCM-13A-004-f2 | 0.043% | 0.001% | | | 0.084% | 0.002% | 0.154% | 0.002% | | | | | | | 0.483% | 0.013% | | | | |
| Week 4 | MPCM-13A-005-a1 | 0.428% | 0.011% | | | 0.117% | 0.002% | 0.578% | 0.002% | | | | | | | 0.070% | 0.000% | 0.041% | 0.001% | | |
| | MPCM-13A-005-a2 | 0.410% | 0.013% | | | 0.128% | 0.005% | 0.667% | 0.031% | | | | | | | 0.146% | 0.008% | 0.113% | 0.006% | | |
| | MPCM-13A-005-b1 | 0.102% | 0.003% | | | 0.118% | 0.004% | 0.374% | 0.008% | | | | | | | 0.639% | 0.036% | 0.172% | 0.005% | | |
| | MPCM-13A-005-b2 | 0.079% | 0.009% | | | 0.115% | 0.012 | 0.252% | 0.019% | | | | | | | 0.710% | 0.069% | 0.128% | 0.012% | | |
| | MPCM-13A-005-c1 | 0.093% | 0.003% | | | 0.066% | 0.001% | 0.672% | 0.020% | | | | | | | 0.212% | 0.006% | 0.361% | 0.015% | | |
| | MPCM-13A-005-c2 | 0.119% | 0.001% | | | 0.080% | 0.001% | 0.686% | 0.012% | | | | | | | 0.252% | 0.001% | 0.345% | 0.004% | | |
| | MPCM-13A-005-d1 | 0.083% | 0.001% | | | 0.089% | 0.003% | 0.333% | 0.010% | 0.019% | 0.001% | 0.013% | 0.001% | 0.010% | 0.001% | 0.222% | 0.008% | 0.214% | 0.006% | | |
| | MPCM-13A-005-d2 | 0.047% | 0.005% | | | 0.069% | 0.006% | 0.170% | 0.011% | | | | | | | 0.105% | 0.009% | 0.163% | 0.013% | | |

TABLE 48-continued

Terpene contents of cannabis blends for Week 3 and Week 4 trials as measured by GC-FID. Blank values indicate undetectable levels or 0.

| Sample | terpinolene | | linalool | | fenchol | | alpha terpineol | | beta caryophyllene | | alpha humulene | | cary oxide | | Total identified oil (wt %) | | Relative myrcene |
|---|---|---|---|---|---|---|---|---|---|---|---|---|---|---|---|---|---|
| | Wt % | 95% CI | Wt % | 95% CI | Wt % | 95% CI | Wt % | 95% CI | Wt % | 95% CI | Wt % | 95% CI | Wt % | 95% CI | Wt % | 95% CI | |
| MPCM-13A-005-e1 | 0.316% | 0.013% | 0.082% | 0.003% | 1.022% | 0.018% | | | | | 0.060% | 0.001% | 0.166% | 0.004% | | | |
| MPCM-13A-005-e2 | 0.312% | 0.011% | 0.098% | 0.002% | 1.125% | 0.010% | | | | | 0.147% | 0.002% | 0.240% | 0.001% | | | |
| MPCM-13A-005-f1 | 0.074% | 0.007% | 0.085% | 0.005% | 0.333% | 0.027% | | | | | 0.437% | 0.022% | 0.080% | 0.011% | | | |
| MPCM-13A-005-f2 | 0.043% | 0.001% | 0.084% | 0.002% | 0.154% | 0.002% | | | | | | | 0.483% | 0.013% | | | |

| | | Terpenes (GC-FID) | | | | | | | | | | | | | Total identified oil (wt %) | | Relative myrcene |
|---|---|---|---|---|---|---|---|---|---|---|---|---|---|---|---|---|---|
| | terpinolene | | linalool | | fenchol | | alpha terpineol | | beta caryophyllene | | alpha humulene | | cary oxide | | | | |
| Sample | Wt % | 95% CI | Wt % | 95% CI | Wt % | 95% CI | Wt % | 95% CI | Wt % | 95% CI | Wt % | 95% CI | Wt % | 95% CI | Wt % | 95% CI | |
| Week 3 | | | | | | | | | | | | | | | | | |
| MPCM-13A-004-a1 | | | 0.047% | 0.001% | | | | | 0.177% | 0.003% | 0.068% | 0.001% | | | 1.523% | 0.026% | 38% |
| MPCM-13A-004-a2 | | | 0.047% | 0.000% | 0.063% | 0.003% | 0.070% | 0.005% | 0.200% | 0.008% | 0.075% | 0.003% | | | 1.690% | 0.074% | 40% |
| MPCM-13A-004-b1 | | | 0.140% | 0.007% | 0.082% | 0.007% | 0.086% | 0.007% | 0.390% | 0.020% | 0.116% | 0.006% | | | 1.973% | 0.114% | 18% |
| MPCM-13A-004-b2 | | | 0.188% | 0.018% | 0.031% | 0.003% | 0.051% | 0.003% | 0.395% | 0.039% | 0.111% | 0.011% | | | 2.208% | 0.245% | 11% |
| MPCM-13A-004-c1 | | | 0.098% | 0.005% | 0.032% | 0.002% | 0.046% | 0.004% | 0.193% | 0.016% | 0.070% | 0.007% | | | 1.848% | 0.072% | 36% |
| MPCM-13A-004-c2 | | | 0.084% | 0.006% | 0.024% | 0.001% | 0.040% | 0.002% | 0.213% | 0.028% | 0.077% | 0.011% | | | 1.751% | 0.058% | 36% |
| MPCM-13A-004-d1 | 0.266% | 0.007% | 0.047% | 0.000% | 0.021% | 0.001% | 0.040% | 0.002% | 0.132% | 0.003% | 0.041% | 0.001% | | | 1.326% | 0.070% | 21% |
| MPCM-13A-004-d2 | 0.379% | 0.028% | 0.049% | 0.002% | | | | | 0.086% | 0.003% | 0.023% | 0.001% | | | 1.222% | 0.058% | 14% |
| MPCM-13A-004-e1 | | | 0.138% | 0.002% | | | | | 0.311% | 0.005% | 0.080% | 0.001% | | | 2.171% | 0.051% | 47% |
| MPCM-13A-004-e2 | | | 0.110% | 0.001% | 0.047% | 0.002% | 0.053% | 0.002% | 0.292% | 0.007% | 0.083% | 0.001% | | | 2.015% | 0.038% | 45% |
| MPCM-13A-004-f1 | | | 0.138% | 0.006% | 0.054% | 0.001% | 0.059% | 0.001% | 0.295% | 0.015% | 0.083% | 0.003% | | | 1.439% | 0.069% | 18% |
| MPCM-13A-004-f2 | | | 0.177% | 0.003% | 0.020% | 0.001% | 0.029% | 0.001% | 0.306% | 0.005% | 0.079% | 0.002% | | | 1.446% | 0.037% | 11% |
| Week 4 | | | | | | | | | | | | | | | | | |
| MPCM-13A-005-a1 | | | 0.047% | 0.001% | | | | | 0.177% | 0.003% | 0.068% | 0.001% | | | 1.523% | 0.026% | 38% |
| MPCM-13A-005-a2 | | | 0.049% | 0.001% | 0.077% | 0.003% | 0.078% | 0.002% | 0.286% | 0.014% | 0.107% | 0.005% | 0.147% | 0.002% | 1.957% | 0.081% | 34% |
| MPCM-13A-005-b1 | | | 0.170% | 0.009% | 0.082% | 0.007% | 0.086% | 0.007% | 0.476% | 0.020% | 0.149% | 0.003% | 0.437% | 0.022% | 2.418% | 0.092% | 15% |
| MPCM-13A-005-b2 | | | 0.188% | 0.018% | | | | | 0.395% | 0.039% | 0.111% | 0.011% | 0.483% | 0.013% | 2.208% | 0.245% | 11% |

TABLE 48-continued

Terpene contents of cannabis blends for Week 3 and Week 4 trials as measured by GC-FID.
Blank values indicate undetectable levels or 0.

| | | | | | | | | | | | |
|---|---|---|---|---|---|---|---|---|---|---|---|
| MPCM-13A-005-c1 | | 0.098% | 0.005% | 0.031% | 0.003% | 0.051% | 0.003% | 0.193% | 0.016% | 0.070% | 0.007% | 1.848% | 0.072% | 36% |
| MPCM-13A-005-c2 | | 0.088% | 0.003% | 0.035% | 0.001% | 0.048% | 0.001% | 0.305% | 0.003% | 0.114% | 0.002% | 1.759% | 0.015% | 39% |
| MPCM-13A-005-d1 | 0.352% | 0.019% | 0.053% | 0.002% | 0.029% | 0.001% | 0.044% | 0.002% | 0.225% | 0.010% | 0.075% | 0.003% | 1.422% | 0.065% | 23% |
| MPCM-13A-005-d2 | 0.379% | 0.028% | 0.049% | 0.002% | 0.021% | 0.001% | 0.040% | 0.002% | 0.086% | 0.003% | 0.023% | 0.001% | 1.222% | 0.058% | 14% |
| MPCM-13A-005-e1 | | 0.138% | 0.002% | | | | | 0.311% | 0.005% | 0.080% | 0.001% | 2.171% | 0.051% | 47% |
| MPCM-13A-005-e2 | | 0.139% | 0.003% | 0.019% | 0.002% | 0.027% | 0.002% | 0.446% | 0.025% | 0.135% | 0.009% | 2.690% | 0.022% | 42% |
| MPCM-13A-005-f1 | | 0.151% | 0.008% | 0.050% | 0.002% | 0.055% | 0.001% | 0.426% | 0.023% | 0.129% | 0.007% | 2.010% | 0.401% | 17% |
| MPCM-13A-005-f2 | | 0.177% | 0.003% | 0.054% | 0.001% | 0.059% | 0.001% | 0.306% | 0.005% | 0.079% | 0.002% | 1.446% | 0.037% | 11% |

The controls (a1, b2, c1, d2, e1, and f2) had only THC while the comparators (a2, b1, c2, d1, e2, and f1) had approximately the same amount of THC plus a small percentage of THCV. In Week Three approximately 1.5% of THCV was added, in Week Four 2.5% of THCV was added. These non-THC cannabinoids have demonstrated pharmacology (such as CB2 agonist and mild antagonist to CB1) that we hypothesized may attenuate some of the negative side effects of THC by blocking the action of THC itself or by activating alternative pathways (RG Pertwee. 2008 "The diverse CB1 and CB2 receptor pharmacology of three plant cannabinoids: delta 9 tetrahydrocannabinol, cannabidiol and delta 9 tetrahydrocannabivarin" Br. J. Pharmacol. 153(2):199-215).

The controls and comparators in Weeks Three and Four were also blended to have very similar terpene profiles in order to ensure both samples had similar aroma, flavor, and putative entourage effects, so as not to predispose the volunteer into thinking one or the other would be different based on organoleptic properties. Both Table 48 and the FIG. 8 (with the controls and comparator sample pairs labeled with brackets) show there is little difference in the terpene profiles of the control and comparator within a group. The blends were always prepared so the myrcene content was below 60% and the total identified essential oil content was about 1.5%.

Thirty volunteers were recruited and asked to fill out demographic surveys. Each week the volunteers were given a control and a comparator, two corresponding surveys as described in Examples 9 and 10. The results were analyzed as the averages along with the 95% confidence intervals (Table 49).

Figure 9:
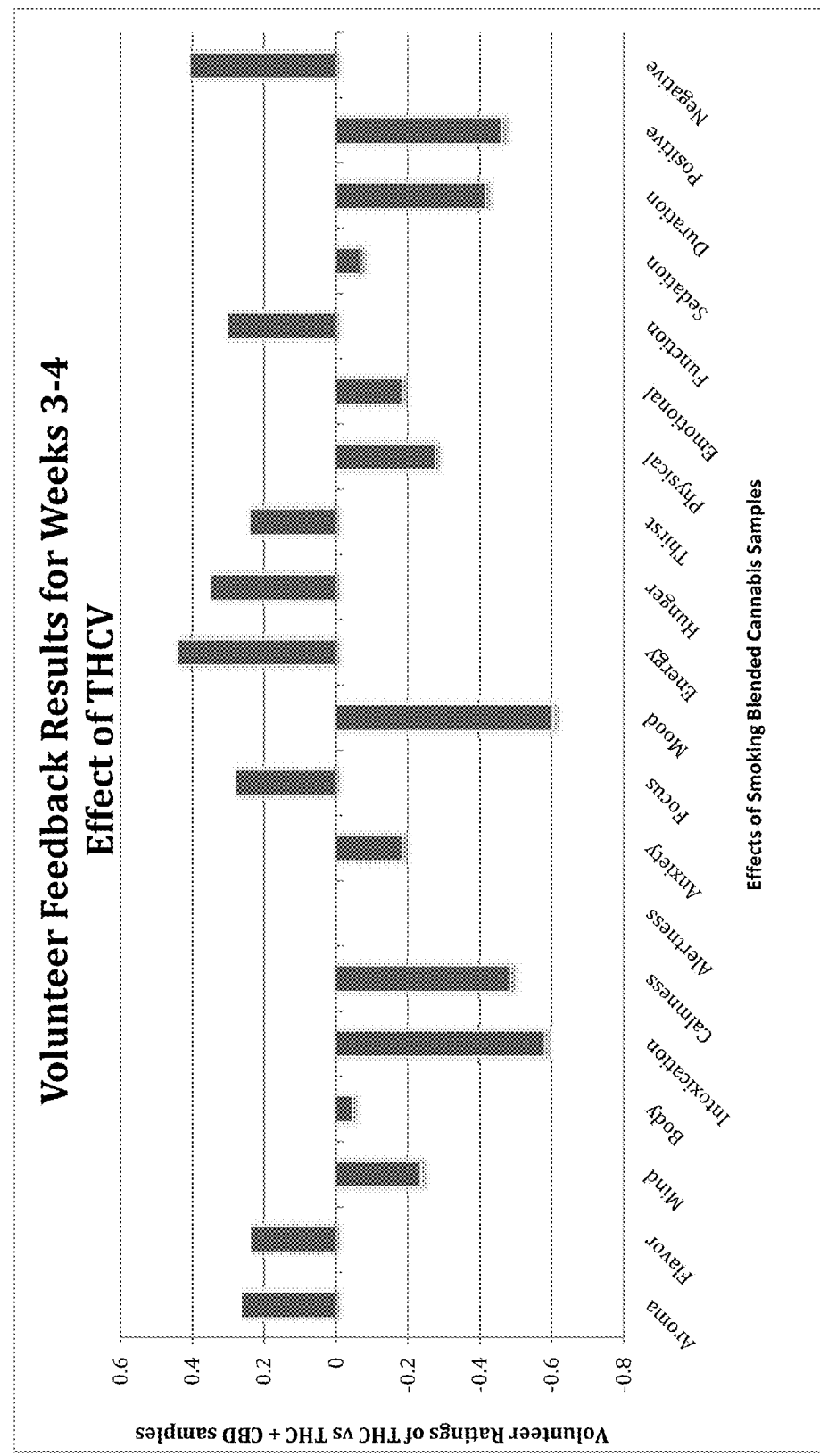
FIG. 9—Bar graph of Weeks 3 and 4 trials feedback results combined. Values are presented as ratings for test sample minus control sample. Higher values indicated increased ratings for a category, while lower values indicate decreased ratings for a category. THCV containing samples showed decrease in mind and body high as well as increased ability to function.

The results are presented as the difference in feedback scores between control samples with just THC cannabinoid, to comparator samples with added THCV cannabinoid (see Table 49 and FIG. 9).

Several feedback trends can be seen in the comparison of the two samples. Most notably, there appeared to be an obvious decrease in the level of "mind high", "intoxication", and "duration" for *cannabis* blends containing THCV. There also appeared to be an increase in the ability to "function normally", "energy", "focus" and "hunger". Each comparison control and comparator sample contained equal amounts of THC and nearly identical terpene profiles. Thus the differences outlined in Table 49 and FIG. 9 are attributed to the small amount of THCV added to comparator samples.

The observed trends suggest that the addition of a non-THC cannabinoid, such as found in THCV cultivars, can help reduce the feelings associated with being "high", reduce "intoxication", reduce the "duration", reduce "sedation", and improve the ability to "function" normally while under the influence. Thus in some embodiments, the specialty *cannabis* of the present invention with THCV has the potential to reduce adverse effects and provide a larger margin of safety for a number of applications. In some embodiments, the THCV containing specialty *cannabis* can be used at times when users wish to still be able to remain functioning normally even after smoking Another use for specialty *cannabis* of the present invention is in medicinal applications. Many times patients attempting to use *cannabis* for medical treatment discontinue use due to the aforementioned "negative" side effects, such as being "high" or intoxicated, and these ratios have demonstrated a clear potential of the present invention to mitigate these effects. In some embodiments, patients could use the specialty *cannabis* of the present invention to experience the hunger inducing effects of *cannabis*,

TABLE 49

Combined feedback results for Week 3 and 4 trials.

Averages for Weeks 3-4

| Question | A | 95% CI | B | 95% CI | C | 95% CI | D | 95% CI | E | 95% CI | F | 95% CI | TOTAL | 95% CI |
|---|---|---|---|---|---|---|---|---|---|---|---|---|---|---|
| Aroma | 2.167 | 2.45 | −0.33 | 0.65 | −0.13 | 0.78 | 0.143 | 1.00 | 0.286 | 2.21 | −0.25 | 1.27 | 0.262 | 0.62 |
| Flavor | 1 | 2.09 | −1.25 | 1.67 | 0.556 | 1.14 | −1.4 | 3.31 | 0.833 | 1.06 | 0.625 | 1.23 | 0.237 | 0.71 |
| Mind | 0.333 | 2.46 | 0.333 | 0.83 | 0 | 0.92 | −1.43 | 1.53 | −1.33 | 2.61 | 0.5 | 1.96 | −0.24 | 0.72 |
| Body | 1 | 1.82 | −0.67 | 0.83 | 0.444 | 1.23 | −0.43 | 1.70 | −1.83 | 1.78 | 0.75 | 1.42 | −0.05 | 0.64 |
| Intoxication | 0 | 2.37 | −0.33 | 0.83 | −0.11 | 0.89 | −2 | 1.86 | −1.57 | 2.30 | 0.375 | 1.77 | −0.58 | 0.71 |
| Calmness | −1 | 1.39 | 0.5 | 2.07 | 0.125 | 1.01 | 0.714 | 2.08 | −1 | 1.05 | −2.13 | 1.55 | −0.49 | 0.68 |
| Alertness | 0 | 1.52 | −1.5 | 1.21 | 0 | 0.65 | 1.714 | 1.58 | 0.286 | 1.64 | −0.63 | 1.92 | 0 | 0.63 |
| Anxiety | −0.67 | 1.80 | 0.833 | 1.38 | −0.56 | 0.74 | −1 | 1.76 | −0.14 | 1.45 | 0.5 | 2.22 | −0.19 | 0.65 |
| Focus | 0.167 | 1.78 | −2 | 1.34 | 0.444 | 1.14 | 1.429 | 1.27 | 0.143 | 1.79 | 1 | 2.19 | 0.279 | 0.70 |
| Mood | 0.833 | 2.17 | −1.83 | 1.55 | 0 | 1.08 | 0.714 | 1.33 | −1.57 | 1.34 | −1.75 | 2.59 | −0.6 | 0.76 |
| Energy | −0.5 | 1.31 | −0.83 | 0.94 | 0.778 | 1.63 | 2.286 | 1.40 | 0.714 | 1.26 | −0.13 | 0.58 | 0.442 | 0.58 |
| Hunger | 1.333 | 2.24 | 1.167 | 1.28 | 0.333 | 1.39 | 0.714 | 1.99 | 0.143 | 0.90 | −1.13 | 1.67 | 0.349 | 0.67 |
| Thirst | 0 | 1.01 | 0 | 1.07 | 0.333 | 1.03 | 0.714 | 1.11 | 0 | 2.05 | 0.25 | 2.18 | 0.238 | 0.61 |
| Physical | −2 | 2.73 | −0.33 | 1.49 | 0.111 | 0.83 | 0.571 | 1.27 | −0.29 | 0.93 | −0.13 | 1.01 | −0.28 | 0.57 |
| Emotional | −0.83 | 1.18 | 0.5 | 1.50 | −0.11 | 0.89 | 1 | 1.05 | −0.43 | 0.58 | −1.13 | 2.58 | −0.19 | 0.62 |
| Function | 0.333 | 1.65 | 0 | 2.68 | −0.33 | 0.65 | 1.857 | 1.68 | 1.143 | 1.17 | −0.88 | 1.31 | 0.302 | 0.64 |
| Sedation | 1.167 | 2.05 | 0 | 1.01 | −0.11 | 1.44 | −1.14 | 1.08 | −0.71 | 2.25 | 0.5 | 1.85 | −0.07 | 0.69 |
| Duration | 0.667 | 2.46 | −0.83 | 0.94 | −0.11 | 0.89 | −0.14 | 2.11 | −1.43 | 0.94 | −0.63 | 0.82 | −0.42 | 0.57 |
| Positive | 0.333 | 2.36 | −0.83 | 1.18 | 0 | 0.86 | 0.714 | 1.26 | −1.71 | 1.53 | −1.25 | 0.61 | −0.47 | 0.56 |
| Negative | 0.6 | 1.00 | 1.167 | 2.11 | −0.33 | 0.57 | −1.29 | 1.46 | 0.857 | 1.79 | 1.625 | 0.90 | 0.405 | 0.59 | with reduced effects of feeling "high" while maintaining an increased ability to function.

THCV has been shown to be a potent CB2 receptor agonist but a mild antagonist for CB1 receptors. THCV's response to with the CB1 receptor is also dose dependent as higher doses of THCV allow the molecule to become a CB1 agonist (Pertwee, R. G. 2008 "The diverse CB1 and CB2 receptor pharmacology of three plant cannabinoids: Δ9-tetrahydrocannabinol, cannabidiol and Δ9-tetrahydrocannabivarin"). The experiments will also be repeated at higher THCV concentrations.

Example 15

Phenotypic Analysis THCV Specialty *Cannabis* Progeny (Prophetic)

The new specialty *cannabis* varieties created through crosses described in Examples 5 and 12 will be subjected to phenotypic analysis as described in Example 2 (indoor growth) and Example 8 (outdoor growth).

Initial selections will be conducted based on measured phenotypes as well as the chemical analyses already conducted in Example 13. Cuttings of desirable progeny will be preserved for subsequent breeding as described in Examples 5, 19 and 20. The data gathering sheet shown in FIG. 2 will be used to guide these phenotype assays. Data that will be collected will include plant height at maturity, plant diameter at maturity, number of leaflets, leaf type, average number of internodes, leaf color, node branching, number of inflorescences, average non-apical inflorescences, apical inflorescence size, flower cluster density, ripening mode, average calyx length, and flower color. Notes about growth and resistance to pests will also be recorded.

Example 16

Development of CBG Specialty *Cannabis* Varieties (Prophetic)

Unique parental chemotype I II, III and CBG lines from Examples 2-4 will be selected and one of the parental cultivars will be treated with silver thiosulfate to coax the pistillate plant to produce staminate, pollen-bearing flowers. The chemotype I, II or III line will then be crossed, the resulting progeny will be screened by TLC to identify plants producing either THC:CBG or CBD:CBG. Progeny exhibiting the desired cannabinoid profile will be allowed to reach maturity and the flowers will be harvested and analyzed via GC-FID and HPLC. Table 50 outlines the initial crosses that will be performed. Progeny from these crosses will also be allowed to "self" to produce CBG producing *cannabis* with desirable terpene profiles and high terpene oil contents of the parental varieties. Progeny will also be backcrossed to parental lines to reinforce parental chemical and morphological phenotypes. For a more thorough description of expected breeding schemes, see Example 5.

TABLE 50

Prophetic crosses with CBG02 parents.

| P Donor | Acceptor Cultivar | Acceptor Trait | Acceptor Cultivar | Acceptor Trait | Acceptor Cultivar | Acceptor Trait | Seed Batch Code |
|---|---|---|---|---|---|---|---|
| CBG02xS- | GOD13 | 1, 2, 3, 12 | GOD02 | 1, 2, 3, 9, 10 | GOD12 | 1, 2, 4, 10 | CBG02xS-XGOLD |
| CBG02xS- | SIL04 | 1, 3, 7, 10, 12 | SIL01 | 1, 3, 12 | SIL08 | 1, 2, 3, 9, 12 | CBG02xS-XSILVER |
| CBG02xS- | WHI02 | 1, 3, 5, 8, 9, 12 | WHI07 | 1, 3, 5, 6, 12 | WHI03 | 1, 3, 5, 6, 12 | CBG02xS-XWHITE |
| CBG02xS- | PUR01 | 1, 6, 8, 10 | PUR03 | 1, 2, 3, 6, 12 | | | CBG02xS-XPURPLE |
| CBG02xS- | RED02 | 1, 3, 4, 5, 12 | RED01 | 1, 3, 4, 5, 12 | | | CBG02xS-XRED |
| CBG02xS- | YEL03 | 1, 2, 3, 8, 9, 10, 12 | YEL04 | 1, 2, 4, 5 | YEL05 | 1, 2, 4, 5, 8, 9, 10 | CBG02xS-XYELLOW |
| CBG02xS- | ORA02 | 1, 4, 7, 8, 12 | ORA03 | 1, 4, 7, 8, 9, 10 | | | CBG02xS-XORANGE |
| CBG02xS- | BLK03 | 1, 2, 3, 6, 10, 12 | | | | | CBG02xS-XBLACK |
| CBG02xS- | FSC01 | 1, 2, 4, 9, 10 | FSC02 | 1, 2, 4, 9, 10 | | | CBG02xS-XFUSCIA |
| CBG02xS- | GRA01 | 1, 2, 4, 7, 8, 10 | GRA03 | 1, 2, 3, 7, 8, 9, 12 | | | CBG02xS-XGRAY |
| CBG02xS- | BRO01 | 1, 4, 5, 6, 12 | BRO04 | 1, 2, 5, 6, 10, 12 | | | CBG02xS-XBRONZE |
| CBG02xS- | GRE01 | 1, 2, 3, 4, 6, 8, 9, 12 | GRE02 | 1, 2, 3, 7, 8, 9, 10 | GRE30 | 1, 2, 4, 5, 9, 10 | CBG02xS-XGREEN |
| CBG02xS- | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBG02xS-XBLUE |
| CBG02xS- | JAD07 | 1, 2, 4, 5, 8, 9, 10 | JAD21 | 1, 2, 4, 5, 8, 9, 10 | JAD04 | 1, 2, 3, 9, 12 | CBG02xS-XJADE |
| CBG02xS- | CBD04 | 1, 2, 6 | CBD05 | 1, 2, 3, 6, 8, 12 | | | CBG02xS-XCBD (Type 2) |
| CBG02xS- | CBD24 | 1, 2, 3, 6, 8, 12 | CBD04xP-09 | 1, 2, 3, 6, 8, 12 | CBD05xP-01 | 1, 2, 3, 6, 8, 12 | CBG02xS-XCBD (Type 3) |
| CBG02xS- | CBD05 | 1, 2, 3, 6, 8, 12 | | | | | CBG02xS-XCBG02xS- |
| CBG02xS- | CBG02xS- | 1, 2, 4, 5, 8, 9, 11 | | | | | CBG02xSXSELF |

In these crosses, the CBG02 line was selected for its accumulation of CBG cannabinoid. Table 50 also lists the some of the major traits (in trait codes) for which the other parental lines were chosen and the expected phenotypes of the progeny. Table 51, lists each of the desired traits alongside the trait codes used to represent them.

TABLE 51

Non-limiting list of traits important for specialty cannabis breeding programs.

| Trait ID | Description |
|---|---|
| 1 | Essential Oil Content (either terpene or overall content) - Selection based on overall oil content >1.5% and/or a singe terpene that accounts over half of total terpene content and/or a determined range of terpene concentrations designed specifically to treat ailment. |
| 2 | Cannabinoid Content (either rare cannabinoid or overall content) - Selection based on overall oil content >1.5% and/or a singe terpene that accounts over half of total terpene content and/or a determined range of terpene concentrations designed specifically to treat ailment. |
| 3 | Structure for Manual Trim/Market - Selections are based on the relative ratio by weight of finished flower: Whole plant. This usually is directly related to dense trichome morphology with very few sun leaves. |
| 4 | Structure for Automated Trimming - Selection based on flower morphology that is more kola with many sun leaves protruding from large inflorescences. Overall flower size is typically large, but trichomes are less densely packed and overall inflorescence is less dense than what is traditionally selected for manual trim. |
| 5 | Structure for Extraction - Selection for this trait is conducted post harvest and post drying. Positive selection is based on copious shedding of trichome heads and stalks. |
| 6 | Color - Selections are based on, but not limited to unique coloration of stem, leaf, inflorescence, calyx, stamen, trichome bodies and finished products including extracts and hash. |
| 7 | Root Structure - Positive root selection is marked by overall root vigor and adventitious root growth, ease of transplant, rate of root development on clonal propagations, and root shooting from tissue culture samples. Also resistance to soil and hydroponic pathogens including pythium. |
| 8 | Vigor - Selection for plant vigor are marked by tremendous growth rates and robust stem/stalk infrastructure. Often times, selection display morphologies that are very much enlarged compared to sibling progeny. |
| 9 | Fungal Resistance - Selections based on plant that exhibit immunity or partial immunity to fungal diseases and pathogens including but not limited to powdery mildew, botrytis, downy mildew, etc. |
| 10 | High Yield Natural Light Production Long Season - Selection based on yield performance for early ripening varieties during long season. |
| 11 | High Yield Natural Light Production Short Season - Selection based on yield performance of late ripening varieties during long season and/or yield of plants that ripen in winter months and at low light levels. |
| 12 | High Yield Indoor Production - Selection based solely on plant yield performance in artificial lighting (HID). |

Example 17

Chemical and Phenotypic Analysis CBG Specialty *Cannabis* Progeny (Prophetic)

The new CBG specialty *cannabis* varieties that will be created through crosses described in Examples 5 and 16 will be subjected to cannabinoid and terpene chemical analysis as described in Example 1. The results of the chemical analyses are expected to show that the crosses described in Example 16 generated specialty *cannabis* that accumulate CBG and have higher oil contents and "desirable" terpene profiles.

The new CBG specialty *cannabis* varieties will also be subjected to phenotypic analysis as described in Example 2 (indoor growth) and Example 8 (outdoor growth).

Initial selections will be conducted based on measured phenotypes as well as the chemical analyses. Cuttings of desirable progeny will be preserved for subsequent breeding as described in Example 5, 19 and 20.

Example 18

Volunteer Trials Using THC:CBG, CBD:CBG, or CBG Only Specialty *Cannabis*. Effect of Added CBG (Prophetic)

In order to demonstrate the added utility of the CBG specialty *cannabis* varieties of the present invention, volunteer comparison trials will conducted. During these trials, volunteers will be provided with *cannabis* blends with varying terpene and cannabinoid profiles to determine the effect of specialty *cannabis* with added CBG.

The volunteer trial for CBG will be conducted similarly to the trial of Example 9. The trial will split volunteers into groups. Each volunteer in the group will be given two samples (a control and a comparator blend). For this trial, the control comparator blends will be prepared to contain nearly identical levels of non-CBG cannabinoids and terpenes, but each week the comparator will have either 1.5% CBG, or 2.5% CBG, added in. Volunteer responses will be measured using the questionnaire of FIG. 2.

CBG has been shown to be a CB1 antagonist (Cascio et al., "Evidence that the plant cannabinoid cannabigerol is a highly potent alpha(2)-adronoceptor agonist and moderately potent 5HT receptor antagonist" British J of Pharma. 159 (1): 129-141). The addition of CBG into *cannabis* blends is thus expected to reduce the side effects of THC.

Example 19

Development of Additional Cannabinoid Producing Specialty *Cannabis* (Prophetic)

In order to develop specialty *cannabis* with unique cannabinoid profiles, additional crosses among the parental varieties disclosed in Example 2-4 will be conducted. These prophetic crosses are indicated below with expected breeding charts describing specific crosses and the traits each cross is expected to produce. Traits for each cross are represented by trait codes which are described in Table 51 of Example 16.

Table 52 is a non-limiting list of expected crosses using parental lines of the present invention to generate new CBD producing specialty *cannabis*. Table 53 is a non-limiting list of expected crosses using progeny CBD lines previously developed in Examples 5 and 6. Each of these crosses will also be followed up by one or more back-crosses to further reinforce the transfer of desired traits.

TABLE 52

Additional example crosses to be conducted for CBD parental lines.

| P Donor | Acceptor Cultivar | Acceptor Trait | Acceptor Cultivar | Acceptor Trait | Acceptor Cultivar | Acceptor Trait | Seed Lot | Qty (g) |
|---|---|---|---|---|---|---|---|---|
| CBD24 | GOD13 | 1, 2, 3, 12 | GOD02 | 1, 2, 3, 9, 10 | GOD12 | 1, 2, 4, 10 | CBD24XGOLD | |
| CBD24 | SIL04 | 1, 3, 7, 10, 12 | SIL01 | 1, 3, 12 | SIL08 | 1, 2, 3, 9, 12 | CBD24XSILVER | |
| CBD24 | WHI02 | 1, 3, 5, 8, 9, 12 | WHI07 | 1, 3, 5, 6, 12 | WHI03 | 1, 3, 5, 6, 12 | CBD24XWHITE | |
| CBD24 | PUR01 | 1, 6, 8, 10 | PUR03 | 1, 2, 3, 6, 12 | | | CBD24XPURPLE | |
| CBD24 | YEL03 | 1, 2, 3, 8, 9, 10, 12 | YEL04 | 1, 2, 4, 5 | YEL05 | 1, 2, 4, 5, 8, 9, 10 | CBD24XYELLOW | |
| CBD24 | ORA02 | 1, 4, 7, 8, 12 | ORA03 | 1, 4, 7, 8, 9, 10 | | | CBD24XORANGE | |
| CBD24 | BLK03 | 1, 2, 3, 6, 10, 12 | | | | | CBD24XBLACK | |
| CBD24 | FSC01 | 1, 2, 4, 9, 10 | FSC02 | 1, 2, 4, 9, 10 | | | CBD24XFUSCIA | |
| CBD24 | GRA01 | 1, 2, 4, 7, 8, 10 | GRA03 | 1, 2, 3, 7, 8, 9, 12 | | | CBD24XGRAY | |
| CBD24 | GRE01 | 1, 2, 3, 4, 6, 8, 9, 12 | GRE02 | 1, 2, 3, 7, 8, 9, 10 | GRE30 | 1, 2, 4, 5, 9, 10 | CBD24XGREEN | |
| CBD24 | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBD24XBLUE | |
| CBD24 | JAD07 | 1, 2, 4, 5, 8, 9, 10 | JAD21 | 1, 2, 4, 5, 8, 9, 10 | JAD04 | 1, 2, 3, 9, 12 | CBD24XJADE | |
| CBD24 | CBD05 | 1, 2, 3, 6, 8, 12 | CBD04 | 1, 2, 6 | | | CBD24XCBD (Type 2) | |
| CBD24 | SIL08xP-02 | 1, 2, 3, 12 | | | | | CBD24xSIL08xP-02 | |
| CBD24 | CBD04xP-09 | 1, 2, 6, 9, 10, 12 | CBD05xP-01 | 1, 2, 3, 8, 9, 10, 12 | CBD24 | 1, 2, 6, 9, 10, 12 | CBD24xCBD (Type 3) | |

TABLE 53

Additional example crosses to be conducted with CBD progeny lines of the present invention.

| P Donor | Acceptor Cultivar | Acceptor Trait | Acceptor Cultivar | Acceptor Trait | Acceptor Cultivar | Acceptor Trait | Seed Lot | Qty (g) |
|---|---|---|---|---|---|---|---|---|
| CBD04xP-09 | GOD13 | 1, 2, 3, 12 | GOD02 | 1, 2, 3, 9, 10 | GOD12 | 1, 2, 4, 10 | CBD04xP-09XGOLD | |
| CBD04xP-09 | SIL04 | 1, 3, 7, 10, 12 | SIL01 | 1, 3, 12 | SIL08 | 1, 2, 3, 9, 12 | CBD04xP-09XSILVER | |
| CBD04xP-09 | WHI02 | 1, 3, 5, 8, 9, 12 | WHI07 | 1, 3, 5, 6, 12 | WHI03 | 1, 3, 5, 6, 12 | CBD04xP-09XWHITE | |
| CBD04xP-09 | PUR01 | 1, 6, 8, 10 | PUR03 | 1, 2, 3, 6, 12 | | | CBD04xP-09XPURPLE | |
| CBD04xP-09 | YEL03 | 1, 2, 3, 8, 9, 10, 12 | YEL04 | 1, 2, 4, 5 | YEL05 | 1, 2, 4, 5, 8, 9, 10 | CBD04xP-09XYELLOW | |
| CBD04xP-09 | ORA02 | 1, 4, 7, 8, 12 | ORA03 | 1, 4, 7, 8, 9, 10 | | | CBD04xP-09X0RANGE | |
| CBD04xP-09 | BLK03 | 1, 2, 3, 6, 10, 12 | | | | | CBD04xP-09XBLACK | |
| CBD04xP-09 | FSC01 | 1, 2, 4, 9, 10 | FSC02 | 1, 2, 4, 9, 10 | | | CBD04xP-09XFUSCIA | |
| CBD04xP-09 | GRA01 | 1, 2, 4, 7, 8, 10 | GRA03 | 1, 2, 3, 7, 8, 9, 12 | | | CBD04xP-09XGRAY | |
| CBD04xP-09 | GRE01 | 1, 2, 3, 4, 6, 8, 9, 12 | GRE02 | 1, 2, 3, 7, 8, 9, 10 | GRE30 | 1, 2, 4, 5, 9, 10 | CBD04xP-09XGREEN | |
| CBD04xP-09 | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBD04xP-09XBLUE | |
| CBD04xP-09 | JAD07 | 1, 2, 4, 5, 8, 9, 10 | JAD21 | 1, 2, 4, 5, 8, 9, 10 | JAD04 | 1, 2, 3, 9, 12 | CBD04xP-09XJADE | |
| CBD04xP-09 | CBD05 | 1, 2, 3, 6, 8, 12 | CBD04 | 1, 2, 6 | | | CBD04xP-09XCBD (Type2) | |
| CBD04xP-09 | SIL08xP-02 | 1, 2, 3, 12 | | | | | CBD04xP-09xSIL08xP-02 | |
| CBD04xP-09 | CBD04xP-09 | 1, 2, 6, 9, 10, 12 | CBD05xP-01 | 1, 2, 3, 8, 9, 10, 12 | CBD24 | 1, 2, 6, 9, 10, 12 | CBD04xP-09xCBD (Type3) | |
| CBD05xP-01 | GOD13 | 1, 2, 3, 12 | GOD02 | 1, 2, 3, 9, 10 | GOD12 | 1, 2, 4, 10 | CBD05xP-01XGOLD | |
| CBD05xP-01 | SIL04 | 1, 3, 7, 10, 12 | SIL01 | 1, 3, 12 | SIL08 | 1, 2, 3, 9, 12 | CBD05xP-01XSILVER | |
| CBD05xP-01 | WHI02 | 1, 3, 5, 8, 9, 12 | WHI07 | 1, 3, 5, 6, 12 | WHI03 | 1, 3, 5, 6, 12 | CBD05xP-01XWHITE | |
| CBD05xP-01 | PUR01 | 1, 6, 8, 10 | PUR03 | 1, 2, 3, 6, 12 | | | CBD05xP-01XPURPLE | |
| CBD05xP-01 | RED02 | 1, 3, 4, 5, 12 | RED01 | 1, 3, 4, 5, 12 | | | CBD05xP-01XRED | |
| CBD05xP-01 | YEL03 | 1, 2, 3, 8, 9, 10, 12 | YEL04 | 1, 2, 4, 5 | YEL05 | 1, 2, 4, 5, 8, 9, 10 | CBD05xP-01XYELLOW | |
| CBD05xP-01 | ORA02 | 1, 4, 7, 8, 12 | ORA03 | 1, 4, 7, 8, 9, 10 | | | CBD05xP-01X0RANGE | |
| CBD05xP-01 | BLK03 | 1, 2, 3, 6, 10, 12 | | | | | CBD05xP-01XBLACK | |
| CBD05xP-01 | FSC01 | 1, 2, 4, 9, 10 | FSC02 | 1, 2, 4, 9, 10 | | | CBD05xP-01XFUSCIA | |
| CBD05xP-01 | GRA01 | 1, 2, 4, 7, 8, 10 | GRA03 | 1, 2, 3, 7, 8, 9, 12 | | | CBD05xP-01XGRAY | |
| CBD05xP-01 | BRO01 | 1, 4, 5, 6, 12 | BRO04 | 1, 2, 5, 6, 10, 12 | | | CBD05xP-01XBRONZE | |
| CBD05xP-01 | GRE01 | 1, 2, 3, 4, 6, 8, 9, 12 | GRE02 | 1, 2, 3, 7, 8, 9, 10 | GRE30 | 1, 2, 4, 5, 9, 10 | CBD05xP-01XGREEN | |
| CBD05xP-01 | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBD05xP-01XBLUE | |
| CBD05xP-01 | JAD07 | 1, 2, 4, 5, 8, 9, 10 | JAD21 | 1, 2, 4, 5, 8, 9, 10 | JAD04 | 1, 2, 3, 9, 12 | CBD05xP-01XJADE | |
| CBD05xP-01 | CBD05 | 2, 4, 9, 10 | CBD04 | 1, 2, 6 | | | CBD05xP-01XCBD03 | |
| CBD05XP-01 | CBD05xP-01 | 1, 2, 3, 6, 8, 12 | | | | | CBD05xP-01XSELF | |

Table 54 is a non-limiting list of expected crosses using parental lines of the present invention to generate new THCV producing specialty *cannabis*. Table 55 is a non-limiting list of expected crosses using parental lines of the present invention to generate new CBDV producing specialty *cannabis*.

Table 56 is a non-limiting list of expected crosses using parental lines of the present invention to generate new CBG producing specialty *cannabis*. Table 57 is a non-limiting list of expected crosses using parental lines of the present invention to generate new CBC producing specialty *cannabis*.

Each of these crosses will also be followed up by one or more back-crosses to further reinforce the transfer of desired traits.

TABLE 54

Additional example crosses to be conducted for THCV lines.

| P Donor | Acceptor Cultivar | Trait | Acceptor Cultivar | Trait | Acceptor Cultivar | Trait | Seed Batch Code |
|---|---|---|---|---|---|---|---|
| THV01xS- | GOd13 | 1, 2, 3, 12 | GOD02 | 1, 2, 3, 9, 10 | GOD12 | 1, 2, 4, 10 | THV01xS-XGOLD |
| THV01xS- | SIL04 | 1, 3, 7, 10, 12 | SIL01 | 1, 3, 12 | SIL08 | 1, 2, 3, 9, 12 | THV01xS-XSILVER |
| THV01xS- | WHI02 | 1, 3, 5, 8, 9, 12 | WHI07 | 1, 3, 5, 6, 12 | WHI03 | 1, 3, 5, 6, 12 | THV01xS-XWHITE |
| THV01xS- | PUR01 | 1, 6, 8, 10 | PUR03 | 1, 2, 3, 6, 12 | | | THV01xS-XPURPLE |
| THV01xS- | RED02 | 1, 3, 4, 5, 12 | RED01 | 1, 3, 4, 5, 12 | | | THV01xS-XRED |
| THV01xS- | YEL03 | 1, 2, 3, 8, 9, 10, 12 | YE0L4 | 1, 2, 4, 5 | YEL05 | 1, 2, 4, 5, 8, 9, 10 | THV01xS-XYELLOW |
| THV01xS- | ORA02 | 1, 4, 7, 8, 12 | ORA03 | 1, 4, 7, 8, 9, 10 | | | THV01xS-XORANGE |
| THV01xS- | BLK03 | 1, 2, 3, 6, 10, 12 | | | | | THV01xS-XBLACK |
| THV01xS- | FSC01 | 1, 2, 4, 9, 10 | FSC02 | 1, 2, 4, 9, 10 | | | THV01xS-XFUSCIA |
| THV01xS- | GRA01 | 1, 2, 4, 7, 8, 10 | GRA03 | 1, 2, 3, 7, 8, 9, 12 | | | THV01xS-XGRAY |
| THV01xS- | BRO01 | 1, 4, 5, 6, 12 | BRO04 | 1, 2, 5, 6, 10, 12 | | | THV01xS-XBRONZE |
| THV01xS- | GRE01 | 1, 2, 3, 4, 6, 8, 9, 12 | GRE02 | 1, 2, 3, 7, 8, 9, 10 | GRE30 | 1, 2, 4, 5, 9, 10 | THV01xS-XGREEN |
| THV01xS- | BLU08 | 1, 2, 4, 6, 8, 10 | BLU05 | 1, 2, 3, 4, 6, 9, 12 | BLU06 | 1, 2, 4, 5, 6, 7, 8, 9, 10 | THV01xS-XBLUE |
| THV01xS- | JAD7 | 1, 2, 4, 5, 8, 9, 10 | JAd21 | 1, 2, 4, 5, 8, 9, 10 | JAD04 | 1, 2, 3, 9, 12 | THV01xS-XJADE |
| THV01xS- | CBD04 | 1, 2, 6 | CBD05 | 1, 2, 3, 6, 8, 12 | | | THV01xS-XCBD (Type 2) |
| THV01xS- | CBD24 | 1, 2, 3, 6, 8, 12 | CBD04xP-09 | 1, 2, 3, 6, 8, 12 | CBD04xP-01 | 1, 2, 3, 6, 8, 12 | THV01xS-XCBD (Type 3) |
| THV01xS- | CBD05 | 1, 2, 3, 6, 8, 12 | | | | | THV01xS-XTHV01xS- |
| THV01xS- | THV01xS- | 1, 2, 4, 5, 8, 9, 11 | | | | | THV01xS-XSELF |
| THV01xS- | CBDV1xS- | 1, 2, 4, 5, 8, 9, 11 | | | | | CBDV1xS-XSHORT |

TABLE 55

Additional example crosses to be conducted for CBDV lines.

| P Donor | Acceptor Cultivar | Trait | Acceptor Cultivar | Trait | Acceptor Cultivar | Trait | Seed Batch Code |
|---|---|---|---|---|---|---|---|
| CBDV1xS- | GOD13 | 1, 2, 3, 12 | GOD02 | 1, 2, 3, 9, 10 | GOD12 | 1, 2, 4, 10 | CBDV1xS-XGOLD |
| CBDV1xS- | SIL04 | 1, 3, 7, 10, 12 | SIL01 | 1, 3, 12 | SIL08 | 1, 2, 3, 9, 12 | CBDV1xS-XSILVER |
| CBDV1xS- | WHI02 | 1, 3, 5, 8, 9, 12 | WHI07 | 1, 3, 5, 6, 12 | WHI03 | 1, 3, 5, 6, 12 | CBDV1xS-XWHITE |
| CBDV1xS- | PUR01 | 1, 6, 8, 10 | PUR03 | 1, 2, 3, 6, 12 | | | CBDV1xS-XPURPLE |
| CBDV1xS- | RED02 | 1, 3, 4, 5, 12 | RED01 | 1, 3, 4, 5, 12 | | | CBDV1xS-XRED |
| CBDV1xS- | YEL03 | 1, 2, 3, 8, 9, 10, 12 | YEL04 | 1, 2, 4, 5 | YEL05 | 1, 2, 4, 5, 8, 9, 10 | CBDV1xS-XYELLOW |
| CBDV1xS- | ORA02 | 1, 4, 7, 8, 12 | ORA03 | 1, 4, 7, 8, 9, 10 | | | CBDV1xS-XORANGE |
| CBDV1xS- | BLK03 | 1, 2, 3, 6, 10, 12 | | | | | CBDV1xS-XBLACK |
| CBDV1xS- | FSC01 | 1, 2, 4, 9, 10 | FSC02 | 1, 2, 4, 9, 10 | | | CBDV1xS-XFUSCIA |
| CBDV1xS- | GRA01 | 1, 2, 4, 7, 8, 10 | GRA03 | 1, 2, 3, 7, 8, 9, 12 | | | CBDV1xS-XGRAY |
| CBDV1xS- | BRO01 | 1, 4, 5, 6, 12 | BRO04 | 1, 2, 5, 6, 10, 12 | | | CBDV1xS-XBRONZE |
| CBDV1xS- | GRE01 | 1, 2, 3, 4, 6, 8, 9, 12 | GRE02 | 1, 2, 3, 7, 8, 9, 10 | GRE30 | 1, 2, 4, 5, 9, 10 | CBDV1xS-XGREEN |
| CBDV1xS- | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBDV1xS-XBLUE |
| CBDV1xS- | JAD07 | 1, 2, 4, 5, 8, 9, 10 | JAD21 | 1, 2, 4, 5, 8, 9, 10 | JAD04 | 1, 2, 3, 9, 12 | CBDV1xS-XJADE |
| CBDV1xS- | CBD04 | 1, 2, 6 | CBD05 | 1, 2, 3, 6, 8, 12 | | | CBDV1xS-XCBD (Type 2) |
| CBDV1xS- | CBD24 | 1, 2, 3, 6, 8, 12 | CBD04xP-09 | 1, 2, 3, 6, 8, 12 | CBD05xP-01 | 1, 2, 3, 6, 8, 12 | CBDV1xS-XCBD (Type 3) |
| CBDV1xS- | CBD05 | 1, 2, 3, 6, 8, 12 | | | | | CBDV1xS-XCBDV1xS- |
| CBDV1xS- | CBDV1xS- | 1, 2, 4, 5, 8, 9, 11 | | | | | CBDV1xS-XSELF |

TABLE 56

Additional example crosses to be conducted for CBG lines.

| P Donor | Acceptor Cultivar | Trait | Acceptor Cultivar | Trait | Acceptor Cultivar | Trait | Seed Batch Code |
|---|---|---|---|---|---|---|---|
| CBG1xS- | GOD13 | 1, 2, 3, 12 | GOD02 | 1, 2, 3, 9, 10 | GOD12 | 1, 2, 4, 10 | CBG1xS-XGOLD |
| CBG1xS- | SIL04 | 1, 3, 7, 10, 12 | SIL01 | 1, 3, 12 | SIL08 | 1, 2, 3, 9, 12 | CBG1xS-XSILVER |
| CBG1xS- | WHI02 | 1, 3, 5, 8, 9, 12 | WHI07 | 1, 3, 5, 6, 12 | WHI03 | 1, 3, 5, 6, 12 | CBG1xS-XWHITE |

TABLE 56-continued

Additional example crosses to be conducted for CBG lines.

| P Donor | Acceptor Cultivar | Acceptor Trait | Acceptor Cultivar | Acceptor Trait | Acceptor Cultivar | Acceptor Trait | Seed Batch Code |
|---|---|---|---|---|---|---|---|
| CBG1xS- | PUR01 | 1, 6, 8, 10 | PUR03 | 1, 2, 3, 6, 12 | | | CBG1xS-XPURPLE |
| CBG1xS- | RED02 | 1, 3, 4, 5, 12 | RED01 | 1, 3, 4, 5, 12 | | | CBG1xS-XRED |
| CBG1xS- | YEL03 | 1, 2, 3, 8, 9, 10, 12 | YEL04 | 1, 2, 4, 5 | YEL05 | 1, 2, 4, 5, 8, 9, 10 | CBG1xS-XYELLOW |
| CBG1xS- | ORA02 | 1, 4, 7, 8, 12 | ORA03 | 1, 4, 7, 8, 9, 10 | | | CBG1xS-XORANGE |
| CBG1xS- | BLK03 | 1, 2, 3, 6, 10, 12 | | | | | CBG1xS-XBLACK |
| CBG1xS- | FSC01 | 1, 2, 4, 9, 10 | FSC02 | 1, 2, 4, 9, 10 | | | CBG1xS-XFUSCIA |
| CBG1xS- | GRA01 | 1, 2, 4, 7, 8, 10 | GRA03 | 1, 2, 3, 7, 8, 9, 12 | | | CBG1xS-XGRAY |
| CBG1xS- | BRO01 | 1, 4, 5, 6, 12 | BRO04 | 1, 2, 5, 6, 10, 12 | | | CBG1xS-XBRONZE |
| CBG1xS- | GRE01 | 1, 2, 3, 4, 6, 8, 9, 12 | GRE02 | 1, 2, 3, 7, 8, 9, 10 | GRE30 | 1, 2, 4, 5, 9, 10 | CBG1xS-XGREEN |
| CBG1xS- | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBG1xS-XBLUE |
| CBG1xS- | JAD07 | 1, 2, 4, 5, 8, 9, 10 | JAD21 | 1, 2, 4, 5, 8, 9, 10 | JAD04 | 1, 2, 3, 9, 12 | CBG1xS-XJADE |
| CBG1xS- | CBD04 | 1, 2, 6 | CBD05 | 1, 2, 3, 6, 8, 12 | | | CBG1xS-XCBD (Type 2) |
| CBG1xS- | CBD24 | 1, 2, 3, 6, 8, 12 | CBD04xP-09 | 1, 2, 3, 6, 8, 12 | CBD05xP-01 | 1, 2, 3, 6, 8, 12 | CBG1xS-XCBD (Type 3) |
| CBG1xS- | CBD05 | 1, 2, 3, 6, 8, 12 | | | | | CBG1xS-XCBG1xS- |
| CBG1xS- | CBG1xS- | 1, 2, 4, 5, 8, 9, 11 | | | | | CBG1xSXSELF |

TABLE 57

Additional example crosses to be conducted for CBC lines.

| P Donor | Acceptor Cultivar | Acceptor Trait | Acceptor Cultivar | Acceptor Trait | Acceptor Cultivar | Acceptor Trait | Seed Batch Code |
|---|---|---|---|---|---|---|---|
| CBC1xS- | GOD13 | 1, 2, 3, 12 | GOD02 | 1, 2, 3, 9, 10 | GOD12 | 1, 2, 4, 10 | CBC1xS-XGOLD |
| CBC1xS- | SIL04 | 1, 3, 7, 10, 12 | SIL01 | 1, 3, 12 | SIL08 | 1, 2, 3, 9, 12 | CBC1xS-XSILVER |
| CBC1xS- | WHI02 | 1, 3, 5, 8, 9, 12 | WHI07 | 1, 3, 5, 6, 12 | WHI03 | 1, 3, 5, 6, 12 | CBC1xS-XWHITE |
| CBC1xS- | PUR01 | 1, 6, 8, 10 | PUR03 | 1, 2, 3, 6, 12 | | | CBC1xS-XPURPLE |
| CBC1xS- | RED02 | 1, 3, 4, 5, 12 | RED01 | 1, 3, 4, 5, 12 | | | CBC1xS-XRED |
| CBC1xS- | YEL03 | 1, 2, 3, 8, 9, 10, 12 | YEL04 | 1, 2, 4, 5 | YEL05 | 1, 2, 4, 5, 8, 9, 10 | CBC1xS-XYELLOW |
| CBC1xS- | ORA02 | 1, 4, 7, 8, 12 | ORA03 | 1, 4, 7, 8, 9, 10 | | | CBC1xS-XORANGE |
| CBC1xS- | BLK03 | 1, 2, 3, 6, 10, 12 | | | | | CBC1xS-XBLACK |
| CBC1xS- | FSC01 | 1, 2, 4, 9, 10 | FSC02 | 1, 2, 4, 9, 10 | | | CBC1xS-XFUSCIA |
| CBC1xS- | GRA01 | 1, 2, 4, 7, 8, 10 | GRA03 | 1, 2, 3, 7, 8, 9, 12 | | | CBC1xS-XGRAY |
| CBC1xS- | BRO01 | 1, 4, 5, 6, 12 | BRO04 | 1, 2, 5, 6, 10, 12 | | | CBC1xS-XBRONZE |
| CBC1xS- | GRE01 | 1, 2, 3, 4, 6, 8, 9, 12 | GRE02 | 1, 2, 3, 7, 8, 9, 10 | GRE30 | 1, 2, 4, 5, 9, 10 | CBC1xS-XGREEN |
| CBC1xS- | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBC1xS-XBLUE |
| CBC1xS- | JAD07 | 1, 2, 4, 5, 8, 9, 10 | JAD21 | 1, 2, 4, 5, 8, 9, 10 | JAD04 | 1, 2, 3, 9, 12 | CBC1xS-XJADE |
| CBC1xS- | CBD04 | 1, 2, 6 | CBD05 | 1, 2, 3, 6, 8, 12 | | | CBC1xS-XCBD (Type 2) |
| CBC1xS- | CBD24 | 1, 2, 3, 6, 8, 12 | CBD04xP-09 | 1, 2, 3, 6, 8, 12 | CBD05xP-01 | 1, 2, 3, 6, 8, 12 | CBC1xS-XCBD (Type 3) |
| CBC1xS- | CBD05 | 1, 2, 3, 6, 8, 12 | | | | | CBC1xS-XCBC1xS- |
| CBC1xS- | CBC1xS- | 1, 2, 4, 5, 8, 9, 11 | | | | | CBC1xS-XSELF |

The progeny of each cross described herein will be analyzed as described in Examples 1 and 2. Progeny with desirable cannabinoid and/or terpene profiles as well as desirable morphologies will be used for production of specialty *cannabis*.

Example 20

Development of Additional Terpene Profile Producing Specialty *Cannabis* (Prophetic)

In order to develop specialty *cannabis* with unique cannabinoid and terpene profiles, additional crosses among the parental varieties disclosed in Example 2-4 and the progeny varieties disclosed will be conducted. These prophetic crosses are indicated below with expected breeding charts describing specific crosses and the traits each cross is expected to produce. Traits for each cross are represented by trait codes which are described in Table 51 of Example 16.

Table 58 through 64 are non-limiting lists of prophetic crosses using parental and progeny lines of the present invention to generate new specialty *cannabis* varieties with terpene profiles dominated by selected terpenes. Each of these crosses will also be followed up by one or more back-crosses to further reinforce the transfer of desired traits.

TABLE 58

Additional example crosses to be conducted for ocimene rich terpene profiles.

| P Donor | Acceptor Cultivar | Acceptor Trait | Acceptor Cultivar | Acceptor Trait | Acceptor Cultivar | Acceptor Trait | Seed Lot | Qty (g) |
|---|---|---|---|---|---|---|---|---|
| YEL3xP-23 | YEL03 | 1, 2, 3, 8, 9, 10, 12 | YEL04 | 1, 2, 4, 5 | YEL05 | 1, 2, 4, 5, 8, 9, 10 | YEL3xP-23XYELLOW | |
| YEL3xP-23 | GOD13 | 1, 2, 3, 12 | GOD02 | 1, 2, 3, 9, 10 | GOD12 | 1, 2, 4, 10 | YEL3xP-23XGOLD | |
| YEL3xP-23 | GRE01 | 1, 2, 3, 4, 6, 8, 9, 12 | | | | | YEL3xP-23XPURPLE | |
| YEL3xP-23 | BLK03 | 1, 2, 3, 6, 10, 12 | | | | | YEL3xP-23XBLK | |
| YEL3xP-23 | CBD05 | 1, 2, 3, 6, 8, 12 | CBD04 | 1, 2, 6 | | | YEL3xP-23XCBDType2 | |
| YEL3xP-23 | CBD04xP-09 | 1, 2, 6, 9, 10, 12 | CBD05xP-01 | 1, 2, 3, 8, 9, 10, 12 | | | YEL3xP-23XCBDType3 | |
| YEL3xP-23 | WHI04xP-02 | 1, 2, 4, 9, 10 | | | | | YEL3xP-23XHighLimonene | |
| YEL3xP-23 | YEL3xP-23 | 1, 2, 4, 9, 10 | | | | | YEL3xP-23xSELF | |

TABLE 59

Additional example crosses to be conducted for terpinolene rich terpene profiles.

| P Donor | Acceptor Cultivar | Acceptor Trait | Acceptor Cultivar | Acceptor Trait | Acceptor Cultivar | Acceptor Trait | Seed Lot | Qty (g) |
|---|---|---|---|---|---|---|---|---|
| YEL3xP-26 | YEL03 | 1, 2, 3, 8, 9, 10, 12 | YEL04 | 1, 2, 4, 5 | YEL05 | 1, 2, 4, 5, 8, 9, 10 | YEL3xP-26XYELLOW | |
| YEL3xP-26 | GOD13 | 1, 2, 3, 12 | GOD02 | 1, 2, 3, 9, 10 | GOD12 | 1, 2, 4, 10 | YEL3xP-26XGOLD | |
| YEL3xP-26 | GRE01 | 1, 2, 3, 4, 6, 8, 9, 12 | | | | | YEL3xP-26XPURPLE | |
| YEL3xP-26 | BLK03 | 1, 2, 3, 6, 10, 12 | | | | | YEL3xP-26XBLK | |
| YEL3xP-26 | CBD05 | 1, 2, 3, 6, 8, 12 | CBD04 | 1, 2, 6 | | | YEL3xP-26XCBDType2 | |
| YEL3xP-26 | CBD04xP-09 | 1, 2, 6, 9, 10, 12 | CBD05xP-01 | 1, 2, 3, 8, 9, 10, 12 | | | YEL3xP-26XCBDType3 | |
| YEL3xP-26 | WHI04xP-02 | 1, 2, 4, 9, 10 | | | | | YEL3xP-26XHighLimonene | |
| YEL3xP-26 | YEL3xP-26 | 1, 2, 4, 9, 10 | | | | | YEL3xP-26xSELF | |

TABLE 60

Additional example crosses to be conducted for Caryophyllene rich terpene profiles.

| P Donor | Acceptor Cultivar | Acceptor Trait | Acceptor Cultivar | Acceptor Trait | Acceptor Cultivar | Acceptor Trait | seed Lot | Qty (g) |
|---|---|---|---|---|---|---|---|---|
| SIL08xP-01 | YEL03 | 1, 2, 3, 8, 9, 10, 12 | YEL04 | 1, 2, 4, 5 | YEL05 | 1, 2, 4, 5, 8, 9, 10 | SIL08xP-01XYELLOW | |
| SIL08xP-01 | GOD13 | 1, 2, 3, 12 | GOD02 | 1, 2, 3, 9, 10 | GOD12 | 1, 2, 4, 10 | SIL08xP-01XGOLD | |
| SIL08xP-01 | GRE01 | 1, 2, 3, 4, 6, 8, 9, 12 | | | | | SIL08xP-01XPURPLE | |
| SIL08xP-01 | WHI07 | 1, 3, 5, 6, 12 | | | | | SIL08xP-01XWHITE | |
| SIL08xP-01 | SIL04 | 1, 3, 7, 10, 12 | SIL01 | 1, 3, 12 | SIL08 | 1, 2, 3, 9, 12 | SIL08xP-01XSILVER | |
| SIL08xP-01 | BLK03 | 1, 2, 3, 6, 10, 12 | | | | | SIL08xP-01XBLK | |
| SIL08xP-01 | CBD05 | 1, 2, 3, 6, 8, 12 | CBD04 | 1, 2, 6 | | | SIL08xP-01XCBDType2 | |
| SIL08xP-01 | CBD04xP-09 | 1, 2, 6, 9, 10, 12 | CBD05xP-01 | 1, 2, 3, 8, 9, 10, 12 | | | SIL08xP-01XCBDType3 | |
| SIL08xP-01 | WHI04xP-02 | 1, 2, 4, 9, 10 | | | | | SIL08xP-01XHighLimonene | |
| SIL08xP-01 | SIL08xP-01 | 1, 2, 4, 9, 10 | | | | | SIL08xP-01xSELF | |
| SIL08xP-08 | SIL08xP-08 | 1, 2, 4, 9, 10 | | | | | SIL08xP-08xSELF | |

TABLE 61

Additional example crosses to be conducted for limonene rich terpene profiles.

| P Donor | Acceptor Cultivar | Acceptor Trait | Acceptor Cultivar | Acceptor Trait | Acceptor Cultivar | Acceptor Trait | seed Lot | Qty (g) |
|---|---|---|---|---|---|---|---|---|
| SIL08xP-37 | YEL03 | 1, 2, 3, 8, 9, 10, 12 | YEL04 | 1, 2, 4, 5 | YEL05 | 1, 2, 4, 5, 8, 9, 10 | SIL08xP-37XYELLOW | |
| SIL08xP-37 | GOD13 | 1, 2, 3, 12 | GOD02 | 1, 2, 3, 9, 10 | GOD12 | 1, 2, 4, 10 | SIL08xP-37XGOLD | |
| SIL08xP-37 | GRE01 | 1, 2, 3, 4, 6, 8, 9, 12 | | | | | SIL08xP-37XPURPLE | |
| SIL08xP-37 | WHI07 | 1, 3, 5, 6, 12 | | | | | SIL08xP-37XWHITE | |

TABLE 61-continued

Additional example crosses to be conducted for limonene rich terpene profiles.

| P Donor | Acceptor Cultivar | Trait | Acceptor Cultivar | Trait | Acceptor Cultivar | Trait | seed Lot | Qty (g) |
|---|---|---|---|---|---|---|---|---|
| SIL08xP-37 | SIL04 | 1, 3, 7, 10, 12 | SIL01 | 1, 3, 12 | SIL08 | 1, 2, 3, 9, 12 | SIL08xP-37XSILVER | |
| SIL08xP-37 | BLK03 | 1, 2, 3, 6, 10, 12 | | | | | SIL08xP-37XBLK | |
| SIL08xP-37 | CBD05 | 1, 2, 3, 6, 8, 12 | CBD04 | 1, 2, 6 | | | SIL08xP-37XCBDType2 | |
| SIL08xP-37 | CBD04xP-09 | 1, 2, 6, 9, 10, 12 | CBD05xP-01 | 1, 2, 3, 8, 9, 10, 12 | | | SIL08xP-37XCBDType3 | |
| SIL08xP-37 | WHI04xP-02 | 1, 2, 4, 9, 10 | | | | | SIL08xP-37XHighLimonene | |
| SIL08xP-37 | SIL08xP-37 | 1, 2, 4, 9, 10 | | | | | SIL08xP-37xSELF | |
| WHI07xP-08 | WHI07xP-08 | 1, 2, 4, 9, 10 | | | | | WHI07xP-08xSELF | |

TABLE 62

Additional example crosses to be conducted for humulene rich terpene profiles.

| P Donor | Acceptor Cultivar | Trait | Acceptor Cultivar | Trait | Acceptor Cultivar | Trait | Seed Lot | Qty (g) |
|---|---|---|---|---|---|---|---|---|
| SIL08xP-03 | YEL03 | 1, 2, 3, 8, 9, 10, 12 | YEL04 | 1, 2, 4, 5 | YEL05 | 1, 2, 4, 5, 8, 9, 10 | SIL08xP-03XYELLOW | |
| SIL08xP-03 | GOD13 | 1, 2, 3, 12 | GOD02 | 1, 2, 3, 9, 10 | GOD12 | 1, 2, 4, 10 | SIL08xP-03XGOLD | |
| SIL08xP-03 | GRE01 | 1, 2, 3, 4, 6, 8, 9, 12 | | | | | SIL08xP-03XPURPLE | |
| SIL08xP-03 | WHI07 | 1, 3, 5, 6, 12 | | | | | SIL08xP-03XWHITE | |
| SIL08xP-03 | SIL04 | 1, 3, 7, 10, 12 | SIL01 | 1, 3, 12 | SIL08 | 1, 2, 3, 9, 12 | SIL08xP-03XSILVER | |
| SIL08xP-03 | BLK03 | 1, 2, 3, 6, 10, 12 | | | | | SIL08xP-03XBLK | |
| SIL08xP-03 | CBD05 | 1, 2, 3, 6, 8, 12 | CBD04 | 1, 2, 6 | | | SIL08xP-03XCBDType2 | |
| SIL08xP-03 | CBD04xP-09 | 1, 2, 6, 9, 10, 12 | CBD05xP-01 | 1, 2, 3, 8, 9, 10, 12 | | | SIL08xP-03XCBDType3 | |
| SIL08xP-03 | WHI04xP-02 | 1, 2, 4, 9, 10 | | | | | SIL08xP-03XHighLimonene | |
| SIL08xP-03 | SIL08xP-03 | 1, 2, 4, 9, 10 | | | | | SIL08xP-03xSELF | |
| SIL08xP-27 | SIL08xP-27 | 1, 2, 4, 9, 10 | | | | | SIL08xP-27xSELF | |

TABLE 63

Additional example crosses to be conducted for linalool rich terpene profiles.

| P Donor | Acceptor Cultivar | Trait | Acceptor Cultivar | Trait | Acceptor Cultivar | Trait | Seed Lot | Qty (g) |
|---|---|---|---|---|---|---|---|---|
| WHI04xP-02 | GOD13 | 1, 2, 3, 12 | GOD02 | 1, 2, 3, 9, 10 | GOD12 | 1, 2, 4, 10 | CBD24XGOLD | |
| WHI04xP-02 | SIL04 | 1, 3, 7, 10, 12 | SIL01 | 1, 3, 12 | SIL08 | 1, 2, 3, 9, 12 | CBD24XSILVER | |
| WHI04xP-02 | WHI02 | 1, 3, 5, 8, 9, 12 | WHI07 | 1, 3, 5, 6, 12 | WHI03 | 1, 3, 5, 6, 12 | CBD24XWHITE | |
| WHI04xP-02 | PUR01 | 1, 6, 8, 10 | PUR03 | 1, 2, 3, 6, 12 | | | CBD24XPURPLE | |
| WHI04xP-02 | YEL03 | 1, 2, 3, 8, 9, 10, 12 | YEL04 | 1, 2, 4, 5 | YEL05 | 1, 2, 4, 5, 8, 9, 10 | CBD24XYELLOW | |
| WHI04xP-02 | ORA02 | 1, 4, 7, 8, 12 | ORA03 | 1, 4, 7, 8, 9, 10 | | | CBD24XORANGE | |
| WHI04xP-02 | BLK03 | 1, 2, 3, 6, 10, 12 | | | | | CBD24XBLACK | |
| WHI04xP-02 | FSC01 | 1, 2, 4, 9, 10 | FSC02 | 1, 2, 4, 9, 10 | | | CBD24XFUSCIA | |
| WHI04xP-02 | GRA01 | 1, 2, 4, 7, 8, 10 | GRA03 | 1, 2, 3, 7, 8, 9, 12 | | | CBD24XGRAY | |
| WHI04xP-02 | GRE01 | 1, 2, 3, 4, 6, 8, 9, 12 | GRE02 | 1, 2, 3, 7, 8, 9, 10 | GRE30 | 1, 2, 4, 5, 9, 10 | CBD24XGREEN | |
| WHI04xP-02 | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBD24XBLUE | |
| WHI04xP-02 | JAD07 | 1, 2, 4, 5, 8, 9, 10 | JAD21 | 1, 2, 4, 5, 8, 9, 10 | JAD04 | 1, 2, 3, 9, 12 | CBD24XJADE | |
| WHI04xP-02 | CBD05 | 1, 2, 3, 6, 8, 12 | CBD04 | 1, 2, 6 | | | CBD24XCBD (Type 2) | |
| WHI04xP-02 | WHI04xP-02 | 1, 2, 3, 12 | | | | | CBD24xSIL08xP-02 | |
| WHI04xP-02 | CBD04xP-09 | 1, 2, 6, 9, 10, 12 | CBD05xP-01 | 1, 2, 3, 8, 9, 10, 12 | CBD24 | 1, 2, 6, 9, 10, 12 | CBD24xCBD (Type 3) | |

TABLE 64

Additional example crosses to be conducted for pinene rich terpene profiles.

| P Donor | Acceptor Cultivar | Trait | Acceptor Cultivar | Trait | Acceptor Cultivar | Trait | Seed Batch Code | Qty (g) |
|---|---|---|---|---|---|---|---|---|
| CBD05 | GOD13 | 1, 2, 3, 12 | GOD02 | 1, 2, 3, 9, 10 | GOD12 | 1, 2, 4, 10 | CBD05XGOLD | 52.1 |
| CBD05 | SIL04 | 1, 3, 7, 10, 12 | SIL01 | 1, 3, 12 | SIL08 | 1, 2, 3, 9, 12 | CBD05XSILVER | 102.2 |
| CBD05 | WHI02 | 1, 3, 5, 8, 9, 12 | WH0I7 | 1, 3, 5, 6, 12 | WHI03 | 1, 3, 5, 6, 12 | CBD05XWHITE | 15.1 |

TABLE 64-continued

Additional example crosses to be conducted for pinene rich terpene profiles.

| P Donor | Acceptor Cultivar | Trait | Acceptor Cultivar | Trait | Acceptor Cultivar | Trait | Seed Batch Code | Qty (g) |
|---|---|---|---|---|---|---|---|---|
| CBD05 | PUR01 | 1, 6, 8, 10 | PUR03 | 1, 2, 3, 6, 12 | | | CBD05XPURPLE | 10.4 |
| CBD05 | RED02 | 1, 3, 4, 5, 12 | RED01 | 1, 3, 4, 5, 12 | | | CBD05XRED | 59 |
| CBD05 | YEL03 | 1, 2, 3, 8, 9, 10, 12 | YEL04 | 1, 2, 4, 5 | YEL05 | 1, 2, 4, 5, 8, 9, 10 | CBD05XYELLOW | 130.1 |
| CBD05 | ORA02 | 1, 4, 7, 8, 12 | ORA03 | 1, 4, 7, 8, 9, 10 | | | CBD05XORANGE | 66.6 |
| CBD05 | BLK03 | 1, 2, 3, 6, 10, 12 | | | | | CBD05XBLACK | 12.1 |
| CBD05 | FSC01 | 1, 2, 4, 9, 10 | FSC02 | 1, 2, 4, 9, 10 | | | CBD05XFUSCIA | 88.9 |
| CBD05 | GRA01 | 1, 2, 4, 7, 8, 10 | GRA03 | 1, 2, 3, 7, 8, 9, 12 | | | CBD05XGRAY | 37.2 |
| CBD05 | BRO01 | 1, 4, 5, 6, 12 | BRO04 | 1, 2, 5, 6, 10, 12 | | | CBD05XBRONZE | 6.1 |
| CBD05 | GRE01 | 1, 2, 3, 4, 6, 8, 9, 12 | GRE02 | 1, 2, 3, 7, 8, 9, 10 | GRE30 | 1, 2, 4, 5, 9, 10 | CBD05XGREEN | 56.6 |
| CBD05 | BLU08 | 1, 2, 4, 6, 8, 10 | BLU05 | 1, 2, 3, 4, 6, 9, 12 | BLU06 | 1, 2, 4, 5, 6, 7, 8, 9, 10 | CBD05XBLUE | 190.7 |
| CBD05 | JAD07 | 1, 2, 4, 5, 8, 9, 10 | JA21 | 1, 2, 4, 5, 8, 9, 10 | JAD04 | 1, 2, 3, 9, 12 | CBD05XJADE | 87.8 |
| CBD05 | CBD02 | 1, 2, 4, 5, 7, 8, 9, 12 | | | | | CBD05XCBD02 | 5.4 |
| CBD05 | CBD03 | 2, 4, 9, 10 | | | | | CBD05XCBD03 | 2.2 |
| CBD05 | CBD04 | 1, 2, 6 | | | | | CBD05XCBD04 | 2.1 |
| CBD05 | CBD05 | 1, 2, 3, 6, 8, 12 | | | | | CBD05XSELF | 10.1 |

The progeny of each cross described herein will be analyzed as described in Examples 1 and 2. Progeny with desirable cannabinoid and/or terpene profiles as well as desirable morphologies will be used for production of specialty *cannabis*.

Example 21

Tracking of *Cannabis* Plants During Production, Processing and Use

Specialty *cannabis* must be easily distinguished from each other as well as from traditional recreational *cannabis* and hemp, allowing it to be tracked from seed to plant to processing to sale ("seed to sale" tracking). This can be accomplished by tagging the seeds or cutting, harvested material, and marketed product in a variety of different ways. According to the present invention it is possible to provide instantaneously the use of forensic-style audit capabilities to indoor horticulture. For example, the compositions and methods of the present invention can be used to track specialty *cannabis* plants, plant parts, ground plant material, compressed plant material, extracts, etc. Thus, according to the present invention, one can track the chemotype for an individual plant or group of plants from seed to flower and beyond.

First, the seeds and plants may be implanted with a tracking device, such as via radio-frequency identification (RFID) using an RFID tag or chip, a telemetric thread, a microchip, or a magnetic tag, which will allow real-time identification of the seed, plant, harvest, or final product.

In one non-limiting example, the seeds and plants are implanted with a very small active MD tag or chip which will emit a unique address fir each seed and/or plant to a reader. RFID is a wireless data collection technology that uses electronic tags for storing substantial amounts of data that can be used for tracking individual items. There are two basic types of REID tags: passive and active. "Passive" tags have no power source but use the electromagnetic waves from a reader (e.g., the receiver) up to approximately 15 feet away to transmit back their contents. "Active" tags use a battery to transmit up to about 1,500 feet. The REID tags are read when they are within the proximity of two-way radio transmitter-receivers, or readers, which send a signal to the tag and read its response. The handheld devices can easily be used to track the REID tags integrated into the *cannabis* seeds, plants, and/or product.

Alternatively, the specialty *cannabis* plants can be tagged by recombinantly engineering them to express a phenotypic trait unique to the strain. For example, a strain can be stably transformed to express bio-markers, generally proteins, that directly, or on contact with suitable substrates, yield a characteristic color, optical density, light emission, or fluorescence. Fluorescent bio-markers can include green fluorescent protein, red fluorescent protein, yellow fluorescent protein, blue fluorescent protein, or variants thereof that, when expressed, will emit a color under a particular wavelength. Other examples of color tagging include the bioengineering of *cannabis* with enzymes for the production of anthocyanins or other colored biosynthetic non-active colored chemicals. Detection devices for fluorescent bio-markers can have one or more excitation light sources for emitting light of a wavelength or a range of wavelengths suitable for inducing the fluorescence, in a non-limiting example, an expression cassette comprising green fluorescent protein is stably transformed into the plant cells using standard laboratory techniques. This protein will be expressed by the seed and/or plant, and when excited by a particular wavelength produced by a simple device, such as a hand-held light, can be easily identified by the red color.

Example 22

Horticultural Practice (Consistency)

All *cannabis* germplasm and cuttings of *cannabis* germplasm are established in identical environmental conditions (~80'C, 80% Humidity, CO2 variable, 3000 k lighting). Once roots are established, plants are transplanted into 1 gallon pots using a proprietary soil mix #1 heavily laded with beneficial microbes, nematodes and predator mites. Our soil system is crucial to establish consistent growth patterns and secondary metabolite production.

Plants are grown under 18 hours of light with 50% Metal Halide & 50% High Pressure Sodium Light bulbs generating the spectrum. The environmental conditions, distance from light, pots and soil are all proprietary.

Once roots are bound, or plants are approximately 12"-18", they are transplanted into 3 gallon pots with proprietary soil mix #2. Again, microbial content of soil and beneficials are a crucial contributor to the consistent production of specialty *cannabis*.

Plants are induced into flowering by undergoing a period of 72 hours of darkness which is followed by the light cycle of 12 hours of light and 12 hours of dark (20% Metal Halide and 80% High Pressure Sodium). Plants are trimmed, pruned and topped similar to fruit tree industry (i.e., a healthy number of budding sites distributed evenly throughout the canopy). The specific techniques employed are cultivar specific.

Environmental conditions, pots, distance from light, trellising techniques, carbon dioxide concentration and nutrient regimen are all proprietary.

Flowering period can last between fifty and ninety days. While plants can exceed 5' in height, canopies are 'shaped' in row crop tradition and kept at 18"-24".

Plants are culled if they are showing expressing stress genes and/or if they are showing any signs of variations. Ripeness is specifically determined by genetics.

Example 23

Feedback-Based Cultivation System

Some embodiments of the present invention are directed to systems, apparatuses, and methods for feedback-based cultivation of the herbal specialty *cannabis* described herein.

Figure 10:
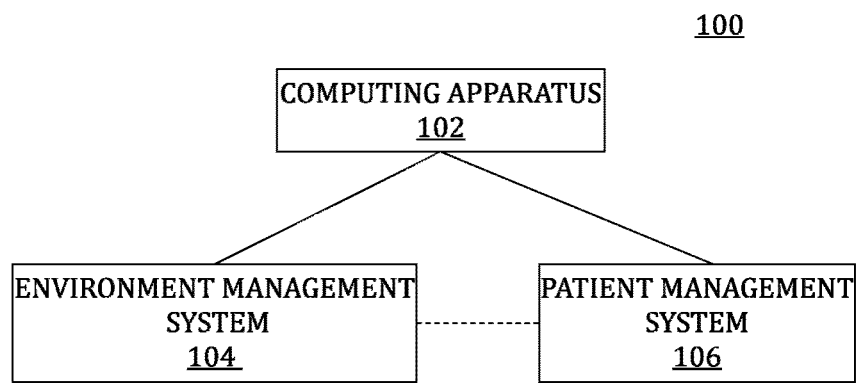
FIG. 10—Diagram outlining major sections of feedback cultivation system. A computing apparatus integrates data from patient management system and plant growth environment management system to produce specialty *cannabis* tailored for various medicinal or recreational purposes.

FIG. 10 illustrates a system 100 for feedback-based cultivation of the herbal specialty *cannabis* described herein, according to some embodiments. The system 100 includes at least a computing apparatus 102, an environment management system 104, and a patient management system 106. The various components of the system 100 can be in communication as indicated by lines in FIG. 10 via a network (wherein a dotted line indicates an optional connection), which may be any type of network (e.g., a local area network or LAN, a wide area network or WAN, a virtual network, a telecommunications network, the internet and/or the like) implemented as a wired network and/or a wireless network. Any or all communications may be secured (e.g., encrypted) or unsecured, as is known in the art.

The environment management system 104 can be configured for production of the specialty *cannabis* plants disclosed herein. In some embodiments, the environment management system 104 can be configured for managing a controlled environment for production of the herbal specialty *cannabis* disclosed herein. The controlled environment can include one or more software and/or hardware components monitored and/or controlled by the environment management system 104 including, but not limited to, one or more sensors, one or more controllers, one or more fertigation systems, and/or the like. For example, in some embodiments, the environment management system 104 can include controlled environment grow rooms, sensors, fertigation devices, and further computer networks and interfaces for monitoring/control of these aspects. In this manner, the disclosed embodiments are configurable to implement a smart grow room, where sensor technology and artificial intelligence-based software combine to assist cultivators to monitor the dozens of parameters that must be optimized to grow the highest quality and healthiest plants producing consistent levels of secondary metabolites (as will be described in more detail later). In some embodiments, the sensors can include soil sensors for taking soil measurements such as, but not limited to, soil moisture, electrical conductivity (EC), available soil moisture, potential gravity, temperature, and/or the like.

In some embodiments, where grow rooms are employed, multiple sensors per room can be employed. For example, the total density or number of sensors in each 'cell' (or room with five 4'×16' rows, ~150 plants, 15 plants per 4'×8' table) can vary from 2-4 per room. The number of sensors in a room can be dictated by the density of plants in each table. Two sensors are needed for each density, whether it is 15 or 21 plants per table, one on a boundary plant and one on a middle plant. Additional pairs of sensors can be added for a specific cultivar if it is known to have substantially different water usage than surrounding plants in the cell.

In some embodiments, the sensors can include sensors for air particulate/contamination measurements. In some embodiments, the sensor(s) includes a Thermo Scientific TEOM 1405 continuous particulate monitor. In some embodiments, the air sensor(s) can include environmental controllers having sensors associated therewith, such as the Sentinel CHHC-4 that measures, in real time, temperature, relative humidity, and carbon dioxide content. In such embodiments, the controller can also be employed for environmental control. For example, the CHHC-4's ability to hold a set point within a certain range of accuracy can be exploited.

In some embodiments, water and/or fertigation parameters can be measured by a variety of sensors, including pH, EC, flow rate, TDS, NPK, ppm of certain compounds, and/or others if desired. Some of these parameters can be determined via direct measurements, while other, such as ppm of some compounds, can be determined via dilution calculations. In some embodiments, water and/or fertigation parameters can be controlled using systems such as, but not limited to, the Hanna Instruments computerized fertigation system (Model HI 10000) that allows for mixing of four nutrient zones and one acid/buffer zone for pH control, and uses reliable and accurate Dosatron D8R venturi style injectors. The HI 10000 can also be hooked to a reservoir style system or in-line flow mixing, where the preferred method is likely reservoir for compost teas and inline for fertigation.

In some embodiments, the environment management system 104 can be configured to track active ingredients from their concentrations on the plant in the field, through production and processing. In some embodiments, the environment management system 104 can be configured to measure the production of key secondary metabolites and/or monitor their flux in concentration over time to better understand and control the mechanisms underlying their biosynthesis. In this manner, aspects of the environment management system 104 overcome challenges associated with the production of herbal specialty *cannabis* that have multiple active ingredients, where consistent production of these active ingredients typically varies from crop to crop. Additional benefits are realized when a highly monitored controlled cultivation environment can be utilized in conjunction with timely chemical fertilizers that trigger the plants to produce these metabolites at the desired concentration. As a result, harvesting at the optimal time can guarantee consistent *cannabis*. In some embodiments, the environment management system 104 can be further configured to optimize for individual metabolites of interest with troubleshooting mechanisms to identify issues before they impact a plant's primary or secondary metabolite production.

Figure 11:
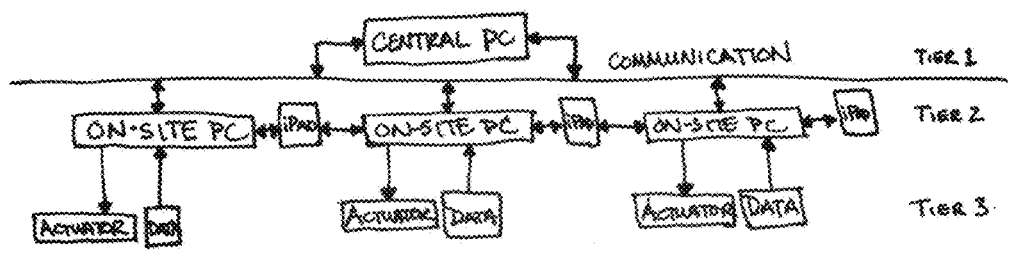
FIG. 11—Diagram outlining environmental management system describing data collection and environmental control.

In some embodiments, the environment management system 104 can be structured in a multi tier manner and particularly in a three tier manner, with the primary order being a central control center/database, second order being an on-site pc interface station, and third order being an individual station such as a tablet interface. The data processing and analysis can be carried out by the more powerful control center computers, which can be equipped with the latest microcomputer needed for bidirectional data transmission, allowing them to communicate with the on-site PC stations and/or to the individual stations. The bidirectional data transmission between different facets of the network, such as the individual stations and on-site PCs, can be accomplished in the manner outlined in FIG. 11, which illustrates an exemplary and non-limiting embodiment of the environment management system 104:

As illustrated in FIG. 11, environmental sensors ("actuator") sense environmental parameters and take in raw data ("data") from their respective system and location therein. This data is then location and time stamped and sent to the on-site PC station ("on-site PC").

The raw sensor data can then be received at the on-site PC. Decision making data analysis may be done on the on-site PC, and/or at the central control center ("central PC"), and/or other network computers as well. The data received at the central PC is sent to the control center, and changes to the data can be made by the on-site PC in conjunction with the applicable system hardware.

Figure 12:
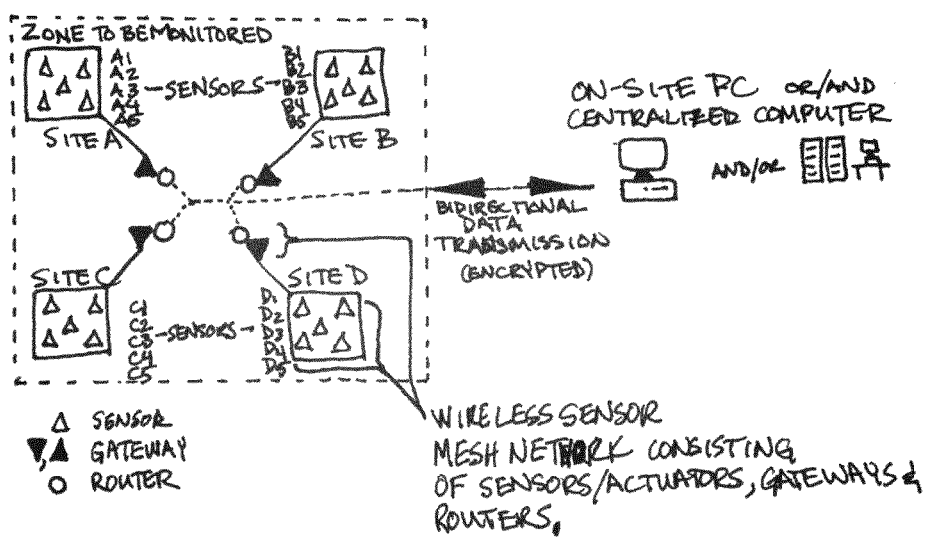
FIG. 12—Diagram outlining wireless data system integrating environmental data cues from sensors at multiple growth sites. Actuators allow for computer responses to adjust environmental conditions.

In some embodiments, a wireless system of sensor-to-PC communication can be used. In some embodiments, as best illustrated in FIG. 12, a wireless mesh network of sensors can be employed that feedback to a centralized pc system.

The wireless system can contain at least three main components; intelligent sensors/actuators, wireless mesh network of routers and gateways with intelligent routing algorithms, and control and actuation.

In some embodiments, functionality and/or data associated with the environment management system 104 can include, but is not limited to, one or more of the following: number of plants put into veg (date, variety); assign lot and plant number; track development—ability to ascertain Inventory of plants at any given time; assign date of flowering (date flowering initiated, variety, lot #, plant #, location); track feeding schedule during flowering (date, six nutrient fields); track environmental conditions (linked to various sensors in the room: soil moisture, temperature, humidity, CO2 level, and Light intensity); cultivator notes field (Date, Note field for cultivator to make notes on specified date, e.g., 'lights were mistakenly left on form 0200 until 2300'); cannabinoid/terpenoid testing log (results, testing date, point in flowering); harvest (date, B&T weight); processing (trim date, weights); bulk packaging; transit; acquisition from MPC—lot #, variety, production reimbursement, total weight, form; receipt (entity, name, date); safety screening results (pass/fail)—molds, pesticides, aflatoxins, microbial; weighing; assembly (units); allocation information (amount, avg. allocation, reimbursement); and popularity indices (rank, velocity, potency/reimbursement—via cross-references with "Patient" data). Table 65 illustrates exemplary and non-limiting embodiments of the cultivation-related information that can be collected.

Referring again to FIG. 10, the patient management system 106 can be configured to acquire patient data in any suitable manner. In some embodiments, the patient management system 106 can be configured to record patient data within the context of a method as illustrated in FIG. 2.

FIG. 2 used in Example 9 illustrates exemplary and non-limiting embodiments of the patient-related information that can be collected, including prescribing physician information.

In some embodiments, functionality and/or data associated with the patient management system 106 can include, but is not limited to, one or more of the following: standardized and compliance messaging to visitors (clients, elected officials, healthcare providers and media) by using recorded images/messages transmitted electronically via tablet (this can include all agreements and consents); collect biographical, contact, health history, and prior non-cannabis treatments electronically (currently collected on handwritten forms); set up patient record automatically; immediately upon completion of registration process, prior to first transaction; assign patient ID automatically and associate that ID with all future activities related to the patient; swipe driver's license upon subsequent visits—swipe can bring up patient's record and enable dispensary staffer to immediately see "attached" scans of physician recommendation, photo ID as well as recommendation expiration date; recommendation date can be color coded to quickly draw attention if out-of-date or if within X days of being out of date so that dispensary staffer can inform patient on the spot that either the recommendation is no longer valid or that it will be invalid in X days/weeks/months and that s/he should take steps to renew it; information regarding allocations to specific patient can be captured (date, variety, amount, $, lot) and accessible by staff by doing a patient "name" query; feedback regarding prior allocations can be captured (noted effects) and ratings of medicines; follow up, correspondence to physicians can be prepared automatically by pulling data from allocation database fields; the ability to query database by age, gender, strain, lot #, feedback (feedback itself and/or condition), etc, and cross reference with production fields below; and the ability to predict/recommend medicine based upon prior ratings/preferences cross-referenced with strain chemistries.

System access can be a concern in such multiuser environments. Accordingly, embodiments directed to system access will be described with respect to the system 100, and unless explicitly stated otherwise, are understood to be directed to aspects of operation of the environment management system 104 (also referred to as the production side), and/or the patient management system 106 (also referred to as the patient side), and/or the computing apparatus 102. In some embodiments, system access (production side and patient side) can include four components of hierarchy; master administrator, regional manager, on-site manager, and cultivator (production side)/counselor (patient side). Communication structure can be cloned from one tier to the next, e.g. from cultivators to master administrators. In some embodiments, the communication structure can include alerts, decision tree confirmations, and/or other clearance restrictions—most restrictive at the cultivator level and least at the master control level. This 'overlapping' of communication in each sector can bring continuity between the chain of command so that major decisions are always cleared on multiple levels. Integrating with the on-site PC and individual PC can condition operation patients to use open communication that they know is backed by system-checked accountability.

The on-site PCs and the individual PCs can have a private communication system therebetween, such as encrypted IM and/or some form of closed/private network. In some embodiments, emails are encrypted for patients that can send notifications to users' email of choice when a new email arrives in their encrypted box.

PC Computer Terminal Interface
Master Administrator Platform:

In some embodiments, the master administrator platform (e.g. the central PC) can be characterized in the following exemplary and non-limiting manner: access to all real-time databases, archived data sets/analysis results, patient information, cameras, etc. No access restrictions, access can be heavily encrypted and access codes can be very limited in number, only to key company patients for example. Access to certain aspects of the master platform can be partitioned off for limited access to other manager(s) if needed. For example, lab managers can have access to analysis data, certain production managers have access to some production data, etc.

Regional Manager Platform

In some embodiments, the regional manager platform allows for control over a number of sites, and over selected parameters that can be delegated by the master administrator platform. For example, the person responsible for formulating fertigation solutions in the lab can have regional access over the fertigation/soil water parameters, but not full 'master' access to all sites. This access can be restricted further to be allowed from on-site network computers.

Site Manager Platform

In some embodiments, the site manager platform (e.g. the on-site PC) provides an access point for data compilation/entry, Excel, Word, system specific software, and/or the like. System access/control will encompass control over master 'filtered' parameters such as fertigation time series/allocation and/or the like. Any independent changes made by the site manager either via their individual PC interface would be sent back to the necessary upper management in the form of an email, 1M, and/or other chosen alert method. In some embodiments, a two method minimum, and preferably three alert methods are preferred for adequate redundancy and accountability.

In some embodiments, no cultivator/counselor access is permitted to on-site PCs or otherwise, and cultivator interaction can take place through the individual PC only. Counselor access will take place through a separate individual PC intended to provide product information to inform counselors and, through the counselors, consumers.

Individual PC Platform

The individual PC will serve different needs for different levels of management and operators, but the main purpose can be for use as a company specific interface and communication tool. At all levels users can populate, manage, and track their tasks, as well as enter data and notes. In some embodiments, all users can also send and receive messages to other users within their realm. At higher levels, users can track data trends, view real time data, and analyze various data components in different graph formats and analysis methods of their choosing. This analysis will tap data on the master database for all sites, allowing regional manager and master administrators to track multiple site data from one device.

The level of interaction at each level can happen via applications in some embodiments, some shared by all users and others only for those with special permissions. A majority of these applications can be specific need-based adaptations of preexisting native apps (i.e.: notepad) or proprietary apps.

Master Access platform: Data input for all areas of production and/or patient side. In some embodiments, the master access platform allows viewing of each site(s) critical data 'at a glance'. The 'at-a-glance' data can be changed in both content and form. For example, one patient may want to compile yield data for all sites that are displayed in a monthly time series linear graphs over a prior year, with a year-to-date production trend graph for comparison (underlined portions represent changeable variables in the at-a-glance screen). Any analysis done by algorithms could also be accessible at the individual PC level, but not necessarily as in depth as is available at the on-site PC level. In some embodiments, the master access platform includes the ability to make changes/overrides that update to selected individual PCs (i.e. a master access change to nighttime temperature schedule for a certain cell would send notifications of the change, if desired, and create a permanent change). In some embodiments, the master access parameter set points, and other system parameter elements that are outside of the regional manager/site manger security clearance will require an encrypted password to change. If needed, this would allow master administrators to grant lower management access to certain elements on per case basis.

In some embodiments, the master access platform includes the ability to access patient records, surveys, survey group data, blood sample data, and all other aspects of the patient side of the system. At-a-glace home screen for patient data will have the ability to show output of algorithmic data mining. A patient system example would be when a patient's makes their first visit and submits their information into the patient database, that information is cross-referenced with an array of other patient 'data points' (such as ailment, age, gender, survey responses, chemovar preference, etc.). Based on the results of one or a few simple data mining algorithms, tailored recommendations can be made and generated on the counselor's individual PC in real time (e.g. a recommendation engine can be implemented).

In some embodiments, the master administrator platform can include the ability to set the recommendation parameters for the algorithm's decision process, but whatever chemovar recommendation parameters are chosen, in some embodiments, they can remain constant for all new patients. In this manner, a consistent reliable database can be built over time, which will increase the 'accuracy' of the system. This ability for the system to 'learn' using AI (artificial intelligence) software programming, likely with evolutionary algorithms, will require a certain amount of time of patient response data to be entered before the programs(s) can discern which decision pattern yields the favorable result a statistically significant amount of times. The eventual result of this system component at the patient/counselor interaction level can be an accountable and consistent decision tree process that is tied in to all levels of management, removing counselor recommendation variance from one to the other and possible misinformation. Although this example pertains to chemovar recommendation, it is understood that it can also be applied to other patient/counselor interactions such as patient/POA (point of allocation) and others.

Regional Manager Platform: The individual PC regional manager platform can allow RMs to have at-a-glance data viewing/comparison capabilities similar in function to that of the master administrator, but restricted in content to that which is job/project related or delegated otherwise. Data input/analysis and system monitoring can be the main use of the individual PC for RMs. Selective control over certain 'master delegated' system parameters could be altered by RMs via the individual PCs similar to the way it would be on the on-site PC, but via a comparatively 'deconstructed/refined' tablet interface.

Site Manager Platform: Can allow for site overview and management of multiple cultivators or cultivation teams.

Cultivator/Counselor platform: Can allows for cultivator notes to be entered into the system, and the system can digitally 'tag' the notes with date, time, batch number, plant number, etc. in the system to be referenced at a later point if needed. Cultivators will need to have fields in the notation application that will be filled out with the appropriate information to create a track record for the entry tag.

Having described system access, referring again to FIG. 10, embodiments directed to software tools will be described with respect to the system 100, and unless explicitly stated otherwise, are understood to be directed to aspects of operation of the environment management system 104 (also referred to as the production side), and/or the patient management system 106 (also referred to as the patient side), and/or the computing apparatus 102.

Decision Tree Analysis Help Tool—Designed with the cultivator/counselor in mind, this application can serve both as a communication pathway between managers and cultivators/counselors as well as a help tool for them as well. A troubleshooting function is in the form of a series of searchable common issues that arise either in daily procedure or possibly on rare occasions. If such an issue arises that someone doesn't know the correct flow of action for a particular task, they can reference this application to see a decision tree/flow chart on how it should be done according to management.

This application can become a communication tool when the managers, whether transitory regional or permanent on-site, choose to upload decision trees into the system. For example, if a regional manager comes through and makes changes to operating procedure or wants to reiterate procedure, they can quickly create a simple decision tree chart (possibly pre-formatted entry fields) while on-site and upload that system onto the network. Once uploaded, it is available for others to view when needed, and managers could even make it into a checklist format in which operators must check off steps in the process until proficient.

Data Entry Portal—The data entry portal can be the data entry application for the individual PC that will have different 'forms' for different operator positions. For example, patient-based entry fields (i.e.: POA data, patient feedback data, etc.) for counselors and plant-based entry fields (i.e.: plant number, lot number, package number, etc.) for cultivators.

Data Analysis Tool—The data analysis tool can allow managers and technicians the ability to alter their at-a-glance home screens and run other analysis on their data in the field. The range of this analysis can be limited in comparison to the pc interface. The results of such an informatics system can be directed and displayed in many ways, to be chosen by the user.

Genetics—Terpene Profiles—System is designed to analyze, characterize and codify the subtleties in terpene differences across a large number of separate genetic groups (as per the color coded system), different populations within those groups, and time series analysis tracking where applicable (i.e.: terpene ratio and/or quantity variation during final weeks of flower development). Individuals will be grouped into different color groups based initially on some qualitative characteristics such as 'nose' (piney, fruity, etc.), and later quantitatively. Quantitative analysis will allow for each individual to be profiled into the database.

Chemotype Profiles—These can have the same framework as the terpene program, but can include cannabinoids and other secondary metabolites of interest.

Bioinformatics—The use of evolutionary algorithms to run computer models of mass breeding programs that can allow for increased efficiency in parent material selection as well as accurately estimating required population sizes for field trials.

Algorithms for Data, Systems and decision Making—Numerous algorithms can be used at any point either singularly, simultaneously or in conjunction to produce new data, maintain system functionality and/or optimization, compilation and execution of fuzzy control programs, analyzing and/or processing data, making system updates and 'intelligent' decision/changes, and monitoring system components/sensors to name a few. Some of the algorithms used to address dynamic data sets and problems can include, but are not limited to; least squares algorithms, direct and/or indirect control evolutionary algorithms, pattern recognition algorithms, data fusion and/or data clustering algorithms.

Referring to FIG. 10 again, the computing apparatus 102 (also referred to as the "central computer", the "central PC", etc. See FIGS. 11, 12) can handle the acquisition, processing, and analysis of data from different components of the system 100, including the environment management system 104 and the patient management system 106. In some embodiments, the computing apparatus 102 can be configured to track both crop and patient trials of chemotypes of potential interest. For example, the computing apparatus 102 can be configured to track the production of metabolites of interest in a crop, while also being configured to track the metabolism of those eventual plant-produced metabolites as they are metabolized by consumers. Thus, active ingredients can be tracked from their concentrations on the plant in the field, through production and processing, to the eventual concentrations as metabolites in the blood of patients, post consumption. In this manner, aspects of operation of the computing apparatus 102 can define the complete chemical relationship between plant and human. In some embodiments, this defined chemical relationship can be used to create maps, multi-dimensional scatter plot to examine and/or analyze patterns within a host of metabolic variables throughout the incredibly complex system.

In some embodiments, once data is received at the computing apparatus 102 any number of actions can be taken, based on a user's needs and based on a user's associated system access parameters as discussed above (i.e. a user of the computing apparatus 102, of the environment management system 104, and/or of the patient management system 106). In some embodiments, the computing apparatus 102 can be configured to implement one or more algorithms to analyze various types and forms of information including, but not limited to; genetic data, breeding data, tissue culture data, field trial data, all computer system-related data, greenhouse data, indoor grow data, environmental sensor-sourced data, environmental data from other sources, all patient-related/sourced data, allocation/reimbursement data, and all other types/forms of proprietary sourced data.

The resulting information can then be transmitted back to the user that requested it in the form of their choosing via bidirectional data transmission. This transmission, either wireless or wired in signal, can be routed through the network (not shown), and/or can be encrypted. The user can then choose to make changes or updates to the controllable/accessible aspects of the system 100, if applicable. For any alterations to system parameters or any other significant system aspect, a feedback system can exist for alerts, timestamps, updates to current/future computational processes, referenced data sets, and other signals.

In this manner, patient feedback data can fuel the production of specialty *cannabis*. For example, the patient feedback data can be used to optimize pharmacologically active plant oil content through a host of breeding and cultivation techniques. In some embodiments, the computing apparatus 104 can be configured to monitor market trends and identifies products' appeal, efficacy, and sell-through as the products' chemotype evolves over time refined by consumer feedback and research studies. In some embodiments, the feedstock that is used to create these products can be selected in response to real-time feedback collected by this system from consumers. The coupling of chemotype development and selection with consumer feedback can enable the identification of market trends of selected chemotypes at the earliest possible stage in product deployment. For example, principal component analysis can be used to identify synergies between groups of pharmacologically active constituents that are gaining traction with consumers for their medicinal effectiveness, their aesthetic appeal or combination of both.

TABLE 65

Exemplary growth data for storage in growth system.

| Exemplary Lot Table(s) | Exemplary Collective Table |
|---|---|
| lot identifier (relates to Collective Table and Patient Table) | collective lot arrival date/time |
| lot location identifier | collective lot identifier (relates to Lot Table) |
| lot plant identifier (relates to Plant Table) | collective break lot up into units date |
| lot date began veg | collective units inventory |
| lot date began flowering | patient unit allocation date |
| lot feeding date(s) | patient unit allocation identifier |
| lot feeding date(s) nutrients (six fields) | patient unit allocation reimbursement |
| lot environmental condition(s) (dates) (soil moisture, temperature, humidity, CO2, light intensity) | Seed to Plasma Constituent Analysis |
| lot cultivator notes | |
| lot cannabinoid/terpenoid testing (results, testing date, point in flowering) | |
| lot safety screening results (pass/fail) | |
| lot harvest date | |
| lot harvest date weight | |
| lot trim date | |
| lot trim date weight | |
| lot bulk packaging date | |
| lot bulk packaging date weight | |
| lot transit departure date/time | |

Example 24

Multiplexed *Cannabis* Mixtures

Some embodiments of the present invention are directed to the production of multiplexed *cannabis* mixtures (MCM). In some embodiments the MCM comprises at least one *cannabis* plant base and one or more stock fortifier(s) to create custom medical *cannabis* mixtures for the treatment of a particular disease or disorder. In some embodiments, said *cannabis* base comprises one of the *cannabis* varieties of the present invention or any other *cannabis* variety known in the art. In some embodiments, the variety chosen as the *cannabis* base is selected for its cannabinoid profile. In other embodiments, the *cannabis* base is selected for its terpene profile creating a desirable aroma/organoleptic feel or desired entourage effect.

In addition to the *cannabis* base, the MCM includes one or more stock fortifiers. In some embodiments the stock fortifiers enhance the MCM by supplementing the *cannabis* base with THC, CBD, CBG or other cannabinoids (for example the addition of CBD fortifiers to supplement a high THC *cannabis* base). In some embodiments, the stock fortifiers enhance the MCM by supplementing the *cannabis* base with terpenes such as limonene, pinene, myrcene, linalool, beta-caryophyllene, phytol, terpinolene, terpene, ocimene, caryophyllene oxide, alpha-humulene, or combinations thereof.

In one embodiment, the fortifying stock comprises plant material that can be blended into the *cannabis* base. Cannabinoid fortifying stocks can include one or more of the *cannabis* varieties of the present invention or any other *cannabis* known in the art. In some embodiments, the variety chosen as the *cannabis* stock fortifier is selected based on its cannabinoid profile. In other embodiments, the *cannabis* fortifier is selected based on its flavor profile. In some embodiments the *cannabis* fortifier is selected based on its ability to reduce side effects due to THC.

In one embodiment, the fortifying stock comprises herbs such as basil, oregano, rosemary, sage, or other herbs with desired terpene profiles. In one embodiment, the fortifying stock is selected based on its flavor profile (for example, to provide the patient with a mixture tailored to their flavor, aroma, and organoleptic preferences for their medicinal or recreational use). In other embodiments, the fortifying stock is selected based on its ability to treat a disease (for example the addition of pinene-containing rosemary for its anti-inflammatory properties). In other embodiments, the fortifying stock is selected based on its entourage effects with *cannabis* (*British Journal of Pharmacology* 163.7 (2011): 1344-1364).

In some embodiments, the *cannabis* stock fortifiers are in the form of extracts such as *cannabis* sludges or essential oils (EO). Any means commonly used in the art to isolate particular *cannabis* agents may be used may be used to prepare the fortifier stocks. For example, stock cannabinoid fortifiers with high THC (I), CBD (II), and/or CBG (IV) contents, can be produced by removing the extract from phenotype I, II, or IV plants that are high in THC, CBD, and/or CBG. The terpenes are distilled from the extract by supercritical extraction to provide a crude sludge, which is then winterized to remove waxes.

To prepare the high terpene EO fortifiers, plants are produced that have the desired concentrations of terpenes: these include, but are not limited to, terpinolene, alpha phelladrene, beta ocimene, carene, limonene, gamma terpinene, alpha pinene, alpha terpinene, beta pinene, fenchol, camphene, alpha terpineol, alpha humulene, beta caryophyllene, linalool, cary oxide, myrcene, and/or phytol. The high terpene extract is removed from the plants, and is then steam distilled to provide stock terpene fortifiers with high limonene, pinene, myrcene, Linalool, caryophyllene, and/or phytol. Since these compounds may extract together it might be necessary to fractionally distill the crude to further enrich for the desired compound.

For small scale extraction of terpenes, a 500 mL round bottom flask is charged with 50-100 g of ground *cannabis* flowers or other terpene producing plant and approximately 300 mL of water. The flask is fitted with a claisen adapter, a distillation head, a water cooled condenser, a 250 mL receiver, a thermometer, and a separatory funnel. Heat is applied until a constant rate of distillation (one drop every 2-5 seconds) is achieved. As the water in the flask is depleted more is added via the separatory funnel. Continue this process until approximately 150 mL of cloudy condensate is obtained. The condensate is transferred to a separatory funnel and extracted twice with 30 mL of diethyl ether. The ether extracts are dried over sodium sulfate and evaporated with very gentle warming on a rotovap or under a gentle flow of nitrogen. The condensate is stored in the dark at −20 C. The neat steam distillate is misted onto the MCM to fortify the terpene content.

In some embodiments the *cannabis* base to which the high cannabinoid or terpene fortified stock is added is prepared from any and all of the various strains described herein, or others known in the art, by supercritical extraction. This provides the foundation cannabinoid ratio which retains the subjective qualities of the strain since all the cannabinoids, terpenes, and waxes are still present.

Although *cannabis* can be used to treat several symptoms, it is not a one size fits all cure. Diseases may treated more effectively if the *cannabis* medicines used to treat the symptoms are tailored to each disease with specific cannabinoid and terpene compositions. It has been suggested for example that various THC: CBD ratios would be most effective at treating a variety of diseases (Table 68, and U.S. patent application Ser. No. 11/628,814). In addition, the present invention has discovered the effect of several terpenes on volunteer mood, anxiety, emotional comfort, etc (Examples 9, 10, 11, and 14). In some embodiments, the tailored medicine is provided through breeding of specialty *cannabis* of the present invention. In other embodiments, the specialty *cannabis* of the present invention are used in MCMs to further enhance the cannabinoid and terpene profiles. In some embodiments, the MCMs are produced using other known *cannabis* varieties. In some embodiments, the MCMs are tailored to a desired medicinal or recreational effect.

Figure 13:
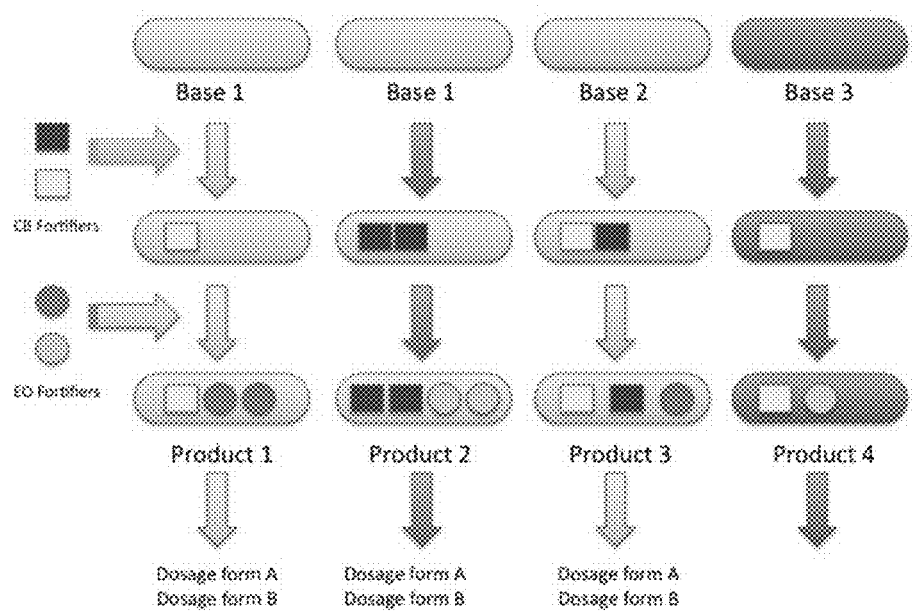
FIG. 13—Example diagram of multiplexed *cannabis* mixtures in which base *cannabis* flower material is enhanced with cannabinoid and/or terpene fortifiers to create custom *cannabis* blends for medicinal or recreational uses.

The concentrations of the various active agents present in the multiplexed *cannabis* medicine will vary depending on what has been determined to be the optimal dosing for any particular disease or disorder being treated. Depending on the condition being treated and the subjective qualities desired (such as aroma, flavor and organoleptic feel), the base is then fortified with high cannabinoid and/or terpene stock to give the final preparation according to the following flowchart in FIG. 13. A non-exhaustive list of examples of MCMs to treat various diseases are outlined in Table 66. In some embodiments, MCM's are a macroscopic method of dosage control through the manipulation of ratios of agonist-antagonist blends that exploit the relationship of each cannabinoid to the cannabinoid receptors of the human body. In some embodiments the MCMs further tailor the effects of the *cannabis* blends through the use of each terpene's unique individual, and entourage effects.

TABLE 66

Example Multiplexed Cannabis Mixtures.

| DISEASE | CB BASE | CB FORTIFIER | TERPENE FORTIFIER |
|---|---|---|---|
| Brachial Plexus Avulsion | THC variety | CBDV variety | myrcene and eucalyptol |
| Arthritis | THC variety | CBD variety | linalool |
| Motion Sickness | THC variety | CBD variety | limonene |
| Seizures | THCV variety | CBDV variety | pinene |
| Neuropathic pain | THC variety | — | myrcene and linalool |
| Weight Loss | THCV variety | CBDV variety | cineol |
| Depression | CBG and CBC varieties | THC variety | linalool |
| Irritable Bowel Syndrome | CBD varieties | THC variety | limonene |
| Cancer Pain | THC variety | CBD variety | myrcene and eucalyptol |
| Low HDL Cholesterol | THCV variety | CBD variety | myrcene |

Example 25

Blended Bubble Pack Doses

It is important that the specialty *cannabis* and MCMs of the present invention be stable and possesses a long shelf-life when prepared for distribution to users for medicinal and recreational uses. This is achieved through proper drying and curing of the processed specialty *cannabis* product. In one embodiment, the shelf-life of the specialty *cannabis*, MCMs, or *cannabis* extracts of the present invention can be increased by proper airtight packaging such as in a bubble pack or a blister pack. One embodiment of the blister pack is diagramed in FIG. 14. In some embodiments, the blister packs of the present invention can be used with any *cannabis* product.

The longevity (i.e., shelf-life) of the packaged *cannabis* can be further extended by Modified Atmosphere Packaging (MAP), a technique used for prolonging the shelf-life of fresh or minimally processed foods. In this preservation technique, the air surrounding the product in the package is removed by vacuum or modified to contain different levels of nitrogen, oxygen, and carbon dioxide.

The specialty *cannabis* products of the present invention, including the blended *cannabis* compositions described herein, can be packaged in a bubble pack in either multi- or single-dose units to increase product longevity. Each single-dose unit packaged in the bubble pack will comprise the optimum cannabinoid and terpene dose identified by the instant invention. In one embodiment, the compositions of the invention are packaged as single-dose units to ensure the patient receives a correct, standardized dose and to protect the product integrity.

Example 26

Use of the Invention as Expectorant

When vaporized and inhaled, the specialty *cannabis* varieties of the present invention are an effective expectorant. Use of CBs containing specialty *cannabis* varieties described herein can be used, for example, in the treatment of congestion and upper respiratory diseases.

One mechanism through which specialty *cannabis* may act as an expectorant is through the activity of terpin hydrate, a precursor to terpineol which has been identified in several *cannabis* strains (See, Ross and ElSohly, (1996). J. Nat. Prod. 59:49-51 and Fischedick et al., (2010) Phytochemistry 71:2058-2073). The presence of terpineol, instead of terpin hydrate, in the samples after the *cannabis* is dried and heated may be due to a dehydration reaction of terpin hydrate to terpineol under thermal conditions. This chemical process may not occur if the *cannabis* is exposed to the lower heat of a vaporizer.

Inhalation of the vapors produced by high CBs containing specialty *cannabis* exposed to a lower heat can act as an effective expectorant and can be useful in the treatment of congestion. Terpin hydrate was commonly used in the treatment of acute and chronic bronchitis, but it was removed from the market by the FDA, which cited a lack of efficacy (See, Code of Federal Regulations, Title 21, Volume 5, Apr. 1, 2009). However, the formulations studied were oral formulations comprising terpin hydrate, not vaporized, inhaled terpin hydrate which may prove more effective.

Example 27

Pelletization of Specialty *Cannabis* for Bowls, Pipes, or Vaporizers

Specialty *cannabis* of the present invention will be used to create pre-pressed bowls of blended and pelletized *cannabis*. In some embodiments the MCMs of Example 24 may also be pelleted. Novel design and pellet density were used to optimize dosage for vapor and combusted cannabinoid delivery. The purpose of this invention is to maximize the exposed surface area of the pelletized material to maximize contact with heated air to achieve optimal vaporization. In one embodiment, the shape of the *cannabis* pellet is a very thin 'coin' shape.

Figure 15:
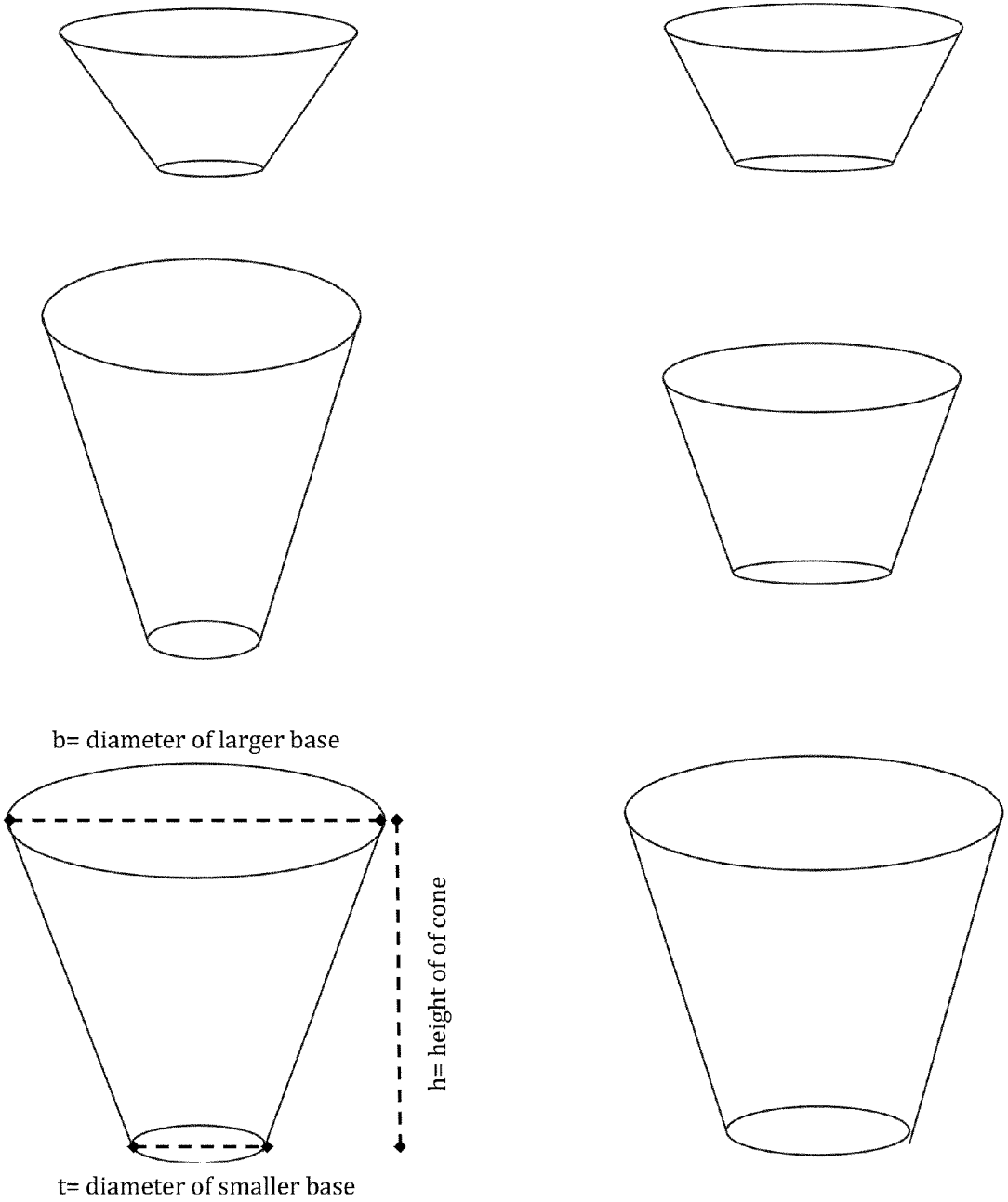
FIG. 15—Example diagrams of "truncated cone" pressed pellet shapes.

In another embodiment, the shape of the *cannabis* pellet of the present invention is a "truncated cone" (FIG. 15). In some embodiments, the dimensions of the *cannabis* pellet shape can vary for use with various smoking methods. In some embodiments the "truncated cone" pellet has a smaller base diameter "t" of 0.5 mm, 1 mm, 1.5 mm, 2 mm, 2.5 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 or 50 millimeters.

In some embodiments the "truncated cone" pellet has a larger base diameter "b" of 0.5 mm, 1 mm, 1.5 mm, 2 mm, 2.5 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 or 50 millimeters.

In some embodiments the "truncated cone" pellet has a cone height "h" of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, 5.1 mm, 5.2 mm, 5.3 mm, 5.4 mm, 5.5 mm, 5.6 mm, 5.7 mm, 5.8 mm, 5.9 mm, 6.0 mm, 6.1 mm, 6.2 mm, 6.3 mm, 6.4 mm, 6.5 mm, 6.6 mm, 6.7 mm, 6.8 mm, 6.9 mm, 7.0 mm, 7.1 mm, 7.2 mm, 7.3 mm, 7.4 mm, 7.5 mm, 7.6 mm, 7.7 mm, 7.8 mm, 7.9 mm, 8.0 mm, 8.1 mm, 8.2 mm, 8.3 mm, 8.4 mm, 8.5 mm, 8.6 mm, 8.7 mm, 8.8 mm, 8.9 mm, 9.0 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 or 50 millimeters.

In another embodiment, the shape of the *cannabis* pellet of the present invention is a "donut shape" (FIG. 16). In some embodiments, the dimensions of the *cannabis* pellet shape can vary for use with various smoking methods. In some embodiments the "donut shape" pellet has a outer donut diameter "od" of 0.5 mm, 1 mm, 1.5 mm, 2 mm, 2.5 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 or 50 millimeters.

In some embodiments the "donut shape" pellet has a inner donut diameter "b" of 0.5 mm, 1 mm, 1.5 mm, 2 mm, 2.5 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 or 50 millimeters.

In some embodiments the "donut shape" pellet has a donut height "dh" of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, 5.1 mm, 5.2 mm, 5.3 mm, 5.4 mm, 5.5 mm, 5.6 mm, 5.7 mm, 5.8 mm, 5.9 mm, 6.0 mm, 6.1 mm, 6.2 mm, 6.3 mm, 6.4 mm, 6.5 mm, 6.6 mm, 6.7 mm, 6.8 mm, 6.9 mm, 7.0 mm, 7.1 mm, 7.2 mm, 7.3 mm, 7.4 mm, 7.5 mm, 7.6 mm, 7.7 mm, 7.8 mm, 7.9 mm, 8.0 mm, 8.1 mm, 8.2 mm, 8.3 mm, 8.4 mm, 8.5 mm, 8.6 mm, 8.7 mm, 8.8 mm, 8.9 mm, 9.0 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 or 50 millimeters.

Figure 17:
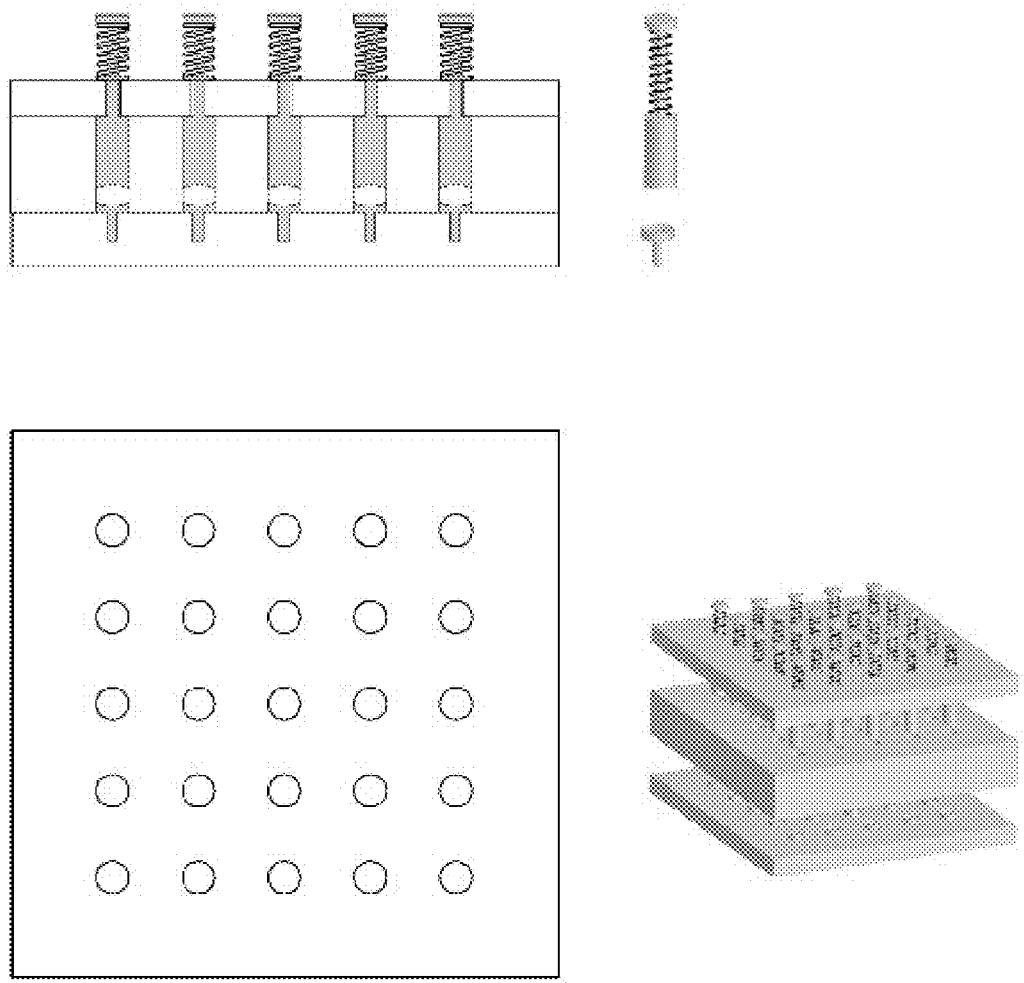
FIG. 17—Example diagram of a die for the production of *cannabis* pellets.

In some embodiments the *cannabis* pellets of the present invention are made with dies to form the specialty *cannabis*, MCM, or extracts into shapes (FIG. 17). In some embodiments the dies of the present invention is a coining die or a blanking die. The dies of the present invention may be made from any material capable of withstanding the pressures of forming pellets such as steel, hard plastic, wood, or ceramic.

In some embodiments, the *cannabis* pellets of the present invention are made with a die press. In some embodiments, the *cannabis* pellets of the present invention are made with commercially-available die presses such as the Across EP40 Pellet press (sold by Across International). In some embodiments, the dies of the present invention are designed to work with the pellet press. In other embodiments the pellet press already includes the shaping tool for *cannabis* pellets.

Example 28

*Cannabis* Extracts/Products

The specialty *cannabis* and MCMs of the present invention can be used to create various extracts or *cannabis* products. *Cannabis* extracts or products include:

Kief—refers to trichomes collected from *cannabis*. The trichomes of *cannabis* are the areas of cannabinoid and terpene accumulation. Kief can be gathered from containers where *cannabis* flowers have been handled. It can be obtained from mechanical separation of the trichomes from inflorescence tissue through methods such as grinding flowers, or collecting and sifting through dust after manicuring or handling *cannabis*. Kief can be pressed into hashish for convenience or storage.

Hash—sometimes known as hashish, is often composed of preparations of *cannabis* trichomes. Hash pressed from kief is often solid.

Bubble Hash—sometimes called bubble melt hash can take on paste-like properties with varying hardness and pliability. Bubble hash is usually made via water separation in which *cannabis* material is placed in a cold water bath and stirred for a long time (around 1 hour). Once the mixture settles it can be sifted to collect the hash.

Solvent reduced oils—also sometimes known as hash oil, honey oil, or full melt hash among other names. This type of *cannabis* oil is made by soaking plant material in a chemical solvent. After separating plant material, the solvent can be boiled or evaporated off, leaving the oil behind. Butane Hash Oil is produced by passing butane over *cannabis* and then letting the butane evaporate. Budder or Wax is produced through isopropyl extraction of *cannabis*. The resulting substance is a wax like golden brown paste.

Tinctures—are alcoholic extracts of *cannabis*. These are usually made by mixing *cannabis* material with high proof ethanol and separating out plant material.

E-juice—are *cannabis* extracts dissolved in either propylene glycol, vegetable glycerin, or a combination of both. Some E-juice formulations will also include polyethylene glycol and flavorings. E-juice tends to be less viscous than solvent reduced oils and is commonly consumed on e-cigarettes or pen vaporizers.

While these types of extracts have become a popular form of consuming *cannabis*, the extraction methods often lead to material with little or no terpene profile. That is, the harvest, storage, handling, and extraction methods produce an extract which is rich in cannabinoids, but often devoid of terpenes.

The extraction methods of the present invention are designed to preserve both the cannabinoids and the terpenes. In some embodiments, the specialty *cannabis* of the present invention is extracted via methods which preserve the cannabinoid and terpenes. In other embodiments, said methods can be used with any *cannabis* plants. The extracts of the present invention are designed to produce products for human or animal consumption via inhalation (via combustion, vaporization and nebulization), buccal absorption within the mouth, oral administration, and topical application delivery methods. The present invention teaches an optimized method at which we extract compounds of interest, by extracting at the point when the drying harvested plant has reached 15% water weight, which minimizes the loss of terpenes and plant volatiles of interest. Stems are typically still 'cool' and 'rubbery' from evaporation taking place. This timeframe (or if frozen at this point in process) allow extractor to minimize terpene loss to evaporation. There is a direct correlation between cool/slow/dry and preservation of essential oils. Thus, there is a direct correlation to EO loss in flowers that dry too fast, or too hot conditions or simply dry out too much (<10% H2O). The chemical extraction of our cultivars can be accomplished employing polar and non-polar solvents in various phases at varying pressures and temperatures to selectively or comprehensively extract terpenes, cannabinoids and other compounds of flavor, fragrance or pharmacological value for use individually or combination in the formulation of our products. The extractions can be shaped and formed into single or multiple dose packages, e.g., dabs, pellets and loads. The solvents employed for selective extraction of our cultivars may include water, carbon dioxide, 1,1,1,2-tetrafluoroethane, butane, propane, ethanol, isopropyl alcohol, hexane, and limonene, in combination or series. We can also extract compounds of interest mechanically by sieving the plant parts that produce those compounds. Measuring the plant part, i.e. trichome gland head, to be sieved via optical or electron microscopy can aid the selection of the optimal sieve pore size, ranging from 30 to 130 microns, to capture the plant part of interest. The chemical and mechanical extraction methods of the present invention can be used to produce products that combine chemical extractions with plant parts containing compounds of interest. The extracts of the present invention may also be combined with pure compounds of interest to the extractions, e.g. cannabinoids or terpenes to further enhance or modify the resulting formulation's fragrance, flavor or pharmacology. In some embodiments the extractions are supplemented with terpenes or cannabinoids to adjust for any loss of those compounds during extraction processes. In some embodiments, the *cannabis* extracts of the present invention mimic the chemistry of the *cannabis* flower material. In some embodiments, the *cannabis* extracts of the present invention will about the same cannabinoid and terpene profile of the dried flowers of the specialty *cannabis* of the present invention.

Extracts of the present invention can be used for vaporization, production of e-juice or tincture for e-cigarettes, or for the production of other consumable products such as edibles or topical spreads.

Example 29

Use of Specialty *Cannabis* in Edibles

*Cannabis* edibles such as candy, brownies, and other foods are a popular method of consuming *cannabis* for medicinal and recreational purposes. In some embodiments, the specialty *cannabis* of the present invention is used to make *cannabis* edibles. Most *cannabis* edible recipes begin with the extraction of cannabinoids and terpenes which are then used as an ingredient in various edible recipes. In one embodiment, the *cannabis* extract used to make edibles out of the specialty *cannabis* of the present invention is *cannabis* butter. *Cannabis* butter is made by melting butter (not margarine) in a container with *cannabis* and letting it simmer for about half an hour, or until the butter turns green. The butter is then chilled and used in normal recipes. Other extraction methods for edibles include extraction into cooking oil, milk, cream, flour (grinding *cannabis* and blending with flour for baking) Lipid rich extraction mediums/edibles are believed to facilitate absorption of cannabinoids into the blood stream. THC absorbed by the body is converted by the liver into 11-hydroxy-THC. This modification increases the ability of the THC molecule to bind to the CB1 receptor and also facilitates crossing of the brain blood barrier thereby increasing the potency and duration of its effects. For additional information on various edibles that can be produced with the specialty *cannabis* of the present invention, please see (Sarah Conrique "The Vegan Stoner Cookbook: 100 easy Vegan Recipes to Much" ISBN 1607744643; "Official High Times *Cannabis* Cookbook" ASIN B00HB7YI8U; Bliss Cameron "Marijuana Cooking: Good Medicine Made Easy" ISBN 1931160325; Tim Pilcher "The *Cannabis* Cookbook: Over 35 Tasty Recipes for Meals, Munchies, and More" ISBN 0762430907)

Example 30

Dosing Regimens of Multiplexed *Cannabis* Medicines

Volunteers

Regardless of the condition being treated, two separate groups of volunteers are evaluated: one composed of novice *cannabis* users and one composed of experienced *cannabis* users. It is helpful to know the past *cannabis* use history of volunteers since tolerance can occur in experienced users, who will therefore experience the therapeutic effects of the multiplexed *cannabis* formulation differently than those with no tolerance. However the rate and duration of tolerance varies with the different effects; a particular individual may have developed tolerance to one *cannabis* agent but not to another. This may actually serve to increase the therapeutic margin depending on the condition. For instance, tolerance to cognitive and psychomotor impairment, the psychological high, tachycardia, and orthostatic hypertension, tends to develop rather quickly and chronic users may not experience these detrimental side effects, while still benefitting from the analgesic or other therapeutic effects of *cannabis*. Conversely, the novice user who has no tolerance, can be slowly subjected to dose escalation (e.g. over 30 days or more) to build tolerance to these effects before given therapeutic doses. Many times the dysphoria experienced by naive users is enough to cause discontinuation of the treatment, and slow dose escalation which helps induce tolerance to the detrimental side effects may alleviate this.

The biodistribution and PK of the *cannabis* active agents administered either orally or through inhalation differ substantially. An acute condition may respond better to an inhaled formulation while a chronic condition may respond better to the prolonged plasma concentrations resulting from oral administration. The higher levels of 11-OH-THC (and/or CBs) formed from first-pass metabolism after oral formulation administration, which is more potent and has better blood brain barrier penetration than the parent compound, has implications for neurological conditions. The dosing studies described herein evaluate the effects of various doses of the multiplexed *cannabis* formulations when administered either orally or through inhalation.

Formulations

The amounts and types of bases, cannabinoid and terpene fortifiers are designed to have a synergistic effect on the conditions being treated. The multiplexed signaling resulting from the synergy of the components may be more effective than any single component alone and are tailored to achieve the desired effects. For instance, analgesia has been shown to be mediated by the $CB_1$, $CB_2$, TRPV-1, and $\alpha_2$-AR receptors, which suggests a component mixture of THC (which acts on $CB_1$ and $CB_2$), TRPV-1 (which acts on CBD), CBG (which acts on $\alpha_2$-AR) and β-myrcene (which acts on $\alpha_2$-AR) will be therapeutic. Similarly if the cause of the pain is inflammation, which is mediated by TNF-α and PGE-1, then the synergistic effects of a multiplexed medicine comprising CBD-rich extract, which counteracts TNF-α and α-pinene, which counteracts PGE-1, proves a more effective therapeutic than extracts not containing both of these compounds. The following Table 67 shows a few examples of the various clinical indications that are treated with *cannabis* formulations, the cannabinoids and terpenoids that are effective therapeutics for each clinical indication, and the pathways each cannabinoid influences.

TABLE 67

Non-exhaustive list of clinical indications that can be treated with *cannabis*.

| Pharmacological Action | Relevant Clinical Indication | Cannabinoid | | | | | | Terpene | | | | |
|---|---|---|---|---|---|---|---|---|---|---|---|---|
| | | THC | CBD | CBG | CBC | CBN | THCV | Limonene | a-pinene | b-myrcene | Linalool | b-caryophyl. |
| Neuroprotective | Parkinson's | ✓ | ✓ | | | | | | | | | |
| | Alzheimer's | Down regulate glutamate | Down regulate [Ca2+] | | | | | | | | | |
| | MS | Down regulate [Ca2+] | Down regulate ROS | | | | | | | | | |
| | Stroke | anti-oxidant | anti-oxidant | | | | | | | | | |
| Vasorelaxant | Glaucoma | ✓ | ✓ | | | | | | | | | |
| Appetite Stimulant | Anorexia | (+)PPARg | (+)PPARg | | | | | | | | | |
| | Cachexia | ✓ | | | | | | | | | | |
| | AIDS wasting | Down regulate leptin | | | | | | | | | | |
| | | (+)PPARg | | | | | | | | | | |
| Anti-proliferative | | (-)TRPM8 | up[Ca2+] | (-)TRPM8 | (-)TRPM8 | ✓ | | | | | | |
| | | | up-ROS | | | | | | | | | |
| | | | (+)CB₂ | | | | | | | | | |
| | | | (-)TRPM8 | | | | | | | | | |
| Intestinal Anti-prokinetic | Diarrhea | ✓ | (-)Ca₁ | | | | | | | | | |
| | | | Down regulate FAAH | | | | | | | | | |
| Immunosuppressive | Allergies | ✓ | | | | | | | | | | |
| | MS | Down regulate T-Cells | Down regulate T-Cells | | | | | | | | | |
| | RA | Down regulate Cytokines | | | | | | | | | | |
| | IBS | Down regulate Interleukins | | | | | | | | | | |
| Anti-Inflammatory | Pain | ✓ | Down regulate TNFa | | (+)TRPA1 | | | | PGE1 | PGE2 | | PGE1 |
| | MS | Down regulate IFNg | Down regulate ADO uptake | | | | | | | | ✓ | |
| | Chron's Arthritis | Down regulate Interleukins (+)PPARg | | | | | ✓ | | | | | |
| Sedative | Sleep disorders | ✓ | ✓ | | | | | | | | | |

TABLE 67-continued

Non-exhaustive list of clinical indications that can be treated with *cannabis*.

| | | Cannabinoid | | | | | | Terpene | | | | |
|---|---|---|---|---|---|---|---|---|---|---|---|---|
| | THC | CBD | CBG | CBC | CBN | THCV | Limonene | a-pinene | b-myrcene | Linalool | b-caryophyl. |
| Anti-epileptic | | | | | | | | | | | | |
| Epilepsy | ✓ | ✓ Down regulate [Ca2+] (+)5HT$_{1A}$ | ✓ Down regulate GABA uptake | | | ✓ (−)CB$_1$ | | | | anti-Glu | ✓ |
| Anti-emetic | | Down regulate ADO uptake | | | | | | | | | |
| CIE | ✓ | ✓ | | | | | | | | | |
| Anxiolytic | | | | | | | | | | | |
| Panic Disorder | ✓ | ✓ (+)5HT$_{1A}$ | ✓ Down regulate GABA uptake | | | | ✓ 5HT$_{1A}$ | | | ✓ | |
| Social Anxiety Disorder | | | | | | | | | | | |
| Generalized Anxiety Disorder | | | | | | | | | | | |
| PTSD | | (+)CB$_1$ | | | | | | | | | |
| Antidepressant | | | | | | | | | | | |
| Depression | ✓ | ✓ | ✓ (−)5HT$_{1A}$ | | | | ✓ | | | | |
| Anti-psychotic | | (+)TRPV1 | | | | | | | | | |
| Anti-spasmodic | | | ✓ | | | | | | | | |
| MS | ✓ | ✓ | Down regulate GABA uptake | | | | | | | | |
| Spinal cord injury | | | | | | | | | | | |
| Cerebral palsy | | | | | | | | | | | |
| Analgesic | | | | | | | | | | | |
| MS | ✓ CB$_1$ | ✓ (+)TRPV1 | ✓ (+)TRPA1 | ✓ | | | | | | | |
| Post-operative pain | CB$_2$ | (+)TRPA1 | (+)TRPA1 | (+)TRPA1 | (+)TRPV2 | | | | | | |
| Migraine | (+)TRPA1 | | Down regulate GABA uptake a2 blockade | | | | | | ✓ | ✓ A$_{2A}$ | |
| Neuropathic pain | | | | | | | | | | | |
| Sciatica | | | | | | | | | | | |
| Bronchodialator | | | | | | | | | | | |
| Asthma | ✓ | | | | | | | | | | |
| Sleep-related breathing disorders | | | | | | | | | | | |
| Muscle relaxant | | | | | | | | | | | |
| MS | ✓ | | ✓ Down regulate GABA uptake | | | | | | | | |

The fortifiers of the present invention are chosen to reinforce the treatment for the given clinical condition and to posses an improved therapeutic margin, through synergy of the various pathways involved in the disease or disorder. Table 67 is a brief, and by no means complete, summary of pharmacological effects of various representative cannabinoids and terpenoids along with the relevant therapeutic applications. In cases where a mechanism has been proposed this has been included in the table.

Another important aspect of this invention is in the combinatorial and synergistic pharmacological effects of the cannabinoids and terpene active ingredients present in *cannabis*. For example, recreational *cannabis* in the U.S. has been selected (through breeding) to contain a high content of tetrahydrocannabinol (THC), ignoring or reducing other cannabinoid and terpenoid compounds regarded as inactive compounds. Although cannabidiol was regarded as an inactive compound in the past, there is now experimental evidence that it has potentially beneficial pharmacological activity different from that of THC. Effects of other terpene compounds as analgesics or anti-microbial substances is also emerging (Russo, Ethan, Br J Pharmacol: 163(7) 1344-1364 (2011)). The therapeutic effects of *cannabis* cannot be satisfactorily explained just in terms of one or the other "active" constituent, but are instead a consequence of the combination of active compounds.

Given the varied above-referenced individual and combinatorial effects of THC and CBD cannabinoids on various diseases, Table 68 outlines preferred ratios of THC:CBD concentrations for treatment of various diseases (see U.S. patent application Ser. No. 11/628,814, and UK patent application GB2377633)

TABLE 68

Preferred THC:CBD ratios for the treatment of various diseases.

| CATEGORY | THC:CBS RATIO | DISEASE |
|---|---|---|
| High THC | >95:5 | Cancer pain; Migraine; Appetite stimulation. |
| Even ratio | 50:50 | Multiple sclerosis; Spinal cord injury; Peripheral neuropathy; Neurogenic pain. |
| Broad ratio | <25:75 | Rheumatoid arthritis; Inflammatory bowel disease. |
| High CBD | <5:95 | Psychotic disorders (schizophrenia); Epilepsy; Movement disorders; Stroke; Head injury; Disease modification in rheumatoid arthritis and other inflammatory conditions; Appetite suppression |

Volunteer Sub-Groups and Controls

Large volunteer groups (75-100 volunteers) are studied to evaluate the subjective effects of the *cannabis* formulations. For all studies, volunteer groups are chosen from several locations and are chosen from various dispensaries and/or solicited, if drug-naïve volunteers are difficult to find. These volunteers are subdivided into experienced and novice *cannabis* users, and then if the clinical indication warrants it, further subdivided into those receiving either the oral and inhaled formulations. Due to the extremely variable bioavailability, dosage regimens are tailored to the indication and the volunteer. All studies are done with the appropriate medical and/or psychological supervision and evaluation. There are several placebo groups, with the volunteers receiving either complete placebos, a placebo containing no cannabinoids and only terpenes, and placebos containing no terpenes and only cannabinoids. This will serve to establish not only efficacy of the cannabinoids and/or terpenes, but also the synergy. The complete placebo is generated from fats and waxes resulting from cannabinoid extraction and is spiked with terpenes fortifiers for exact and reproducible levels of terpenes to make the placebo without cannabinoids, or it is spiked with cannabinoid fortifiers to make exact and reproducible levels of cannabinoids without the terpenes. *Cannabis* treatments for these studies will include inhaled, oral buccal, or ingested *cannabis*. In some embodiments, the inhaled *cannabis* formulations are the specialty *cannabis* of the present invention. In other embodiments, the inhaled *cannabis* formulations are extracts derived from the specialty *cannabis* of the present invention. In other embodiments, the oral dose of *cannabis* is prepared from extracts of the specialty *cannabis* of the present invention.

Proposed Clinical Indications

The studies first evaluate the predictable and reproducible plasma levels of *cannabis* active agents both in a volunteer, and between different volunteers, who received the multiplexed medicines either orally or through inhalation. Once this is evaluated, the mitigation of adverse effects is studied through dose escalation and/or examining the ratios of active ingredients in the multiplexed *cannabis* formulation. Once this is established, the various clinical indications are examined.

Based on proposed pharmacological mechanisms of action, there are a number of clinical indications that are evaluated for treatment with *cannabis*-based medicines. These include, but are not limited to, Parkinson's, Alzheimer's, MS, stroke, glaucoma, anorexia, cachexia (from AIDS, cancer, Multiple Sclerosis, congestive heart failure), diarrhea, allergies, arthritis, irritable bowel syndrome, Crohn's disease, sleep disorders, epilepsy, chemotherapy induced emesis, panic disorder, social anxiety disorder, generalized anxiety disorder, post-traumatic stress disorder, depression, spinal cord injury, cerebral palsy, post-operative pain, migraine, neuropathic pain, sciatica, asthma, and/or sleep-related breathing disorders.

Terminology

In the studies below, the medicines are referred to by the principal components of the base and fortifiers.

Study 1: Precision of Dosing Regimens and Bioavailability

Traditionally, administration of *cannabis* has resulted in unpredictable bioavailabilities, resulting in frequent occurrences of overdosing and/or under dosing which make it difficult to attain therapeutic blood levels while mitigating adverse events in a predictable manner. Therefore, the ability to provide predictable and consistent blood plasma levels has great utility.

In this study, volunteers are divided into two groups: one receiving inhaled *cannabis* formulations, and one receiving oral *cannabis* formulations. Those receiving the oral dose of *cannabis* abide by strict pre-dosing dieting. The dose amount is scaled to body weight (0.05 and 0.1 mg/kg) and, since *cannabis* active components are highly lipophillic, the dose amount further scaled based on BMI and/or body fat measurements. For example, the dose based on body weight can be multiplied based on the volunteer's BMI (e.g. multiplying the dose by 0.9 for BMI <18, 1.0 for BMI=18-25, 1.1 for BMI 25-30, and 1.3 for BMI>30). Each study is performed in triplicate to determine intra-volunteer variability and each volunteer first undergoes i.v. dosing with the prescribed amount of drug. The oral formulation is given in a single dose, and to minimize the effect of smoking characteristics, the inhaled formulation is given in tabs of sufficient size to be vaporized and administered in a single dose. Alternatively, the tabs to be vaporized are subdivided into "unit sizes" that are administered in rapid succession. Blood samples are taken at various intervals and assayed for the *cannabis* active agent as well as the appropriate metabolites. From the data biodistribution and appropriate PK parameters are determined. This will be done by measuring cannabinoid levels of volunteer plasma over time after receiving said multiplexed treatments (see U.S. Pat. No. 6,946,150; Huestis et al., Blood cannabinoids. I. Absorption of THC and formation of 11-OH-THC and THCCOOH during and after smoking marijuana. J Anal Toxicol. 1992 September-October; 16(5):276-82; Huestis, Marilyn, Human Cannabinoid Pharmacokinetics. Chem. Biodivers. 2007 August; 4(8): 1770-1804). Cannabinoid plasma levels will be compared for same-volunteers across different treatments to measure the combinatorial drug adsorption effects of different multiplexed cannabinoid and terpenoid combinations. Cannabinoid plasma levels will also be compared between volunteers to further tailor treatments to volunteers based on their different absorption of each cannabinoid.

Study 2: Mitigation of Adverse Effects

This study establishes the development of tolerance to the possible adverse effects of *cannabis*, such as cognitive and psychomotor impairment, the psychological high, anxiety, and tachycardia. This is important as many times the therapeutic dose approaches the intoxicating dose and may cause discontinuation of treatment. Only inhaled formulations are employed in this study since the onset of the drug effect is rapid and the duration is shorter, which provides easier monitoring. Inhalation of the drug formulation is preferably done with a Volcano® or other vaporizer with consistent vapor production. Subjects will be asked to take timed inhalations, timed 10-second breath-holds, and/or timed intermediate duration. Subjective questionnaires and heart-rate monitoring are used for evaluation.

The subjects are divided into a number of groups, and are administered either complete placebo, placebo with only terpenes, THC base, THC:CBD base, or THC base with varying levels and combinations of CBs such as CBD, THCV, CBDV, CBGV or, CBG, and chosen terepenes such as limonene, and/or linalool fortifiers. Terpenes will be chosen based on their ability to mitigate pain as described in Table 2 or based on the results of the volunteer trials of earlier examples. The subjects are administered with 3 mg, 6 mg, or 12 mg of the drug formulation (or dosage levels determined from Study 1). The subjects are further subdivided into those who are administered the maximum dose at the first treatment and those who undergo a slow dose escalation. This establishes the proper dosing regimens and ratios of anxiolytic ingredients in the multiplexed formulations if adverse events are noted in future studies.

Study 3: Pain

Volunteers are grouped into those suffering from Multiple Sclerosis, post-operative pain, migraine, arthritis, and neuropathic pain (such as sciatica) and then subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered with the placebos, THC base, THC/CBD base, or various amounts of CBs such as CBD, THCV, CBDV, CBGV or, CBG, and chosen terepenes such as limonene, and/or linalool fortifiers. Terpenes will be chosen based on their ability to mitigate pain as described in Table 2 or based on the results of the volunteer trials of earlier examples. Volunteers are evaluated via questionnaire and/or medical examination.

Study 4: Anxiety

Volunteers are grouped into those suffering from generalized anxiety disorder (GAD), seasonal affective disorder (SAD), panic disorder, and post-traumatic stress disorder (PTSD). Volunteers are subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers with SAD receive a lower dosing regimen. Volunteers are administered either the placebos, THC base, THC/CBD base, or various amounts of CBs such as CBD, THCV, CBDV, CBGV or, CBG, and chosen terepenes such as limonene, and/or linalool fortifiers. Terpenes will be chosen based on their ability to mitigate pain as described in Table 2 or based on the results of the volunteer trials of earlier examples. Volunteers are evaluated via questionnaire and/or psychological examination.

Study 5: Depression

Volunteers are subdivided into those receiving either oral (2.5 mg and 5 mg THC) or inhaled (2.5 mg and 5 mg THC) administration routes. Dosage levels can also be determined based on Study 1. In this study, higher doses are not examined since only low doses of *cannabis* have been implicated in relieving depression. Volunteers are administered either the placebos, THC base, THC/CBD base, or various amounts of CBs such as CBD, THCV, CBDV, CBGV or, CBG, and chosen terepenes such as limonene, and/or linalool fortifiers. Terpenes will be chosen based on their ability to mitigate pain as described in Table 2 or based on the results of the volunteer trials of earlier examples. Volunteers are evaluated via questionnaire and/or psychological examination.

Study 6: Allergies, Rheumatoid Arthritis, Irritable Bowel Syndrome, Pain, MS, Crohn's Disease, Arthritis Volunteers are grouped into those suffering from allergies, rheumatoid arthritis, irritable bowel syndrome, pain, MS, Crohn's disease, and arthritis and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered either the placebos, THC base, THC/CBD base, or various amounts of CBS, or terpenes such as pinene, myrcene, and/or beta-caryophyllene fortifiers, all of which have been suggested to be inhibit pro-inflammatory and immune response pathways. Other terpenes will be chosen based on their ability to mitigate pain as described in Table 2 or based on the results of the volunteer trials of earlier examples. Volunteers are evaluated via questionnaire and/or medical examination.

Study 7: Asthma, Sleep Disorders, and Sleep Apnea

Volunteers are grouped into those suffering from mild asthma, central sleep apnea, and obstructive sleep apnea and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered either the placebos, THC base, THC/CBD base, or various amounts of pinene, which has been implicated in bronchodillation and of myrcene and linalool, which have been suggested to be sedatives. Other terpenes and cannabinoids will be chosen based on their ability to mitigate pain as described in Tables 1 and 2 or based on the results of the volunteer trials of earlier examples. Volunteers are evaluated via questionnaire and/or medical examination.

Study 8: Appetite Stimulant

Volunteers are grouped into those suffering from anorexia, AIDS Wasting Syndrome, and cachexia resulting from MS or CHF and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered either the placebos, THC base, THC/CBD base, limonene or pinene for associated anxiety, and CBG, or limonene for associated depression. Other terpenes and cannabinoids will be chosen based on their ability to mitigate pain as described in Tables 1 and 2 or based on the results of the volunteer trials of earlier examples. Volunteers are evaluated via questionnaire and/or medical examination.

Study 9: Neuroprotection

Volunteers are grouped into those suffering from mild Parkinson's, Alzheimer's, Multiple Sclerosis, and possible recent stroke and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered either the placebos, THC base, THC/CBD base, limonene or pinene for associated anxiety, and CBG or limonene for associated depression. Other terpenes and cannabinoids will be chosen based on their ability to mitigate pain as described in Tables 1 and 2 or based on the results of the volunteer trials of earlier examples. Volunteers are evaluated via questionnaire and/or medical examination.

Study 10: Multiple Sclerosis

Volunteers are subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered either the placebos, THC base, THC/CBD base, or various ratios of THC fortifiers (associated with neuro-protective, immunosuppressive, anti-inflammatory, anti-spasmodic, analgesic, and muscle relaxant effects), CBD fortifiers (associated with neuro-protective, immunosuppressive, anti-inflammatory, anti-spasmodic, and analgesic effects), CBG fortifiers (associated with anti-spasmodic, analgesic, and muscle-relaxant effects), pinene (associated with anti-inflammatory effects), myrcene (associated with anti-inflammatory and analgesic effects), linalool (associated with analgesic effects), and beta-caryophyllene (associated with anti-inflammatory effects). Volunteers are evaluated via questionnaire and/or medical examination.

Study 11: Epilepsy/Migraine

Volunteers are grouped into those suffering from seizure disorders of different classifications and migraine headaches of different classifications, and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Volunteers are administered either the placebos, THC base, THC/CBD base and CBD, CBG, or linalool fortifiers, all of which are implicated in anti-epileptic pathways. Other terpenes and cannabinoids will be chosen based on their ability to mitigate pain as described in Tables 1 and 2 or based on the results of the volunteer trials of earlier examples. Volunteers are evaluated via questionnaire and/or medical examination.

Example 31

Use of Multiplexed *Cannabis* Mixtures to Treat Brachial Plexus Avulsion (Prophetic)

In one embodiment of this invention the multiplexed *cannabis* mixtures or specialty *cannabis* plants of the present invention are tailored to treat the symptoms of brachial plexus avulsion. Effectiveness of the treatment will be confirmed by conducting a trial using double blind, randomized treatments comparing the effects of multiplexed *cannabis* mixtures containing THC and/or CBD, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on both their therapeutic activity (e.g. analgesic effects of myrcene and linalool) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which pain relief is obtained.

Volunteers will be screened to determine eligibility during their first visit at which baseline pain assessments will be made prior to randomizing subjects into each treatment. Volunteers will also be assigned to receive placebos, including complete placebos (no active ingredient), a placebo containing no cannabinoids and only terpenes, and placebos containing no terpenes and only cannabinoids. This will establish not only efficacy of the cannabinoids and/or terpenes, but also the synergy among the active compounds inherent in each *cannabis* line used.

The effectiveness of each treatment will be scored using volunteer diaries and by accepted pain measuring scales such as the box score 11 (BS11), McGill Pain Questionnaire (MPQ), Numeric Rating Scale (NRS-11), and Visual Analog Scale (VAS), among others (Jensen et al., Clin J Pain, 5(2): 153-9 1989; Melzack R, Pain, 1(3):277-99 1975; Hartrick et al., Pain Pract 3(4):310-6, 2003; Huskisson E, Rheumatol. 9 (5): 768-9, 1982). Particular emphasis will be placed on pain relief and satisfaction scores comparing oral and inhalatory routes of each treatment. The effectiveness of THC and CBD cannabinoids for the treatment of brachial plexus avulsion symptoms has already been demonstrated using *cannabis* based medicinal extracts (CBME, see U.S. patent application Ser. No. 10/533,504). A key aspect of this invention is that multiplexed *cannabis* mixtures use unextracted, natural plant material as a medicine that is both effective at treating symptoms as well as pleasurable to the volunteer; in this case by providing pain relief and a satisfying organoleptic feel.

Example 32

Use of Multiplexed *Cannabis* Mixtures to Treat Arthritis

In one embodiment of this invention the multiplexed *cannabis* mixtures or specialty *cannabis* plants of the present invention are tailored to treat the disease and/or symptoms of arthritis. Effectiveness of the treatment will be confirmed by conducting a trial using double blind, randomized treatments comparing the effects of multiplexed *cannabis* mixtures containing THC and/or CBD, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on both their therapeutic activity (e.g. analgesic effects of myrcene and linalool) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which pain relief is obtained.

Volunteers will be screened to determine eligibility during their first visit at which baseline pain assessments will be made prior to randomizing subjects into each treatment. Volunteers will also be assigned to receive placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by using volunteer diary self-assessments scoring quality of sleep, morning pain at rest, morning pain on movement, morning stiffness, and quality of sleep. McGill Questionnaires or other pain scale questionnaires (e.g. VAS, BS11, NRS-11, etc) will be completed in at least two experimental time points to compare changes in present intensity of pain, and overall impression of pain. Particular emphasis will be placed on pain and overall satisfaction scores comparing oral and inhalatory routes of each treatment. The effectiveness of THC and CBD cannabinoids on treating arthritic symptoms has already been demonstrated using *cannabis* based medicinal extracts (CBME, see U.S. patent application Ser. No. 11/628,814). A key aspect of this invention is that multiplexed *cannabis* mixtures use unextracted natural plant material as a medicine that is both effective at treating symptoms as well as pleasurable to the volunteer; in this case by providing pain relief, extended and better quality sleep, and a satisfying organoleptic feel.

Example 33

Use of Multiplexed *Cannabis* Mixtures to Treat Motion Sickness

In one embodiment of this invention the multiplexed *cannabis* mixtures or specialty *cannabis* plants of the present invention are tailored to prevent and/or treat the symptoms of motion sickness. Effectiveness of the treatment will be confirmed by conducting a trial using double blind, randomized treatments comparing the effects of multiplexed *cannabis* mixtures containing THC and/or CBD, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on both their therapeutic activity (e.g. stomach reflux calming effects of limonene) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20 or lower. Treatments will be administered via oral or inhaled routes. Dosage levels will be determined based on Study 1 of Example 30 of this application, or by individually tailoring doses up to the level at which motion sickness relief is obtained.

Volunteers susceptible to motion sickness will be screened via a questionnaire and then subjected to nausea-inducing trials without any treatment in order to obtain baseline assessments. Nausea inducing trials will include a variety of non-chemical conditions known to induce nausea in volunteers (Griffin et al. *Aviat Space Environ Med.* 75(9):739-748 (2004), Dornhoffer et al., *Otol Neurotol.* 25(5):740-745 (2004), Donohew et al., *Aviat Space Environ Med* 75(8):649-656 (2004), and Duh et al., *Hum Factors* 46(1):142-153 (2004)). In one embodiment, volunteers will be administered a multiplex *cannabis* medicine treatment followed by a 30 minute suburban car journey with artificial restrictions to their view (e.g. blindfolded), and/or in different seating positions. Volunteers will be asked to rate their level of motion sickness at 1 minute intervals and vehicle motion conditions will be recorded in three axis to ensure similar motion conditions across trials. Volunteers will also be assigned to receive placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by comparing volunteer motion sickness scores across treatments. Emphasis will be placed on treatments that reduce motion sickness and also excel at overall satisfaction scores including flavor and organoleptic feel. The effectiveness of THC and CBD cannabinoids on treating motion sickness has already been demonstrated using *cannabis* based medicinal extracts (CBME, see U.S. Pat. No. 8,034,843, and). A key aspect of this invention is that multiplexed *cannabis* mixtures use unextracted natural plant material as a medicine that is both effective at treating symptoms as well as pleasurable to the volunteer; in this case by motion sickness relief, and a satisfying organoleptic feel.

Example 34

Use of Multiplexed *Cannabis* Mixtures to Treat Seizures

In one embodiment of this invention the multiplexed *cannabis* mixtures or specialty *cannabis* plants of the present invention are tailored to prevent and/or treat seizures. Effectiveness of the treatment will be confirmed by conducting a trial using double blind, randomized treatments comparing the effects of multiplexed *cannabis* mixtures containing THCV and/or CBDV, or combinations of other cannabinoid variants, and/or a combination of various terpenes. Concentrations used for this study will be (2 mg, 5 mg, 10 mg, 15 mg, 20 mg or more THCV) and/or (2 mg, 5 mg, 10 mg, 15 mg, 20 mg or more CBDV) alone, or in combination with terpenes such as myrcene, limonene, pinene, and/or linalool fortifiers. Terpene combinations will be chosen based on both their therapeutic activity (e.g. anti convulsant properties of linalool) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which seizure relief is obtained.

Volunteers used for this study will be screened via a questionnaire to determine their severity of their seizure symptoms. Optimal volunteers will be those who have at least 3 partial seizures the month prior to beginning the study. An multi-day baseline assessment period without any treatment will be conducted prior to the randomized study to obtain baseline seizure information from each volunteer. Volunteers will then be randomized and provided with experimental treatments including various multiplex *cannabis* medicine combinations. Volunteers will also be assigned to receive placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

As is common to other seizure studies, treatments will be compared using volunteer diary self-assessments scoring seizure frequency, severity, type, and overall quality of life assessment (Arroyo et al., Epilepsia, Vol. 45:1, 20-27 2004). Particular emphasis will be placed on seizure number, severity, and as quality of life scores, comparing oral and inhalatory routes of each treatment. The effectiveness of THCv and CBDv cannabinoids on treating seizures has already been demonstrated using *cannabis* based medicinal extracts (CBME, see U.S. patent application Ser. No. 13/075,873). A key aspect of this invention is that multiplexed *cannabis* mixtures use unextracted natural plant material as a medicine that is both effective at treating symptoms as well as pleasurable to the volunteer; in this case by providing seizure symptom relief, and a satisfying organoleptic feel.

Example 35

Use of Multiplexed *Cannabis* Mixtures to Treat Neuropathic Pain

In one embodiment of this invention the multiplexed *cannabis* mixtures or specialty *cannabis* plants of the present invention are tailored to treat neuropathic pain such as that related to fibromyalgia, allodynia, parasthesia, post herpetic neuralgia, painful diabetic neuropathy, painful HIV-distal sensory polyneuropathy, among others. Effectiveness of the treatment will be confirmed by conducting a trial using double blind, randomized treatments comparing the effects of multiplexed *cannabis* mixtures containing THC and/or CBD, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on their therapeutic activity (e.g. analgesic effects of myrcene and linalool) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which pain relief is obtained.

Volunteers will be screened to determine eligibility during their first visit at which baseline assessments will be made prior to randomizing subjects into each treatment. Volunteers will also be assigned to receive placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by using volunteer diary self-assessments and by accepted pain measuring scales such as the box score 11 (BS11), McGill Pain Questionnaire (MPQ), Numeric Rating Scale (NRS-11), and Visual Analog Scale (VAS), among others (Jensen et al., Clin J Pain, 5(2):153-9 1989; Melzack R, Pain, 1(3):277-99 1975; Hartrick et al., Pain Pract 3(4):310-6, 2003; Huskisson E, Rheumatol. 9 (5): 768-9, 1982). Other measures may include point questionnaires for quality of sleep, and overall quality of life. Questionnaires will be completed in at least two experimental time points to compare changes in present intensity of pain, and overall impression of pain. Particular emphasis will be placed on pain, sleep, quality of life and overall satisfaction scores comparing oral and inhalatory routes of each treatment. The effectiveness of THC and CBD cannabinoids on treating neuropathic pain has already been demonstrated using *cannabis* based medicinal extracts (CBME, see U.S. patent application Ser. Nos. 12/084,454, 13/491,077, 12/308,776). A key aspect of this invention is that multiplexed *cannabis* mixtures use unextracted natural plant material as a medicine that is both effective at treating symptoms as well as pleasurable to the volunteer; in this case by providing pain relief, extended and better quality sleep, and a satisfying organoleptic feel.

Example 36

Use of Multiplexed *Cannabis* Mixtures to Aid in Weight Loss

In one embodiment of this invention the multiplexed *cannabis* medicine can be used to treat obesity or to aid in cosmetically beneficial weight loss. Effectiveness of the treatment will be confirmed by conducting a trial using double blind, randomized treatments comparing the effects of multiplexed *cannabis* mixtures containing THCV and/or CBDV, or combinations of other cannabinoid variants, and/or a combination of various terpenes. Concentrations used for this study will be (2 mg, 5 mg, 10 mg, 15 mg, 20 mg or more THCV) and/or (2 mg, 5 mg, 10 mg, 15 mg, 20 mg or more CBDV) alone, or in combination with terpenes such as myrcene, limonene, pinene, and/or linalool fortifiers. Terpene combinations will be chosen based on their therapeutic activity (e.g. analgesic effects of myrcene and linalool) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which reduced appetite is obtained.

Volunteers will be screened to determine eligibility based on high body mass indices during their first visit at which baseline weight and health assessments will be made prior to beginning the study. Prior to any treatments, volunteers will be placed on a 600 kcal/day deficit diet without treatments. After 3 weeks, volunteers adhering to the diet and experiencing weight loss will be randomized into each treatment. Volunteers will also be assigned to receive placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

Weight loss will be tracked using standard protocols as those found in (James et al., The Lancet, Vol 356:9248, 2119-2125 2000; Jurgens et al., Cochrane Database Syst Rev Dec. 12, 2012; Patrick et al., J Diabetes Sci Technol, May 17(3): 759-70 2013). The trial will be conducted over for several weeks and the effectiveness of each treatment will be compared. Volunteer diary self-assessments will also be compared to normalize for physical activity and diet, as well as to evaluate the overall satisfaction with each treatment. Volunteer dropout rates will also be measure volunteer motivation. Particular emphasis will be placed on normalized weight loss and overall satisfaction scores comparing oral and inhalatory routes of each treatment. The effectiveness of THCV and CBDV cannabinoids as CB1 and CB2 antagonists and weight loss agents has already been demonstrated using *cannabis* based medicinal extracts (CBME, see U.S. patent application Ser. Nos. 11/667,890, 12/087,847, and US20110082195). A key aspect of this invention is that multiplexed *cannabis* mixtures use unextracted natural plant material as a medicine that is both effective at treating symptoms as well as pleasurable to the volunteer; in this case by helping volunteers with weight loss rate and commitment, and providing a satisfying organoleptic feel.

Example 37

Use of Multiplexed *Cannabis* Mixtures to Treat Depression

In one embodiment of this invention the multiplexed *cannabis* mixtures or specialty *cannabis* plants of the present invention are tailored to treat depression such as morbid or clinical depression, unipolar mood disorder, bipolar mood disorder, syndromal depression, and panic disorder and anxiety among others. Effectiveness of the treatment will be confirmed by conducting a trial using double blind, randomized treatments comparing the effects of multiplexed *cannabis* mixtures containing THC and/or CBG, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBG) and/or (2 mg, 5 mg, 10 mg, 15 mg, 20 mg or more CBC) alone, or in combination with terpenes such as myrcene, limonene, pinene, and/or linalool fortifiers. Terpene combinations will be chosen based on their therapeutic activity (e.g. anti-anxiety effects of linalool; Russo et al., Handbook of Psychotropic Herbs, Haworth Press, December 2000) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which mood improvement is obtained.

Volunteers will be screened to determine eligibility during their first visit. Eligible volunteers will exhibit at least one somatic symptom of depression found on the Bradford Somatic Inventory (Garcia-Campayo et al., British Journal of Psychiatry 168:348-353 1996). Prior to conducting the study, volunteer depression baseline assessments will be made using any of the accepted medical measures such as 17-item Hamilton Depression Rating Scale Interview, Beck Depression Inventory, Bradford Somatic Inventory, etc (see Chatwin et al., BMC family practice 8:2 2007). Volunteers will be randomized into treatment as well as placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by using depression assessments as used for baseline assessments and described above, as well as with the use of volunteer diary self-assessments, and overall satisfaction scores. Depression assessments will be completed in at least two experimental time points. Particular emphasis will be placed on depression and overall satisfaction scores comparing oral and inhalatory routes of each treatment. The effectiveness of CBG and CBC cannabinoids on treating depression has already been demonstrated in animal models using *cannabis* based medicinal extracts (CBME, see U.S. Patent Applications 60/813,814 and 11/760,364 and international patent application WO 2005/000830). A key aspect of this invention is that multiplexed *cannabis* mixtures use unextracted natural plant material as a medicine that is both effective at treating symptoms as well as pleasurable to the volunteer; in this case by improving volunteer mood as an anti-depressant and by providing a pleasurable and satisfying organoleptic feel.

Example 38

Use of Multiplexed *Cannabis* Mixtures to Irritable Bowel Syndrome

In one embodiment of this invention the multiplexed *cannabis* mixtures or specialty *cannabis* plants of the present invention are tailored to treat the symptoms of Irritable Bowel Syndrome (IBS) such as those related to Crohn's disease among others. Effectiveness of the treatment will be confirmed by conducting a trial using double blind, randomized treatments comparing the effects of multiplexed *cannabis* mixtures containing THC and/or CBD, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on their therapeutic activity (e.g. analgesic effects of pinene) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which symptom relief is obtained.

Volunteers will be screened to determine eligibility during their first visit. Eligible volunteers will exhibit IBS symptoms as determined via a Crohn's disease activity index (CDAI) (Best et al., Gastroenterology 70 (3):439-444 1976). Prior to conducting the study, volunteer baseline assessments will be made using any of the accepted medical measures such as CDAI, Harvey-Bradshaw index, and the Inflammatory Bowel Disease Questionnaire (IBDQ), among others (see Harvey and Bradshaw, Lancet 1 (8167):514 1990; and Irvine et al., Gastroenterology 106 (2):287-96, 1994). Volunteers will be randomized into treatment as well as placebo groups, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by using IBS symptom assessments as used for baseline measurements and as described above, as well as with the use of volunteer diary self-assessments, and overall satisfaction scores. IBS symptomatic assessments will be completed in at least two experimental time points. Particular emphasis will be placed on number of soft or liquid stools per day, abdominal pain scores (1-3), and overall satisfaction scores comparing oral and inhalatory routes of each treatment. The effectiveness of CBG cannabinoids on treating depression has already been demonstrated in animal models and in trials using *cannabis* based medicinal extracts (CBME, see U.S. patent application Ser. No. 12/667,561). A key aspect of this invention is that multiplexed *cannabis* mixtures use unextracted natural plant material as a medicine that is both effective at treating symptoms as well as pleasurable to the volunteer; in this case by improving gastrointestinal health and by providing a pleasurable and satisfying organoleptic feel that encourages volunteers to continue treatments.

Example 39

Use of Multiplexed *Cannabis* Mixtures to Treat Pain from Cancer

In one embodiment of this invention the multiplexed *cannabis* mixtures or specialty *cannabis* plants of the present invention are tailored to treat pain such as that related to cancer or other potentially terminal diseases. Effectiveness of the treatment will be confirmed by conducting a trial using double blind, randomized treatments comparing the effects of multiplexed *cannabis* mixtures containing THC and/or CBD, or combinations of other cannabinoid variants, and/or a combination of various terpenes. Concentrations used for this study will be (2 mg, 5 mg, 10 mg, 15 mg, 20 mg or more THC) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on their therapeutic activity (e.g. analgesic effects of myrcene and linalool) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which pain relief is obtained.

Volunteers will be screened to determine eligibility during their first visit at which baseline assessments will be made prior to randomizing subjects into each treatment. Volunteers will also be assigned to receive placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by using volunteer diary self-assessments scoring Numerical Rate Score (NRS) 11-point pain scores, quality of sleep, and overall quality of life. Questionnaires will be completed in at least two experimental time points to compare changes in present intensity of pain, and overall impression of pain. Particular emphasis will be placed on pain, sleep, quality of life and overall satisfaction scores comparing oral and inhalatory routes of each treatment. The effectiveness of THC and CBD cannabinoids on treating pain has already been demonstrated using *cannabis* based medicinal extracts (CBME, see U.S. patent application Ser. Nos. 12/084,454, 13/491,077, 12/308,776, and 12/863,842). A key aspect of this invention is that multiplexed *cannabis* mixtures use unextracted natural plant material as a medicine that is both effective at treating symptoms as well as pleasurable to the volunteer; in this case by providing pain relief, extended and better quality sleep, and a satisfying organoleptic feel.

Example 40

Use of Multiplexed *Cannabis* Mixtures to Improve Cholesterol Levels

In one embodiment of this invention the multiplexed *cannabis* medicine can be used to lower total cholesterol and increase high density lipoprotein (HDL) "good" cholesterol as an effective treatment for diseases such as obesity, heart disease, and diabetes, among others. Effectiveness of the treatment will be confirmed by conducting a trial using double blind, randomized treatments comparing the effects of multiplexed *cannabis* mixtures containing THCV and/or CBD, or combinations of other cannabinoid variants, and/or a combination of various terpenes. Concentrations used for this study will be (2 mg, 5 mg, 10 mg, 15 mg, 20 mg or more THCV) and/or (2 mg, 5 mg, 10 mg, 15 mg, 20 mg or more CBD) alone, or in combination with other terpenes such as myrcene, limonene, pinene, and/or linalool fortifiers. Terpene combinations will be chosen based on their therapeutic activity (e.g. decreases in platelet aggregation effects of myrcene, Lin et al., Planta Med, 69:757-764 2003) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which reduced appetitive or reduced cholesterol levels are obtained.

Volunteers will be screened to determine eligibility based on cholesterol levels and baseline weight and health assessments will be made prior to beginning the study. Volunteer volunteers will be randomized into each treatment groups and placebo groups, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

Cholesterol levels will be measured weekly using any over the counter consumer measuring kits such as the SURESIGN Cholesterol++Test™, Cholesterol Home Scan™, and CheckUp America Cholesterol Panel™, among others. The trial will be conducted over for several weeks and the effectiveness of each treatment will be compared. Volunteer diary self-assessments will also be compared to normalize for physical activity and diet, as well as to evaluate the overall satisfaction with each treatment. Particular emphasis will be placed on total cholesterol and HDL levels, and overall satisfaction scores comparing oral and inhalatory routes of each treatment. The effectiveness of THCV and CBD cannabinoids as CB1 and CB2 antagonists and at lowering cholesterol levels has already been demonstrated using *cannabis* based medicinal extracts (CBME, see U.S. patent application Ser. No. 12/865,842). A key aspect of this invention is that multiplexed *cannabis* mixtures use unextracted natural plant material as a medicine that is both effective at treating symptoms as well as pleasurable to the volunteer; in this case by helping volunteers improve their cholesterol while providing a satisfying organoleptic feel.

Example 41

Use of Multiplexed *Cannabis* Mixtures to Treat Psychosis Related Diseases

In one embodiment of this invention the multiplexed *cannabis* mixtures or specialty *cannabis* plants of the present invention are tailored to treat psychosis related diseases such as schizophrenia, schizophreniform disorder, schizoaffective disorder, bipolar I disorder, bipolar II disorder, major depressive disorder with psychotic feature, delusional disorders, shared psychotic disorder, brief psychotic disorder, among others. Effectiveness of the treatment will be confirmed by conducting a trial using double blind, randomized treatments comparing the effects of multiplexed *cannabis* mixtures containing THCV and/or CBD, or combinations of other cannabinoid variants, and/or a combination of various terpenes. Concentrations used for this study will be (2 mg, 5 mg, 10 mg, 15 mg, 20 mg or more THCV) and/or (2 mg, 5 mg, 10 mg, 15 mg, 20 mg or more CBD) alone, or in combination with terpenes such as myrcene, limonene, pinene, and/or linalool fortifiers. Terpene combinations will be chosen based on their therapeutic activity (e.g. anti-anxiety effects of linalool, Russo et al., Handbook of Psychotropic Herbs, Haworth Press, December 2000) as well as flavor and organoleptic feel (e.g. cineole/eucalyptol for spicy flavor and cooling feel). In some embodiments, the THC:CBS ratio of the MCM or specialty *cannabis* will be greater than or equal to 20:1, or 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, or lower. Treatments will be administered via oral or inhaled routes. Dosage levels will be determined based on Study 1 of Example 30 of this application, or by individually tailoring doses up to the level at which mood improvement is obtained.

Volunteers will be screened to determine eligibility during their first visit. Eligible volunteers will fulfill DSM-IV criteria for a primary diagnosis of psychotic disorder as established by a semi structured interview (McEvoy et al., J. Clinical Psychiatry, Vol 74:-02 (2013)). Prior to conducting the study, volunteer psychosis baseline assessments will be made using any of the accepted medical measures of psychosis such as the Minnesota Multiphasic Personality Inventory-2 (MMPI-2), Barnes Akathisia Scale, Simpson-Angus Scale Positive and Negative Syndrome Scale, etc (see Drayton, M, Occupational Medicine, Vol 59-2:135-136 2009; Munetz et al., Hosp Community Psychiatry, 1988; 39(11): 1172-1177; Barnes, Br J Psychiatry, 1989; 154(5):672-676; Simpson et al., Acta Psychiatr Scand suppl, 1970; 212(5212):11-19; Kay et al., Multi-Health Systems 1994). Volunteers will be randomized into treatment as well as placebos, including complete placebos (no active ingredient), a placebo containing no cannabinoids and only terpenes, and placebos containing no terpenes and only cannabinoids. This approach will establish not only efficacy of the cannabinoids and/or terpenes, but also the synergy among the active compounds inherent in each *cannabis* line used.

The effectiveness of each treatment will be determined by using psychosis assessments as used for baseline assessments and described above, as well as with the use of volunteer diary self-assessments, and overall life quality and satisfaction scores. Psychosis assessments will be completed in at least two experimental time points. Particular emphasis will be placed on psychosis and overall life quality scores comparing oral and inhalatory routes of each treatment. The effectiveness of THCV and CBD cannabinoids on treating psychosis has already been demonstrated in animal models using *cannabis* based medicinal extracts (CBME, see U.S. patent application Ser. No. 12/811,393). A key aspect of this invention is that multiplexed *cannabis* mixtures use unextracted natural plant material as a medicine that is both effective at treating symptoms as well as pleasurable to the volunteer; in this case by reducing volunteer psychosis and providing a pleasurable and satisfying organoleptic feel.

Example 42

Zero-point Delivery Device and Principles

Vaporization is the process of heating a substance to its boiling point to release vapor containing the active constituents in a gaseous state. This vapor can be inhaled to deliver the active agents in the drug, but without the harmful irritants and carcinogens found in smoke that results from combustion of the plant material, and without the alcohol and preserved water that serves as a base for nebulizer solutions. There is a need for a convenient handheld and/or tabletop vaporization device that vaporizes designer 'sludges' (i.e. material to be vaporized) that are created with predetermined and calculated resistances to work best with the vaporization device. The internal resistance of the sludge, in concert with the high voltage current and the aluminum dosage strip technology described in the next Example below, generates the necessary heat of vaporization to volatilize all of the active components in the sludge.

The vaporization device requires, at its most basic, a source of heat that is emitted when an electric current is passed through a wire or a fluid, and a dosage strip containing the *cannabis* sludge to be vaporized that has been optimized for consumption in the vaporization device. The design of the delivery device comprises components that are similar to that of a basic taser or stun gun, which have been used in the laboratory to vaporize *cannabis* oils or sludges.

In some embodiments the electronic design of the zero point delivery device is similar to the stun gun as shown in WO2005076734, U.S. Patent Application Serial No. US 2006/0067026, or U.S. Pat. No. 5,467,247.

At its simplest, the ergo-dynamic vaporization device described herein comprises a space for depositing the dosage strip, a dose selector switch, a micro-computer which activates any one or more four activation sites present on the dosing strip, an activation switch, a battery, a speaker, a LED light, and an area through which the patient inhales the vapor.

Figure 18:
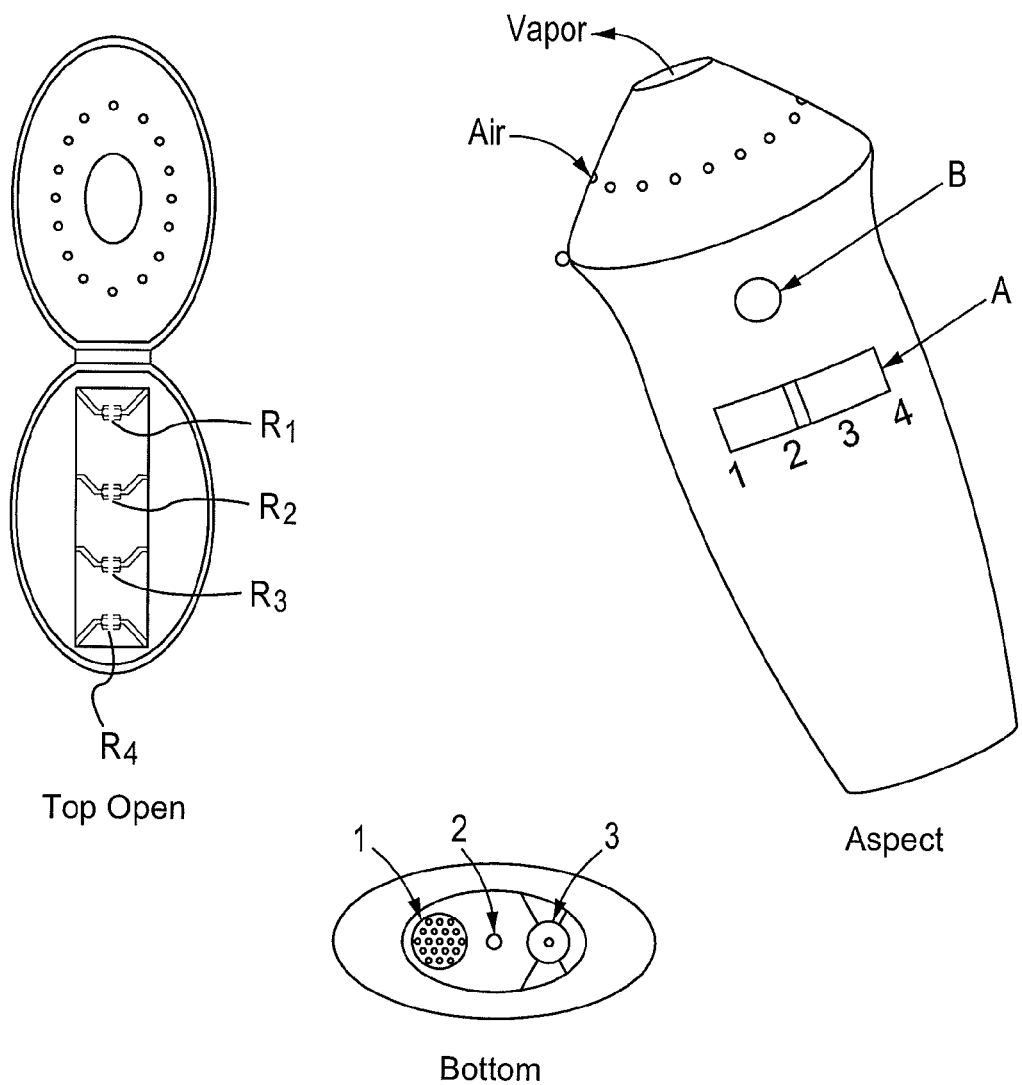
FIG. 18—Example diagram of one embodiment of the vaporizer device of the present invention. The vaporizer may include dosage selection switches allowing the user to switch between, or combine various vaporizable substrates. R1-R4 on the diagram indicate the activation sites for the corresponding dosage strips. A on the diagram is the dose selector. B on the diagram is the dose activator. 1 on the diagram is the speaker. 2 on the diagram is the LED light. 3 on the diagram is the DC dock.

An example of one manifestation of the vaporizer device is shown in FIG. 18. The user chooses the proper dosage on the dose selector switch, and pushes the activation switch, thereby delivering a high voltage current through the aluminum electrodes on the dosage strip to heat and vaporize the sludge. Intake air passes in through small holes located around the central mouth piece. This air flow creates an upward current that allows the essential oil vapor to be inhaled.

The vaporizer may also comprise a selector switch which is designed to select the desired *cannabis* dosage. This switch communicates with the microchip to control how many of the activation sites on the dosing strip are activated and activates the activation sites in any possible combination. In non-limiting examples, the switch activates each of the four sites individually, one, two, three or four of the sites consecutively or serially, or one, two, three, or four sites with a delay between them. The orders in which the activation sites are activated, and/or the delay between the activation of one or more sites, are calculated based on dosage studies.

Example 43

Zero-Point Delivery Doses

Figure 19:
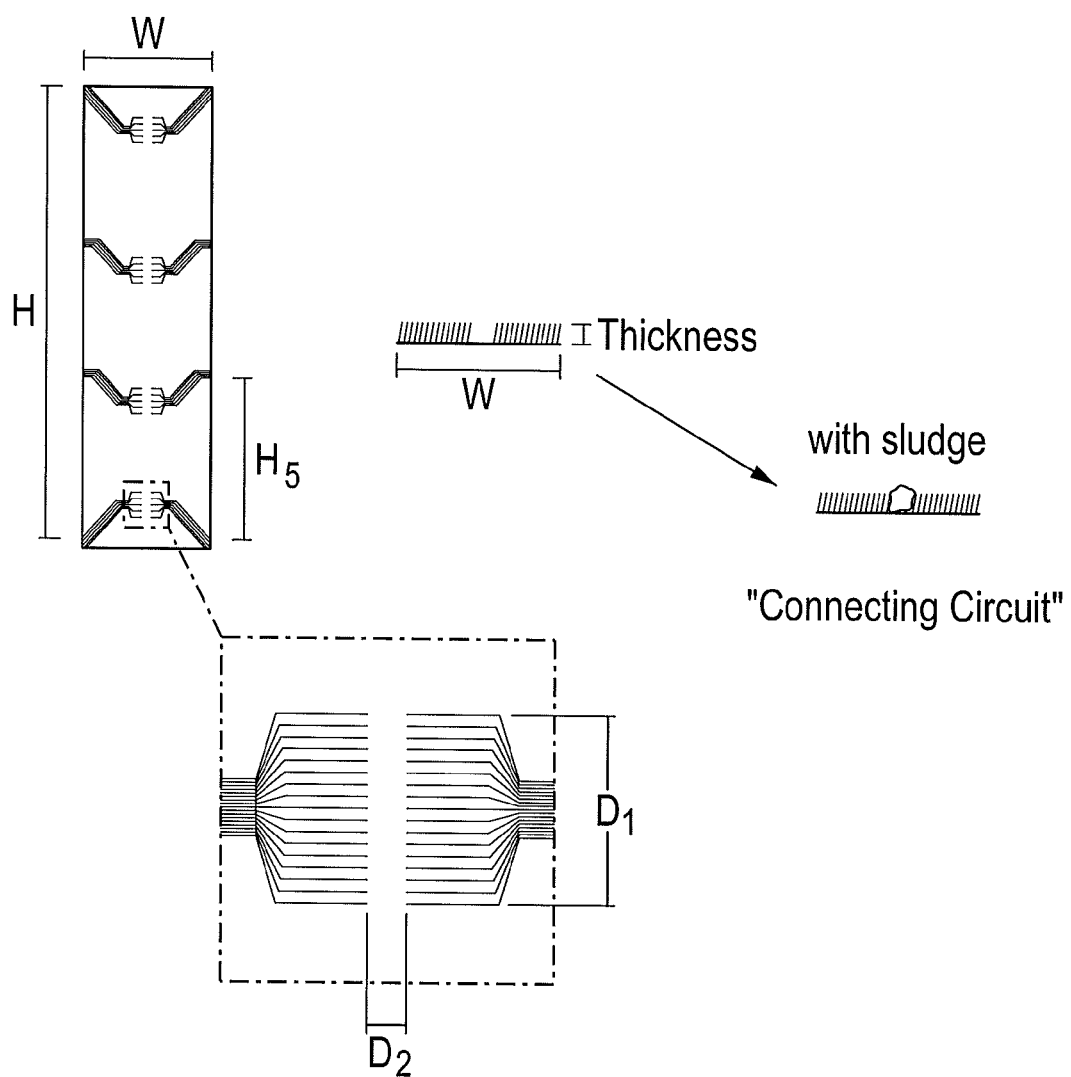
FIG. 19—Example diagram of one embodiment of the dosage strips of the present invention. Each sample is placed with its own heating element so as to be able to switch between, or combine various vaporizing substrates.

The vaporization device described in the above example is designed to work with dosage strips engineered specifically for efficient vaporization at the particular voltage and current supplied by the device. An example of a dosing strip is shown in FIG. 19.

The strips are composed of a non-conductive material such as ceramic or glass, and contain sludge from a whole plant liquid-gas extract at the particular resistance that is vaporized by the device. The dosage strips comprise an aluminum conductor with four (4) or more resistance sites, each of which consists of bundles of frayed aluminum which conduct the high voltage current produced by the vaporization device to the sludge to vaporize it.

The amount of sludge on each dosing strip is predetermined based on the volunteer and the disease and/or disorder being treated, to provide accurate and consistent dosing. The solvent-free sludge is extracted via multigas extraction and comprises the refrigerant 134A, butane, iso-butane and propane in a ratio that delivers a very complete and balanced extraction of essential oils.

The predetermined quantity of sludge is applied onto each of four or more ($R_1$-$R_4$) connections (activation sites) on the dosage strip. The dosage strips are inserted into a vaporization device and are activated by the device's microchip at any number of the sludge activation sites on each dosage strip. The amount of dose administered to the volunteer is selected and altered using the dosing switch on the vaporizer. The settings on the selector switch communicate with the microchip to control how many activation sites on the strip are activated.

The dosing strips and the vaporization device described herein, allow the *cannabis* active compounds to be delivered to the volunteer in a method that is capable of reproducible and accurate dosing for essential oil and cannabinoid medications.

DEPOSIT INFORMATION

A deposit of the *cannabis* varieties of the present invention, including the Classes of *Cannabis* Varieties, is maintained by the Biotech Institute, LLC 5655 Lindero Canyon Road, Suite 226, Westlake Village, Calif. 91362.

In addition, a sample of one or more varieties of this invention, including deposits NCIMB 42246, NCIMB 42247, NCIMB 42248, NCIMB 42249, NCIMB 42250, NCIMB 42254, NCIMB 42255, NCIMB 42256, NCIMB 42257, and NCIMB 42258, has been deposited with an International Depositary Authority as established under the Budapest Treaty according to 37 CFR 1.803(a)(1), at the National Collections of Industrial, Food and Marine Bacteria Ltd. (NCIMB) in Aberdeen Scotland.

To satisfy the enablement requirements of 35 U.S.C. 112, and to certify that the deposit of the isolated strains (i.e., *cannabis* varieties) of the present invention meets the criteria set forth in 37 CFR 1.801-1.809 and Manual of Patent Examining Procedure (MPEP) 2402-2411.05, Applicants hereby make the following statements regarding the deposited *cannabis* varieties:

If the deposit is made under the terms of the Budapest Treaty, the instant invention will be irrevocably and without restriction released to the public upon the granting of a patent.

If the deposit is made not under the terms of the Budapest Treaty, Applicant(s) provides assurance of compliance by following statements:

1. During the pendency of this application, access to the invention will be afforded to the Commissioner upon request;

2. All restrictions on availability to the public will be irrevocably removed upon granting of the patent under conditions specified in 37 CFR 1.808;

3. The deposit will be maintained in a public repository for a period of 30 years or 5 years after the last request or for the effective life of the patent, whichever is longer;

4. A test of the viability of the biological material at the time of deposit will be conducted by the public depository under 37 CFR 1.807; and 5. The deposit will be replaced if it should ever become unavailable.

Access to this deposit will be available during the pendency of this application to persons determined by the Commissioner of Patents and Trademarks to be entitled thereto under 37C.F.R. §1.14 and 35 U.S.C. §122. Upon granting of any claims in this application, all restrictions on the availability to the public of the variety will be irrevocably removed by affording access to a deposit of at least 2,500 seeds of the same variety with the depository.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present invention is not entitled to antedate such publication by virtue of prior invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A hybrid cannabis plant, or an asexual clone of said hybrid cannabis plant, or a plant part, tissue, or cell thereof, which produces a female inflorescence, said inflorescence comprising:
   a) a $B_T/B_D$ genotype;
   b) a terpene profile in which myrcene is not the dominant terpene;
   c) a terpene oil content greater than about 1.0% by weight; and
   d) a CBD content greater than 3%;
wherein the terpene profile is defined as terpinolene, alpha phelladrene, beta ocimene, careen, limonene, gamma terpinene, alpha pinene, alpha terpinene, beta pinene, fenchol, camphene, alpha terpineol, alpha humulene, beta caryophyllene, linalool, cary oxide, and myrcene, and wherein the terpene oil content is determined by the additive content of the terpenes in the terpene profile; and wherein the terpene contents and CBD content are measured by gas chromatography-flame ionization detection (GC-FID) and calculated based on dry weight of the inflorescence; wherein a representative sample of seed producing said plants has been deposited under NCIMB Nos. 42246, 42247, 42248, 42249, 42250, and 42254.

2. The hybrid cannabis plant, or an asexual clone of said hybrid cannabis plant, or a plant part, tissue, or cell thereof of claim 1 wherein the plant, plant part, tissue, or cell comprises a terpene oil content greater than about 1.5% by weight.

3. The hybrid cannabis plant, or an asexual clone of said hybrid cannabis plant, or a plant part, tissue, or cell thereof of claim 1, wherein the hybrid cannabis plant, or an asexual clone of said hybrid cannabis plant, or a plant part, tissue, or cell thereof comprises a tetrahydrocannabinol (THC) content that is at least 3.0% by weight as measured by GC-FID and calculated based on dry weight of the inflorescence.

4. The hybrid cannabis plant, or an asexual clone of said hybrid cannabis plant, or a plant part, tissue, or cell thereof of claim 1, wherein the hybrid cannabis plant, or an asexual clone of said hybrid cannabis plant, or a plant part, tissue, or cell thereof comprises a tetrahydrocannabinol (THC) content that is at least 6.0% by weight as measured by GC-FID and calculated based on dry weight of the inflorescence.

5. The hybrid cannabis plant, or an asexual clone of said hybrid cannabis plant, or a plant part, tissue, or cell thereof of claim 1, wherein the hybrid cannabis plant, or an asexual clone of said hybrid cannabis plant, or a plant part, tissue, or cell thereof comprises a cannabidiol CBD content that is at least 6.0% by weight as measured by GC-FID and calculated based on dry weight of the inflorescence.

6. The hybrid cannabis plant, or an asexual clone of said hybrid cannabis plant, or a plant part, tissue, or cell thereof of claim 1, wherein limonene is the most abundant terpene in said terpene profile.

7. The hybrid cannabis plant, or an asexual clone of said hybrid cannabis plant, or a plant part, tissue, or cell thereof of claim 1, wherein terpinolene is the most abundant terpene in said terpene profile.

8. The hybrid cannabis plant, or an asexual clone of said hybrid cannabis plant, or a plant part, tissue, or cell thereof of claim 1, wherein alpha pinene is the most abundant terpene in said terpene profile.

9. The hybrid cannabis plant, or an asexual clone of said hybrid cannabis plant, or a plant part, tissue, or cell thereof of claim 1, wherein beta caryophyllene is the most abundant terpene in said terpene profile.

10. A method of breeding chemotype II cannabis plants with a non-myrcene dominant terpene profile, said method comprising:
    (i) making a cross between a first hybrid cannabis plant, or an asexual clone of said hybrid cannabis plant of claim 1 and a second cannabis plant to produce an F1 seed:
    (ii) harvesting the resulting seed;
    (iii) growing said seed; and
    (iv) selecting a cannabis plant with a desired phenotype;
    wherein the resulting selected cannabis plant is a chemotype II cannabis plant with a non-myrcene dominant terpene profile.

11. A method of producing a chemotype II cannabis plant with a non-myrcene dominant terpene profile, said method comprising:
    (i) obtaining a cannabis seed, cutting, or plant cell, from a hybrid cannabis plant, or an asexual clone of said hybrid cannabis plant of claim 1;
    (ii) placing said cannabis seed, cutting, or plant cell in an environment conducive to growth; and
    (iii) allowing said cannabis seed, cutting, or plant cell to produce a cannabis plant;
    wherein said produced cannabis plant is a chemotype II cannabis plant with a non-myrcene dominant terpene profile.

12. A cannabis extract from the hybrid cannabis plant, or an asexual clone of said hybrid cannabis plant, or a plant part, tissue, or cell thereof of claim 1.

13. The cannabis extract of claim 12, wherein said extract is selected from the group consisting of kief, hashish, bubble hash, solvent reduced oils, sludges, e-juice, and tinctures.

14. An edible product comprising cannabis tissue from the hybrid cannabis plant, or an asexual clone of said hybrid cannabis plant, or a plant part, tissue, or cell thereof of claim 1.

15. An edible product comprising the cannabis extract of claim 12.

16. The hybrid cannabis plant, or an asexual clone of said hybrid cannabis plant, or a plant part, tissue, or cell thereof of claim 1, wherein said plant part is selected from the group consisting of: trichomes, sun leaves, or inflorescences.

\* \* \* \* \*

UNITED STATES PATENT AND TRADEMARK OFFICE
CERTIFICATE OF CORRECTION

PATENT NO.         : 9,095,554 B2                                            Page 1 of 2
APPLICATION NO.    : 14/216744
DATED              : August 4, 2015
INVENTOR(S)        : Mark Anthony Lewis It is certified that error appears in the above-identified patent and that said Letters Patent is hereby corrected as shown below:

In the Specification

Column 4, line 55: "alpha phelladrene" should be -- alpha phellandrene --.
Column 4, line 55: "careen" should be -- carene --.
Column 4, line 58: "cary oxide" should be -- caryophyllene oxide --.
Column 5, line 26: "alpha phelladrene" should be -- alpha phellandrene --.
Column 5, line 26: "careen" should be -- carene --.
Column 5, line 29: "cary oxide" should be -- caryophyllene oxide --.
Column 5, line 39: "alpha phelladrene" should be -- alpha phellandrene --.
Column 5, line 39: "careen" should be -- carene --.
Column 5, line 42: "cary oxide" should be -- caryophyllene oxide --.
Column 5, line 59: "alpha phelladrene" should be -- alpha phellandrene --.
Column 5, line 60: "careen" should be -- carene --.
Column 5, line 62: "cary oxide" should be -- caryophyllene oxide --.
Column 6, line 40: "alpha phelladrene" should be -- alpha phellandrene --.
Column 6, line 40: "careen" should be -- carene --.
Column 6, line 43: "cary oxide" should be -- caryophyllene oxide --.
Column 7, line 4: "alpha phelladrene" should be -- alpha phellandrene --.
Column 7, line 8: "careen" should be -- carene --.
Column 7, line 56: "cary oxide" should be -- caryophyllene oxide --.
Column 8, line 2: "alpha phelladrene" should be -- alpha phellandrene --.
Column 8, line 2: "careen" should be -- carene --.
Column 8, line 5: "cary oxide" should be -- caryophyllene oxide --.
Column 8, line 46: "alpha phelladrene" should be -- alpha phellandrene --.
Column 8, line 47: "careen" should be -- carene --.
Column 8, line 65: "alpha phelladrene" should be -- alpha phellandrene --.
Column 8, line 66: "careen" should be -- carene --.
Column 9, line 1: "cary oxide" should be -- caryophyllene oxide --.
Column 9, line 28: "alpha phelladrene" should be -- alpha phellandrene --.

Signed and Sealed this
Twelfth Day of January, 2016

Michelle K. Lee
*Director of the United States Patent and Trademark Office*

CERTIFICATE OF CORRECTION (continued)
U.S. Pat. No. 9,095,554 B2

Column 9, line 29: "careen" should be -- carene --.
Column 9, line 32: "cary oxide" should be -- caryophyllene oxide --.
Column 10, line 37: "alpha phelladrene" should be -- alpha phellandrene --.
Column 10, line 37: "careen" should be -- carene --.
Column 10, line 40: "cary oxide" should be -- caryophyllene oxide --.
Column 13, line 11: "alpha phelladrene" should be -- alpha phellandrene --.
Column 13, line 12: "careen" should be -- carene --.
Column 13, line 14: "cary oxide" should be -- caryophyllene oxide --.
Column 41, line 56: "alpha phelladrene" should be -- alpha phellandrene --.
Column 42, line 60: "cary oxide" should be -- caryophyllene oxide --.
Column 45, line 54: "alpha phelladrene" should be -- alpha phellandrene --.
Column 45, line 57: "cary oxide" should be -- caryophyllene oxide --.
Column 92, Table 8: "cary oxide" should be -- caryophyllene oxide --.
Column 95, Table 9: "cary oxide" should be -- caryophyllene oxide --.
Column 97, Table 9: "cary oxide" should be -- caryophyllene oxide --.
Column 103, Table 12: "cary oxide" should be -- caryophyllene oxide --.
Column 104, Table 13: "cary oxide" should be -- caryophyllene oxide --.
Column 105, Table 16: "cary oxide" should be -- caryophyllene oxide --.
Column 108, Table 17: "cary oxide" should be -- caryophyllene oxide --.
Column 110, Table 21: "cary oxide" should be -- caryophyllene oxide --.
Column 151, Table 33: "cary oxide" should be -- caryophyllene oxide --.
Column 176, Table 44: "cary oxide" should be -- caryophyllene oxide --.
Column 184, Table 48: "cary oxide" should be -- caryophyllene oxide --.
Column 214, line 26: "alpha phelladrene" should be -- alpha phellandrene --.
Column 214, line 30: "cary oxide" should be -- caryophyllene oxide --.

In the Claims
Claim 1, in column 245, line 45: "alpha phelladrene" should be -- alpha phellandrene --.
Claim 1, in column 245, line 45: "careen" should be -- carene --.
Claim 1, in column 245, line 48: "cary oxide" should be -- caryophyllene oxide --.